(12) United States Patent
Kobayashi et al.

(10) Patent No.: US 9,079,901 B2
(45) Date of Patent: Jul. 14, 2015

(54) FUSED HETEROCYCLIC COMPOUNDS AS ION CHANNEL MODULATORS

(71) Applicant: Gilead Sciences, Inc., Foster City, CA (US)

(72) Inventors: Tetsuya Kobayashi, Sunnyvale, CA (US); Dmitry Koltun, Foster City, CA (US); Gregory Notte, San Mateo, CA (US); Eric Parkhill, San Francisco, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/217,011

(22) Filed: Mar. 17, 2014

(65) Prior Publication Data

US 2015/0080370 A1   Mar. 19, 2015

Related U.S. Application Data

(63) Continuation of application No. 13/174,587, filed on Jun. 30, 2011, now Pat. No. 8,703,759.

(60) Provisional application No. 61/361,056, filed on Jul. 2, 2010.

(51) Int. Cl.
*C07D 401/14* (2006.01)
*A61K 31/437* (2006.01)
*C07D 471/04* (2006.01)
*C07D 519/00* (2006.01)

(52) U.S. Cl.
CPC ............ *C07D 471/04* (2013.01); *C07D 519/00* (2013.01)

(58) Field of Classification Search
CPC ........................... C07D 401/14; A61K 31/437
USPC ............... 514/211.04, 211.05, 211.09, 211.1, 514/211.13, 303
See application file for complete search history.

(56) References Cited

U.S. PATENT DOCUMENTS

| | | | |
|---|---|---|---|
| 4,230,705 A | 10/1980 | Allen et al. |
| 4,242,515 A | 12/1980 | Trust et al. |
| 4,244,953 A | 1/1981 | Trust et al. |
| 4,326,525 A | 4/1982 | Swanson et al. |
| 4,654,343 A | 3/1987 | Albright et al. |
| 4,746,655 A | 5/1988 | Cale, Jr. |
| 4,812,565 A | 3/1989 | Cale, Jr. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,449 A | 10/1996 | Blackburn et al. |
| 5,616,345 A | 4/1997 | Geoghegan et al. |
| 5,939,412 A | 8/1999 | Bondinell et al. |
| 6,011,150 A | 1/2000 | Iwasaki et al. |
| 6,908,917 B2 | 6/2005 | Ortwine |
| 6,998,408 B2 | 2/2006 | Pinto |
| 7,005,523 B2 | 2/2006 | Dombroski et al. |
| 7,157,490 B2 | 1/2007 | Colandrea et al. |
| 7,306,631 B2 | 12/2007 | Glenn, Jr. et al. |
| 7,456,187 B2 | 11/2008 | Ford et al. |
| 7,572,807 B2 | 8/2009 | Li et al. |
| 7,579,348 B2 | 8/2009 | Wang et al. |
| 7,790,741 B2 | 9/2010 | Calderwood et al. |
| 8,212,041 B2 | 7/2012 | Albrecht et al. |
| 8,389,500 B2 | 3/2013 | Abelman et al. |
| 2004/0063580 A1 | 4/2004 | Kuragano et al. |
| 2004/0204404 A1 | 10/2004 | Zelle et al. |
| 2005/0239767 A1 | 10/2005 | Chan et al. |
| 2007/0066584 A1 | 3/2007 | Yao et al. |
| 2007/0142376 A1 | 6/2007 | Fleenor et al. |
| 2009/0012095 A1 | 1/2009 | Zelle et al. |
| 2009/0069300 A1 | 3/2009 | Zhou et al. |
| 2009/0203707 A1 | 8/2009 | Rajamani et al. |
| 2009/0221555 A1 | 9/2009 | Ahmed et al. |
| 2009/0253689 A1 | 10/2009 | Baeschlin et al. |
| 2010/0056536 A1 | 3/2010 | Antzelevitch et al. |
| 2010/0099676 A1 | 4/2010 | Endoh et al. |
| 2010/0113461 A1 | 5/2010 | Koltun et al. |
| 2010/0144745 A1 | 6/2010 | Bamberg et al. |
| 2010/0240635 A1 | 9/2010 | Cordi et al. |

(Continued)

FOREIGN PATENT DOCUMENTS

| | | |
|---|---|---|
| CA | 2068255 | 11/1992 |
| DE | 4010488 | 10/1991 |

(Continued)

OTHER PUBLICATIONS

Barsky, et al., "Hypoglycemic Cyclic Amidines," J. Med. Chem., 14(1): 40-44 (1971).

(Continued)

*Primary Examiner* — Niloofar Rahmani
(74) *Attorney, Agent, or Firm* — Francis O. Ginah; J. Elin Hartrum

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

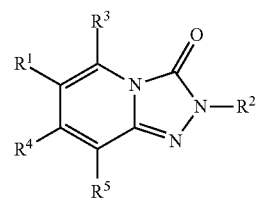

I wherein $R^1$, $R^2$, $R^3$, $R^4$, and $R^5$ are as described herein, to methods for the preparation and use of the compounds and to pharmaceutical compositions containing the same.

24 Claims, No Drawings

(56) References Cited

U.S. PATENT DOCUMENTS

| | | |
|---|---|---|
| 2011/0021521 A1 | 1/2011 | Corkey |
| 2011/0076292 A1 | 3/2011 | Blaquiere et al. |
| 2011/0183990 A1 | 7/2011 | Antzelevitch et al. |
| 2012/0010192 A1 | 1/2012 | Kobayashi et al. |
| 2012/0289493 A1 | 11/2012 | Corkey et al. |
| 2013/0005706 A1 | 1/2013 | Corkey et al. |
| 2013/0012492 A1 | 1/2013 | Corkey et al. |
| 2013/0184255 A1 | 7/2013 | Elzein et al. |
| 2014/0135317 A1 | 5/2014 | Corkey et al. |

FOREIGN PATENT DOCUMENTS

| | | |
|---|---|---|
| DE | 10317526 | 11/2004 |
| EP | 0017438 | 3/1983 |
| EP | 0464572 | 1/1992 |
| EP | 477789 | 4/1992 |
| EP | 540334 | 5/1993 |
| EP | 635488 | 1/1995 |
| EP | 1182195 | 2/2002 |
| EP | 597423 | 6/2002 |
| EP | 1333031 | 8/2003 |
| EP | 1354602 | 10/2003 |
| EP | 1803748 | 7/2007 |
| JP | 06107647 | 4/1994 |
| JP | 04209692 | 6/1997 |
| JP | 09157262 | 6/1997 |
| JP | 11100394 | 4/1999 |
| JP | 2003277384 | 2/2003 |
| JP | 2003321461 | 11/2003 |
| JP | 2006063064 | 9/2006 |
| WO | WO 93/00095 | 1/1993 |
| WO | WO 93/08174 | 4/1993 |
| WO | WO 94/13272 | 6/1994 |
| WO | WO 94/13292 | 6/1994 |
| WO | WO 97/03975 | 2/1997 |
| WO | WO 98/11890 | 3/1998 |
| WO | WO 98/47885 | 10/1998 |
| WO | WO 99/13038 | 3/1999 |
| WO | WO 99/41246 | 8/1999 |
| WO | WO 99/42456 | 8/1999 |
| WO | WO 00/23451 | 4/2000 |
| WO | WO 01/16110 | 3/2001 |
| WO | WO 01/16263 | 3/2001 |
| WO | WO 01/16274 | 3/2001 |
| WO | WO 01/16275 | 3/2001 |
| WO | WO 01/16276 | 3/2001 |
| WO | WO 01/16277 | 3/2001 |
| WO | WO 01/16278 | 3/2001 |
| WO | WO 01/87883 | 11/2001 |
| WO | WO 02/18377 | 3/2002 |
| WO | WO 02/38562 | 5/2002 |
| WO | WO 02/010135 | 7/2002 |
| WO | WO 02/072579 | 9/2002 |
| WO | WO 02/096873 | 12/2002 |
| WO | WO 03/024941 | 3/2003 |
| WO | WO 03/075858 | 9/2003 |
| WO | WO 2004/020440 | 3/2004 |
| WO | WO 2004/026292 | 4/2004 |
| WO | WO 2004/037192 | 5/2004 |
| WO | WO 2004/043940 | 5/2004 |
| WO | WO 2004/062616 | 7/2004 |
| WO | WO 2004/083190 | 9/2004 |
| WO | WO 2004/094371 | 11/2004 |
| WO | WO 2004/096767 | 11/2004 |
| WO | WO 2005/002520 | 1/2005 |
| WO | WO 2005/014558 | 2/2005 |
| WO | WO 2005/060967 | 7/2005 |
| WO | WO 2005/097052 | 10/2005 |
| WO | WO 2006/002470 | 1/2006 |
| WO | WO 2006/011669 | 2/2006 |
| WO | WO 2006/020959 | 2/2006 |
| WO | WO 2006/021544 | 3/2006 |
| WO | WO 2006/023750 | 3/2006 |
| WO | WO 2006/031676 | 3/2006 |
| WO | WO 2006/048727 | 5/2006 |
| WO | WO 2006/091897 | 8/2006 |
| WO | WO 2006/095014 | 9/2006 |
| WO | WO 2006/113864 | 10/2006 |
| WO | WO 2006/125119 | 11/2006 |
| WO | WO 2006/125972 | 11/2006 |
| WO | WO 2006/138549 | 12/2006 |
| WO | WO 2006/138657 | 12/2006 |
| WO | WO 2006/138695 | 12/2006 |
| WO | WO 2007/004028 | 1/2007 |
| WO | WO 2007/023750 | 3/2007 |
| WO | WO 2007/038209 | 4/2007 |
| WO | WO 2007/047604 | 4/2007 |
| WO | WO 2007/058583 | 5/2007 |
| WO | WO 2007/061677 | 5/2007 |
| WO | WO 2007/061696 | 5/2007 |
| WO | WO 2007/069986 | 6/2007 |
| WO | WO 2007/070866 | 6/2007 |
| WO | WO 2007/113226 | 10/2007 |
| WO | WO 2007/146284 | 12/2007 |
| WO | WO 2008/005338 | 1/2008 |
| WO | WO 2008/005457 | 1/2008 |
| WO | WO 2008/006540 | 1/2008 |
| WO | WO 2008/007661 | 1/2008 |
| WO | WO 2008/055068 | 5/2008 |
| WO | WO 2008/079570 | 7/2008 |
| WO | WO 2008/080012 | 7/2008 |
| WO | WO 2008/094909 | 8/2008 |
| WO | WO 2008/108445 | 9/2008 |
| WO | WO 2008/117061 | 10/2008 |
| WO | WO 2008/118141 | 10/2008 |
| WO | WO 2008/134553 | 11/2008 |
| WO | WO 2008/144483 | 11/2008 |
| WO | WO 2009/005675 | 1/2009 |
| WO | WO 2009/026444 | 2/2009 |
| WO | WO 2009/045753 | 4/2009 |
| WO | WO 2009/085980 | 7/2009 |
| WO | WO 2009/089027 | 7/2009 |
| WO | WO 2009/091374 | 7/2009 |
| WO | WO 2009/137462 | 11/2009 |
| WO | WO 2009/137499 | 11/2009 |
| WO | WO 2009/141026 | 11/2009 |
| WO | WO 2009/153589 | 12/2009 |
| WO | WO 2010/006292 | 1/2010 |
| WO | WO 2010/018686 | 2/2010 |
| WO | WO 2010/022001 | 2/2010 |
| WO | WO 2010/077680 | 7/2010 |
| WO | WO 2010/077686 | 7/2010 |
| WO | WO 2010/111534 | 9/2010 |
| WO | WO 2010/118208 | 10/2010 |
| WO | WO 2011/036280 | 3/2011 |
| WO | WO 2011/075607 | 6/2011 |
| WO | WO 2011/084733 | 7/2011 |
| WO | WO 2012/019071 | 2/2012 |
| WO | WO 2012/019076 | 2/2012 |
| WO | WO 2012/037105 | 3/2012 |
| WO | WO 2012/050918 | 4/2012 |
| WO | WO 2012/071509 | 5/2012 |
| WO | WO 2013/006485 | 1/2013 |
| WO | WO 2013/112932 | 8/2013 |

OTHER PUBLICATIONS

Belardinelli, et al:, "A Novel, Potent, and Selective Inhibitor of Cardiac Late Sodium Current Suppresses Experimental Arrhythmias," J. Pharm. Exp. Ther., 344(1): 23-32 (2013).

Benson, et al., "SUMO modification regulates inactivation of the voltage-gated potassium channel Kv1.5", Proc. Nat. Acad. Sci., 104(6): 1805-1810 (2007).

Burashnikov, et al., "Role of late sodium channel current block in the management of atrial fibrillation," Cardiovascular Drugs and Therapy / Sponsored by the International Society of Cardiovascular Pharmacotherapy, 27(1): 79-89 (2013).

Chiu, et al., "Cycloaddition of Alpha-Chloroformylarlhydrazines with Pyridines Afford 2-Aryl-2H-[1,2,4]triazolo[4,3-a]pyridine-3-ones", Journal of the Chinese Chemical Society, Chinese Electronic Periodical Services, China, 48: 1135-1142 (2001).

(56) References Cited

OTHER PUBLICATIONS

Chouhan, et al., "Domino Ring-Opening/Carboxamidation Reactions of N-Tosyl Aziridines and 2-Halophenols/Pyridinol: Efficient Synthesis of 1,4-Benzo- and Pyrido-oxazepinones", Organic Letters, 12(1): 192-195 (2010).
Cleator, et al., "Synthesis of Novel Benzoxathiazepine-1,1-dioxides by Means of a One-pot Multicomponent Reaction," Tetrahedron Letters, 51: 1079-1082 (2010).
Elzein, et al., "Novel 1,3-dipropyl-8-(1-heteroarylmethyl-1$H$-pyrazol-4-yl)-xanthine derivatives as high affinity and selective $A_{2B}$ adenosine receptor antagonists," Bioorganic & Medical Chemistry Letters, 16: 302-306 (2006).
Foster, "Deuterium Isotope Effects in Studies of Drug Metabolism", Trends Pharmacol. Sci., 5(12): 524-527 (1984).
Hale, et al., Journal of Molecular and Cellular Cardiology, 44: 954-967 (2008).
International Search Report and Written Opinion for PCT/US2012/045021 dated Oct. 9, 2012.
International Search Report and Written Opinion from PCT/US2013/02329, dated Mar. 7, 2013.
International Search Report and Written Opinion for PCT/US2010/043264, dated Sep. 28, 2010.
International Search Report and Written Opinion for PCT/US2011/042700, dated Aug. 17, 2011.
International Search Report and Written Opinion from PCT/US2012/036976, dated Jul. 2, 2012.
International Search Report and Written Opinion from PCT/US2012/045086, dated Sep. 19, 2012.
Kumar, et al., "New and emerging antiarrhythmic drugs for atrial fibrillation: what may become available to the clinician in the near future," Curr. Treat. Options Cardiovasc. Med., pp. 11(5) (2009).
Ning, et al., "Ranolazine Increases Beta-Cell Survival and Improves Glucose Homeostasis in Low-Dose Streptozotocin-induced Diabetes in Mice," J. Pharmacol. Exp. Ther., 337(1): 50-58 (2011).
Rudolph, et al., "Quinazolinone Derivatives as Orally Available Ghrelin Receptor Antagonists for the Treatment of Diabetes and Obesity," Journal of Medical Chemistry, 50(21): 5202-5216 (2007).
Shin, et al., Heteroatom Chemistry, 18(3): 212-219 (2007).
Shin, et al., "Synthesis and Characterization of New Bluish-Green Electroluminescent Materials Based on 1,3,4-Oxadiazole Triazolopyridinone Hybrids," Heteroatom Chemistry, Wiley Periodicals, Inc., 10(3): 212-219 (2007).
Shin, et al., "New Synthesis of Highly Potential Efficient Bluish-Green Electroluminescent Materials Based on 1,3,4-Oxadiazole Triazolopyridinone Carbazole Derivatives for Single-Layer Devices," Heteroatom Chemistry, Wiley Periodicals, Inc., 17(2) 160-166 (2006).
Sircar, "Synthesis of New 1,2,4-Triazolo[4,3-b]pyridazines and Related Compounds," Journal of Heterocyclic Chemistry 22(1): 1045-1048 (1985).
Toussaint, et al., "Late sodium current as a promising antiarrhythmic drug target for treatment of atrial fibrilolation?" Naunyn-Schmiedeberg's Archives of Pharmacology, 383(1): 61, 20117 77th Annual Meeting on German-Society-for Experimental- and-Clinical-Pharmacology- and Toxicology; Frankfurt, Germany: Mar. 30-Apr. 2, 2011, the whole document.
U.S. Office Action dated Jul. 17, 2012 for U.S. Appl. No. 12/843,702.
U.S. Office Action dated Jul. 31, 2013 for U.S. Appl. No. 12/843,702.
Vippagunta, et al., "Crystalline Solids," Advanced Drug Delivery Reviews, 48: 3-26 (2001).
Wu, et al. "Late Sodium Current Contributes to the Reverse Rate-Dependent Effect of I-Kr Inhibition on Ventricular Repolarization", *Circulation*, 123 (16), pp. 1713-1720, 2011.
Yang, et al., "Synthesis of Dibenzo[b,f][1,4]oxazepin-11(10H)-ones via Intramolecular Cyclocarbonylation Reactions Using pfl2/Cytop 292 as the Catalytic Systems," Journal of Organic Chemistry, 75(18): 6297-6299 (2010).
Zaza, et al., Pathophysiology and Pharmacology of the Cardiac "Late Sodium Current," Pharmacology and Therapeutics, 119: 326-339 (2008).
U.S. Appl. No. 14/274,422, filed May 9, 2014, Corkey et al.
U.S. Appl. No. 14/345,893, filed Sep. 20, 2012, Belardinelli et al.
Clare et al, Drug Discovery Today 2000, vol. 5, No. 11, 506-520.
Database WPI, Week 198132, Thomson Scientific, London, abstract, 1981, XP-002690413, JP56075428.
Database WPI, Week 199346, Thomson Scientific, London, abstract, 1993, XP-002690414, JP5271069.
Dermer et al., Bio/Technology, 1994, 12:320.
Freshney et al., Culture of Animal Cells, A Manual of Basic Technique, Alan R. Liss, Inc., 1983, New York, pp. 1-6.
International Search Report and Written Opinion for PCT/US2012/056419, dated Jan. 30, 2013.
Krafte et al., Current Opinion in Pharmacology 2008, 8:50-56.
Nagashima et al., "Dual effects of disopyramide to the glycemic control in patients with diabetes mellitus", Diabetes, American Diabetes Association, vol. 53, No. Suppl. 2, 2004.
Office Action, U.S. Appl. No. 12/843,702, dated Jan. 15, 2013.
Office Action, U.S. Appl. No. 13/466,995, dated Jun. 9, 2014.
Office Action, U.S. Appl. No. 13/538,307, mailed on Apr. 24, 2014.
Office Action, U.S. Appl. No. 13/538,847, dated May 3, 2013.
Rush et al., Molecular Interventions 2007, vol. 4, issue 7, 192-195.
Toyofuku et al. JP 06001779, Jan. 11, 1995; CA 122;10048, 1995. Abstract provided.
Office Action, IL Application No. 223724, dated Jan. 27, 2015.

FUSED HETEROCYCLIC COMPOUNDS AS ION CHANNEL MODULATORS

CROSS-REFERENCE TO RELATED APPLICATIONS

This application claims the benefit under 35 U.S.C. §119(e) of U.S. Provisional Application Ser. No. 61/361,056, filed Jul. 2, 2010, the contents of which are hereby incorporated by reference in their entirety.

FIELD

The present disclosure relates to novel compounds and to their use in the treatment of various disease states, including cardiovascular diseases and diabetes. The disclosure also relates to methods for their preparation, and to pharmaceutical compositions containing such compounds.

BACKGROUND

The late sodium current (INaL) is a sustained component of the fast $Na^+$ current of cardiac myocytes and neurons. Many common neurological and cardiac conditions are associated with abnormal (INaL) enhancement, which contributes to the pathogenesis of both electrical and contractile dysfunction in mammals. See, for example, Pathophysiology and Pharmacology of the Cardiac "Late Sodium Current", Pharmacology and Therapeutics 119 (2008) 326-339. Accordingly, pharmaceutical compounds that selectively inhibit (INaL) in mammals are useful in treating such disease states.

One example of a selective inhibitor of (INaL) is RANEXA®, a compound approved by the FDA for the treatment of chronic stable angina pectoris. RANEXA® has also been shown to be useful for the treatment of a variety of cardiovascular diseases, including ischemia, reperfusion injury, arrhythmia and unstable angina, and also for the treatment of diabetes. It would be desirable to provide novel compounds that selectively inhibit (INaL) in mammals and that have the same selectivity over peak INa inhibition as RANEXA®.

SUMMARY

Accordingly, the present disclosure provides novel compounds that function as late sodium channel blockers. In one embodiment, the disclosure provides compounds of A compound Formula I:

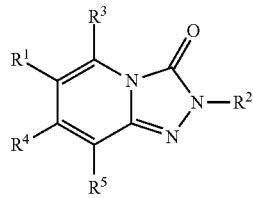

I wherein:
$R^1$ is aryl or heteroaryl,
wherein said aryl or heteroaryl are optionally substituted with one, two, or three substituents independently selected from the group consisting of hydroxyl, halo, $-NO_2$, CN, $-SF_5$, $-Si(CH_3)_3$, $-O-CF_3$, $-O-R^{20}$, $-S-R^{20}$, $-C(O)-R^{20}$, $-N(R^{20})(R^{22})$, $-C(O)-N(e)(R^{22})$, $-N(R^{20})-C(O)-R^{22}$, $-N(R^{20})-S(O)_2-R^{26}$, $-S(O)_2-R^{20}$, $-S(O)_2-N(R^{20})(R^{22})$, $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and
wherein said $C_{1-3}$ alkoxy, $C_{1-4}$ alkyl, $C_{2-4}$ alkenyl, $C_{2-4}$ alkynyl, cycloalkyl, aryl, heteroaryl, or heterocyclyl are optionally substituted with one, two, or three substituents independently selected from hydroxyl, halo, $-NO_2$, $-O-CF_3$, $-O-CHF_2$, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$;

$R^2$ is hydrogen, $C_{1-15}$ alkyl, $C_{1-8}$ alkoxy, $-C(O)-O-R^{26}$, $-C(O)-N(R^{26})(R^{28})$, $-N(R^{20})-S(O)_2-R^{20}$, cycloalkyl, aryl, heteroaryl, or heterocyclyl,
wherein said $C_{1-15}$ alkyl is optionally substituted with one, two, or three substituents independently selected from hydroxyl, $C_{1-8}$ alkoxy, halo, $-NO_2$, $O-CF_3$, $-O-CHF_2$, $C_{2-4}$ alkenyl, $C_{2-4}$ alkynyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
wherein said $C_{1-8}$ alkoxy, $C_{2-4}$ alkenyl, $C_{2-4}$ alkynyl, aryl, heterocyclyl, heteroaryl, or cycloalkyl are optionally further substituted with one, two, or three substituents independently selected from hydroxyl, halo, $-NO_2$, $-O-CF_3$, $C_{1-6}$ alkyl, $C_{1-4}$ alkoxy, aralkyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from deuterium, hydroxyl, halo, $-NO_2$, $-O-CF_3$, $-CF_3$, $-O-CHF_2$, $-N(R^{20})(R^{22})$, $-C(O)-R^{20}$, $-C(O)-O-R^{20}$, $-C(O)-N(R^{20})(R^{22})$, $-CN$, and $-O-R^{20}$;

$R^3$ is selected from the group consisting of hydrogen, hydroxyl, halo, $C_{1-4}$ alkyl, $C_{1-4}$ alkoxy, $-R^{25}-N(R^{20})(R^{22})$, $-R^{25}-O-R^{20}$, $-R^{25}-C(O)-O-R^{20}$, $-R^{25}-C(O)-N(R^{20})(R^{22})$, $-R^{25}-C(O)-O-N(R^{20})(R^{22})$, $-R^{25}-N(R^{20})-C(O)-R^{22}$, and $-R^{25}-O-C(O)-N(R^{20})(R^{22})$, and
wherein said $C_{1-4}$ alkyl is optionally substituted with one, two, or three substituents independently selected from hydroxyl, halo;

$R^4$ is selected from the group consisting of hydrogen, optionally substituted $C_{1-4}$ alkyl, aryl, $-CF_3$, -halo, and $-O-R^{24}$, and
wherein said aryl is optionally further substituted with one, two, or three substituents independently selected from hydroxyl, halo, $-NO_2$, $-O-CF_3$, $C_{1-6}$ alkyl, $C_{1-4}$ alkoxy, aralkyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, $-NO_2$, $-O-CF_3$, $-CF_3$, $-O-CHF_2$, $-N(R^{20})(R^{22})$, $-C(O)-R^{20}$, $-C(O)-O-R^{20}$, $-C(O)-N(R^{20})(R^{22})$, $-CN$, and $-O-R^{20}$;

$R^5$ is selected from the group consisting of hydrogen, optionally substituted alkyl, amino, optionally substituted alkoxy, —$CF_3$, —O—$CF_3$, —CN, and —N($R^{20}$)C(O)—$R^{22}$;

$R^{20}$ and $R^{22}$ are in each instance independently selected from the group consisting of hydrogen, acyl, $C_{1-15}$ alkyl, $C_{2-15}$ alkenyl, $C_{2-15}$ alkynyl, cycloalkyl, heterocyclyl, aryl, and heteroaryl, and wherein said $C_{1-15}$ alkyl, $C_{2-15}$ alkenyl, $C_{2-15}$ alkynyl, cycloalkyl, heterocyclyl, aryl or heteroaryl are optionally substituted with one, two, or three substituents independently selected from hydroxyl, halo, $C_{1-4}$ alkyl, mono- or dialkylamino, aminocarbonyl, —$NO_2$, —$SO_2R^{26}$, —CN, $C_{1-3}$ alkoxy, —$CF_3$, —$OCF_3$, aryl, cycloalkyl, and heteroaryl; or;

when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, aralkyl, aryl, aryloxy, aralkyloxy, mono- or dialkylamino, aminocarbonyl, —$NO_2$, —$SO_2R^{26}$, —CN, $C_{1-3}$ alkoxy, —$CF_3$, —$OCF_3$, and cycloalkyl;

$R^{25}$ is in each instance independently a bond or selected from $C_{1-6}$ alkylene optionally substituted with one or two $C_{1-3}$ alkyl groups; and $R^{24}$, $R^{26}$, and $R^{28}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, $C_{1-4}$ alkoxy, —$CF_3$, and —$OCF_3$;

or a pharmaceutically acceptable salt, ester, prodrug, stereoisomer, solvate, or hydrate thereof, with the proviso that the compound is not 1-(3,4-difluorobenzyl)-2-oxo-N-(3-(3-oxo-2,3-dihydro-[1,2,4]triazolo[4,3-a]pyridin-6-yl)benzyl)-1,2-dihydropyridine-3-carboxamide.

In some embodiments, the disclosure provides compounds of Formula I':

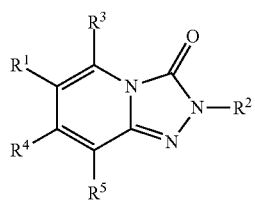

I' wherein:

$R^1$ is aryl or heteroaryl, wherein said aryl or heteroaryl are optionally substituted with one, two, or three substituents independently selected from the group consisting of hydroxyl, halo, —$NO_2$, CN, —$SF_5$, —$Si(CH_3)_3$ —O—$CF_3$, —O—$R^{20}$, —S—$R^{20}$, —C(O)—$R^{20}$, C(O)OH, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{26}$, —S(O)$_2$—$R^{20}$, —S(O)$_2$—N($R^{20}$)($R^{22}$), $C_{1-3}$ alkoxy, $C_{1-4}$ alkyl, $C_{2-4}$ alkenyl, $C_{2-4}$ alkynyl, cycloalkyl, heteroaryl, and heterocyclyl;

wherein said alkoxy, alkyl, alkenyl, alkynyl, heteroaryl, cycloalkyl, or heterocyclyl are optionally substituted with one, two, or three substituents independently selected from hydroxyl, halo, —$NO_2$, —O—$CF_3$, —O—$CF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, $R^2$ is hydrogen, $C_{1-15}$ alkyl, $C_{1-4}$ alkoxy, —C(O)—O—$R^{26}$, —C(O)—N($R^{26}$)($R^{28}$), —N($R^{20}$)—S(O)$_2$—$R^{20}$, cycloalkyl, aryl, heteroaryl, heterocyclyl, wherein said $C_{1-15}$ alkyl is optionally substituted with one, two, or three substituents independently selected from hydroxyl, $C_{1-4}$ alkoxy, halo, —$NO_2$, —O—$CF_3$, —O—$CF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said $C_{1-4}$ alkoxy, cycloalkyl, aryl, heterocyclyl, or heteroaryl are optionally further substituted with one, two, or three substituents independently selected from hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, cycloalkyl, are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$ $R^3$ is selected from the group consisting of hydrogen, hydroxyl, halo, $C_{1-4}$ alkyl, $C_{1-3}$ alkoxy, —$R^{25}$—N($R^{20}$)($R^{22}$), —$R^{25}$—O—$R^{20}$, —$R^{25}$—C(O)—O—$R^{20}$, —$R^{25}$—C(O)—N($R^{20}$)($R^{22}$), —$R^{25}$—C(O)—O—N($R^{20}$)($R^{22}$), —$R^{25}$—N($R^{20}$)—C(O)—$R^{22}$, and —$R^{25}$—O—C(O)—N($R^{20}$)($R^{22}$), wherein said alkyl are optionally substituted with one, two, or three substituents independently selected from hydroxyl, halo, $R^4$ is selected from the group consisting of hydrogen, optionally substituted alkyl, —$CF_3$, -halo, and —O—$R^{24}$;

$R^5$ is selected from the group consisting of hydrogen, optionally substituted alkyl, amino, optionally substituted alkoxy, —$CF_3$, —O—$CF_3$, —CN, and —N($R^{20}$)C(O)—$R^{22}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl, and heteroaryl, wherein said $C_{1-15}$ alkyl, $C_{2-15}$ alkenyl, $C_{2-15}$ alkynyl, cycloalkyl, heterocyclyl, aryl, or heteroaryl are optionally substituted with one, two, or three substituents independently selected from hydroxyl, halo, $C_{1-4}$ alkyl, mono- or dialkylamino, aminocarbonyl, —$NO_2$, —$SO_2R^{26}$, —CN, $C_{1-3}$ alkoxy, —$CF_3$, —$OCF_3$, aryl, cycloalkyl, and heteroaryl; or;

when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, benzyl, phenyl, phenoxy, benzyloxy, mono- or dialkylamino, aminocarbonyl, —$NO_2$, —$SO_2R^{26}$, —CN, $C_{1-3}$ alkoxy, —$CF_3$, —$OCF_3$, aryl, and cycloalkyl;

$R^{25}$ is in each instance independently a bond or selected from $C_{1-6}$ alkylene optionally substituted with one or two $C_{1-3}$ alkyl groups; and $R^{26}$ and $R^{28}$ are in each instance independently selected from hydrogen, alkyl, or cycloalkyl, wherein the alkyl, phenyl and cycloalkyl may be further substituted with from 1 to 3 substituents independently selected from hydroxyl, halo, $C_{1-4}$ alkoxy, —$CF_3$, and —$OCF_3$;

or a pharmaceutically acceptable salt, ester, prodrug, or solvate thereof.

Some embodiments of this disclosure provide a method of treating a disease state in a mammal that is alleviable by treatment with an agent capable of reducing late sodium current, comprising administering to a mammal in need thereof a therapeutically effective dose of the compound of Formula I or a pharmaceutically acceptable salt, ester, prodrug, stereoisomer, solvate, or hydrate thereof. In some embodiments, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication. In some embodiments, the disease state is diabetes or diabetic peripheral neuropathy. In some embodiments, the disease state results in one or more of neuropathic pain, epilepsy, seizures, or paralysis.

In certain embodiments, the disclosure provides pharmaceutical compositions comprising a therapeutically effective amount of a compound of the disclosure (e.g. a compound of Formula I or a pharmaceutically acceptable salt, ester, prodrug, stereoisomer, solvate, or hydrate thereof and at least one pharmaceutically acceptable excipient).

Compounds of Formula I include, but are not limited to:
2-((3-methyl-1,2,4-oxadiazol-5-yl)methyl)-6-(4-(trifluoromethoxy)phenyl)-[1,2,4]triazolo[4,3-a]pyridin-3(2H)-one;
2-((4-methyl-1,2,5-oxadiazol-3-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethoxy)phenyl)-[1,2,4]triazolo[4,3-a]pyridin-3(2H)-one;
2-(2-hydroxy-3-(2-methoxyphenoxy)propyl)-6-(4-(trifluoromethoxy)phenyl)-[1,2,4]triazolo[4,3-a]pyridin-3(2H)-one;
2-((5-methylisoxazol-3-yl)methyl)-6-(4-(trifluoromethoxy)phenyl)-[1,2,4]triazolo[4,3-a]pyridin-3(2H)-one;
2-((3,5-dimethylisoxazol-4-yl)methyl)-6-(4-(trifluoromethoxy)phenyl)-[1,2,4]triazolo[4,3-a]pyridin-3(2H)-one;
6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one;
2-(3-(5-methyl-1,2,4-oxadiazol-3-yl)benzyl)-6-(4-(trifluoromethoxy)phenyl)-[1,2,4]triazolo[4,3-a]pyridin-3(2H)-one;
2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one;
2-(benzo[c][1,2,5]oxadiazol-5-ylmethyl)-6-(4-(trifluoromethoxy)phenyl)-[1,2,4]triazolo[4,3-a]pyridin-3(2H)-one;
2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one;
2-(4-(trifluoromethoxy)benzyl)-6-(4-(trifluoromethoxy)phenyl)-[1,2,4]triazolo[4,3-a]pyridin-3(2H)-one;
2-(quinolin-2-ylmethyl)-6-(4-(trifluoromethoxy)phenyl)-[1,2,4]triazolo[4,3-a]pyridin-3(2H)-one;
2-(1-(3-ethyl-1,2,4-oxadiazol-5-yl)ethyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethoxy)phenyl)-[1,2,4]triazolo[4,3-a]pyridin-3(2H)-one;
2-(pyridin-2-ylmethyl)-6-(4-(trifluoromethoxy)phenyl)-[1,2,4]triazolo[4,3-a]pyridin-3(2H)-one;
2-((4-phenyl-1,2,5-oxadiazol-3-yl)methyl)-6-(4-(trifluoromethoxy)phenyl)-[1,2,4]triazolo[4,3-a]pyridin-3(2H)-one;
2-((5-methyl-1,3,4-oxadiazol-2-yl)methyl)-6-(4-(trifluoromethoxy)phenyl)-[1,2,4]triazolo[4,3-a]pyridin-3(2H)-one;
2-(oxazol-2-ylmethyl)-6-(4-(trifluoromethoxy)phenyl)-[1,2,4]triazolo[4,3-a]pyridin-3(2H)-one;
2-(benzo[d]thiazol-2-ylmethyl)-6-(4-(trifluoromethoxy)phenyl)-[1,2,4]triazolo[4,3-a]pyridin-3(2H)-one;
2-((5-methyl-2-phenyloxazol-4-yl)methyl)-6-(4-(trifluoromethoxy)phenyl)-[1,2,4]triazolo[4,3-a]pyridin-3(2H)-one;
2-((4,5-dimethyloxazol-2-yl)methyl)-6-(4-(trifluoromethoxy)phenyl)-[1,2,4]triazolo[4,3-a]pyridin-3(2H)-one;
2-(2-methoxy-3-(2-methoxyphenoxy)propyl)-6-(4-(trifluoromethoxy)phenyl)-[1,2,4]triazolo[4,3-a]pyridin-3(2H)-one;
2-(3-phenoxypropyl)-6-(4-(trifluoromethoxy)phenyl)-[1,2,4]triazolo[4,3-a]pyridin-3(2H)-one;
2-((5-methyloxazol-2-yl)methyl)-6-(4-(trifluoromethoxy)phenyl)-[1,2,4]triazolo[4,3-a]pyridin-3(2H)-one;
2-((3-cyclopropyl-1-methyl-1H-pyrazol-5-yl)methyl)-6-(4-(trifluoromethoxy)phenyl)-[1,2,4]triazolo[4,3-a]pyridin-3(2H)-one;
2-((1,2,4-oxadiazol-3-yl)methyl)-6-(4-(trifluoromethoxy)phenyl)-[1,2,4]triazolo[4,3-a]pyridin-3(2H)-one;
2-(2-phenoxyethyl)-6-(4-(trifluoromethoxy)phenyl)-[1,2,4]triazolo[4,3-a]pyridin-3(2H)-one;
2-((3-benzyl-1,2,4-oxadiazol-5-yl)methyl)-6-(4-(trifluoromethoxy)phenyl)-[1,2,4]triazolo[4,3-a]pyridin-3(2H)-one;
5-methoxy-2-((3-methyl-1,2,4-oxadiazol-5-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(3-phenoxyphenyl)-[1,2,4]triazolo[4,3-a]pyridin-3(2H)-one;
6-(4-(4-chlorophenoxy)phenyl)-2-((5-methyl-1,2,4-oxadiazol-3-yl)methyl)-[1,2,4]triazolo[4,3-a]pyridin-3(2H)-one;
2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one;
2-(pyridin-2-yl)-6-(4-(trifluoromethoxy)phenyl)-[1,2,4]triazolo[4,3-a]pyridin-3(2H)-one;
2-(2-(1H-pyrazol-1-yl)ethyl)-6-(4-(trifluoromethoxy)phenyl)-[1,2,4]triazolo[4,3-a]pyridin-3(2H)-one;
2-(2-(pyridin-2-yl)ethyl)-6-(4-(trifluoromethoxy)phenyl)-[1,2,4]triazolo[4,3-a]pyridin-3(2H)-one;
2-(3-(2-methoxyphenoxy)propyl)-6-(4-(trifluoromethoxy)phenyl)-[1,2,4]triazolo[4,3-a]pyridin-3(2H)-one;
2-(3-(4-chlorophenoxy)-2-hydroxypropyl)-6-(4-(trifluoromethoxy)phenyl)-[1,2,4]triazolo[4,3-a]pyridin-3(2H)-one;
2-(2-(3-phenoxypyrrolidin-1-yl)ethyl)-6-(4-(trifluoromethoxy)phenyl)-[1,2,4]triazolo[4,3-a]pyridin-3(2H)-one;
2-(2-(4-chlorophenoxy)ethyl)-6-(4-(trifluoromethoxy)phenyl)-[1,2,4]triazolo[4,3-a]pyridin-3(2H)-one;

2-(2-(4-chloro-1H-pyrazol-1-yl)ethyl)-6-(4-(trifluoromethoxy)phenyl)-[1,2,4]triazolo[4,3-a]pyridin-3(2H)-one;
2-(2-(3-methyl-1H-pyrazol-1-yl)ethyl)-6-(4-(trifluoromethoxy)phenyl)-[1,2,4]triazolo[4,3-a]pyridin-3(2H)-one;
2-(2-hydroxy-3-phenoxypropyl)-6-(4-(trifluoromethoxy)phenyl)-[1,2,4]triazolo[4,3-a]pyridin-3(2H)-one;
2-(2-(2,6-dimethylphenoxy)ethyl)-6-(4-(trifluoromethoxy)phenyl)-[1,2,4]triazolo[4,3-a]pyridin-3(2H)-one;
2-(2-(4-phenyl-1H-imidazol-1-yl)ethyl)-6-(4-(trifluoromethoxy)phenyl)-[1,2,4]triazolo[4,3-a]pyridin-3(2H)-one;
2-(2-(2-chlorophenoxy)ethyl)-6-(4-(trifluoromethoxy)phenyl)-[1,2,4]triazolo[4,3-a]pyridin-3(2H)-one;
6-(4-(trifluoromethoxy)phenyl)-2-(2-(3-(trifluoromethyl)pyridin-2-yloxy)ethyl)-[1,2,4]triazolo[4,3-a]pyridin-3(2H)-one;
2-(2-(6-methylpyridin-2-yl)ethyl)-6-(4-(trifluoromethoxy)phenyl)-[1,2,4]triazolo[4,3-a]pyridin-3(2H)-one;
2-(2-(pyridin-2-yloxy)ethyl)-6-(4-(trifluoromethoxy)phenyl)-[1,2,4]triazolo[4,3-a]pyridin-3(2H)-one;
2-(2-(4,4-difluoropiperidin-1-yl)ethyl)-6-(4-(trifluoromethoxy)phenyl)-[1,2,4]triazolo[4,3-a]pyridin-3(2H)-one;
2-(3-(2-fluorophenoxy)propyl)-6-(4-(trifluoromethoxy)phenyl)-[1,2,4]triazolo[4,3-a]pyridin-3(2H)-one;
2-(3-(2-chlorophenoxy)propyl)-6-(4-(trifluoromethoxy)phenyl)-[1,2,4]triazolo[4,3-a]pyridin-3(2H)-one;
6-(4-(4-chlorophenoxy)phenyl)-2-((3-methyl-1,2,4-oxadiazol-5-yl)methyl)-[1,2,4]triazolo[4,3-a]pyridin-3(2H)-one;
2-(2-(3-chlorophenoxy)ethyl)-6-(4-(trifluoromethoxy)phenyl)-[1,2,4]triazolo[4,3-a]pyridin-3(2H)-one;
2-(2-(4-fluorophenoxy)ethyl)-6-(4-(trifluoromethoxy)phenyl)-[1,2,4]triazolo[4,3-a]pyridin-3(2H)-one;
2-(2-(3-bromopyridin-2-yl)ethyl)-6-(4-(trifluoromethoxy)phenyl)-[1,2,4]triazolo[4,3-a]pyridin-3(2H)-one;
2-(2-(4-cyclopropylpyridin-2-yl)ethyl)-6-(4-(trifluoromethoxy)phenyl)-[1,2,4]triazolo[4,3-a]pyridin-3(2H)-one;
2-(2-(4-methylpyridin-2-yl)ethyl)-6-(4-(trifluoromethoxy)phenyl)-[1,2,4]triazolo[4,3-a]pyridin-3(2H)-one;
2-(4-fluorophenethyl)-6-(4-(trifluoromethoxy)phenyl)-[1,2,4]triazolo[4,3-a]pyridin-3(2H)-one;
2-(2-(3-cyclopropylpyridin-2-yl)ethyl)-6-(4-(trifluoromethoxy)phenyl)-[1,2,4]triazolo[4,3-a]pyridin-3(2H)-one;
2-(2-(3-methylpyridin-2-yl)ethyl)-6-(4-(trifluoromethoxy)phenyl)-[1,2,4]triazolo[4,3-a]pyridin-3(2H)-one;
6-(4-(trifluoromethoxy)phenyl)-2-((6-(trifluoromethyl)pyridin-2-yl)methyl)-[1,2,4]triazolo[4,3-a]pyridin-3(2H)-one;
2-(2,6-difluorophenethyl)-6-(4-(trifluoromethoxy)phenyl)-[1,2,4]triazolo[4,3-a]pyridin-3(2H)-one;
2-(3-(3-bromo-4-fluorophenyl)propyl)-6-(4-(trifluoromethoxy)phenyl)-[1,2,4]triazolo[4,3-a]pyridin-3(2H)-one;
6-(4-(trifluoromethoxy)phenyl)-2-(2-(6-(trifluoromethyl)pyridin-2-yloxy)ethyl)-[1,2,4]triazolo[4,3-a]pyridin-3(2H)-one;
6-(4-(trifluoromethoxy)phenyl)-2-(3-(2-(trifluoromethyl)phenoxy)propyl)-[1,2,4]triazolo[4,3-a]pyridin-3(2H)-one;
2-(3-(4-fluoro-2-methoxyphenoxy)propyl)-6-(4-(trifluoromethoxy)phenyl)-[1,2,4]triazolo[4,3-a]pyridin-3(2H)-one
2-(3-(4-chloropyridin-3-yl)prop-2-ynyl)-6-(4-(trifluoromethoxy)phenyl)-[1,2,4]triazolo[4,3-a]pyridin-3(2H)-one;
2-(2-(2-methoxyphenoxy)ethyl)-6-(4-(trifluoromethoxy)phenyl)-[1,2,4]triazolo[4,3-a]pyridin-3(2H)-one;
2-(3-(3-oxo-6-(4-(trifluoromethoxy)phenyl-[1,2,4]triazolo[4,3-a]pyridin-2(3H)-yl)propoxy)benzonitrile;
6-(4-(trifluoromethoxy)phenyl)-2-(3-(2-(trifluoromethyl)phenoxy)propyl)-[1,2,4]triazolo[4,3-a]pyridin-3(2H)-one;
(R)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;
2-(2-(pyridin-3-yl)ethyl)-6-(4-(trifluoromethoxy)phenyl)-[1,2,4]triazolo[4,3-a]pyridin-3(2H)-one;
2-(2-(3,3'-bipyridin-6-yl)ethyl)-6-(4-(trifluoromethoxy)phenyl)-[1,2,4]triazolo[4,3-a]pyridin-3(2H)-one;
2-(2-(p-tolyloxy)ethyl)-6-(4-(trifluoromethoxy)phenyl)-[1,2,4]triazolo[4,3-a]pyridin-3(2H)-one;
2-(3-(4-fluorophenyl)propyl)-6-(4-(trifluoromethoxy)phenyl)-[1,2,4]triazolo[4,3-a]pyridin-3(2H)-one;
2-(chroman-2-ylmethyl)-6-(4-(trifluoromethoxy)phenyl)-[1,2,4]triazolo[4,3-a]pyridin-3(2H)-one;
2-(2,4-difluorophenethyl)-6-(4-(trifluoromethoxy)phenyl)-[1,2,4]triazolo[4,3-a]pyridin-3(2H)-one;
2-(3-(pyridazin-3-yloxy)propyl)-6-(4-(trifluoromethoxy)phenyl)-[1,2,4]triazolo[4,3-a]pyridin-3(2H)-one;
2-(3-(2-chlorophenoxy)-2-methoxypropyl)-6-(4-(trifluoromethoxy)phenyl)-[1,2,4]triazolo[4,3-a]pyridin-3(2H)-one
2-(2-(pyridazin-3-yloxy)ethyl)-6-(4-(trifluoromethoxy)phenyl)-[1,2,4]triazolo[4,3-a]pyridin-3(2H)-one
2-(2-(5-methylpyrimidin-2-yloxy)ethyl)-6-(4-(trifluoromethoxy)phenyl)-[1,2,4]triazolo[4,3-a]pyridin-3(2H)-one;
2-((3-methyl-1,2,4-oxadiazol-5-yl)methyl)-6-(4-(2,2,2-trifluoroethoxy)phenyl)-[1,2,4]triazolo[4,3-a]pyridin-3(2H)-one;
2-(2-(2-(3-methyl-1,2,4-oxadiazol-5-yl)phenoxy)ethyl)-6-(4-(trifluoromethoxy)phenyl)-[1,2,4]triazolo[4,3-a]pyridin-3(2H)-one;
2-(3-(pyrazin-2-yloxy)propyl)-6-(4-(trifluoromethoxy)phenyl)-[1,2,4]triazolo[4,3-a]pyridin-3(2H)-one;
2-(2-((5-methyl-1,2,4-oxadiazol-3-yl)methoxy)ethyl)-6-(4-(trifluoromethoxy)phenyl)-[1,2,4]triazolo[4,3-a]pyridin-3(2H)-one;
2-((3-methyl-1,2,4-oxadiazol-5-yl)methyl)-6-(2-methyl-4-(trifluoromethoxy)phenyl)-[1,2,4]triazolo[4,3-a]pyridin-3(2H)-one;
2-(2-(4,6-dimethylpyrimidin-2-yloxy)ethyl)-6-(4-(trifluoromethoxy)phenyl)-[1,2,4]triazolo[4,3-a]pyridin-3(2H)-one;
2-(3-(2-chlorophenoxy)-2-(pyrimidin-2-yloxy)propyl)-6-(4-(trifluoromethoxy)phenyl)-[1,2,4]triazolo[4,3-a]pyridin-3(2H)-one;
2-(2-(4-cyclopropylpyrimidin-2-yloxy)ethyl)-6-(4-(trifluoromethoxy)phenyl)-[1,2,4]triazolo[4,3-a]pyridin-3(2H)-one;
(S)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;
2-(2-(5-chloropyrimidin-2-yloxy)ethyl)-6-(4-(trifluoromethoxy)phenyl)-[1,2,4]triazolo[4,3-a]pyridin-3(2H)-one
6-(4-(4-fluorophenoxy)phenyl)-2-((3-methyl-1,2,4-oxadiazol-5-yl)methyl)-[1,2,4]triazolo[4,3-a]pyridin-3(2H)-one;

(3-((3-oxo-6-(4-(trifluoromethoxy)phenyl)-[1,2,4]triazolo[4,3-a]pyridin-2(3H)-yl)methyl)-1,2,4-oxadiazol-5-yl)methyl acetate;

(S)-2-(3-(2-chlorophenoxy)-2-methoxypropyl)-6-(4-(trifluoromethoxy)phenyl)-[1,2,4]triazolo[4,3-a]pyridin-3(2H)-one;

(R)-2-(3-(2-chlorophenoxy)-2-methoxypropyl)-6-(4-(trifluoromethoxy)phenyl)-[1,2,4]triazolo[4,3-a]pyridin-3(2H)-one;

2-(2-(1-methyl-1H-benzo[d]imidazol-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-hydroxypropyl)-6-(4-(trifluoromethoxy)phenyl)-[1,2,4]triazolo[4,3-a]pyridin-3(2H)-one;

2-(3-(2-ethoxyphenoxy)-2-hydroxypropyl)-6-(4-(trifluoromethoxy)phenyl)-[1,2,4]triazolo[4,3-a]pyridin-3(2H)-one;

2-(3-(biphenyl-2-yloxy)-2-hydroxypropyl)-6-(4-(trifluoromethoxy)phenyl)-[1,2,4]triazolo[4,3-a]pyridin-3(2H)-one;

2-(2-hydroxy-3-(3-oxo-6-(4-(trifluoromethoxy)phenyl)-[1,2,4]triazolo[4,3-a]pyridin-2(3H)-yl)propoxy)benzonitrile;

2-(2-(pyridin-2-yl)propyl)-6-(4-(trifluoromethoxy)phenyl)-[1,2,4]triazolo[4,3-a]pyridin-3(2H)-one;

2-(2-(6-methoxypyridin-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-methoxypropyl)-6-(4-(trifluoromethoxy)phenyl)-[1,2,4]triazolo[4,3-a]pyridin-3(2H)-one;

2-(2-ethoxy-3-(4-fluoro-2-methoxyphenoxy)propyl)-6-(4-(trifluoromethoxy)phenyl)-[1,2,4]triazolo[4,3-a]pyridin-3(2H)-one;

2-(2-(4-ethoxypyrimidin-2-yloxy)ethyl)-6-(4-(trifluoromethoxy)phenyl)-[1,2,4]triazolo[4,3-a]pyridin-3(2H)-one;

2-(2-hydroxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(2-hydroxy-3-(2-isopropoxyphenoxy)propyl)-6-(4-(trifluoromethoxy)phenyl)-[1,2,4]triazolo[4,3-a]pyridin-3(2H)-one;

2-(4-(pyrimidin-2-yloxy)tetrahydrofuran-3-yl)-6-(4-(trifluoromethoxy)phenyl)-[1,2,4]triazolo[4,3-a]pyridin-3(2H)-one;

2-((3-methyl-1,2,4-oxadiazol-5-yl)methyl)-6-(4-(trimethylsilyl)phenyl)-[1,2,4]triazolo[4,3-a]pyridin-3(2H)-one;

2-(2-(pyrimidin-2-yl)ethyl)-6-(4-(trifluoromethoxy)phenyl)-[1,2,4]triazolo[4,3-a]pyridin-3(2H)-one;

2-(2-(2-oxo-3-phenoxypyrrolidin-1-yl)ethyl)-6-(4-(trifluoromethoxy)phenyl)-[1,2,4]triazolo[4,3-a]pyridin-3(2H)-one;

2-(2-(pyrimidin-4-yl)ethyl)-6-(4-(trifluoromethoxy)phenyl)-[1,2,4]triazolo[4,3-a]pyridin-3(2H)-one;

2-(2-(pyrazin-2-yl)ethyl)-6-(4-(trifluoromethoxy)phenyl)-[1,2,4]triazolo[4,3-a]pyridin-3(2H)-one;

2-(2-(4-phenylpyrimidin-2-yloxy)ethyl)-6-(4-(trifluoromethoxy)phenyl)-[1,2,4]triazolo[4,3-a]pyridin-3(2H)-one;

2-(2-(5-methoxypyrimidin-2-yloxy)ethyl)-6-(4-(trifluoromethoxy)phenyl)-[1,2,4]triazolo[4,3-a]pyridin-3(2H)-one 2-(2-(3-methylpyrazin-2-yl)ethyl)-6-(4-(trifluoromethoxy)phenyl)-[1,2,4]triazolo[4,3-a]pyridin-3(2H)-one;

2-(2-(3-bromo-6-methoxypyridin-2-yl)ethyl)-6-(4-(trifluoromethoxy)phenyl)-[1,2,4]triazolo[4,3-a]pyridin-3(2H)-one;

2-(3-(4-fluoro-3-(oxazol-2-yl)phenyl)propyl)-6-(4-(trifluoromethoxy)phenyl)-[1,2,4]triazolo[4,3-a]pyridin-3(2H)-one;

6-(4-(4-chlorophenoxy)phenyl)-2-(2-(pyrimidin-2-yloxy)ethyl)-[1,2,4]triazolo[4,3-a]pyridin-3(2H)-one;

2-(3-(4-fluoro-3-(pyridin-3-yl)phenyl)propyl)-6-(4-(trifluoromethoxy)phenyl)-[1,2,4]triazolo[4,3-a]pyridin-3(2H)-one;

6-(4-(4-fluorophenoxy)phenyl)-2-(2-(pyrimidin-2-yloxy)ethyl)-[1,2,4]triazolo[4,3-a]pyridin-3(2H)-one;

2-(2-(pyrimidin-2-yloxy)ethyl)-6-(4-(trimethylsilyl)phenyl)-[1,2,4]triazolo[4,3-a]pyridin-3(2H)-one;

2-(2-ethoxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(4-(4-ethoxypyrimidin-2-yloxy)tetrahydrofuran-3-yl)-6-(4-(trifluoromethoxy)phenyl)-[1,2,4]triazolo[4,3-a]pyridin-3(2H)-one;

2-(2-(4-(dimethylamino)-5-fluoropyrimidin-2-yloxy)ethyl)-6-(4-(trifluoromethoxy)phenyl)-[1,2,4]triazolo[4,3-a]pyridin-3(2H)-one;

6-(3,5-difluoro-4-phenoxyphenyl)-2-((3-methyl-1,2,4-oxadiazol-5-yl)methyl)-[1,2,4]triazolo[4,3-a]pyridin-3(2H)-one;

2-((5-(methoxymethyl)-1,2,4-oxadiazol-3-yl)methyl)-6-(4-(trifluoromethoxy)phenyl)-[1,2,4]triazolo[4,3-a]pyridin-3(2H)-one;

2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidine-4-carbonitrile;

2-(2-(5-chloro-4-methoxypyrimidin-2-yloxy)ethyl)-6-(4-(trifluoromethoxy)phenyl)-[1,2,4]triazolo[4,3-a]pyridin-3(2H)-one;

6-(4-benzoylphenyl)-2-((3-methyl-1,2,4-oxadiazol-5-yl)methyl)-[1,2,4]triazolo[4,3-a]pyridin-3(2H)-one;

2-(2-(4-(4-chlorophenoxy)pyrimidin-2-yloxy)ethyl)-6-(4-(trifluoromethoxy)phenyl)-[1,2,4]triazolo[4,3-a]pyridin-3(2H)-one;

2-(2-(4-(3,3-difluoroazetidin-1-yl)-5-fluoropyrimidin-2-yloxy)ethyl)-6-(4-(trifluoromethoxy)phenyl)-[1,2,4]triazolo[4,3-a]pyridin-3(2H)-one;

6-(3,4-dichlorophenyl)-2-((3-methyl-1,2,4-oxadiazol-5-yl)methyl)-[1,2,4]triazolo[4,3-a]pyridin-3(2H)-one;

2-(2-(pyrrolo[1,2-a]pyrazin-1-yloxy)ethyl)-6-(4-(trifluoromethoxy)phenyl)-[1,2,4]triazolo[4,3-a]pyridin-3(2H)-one;

2-((3-((3-oxo-6-(4-(trifluoromethoxy)phenyl)-[1,2,4]triazolo[4,3-a]pyridin-2(3H)-yl)methyl)-1,2,4-oxadiazol-5-yl)methyl)isoindoline-1,3-dione 2-((3-methyl-1,2,4-oxadiazol-5-yl)methyl)-6-(4-(trifluoromethyl)phenyl)-[1,2,4]triazolo[4,3-a]pyridin-3(2H)-one;

2-(2-(5-fluoropyrimidin-2-yloxy)ethyl)-6-(4-(trifluoromethoxy)phenyl)-[1,2,4]triazolo[4,3-a]pyridin-3(2H)-one;

2-(2-(2-chloropyrimidin-5-yloxy)ethyl)-6-(4-(trifluoromethoxy)phenyl)-[1,2,4]triazolo[4,3-a]pyridin-3(2H)-one;

6-(4-(4-fluorophenoxy)phenyl)-2-((5-methyl-1,2,4-oxadiazol-3-yl)methyl)-[1,2,4]triazolo[4,3-a]pyridin-3(2H)-one;

2-(2-(isoquinolin-1-yloxy)ethyl)-6-(4-(trifluoromethoxy)phenyl)-[1,2,4]triazolo[4,3-a]pyridin-3(2H)-one;

2-((5-cyclopropyl-1,2,4-oxadiazol-3-yl)methyl)-6-(4-(trifluoromethoxy)phenyl)-[1,2,4]triazolo[4,3-a]pyridin-3(2H)-one;
6-(4-(4-fluorophenoxy)phenyl)-[1,2,4]triazolo[4,3-a]pyridin-3(2H)-one;
2-((5-(pyridin-2-yl)isoxazol-3-yl)methyl)-6-(4-(trifluoromethoxy)phenyl)-[1,2,4]triazolo[4,3-a]pyridin-3(2H)-one;
2-((5-(3-methylpyridin-2-yl)isoxazol-3-yl)methyl)-6-(4-(trifluoromethoxy)phenyl)-[1,2,4]triazolo[4,3-a]pyridin-3(2H)-one;
6-(4-(4-fluorophenoxy)phenyl)-2-((5-(hydroxymethyl)-1,2,4-oxadiazol-3-yl)methyl)-[1,2,4]triazolo[4,3-a]pyridin-3(2H)-one;
2-(1-(3-methyl-1,2,4-oxadiazol-5-yl)ethyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethyl)phenyl)-[1,2,4]triazolo[4,3-a]pyridin-3(2H)-one;
6-(4-chlorophenyl)-2-((3-methyl-1,2,4-oxadiazol-5-yl)methyl)-[1,2,4]triazolo[4,3-a]pyridin-3(2H)-one;
6-(3,4-difluorophenyl)-2-((3-methyl-1,2,4-oxadiazol-5-yl)methyl)-[1,2,4]triazolo[4,3-a]pyridin-3(2H)-one;
2-cinnamyl-6-(4-(trifluoromethoxy)phenyl)-[1,2,4]triazolo[4,3-a]pyridin-3(2H)-one;
(S)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one
2-((3-(methoxymethyl)-1,2,4-oxadiazol-5-yl)methyl)-6-(4-(trifluoromethoxy)phenyl)-[1,2,4]triazolo[4,3-a]pyridin-3(2H)-one;
2-((5-(difluoromethyl)-1,2,4-oxadiazol-3-yl)methyl)-6-(4-(trifluoromethoxy)phenyl)-[1,2,4]triazolo[4,3-a]pyridin-3(2H)-one;
6-(3-fluoro-4-(trifluoromethoxy)phenyl)-2-((3-methyl-1,2,4-oxadiazol-5-yl)methyl)-[1,2,4]triazolo[4,3-a]pyridin-3(2H)-one;
2-(2-(4-(2-hydroxyethoxy)pyrimidin-2-yloxy)ethyl)-6-(4-(trifluoromethoxy)phenyl)-[1,2,4]triazolo[4,3-a]pyridin-3(2H)-one;
2-((5-(chloromethyl)-1,2,4-oxadiazol-3-yl)methyl)-6-(4-(trifluoromethoxy)phenyl)-[1,2,4]triazolo[4,3-a]pyridin-3(2H)-one;
(R)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one
2-(2-(4-(methylthio)pyrimidin-2-yloxy)ethyl)-6-(4-(trifluoromethoxy)phenyl)-[1,2,4]triazolo[4,3-a]pyridin-3(2H)-one;
2-(2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidin-4-yloxy)acetonitrile;
6-(4-chloro-3-fluorophenyl)-2-((3-methyl-1,2,4-oxadiazol-5-yl)methyl)-[1,2,4]triazolo[4,3-a]pyridin-3(2H)-one;
2-((5-((pyrimidin-2-yloxy)methyl)-1,2,4-oxadiazol-3-yl)methyl)-6-(4-(trifluoromethoxy)phenyl)-[1,2,4]triazolo[4,3-a]pyridin-3(2H)-one;
2-((1-methyl-1H-pyrazol-4-yl)methyl)-6-(4-(trifluoromethoxy)phenyl)-[1,2,4]triazolo[4,3-a]pyridin-3(2H)-one;
2-((3-methylisoxazol-5-yl)methyl)-6-(4-(trifluoromethoxy)phenyl)-[1,2,4]triazolo[4,3-a]pyridin-3(2H)-one;
2-((1-methyl-1H-pyrazol-3-yl)methyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethyl)phenyl)-[1,2,4]triazolo[4,3-a]pyridin-3(2H)-one;
2-((3-(methoxymethyl)-1,2,4-oxadiazol-5-yl)methyl)-6-(4-(trifluoromethyl)phenyl)-[1,2,4]triazolo[4,3-a]pyridin-3(2H)-one;
2-((3-trideuteromethyl-1,2,4-oxadiazol-5-yl)methyl)-6-(4-(trifluoromethoxy)phenyl)-[1,2,4]triazolo[4,3-a]pyridin-3(2H)-one;
2-((5-cyclopropyl-1,3,4-thiadiazol-2-yl)methyl)-6-(4-(trifluoromethoxy)phenyl)-[1,2,4]triazolo[4,3-a]pyridin-3(2H)-one;
6-(4-(trifluoromethyl)phenyl)-[1,2,4]triazolo[4,3-a]pyridin-3(2H)-one;
2-((5-methyloxazol-2-yl)methyl)-6-(4-(trifluoromethyl)phenyl)-[1,2,4]triazolo[4,3-a]pyridin-3(2H)-one;
2-((4,5-dimethyloxazol-2-yl)methyl)-6-(4-(trifluoromethyl)phenyl)-[1,2,4]triazolo[4,3-a]pyridin-3(2H)-one;
2-(2-(imidazo[1,2-a]pyrazin-8-yloxy)ethyl)-6-(4-(trifluoromethoxy)phenyl)-[1,2,4]triazolo[4,3-a]pyridin-3(2H)-one;
2-((5-((pyridin-2-yloxy)methyl)-1,2,4-oxadiazol-3-yl)methyl)-6-(4-(trifluoromethoxy)phenyl)-[1,2,4]triazolo[4,3-a]pyridin-3(2H)-one;
2-((5-((2-ethoxyphenoxy)methyl)-1,2,4-oxadiazol-3-yl)methyl)-6-(4-(trifluoromethoxy)phenyl)-[1,2,4]triazolo[4,3-a]pyridin-3(2H)-one;
2-(2-(4-isopropoxypyrimidin-2-yloxy)ethyl)-6-(4-(trifluoromethoxy)phenyl)-[1,2,4]triazolo[4,3-a]pyridin-3(2H)-one;
2-(2-(4-(2,2,2-trifluoro ethoxy)pyrimidin-2-yloxy)ethyl)-6-(4-(trifluoromethoxy)phenyl)-[1,2,4]triazolo[4,3-a]pyridin-3(2H)-one;
2-(2-(4-(cyclopropylmethoxy)pyrimidin-2-yloxy)ethyl)-6-(4-(trifluoromethoxy)phenyl)-[1,2,4]triazolo[4,3-a]pyridin-3(2H)-one;
6-(4-(trifluoromethoxy)phenyl)-2-(2-(5-(trifluoromethyl)pyrimidin-2-yloxy)ethyl)-[1,2,4]triazolo[4,3-a]pyridin-3(2H)-one;
2-((2-cyclopropyloxazol-4-yl)methyl)-6-(4-(trifluoromethoxy)phenyl)-[1,2,4]triazolo[4,3-a]pyridin-3(2H)-one;
2-((5-cyclopropyl-1,3,4-oxadiazol-2-yl)methyl)-6-(4-(4-fluorophenoxy)phenyl)-[1,2,4]triazolo[4,3-a]pyridin-3(2H)-one;
2-((5-tert-butyloxazol-2-yl)methyl)-6-(4-(trifluoromethoxy)phenyl)-[1,2,4]triazolo[4,3-a]pyridin-3(2H)-one;
2-((5-tert-butyloxazol-2-yl)methyl)-6-(4-(trifluoromethyl)phenyl)-[1,2,4]triazolo[4,3-a]pyridin-3(2H)-one;
2-methyl-6-(4-(trifluoromethyl)phenyl)-[1,2,4]triazolo[4,3-a]pyridin-3(2H)-one;
(R)-2-(2-(3-(4-fluorophenoxy)pyrrolidin-1-yl)ethyl)-6-(4-(trifluoromethoxy)phenyl)-[1,2,4]triazolo[4,3-a]pyridin-3(2H)-one;
5-methyl-6-(4-(trifluoromethoxy)phenyl)-[1,2,4]triazolo[4,3-a]pyridin-3(2H)-one;
5-methyl-2-((3-methyl-1,2,4-oxadiazol-5-yl)methyl)-6-(4-(trifluoromethoxy)phenyl)-[1,2,4]triazolo[4,3-a]pyridin-3(2H)-one;
2-(2,2,2-trifluoroethyl)-6-(4-(trifluoromethoxy)phenyl)-[1,2,4]triazolo[4,3-a]pyridin-3(2H)-one;
2-isopropyl-6-(4-(trifluoromethoxy)phenyl)-[1,2,4]triazolo[4,3-a]pyridin-3(2H)-one;
2-((4-methyloxazol-2-yl)methyl)-6-(4-(trifluoromethoxy)phenyl)-[1,2,4]triazolo[4,3-a]pyridin-3(2H)-one;

2-((4-methyloxazol-2-yl)methyl)-6-(4-(trifluoromethyl)phenyl)-[1,2,4]triazolo[4,3-a]pyridin-3(2H)-one;
2-((4-cyclopropyloxazol-2-yl)methyl)-6-(4-(trifluoromethoxy)phenyl)-[1,2,4]triazolo[4,3-a]pyridin-3(2H)-one
2-((4-cyclopropyloxazol-2-yl)methyl)-6-(4-(trifluoromethyl)phenyl)-[1,2,4]triazolo[4,3-a]pyridin-3(2H)-one;
6-(4-chlorophenyl)-2-((5-methyloxazol-2-yl)methyl)-[1,2,4]triazolo[4,3-a]pyridin-3(2H)-one;
8-methyl-6-(4-(trifluoromethoxy)phenyl)-[1,2,4]triazolo[4,3-a]pyridin-3(2H)-one;
2-((2-methyloxazol-5-yl)methyl)-6-(4-(trifluoromethyl)phenyl)-[1,2,4]triazolo[4,3-a]pyridin-3(2H)-one;
2-(3-(4,5-dichloro-2-methoxyphenoxy)-2-hydroxypropyl)-6-(4-(trifluoromethyl)phenyl)-[1,2,4]triazolo[4,3-a]pyridin-3(2H)-one;
2-((5-cyclopropyloxazol-2-yl)methyl)-6-(4-(trifluoromethoxy)phenyl)-[1,2,4]triazolo[4,3-a]pyridin-3(2H)-one;
6-(4-(trifluoromethoxy)phenyl)-[1,2,4]triazolo[4,3-a]pyridin-3(2H)-one; and
2-methyl-6-(4-(trifluoromethoxy)phenyl)-[1,2,4]triazolo[4,3-a]pyridin-3(2H)-one, or a pharmaceutically acceptable salt, ester, prodrug, stereoisomer, solvate, or hydrate thereof.

DETAILED DESCRIPTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (in some embodiments, 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-10 atoms (e.g. 1, 2, 3, 4, or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, in some embodiments, having from 1 to 20 carbon atoms (e.g. 1-10 carbon atoms, or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5, or 6 carbon atoms.

The term "substituted alkylene" refers to:
(1) an alkylene group as defined above having 1, 2, 3, 4, or 5 substituents (in some embodiments, 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NR$^a$, where R$^a$ is chosen from hydrogen, optionally substituted alkyl, cycloalkyl, cycloalkenyl, aryl, heteroaryl and heterocyclyl; or
(3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$—N(CH$_3$)—CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. In some embodiments, alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2, or 3 carbon-carbon double bonds. In some embodiments, alkenyl groups include ethenyl (or vinyl, i.e. —CH═CH$_2$), 1-propylene (or allyl, —CH$_2$CH═CH$_2$), isopropylene (—C(CH$_3$)═CH$_2$), bicyclo [2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (in some embodiments, 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2, or 3 carbon-carbon triple bonds. In some embodiments, alkynyl groups include ethynyl (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (in some embodiments, 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O) NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$^a$, in which R$^a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R$^a$ is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group $—NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or $—S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "susbstituted cycloalkenyl" refer to cycloalkyl or cycloalkenyl groups having 1, 2, 3, 4 or 5 substituents (in some embodiments, 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—SO_2$-alkyl, $SO_2$-aryl and $—SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and $—S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "alkoxycarbonylamino" refers to a group $—N(R^d)C(O)OR$ in which R is optionally substituted alkyl and $R^d$ is hydrogen or optionally substituted alkyl.

The term "alkyl amine" refers to $R—NH_2$ in which R is optionally substituted alkyl.

The term "dialkyl amine" refers to R—NHR in which each R is independently an optionally substituted alkyl.

The term "trialkyl amine" refers to $NR_3$ in which each R is independently an optionally substituted alkyl.

The term "azido" refers to a group

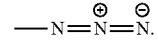

The term "hydroxy" or "hydroxyl" refers to a group —OH.

The term "arylthio" refers to the group —S-aryl.

The term "heterocyclylthio" refers to the group —S-heterocyclyl.

The term "alkylthio" refers to the group —S-alkyl.

The term "aminosulfonyl" refers to the group $—S(O)_2NRR$, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—S(O)_2$-alkyl, $S(O)_2$-aryl and $S(O)_2$-heteroaryl.

The term "aminocarbonylamino" refers to the group $—NR^cC(O)NRR$, wherein $R^c$ is hydrogen or alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, $—S(O)_2$-alkyl, $—S(O)_2$-aryl and $S(O)_2$-heteroaryl.

The term "heterocyclooxy" refers to the group —O-heterocyclyl.

The term "alkoxyamino" refers to the group —NHOR in which R is optionally substituted alkyl.

The term "hydroxyamino" refers to the group —NHOH.

The term "heteroaryl" refers to a group comprising single or multiple rings comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, and the like.

Unless otherwise constrained by the definition for the heteroaryl substituent, such heteroaryl groups can be optionally substituted with 1 to 5 substituents (in some embodiments, 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (in some embodiments, 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —S(O)$_2$-alkyl, S(O)$_2$-aryl and S(O)$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Examples of heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)$_n$R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" or "oxo" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

A compound of a given Formula (e.g. the "compound of Formula I") is intended to encompass the compounds of the disclosure, and the pharmaceutically acceptable salts, pharmaceutically acceptable esters, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers, and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the triazolone containing compounds (when $R^2$ is H) are understood to include their triazolol tautomers. Likewise, the triazolol containing compounds are understood to include their triazolone tautomers. Non-limiting examples of these tautomers are shown below:

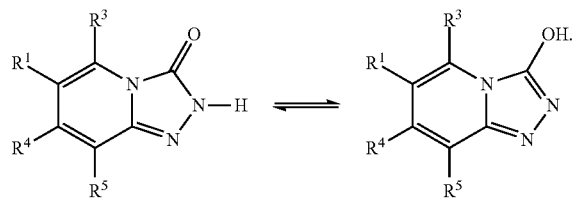

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I and a solvent.

The term "hydrate" refers to the complex formed by the combining of a compound of Formula I and water.

The term "prodrug" refers to compounds of Formula I-IV that include chemical groups which, in vivo, can be converted and/or can be split off from the remainder of the molecule to provide for the active drug, a pharmaceutically acceptable salt thereof, or a biologically active metabolite thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I.

Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients.

Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I).

The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$, and $R^{32}$) as hydrogen, di-substituted amines have 1 of the three substituents on nitrogen ($R^{30}$, $R^{31}$, and $R^{32}$) as hydrogen, whereas tri-substituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroayl, cycloalkyl, cycloalkenyl, heterocyclyl, and the like. The above-mentioned amines refer to the compounds wherein either one, two, or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein, and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to-substituted aryl-(substituted aryl)-substituted aryl.

Nomenclature

Names of compounds of the present disclosure are provided using ACD/Name software for naming chemical compounds (Advanced Chemistry Development, Inc., Toronto). Other compounds or radicals may be named with common names, or systematic or non-systematic names. The naming and numbering of the compounds of the disclosure is illustrated with a representative compound of Formula I:

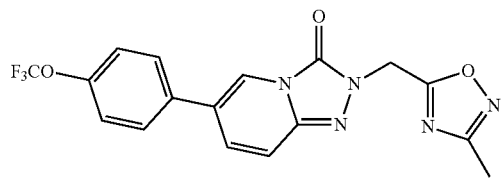 [SMILES: Cc1noc(Cn2nc3ccc(-c4ccc(OC(F)(F)F)cc4)cn3c2=O)n1]

which is named 2-((3-methyl-1,2,4-oxadiazol-5-yl)methyl)-6-(4-(trifluoromethoxy)phenyl)-[1,2,4]triazolo[4,3-a]pyridin-3(2H)-one.

Compounds

Accordingly, in some embodiments the present disclosure provides compounds that function as sodium channel blockers. In some embodiments the disclosure relates to compounds of Formula I':

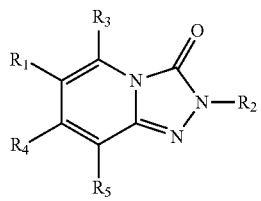

wherein:
R$^1$ is aryl or heteroaryl,
  wherein said aryl or heteroaryl are optionally substituted with one, two, or three substituents independently selected from the group consisting of hydroxyl, halo, —NO$_2$, CN, —SF$_5$, —Si(CH$_3$)$_3$ —O—CF$_3$, —O—R$^{20}$, —S—R$^{20}$, —C(O)—R$^{20}$, C(O)OH, —N(R$^{20}$)(R$^{22}$), —C(O)—N(R$^{20}$)(R$^{22}$), —N(R$^{20}$)—C(O)—R$^{22}$, —N(R$^{20}$)—S(=O)$_2$—R$^{26}$, —S(=O)$_2$—R$^{20}$, —S(=O)$_2$—N(R$^{20}$)(R$^{22}$), C$_{1-3}$ alkoxy, C$_{1-4}$ alkyl, C$_{2-4}$ alkenyl, C$_{2-4}$ alkynyl, cycloalkyl, heteroaryl, and heterocyclyl;
    wherein said alkoxy, alkyl, alkenyl, alkynyl, heteroaryl, cycloalkyl, or heterocyclyl are optionally substituted with one, two, or three substituents independently selected from hydroxyl, halo, —NO$_2$, —O—CF$_3$, —O—CF$_2$, phenyl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, R$^2$ is hydrogen, C$_{1-15}$ alkyl, C$_{1-4}$ alkoxy, —C(O)—O—R$^{26}$, —C(O)—N(R$^{26}$)(R$^{28}$), —N(R$^{20}$)—S(=O)$_2$—R$^{20}$, cycloalkyl, aryl, heteroaryl, heterocyclyl,
  wherein said alkyl is optionally substituted with one, two, or three substituents independently selected from hydroxyl, alkoxy, halo, —NO$_2$, —O—CF$_3$, —O—CF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and
    wherein said alkoxy, cycloalkyl, aryl, heterocyclyl, or heteroaryl are optionally further substituted with one, two, or three substituents independently selected from hydroxyl, halo, —NO$_2$, —O—CF$_3$, C$_{1-6}$ alkyl, C$_{1-4}$ alkoxy, benzyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and
      wherein said C$_{1-6}$ alkyl, C$_{1-4}$ alkoxy, benzyl, aryl, heterocyclyl, heteroaryl, cycloalkyl, are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$ R$^3$ is selected from the group consisting of hydrogen, hydroxyl, halo, C$_{1-4}$ alkyl, C$_{1-3}$ alkoxy, —R$^{25}$—N(R$^{20}$)(R$^{22}$), —R$^{25}$—O—R$^{20}$, —R$^{25}$—C(O)—O—R$^{20}$, —R$^{25}$—C(O)—N(R$^{20}$)(R$^{22}$), —R$^{25}$—C(O)—O—N(R$^{20}$)(R$^{22}$), —R$^{25}$—N(R$^{20}$)—C(O)—R$^{22}$, and —R$^{25}$—O—C(O)—N(R$^{20}$)(R$^{22}$),
  wherein said alkyl are optionally substituted with one, two, or three substituents independently selected from hydroxyl, halo, R$^4$ is selected from the group consisting of hydrogen, optionally substituted alkyl, —CF$_3$, -halo, and —O—R$^{24}$;

R$^5$ is selected from the group consisting of hydrogen, optionally substituted alkyl, amino, optionally substituted alkoxy, —CF$_3$, —O—CF$_3$, —CN, and —N(R$^{20}$)C(O)—R$^{22}$;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl, and heteroaryl,
  wherein the C$_{1-15}$ alkyl, C$_{2-15}$ alkenyl, C$_{2-15}$ alkynyl, heterocyclyl, aryl, and heteroaryl are optionally substituted with one, two, or three substituents independently selected from hydroxyl, halo, C$_{1-4}$ alkyl, mono- or dialkylamino, aminocarbonyl, —NO$_2$, —SO$_2$R$^{26}$, —CN, C$_{1-3}$ alkoxy, —CF$_3$, —OCF$_3$, aryl, cycloalkyl, and heteroaryl; or;

when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, benzyl, phenyl, phenoxy, benzyloxy, mono- or dialkylamino, aminocarbonyl, —NO$_2$, —SO$_2$R$^{26}$, —CN, C$_{1-3}$ alkoxy, —CF$_3$, and —OCF$_3$, aryl, cycloalkyl;

R$^{25}$ is in each instance independently a covalent bond or selected from C$_{1-6}$ alkylene optionally substituted with one or two C$_{1-3}$ alkyl groups; and R$^{26}$ and R$^{28}$ are in each instance independently selected from hydrogen, alkyl, or cycloalkyl, wherein the alkyl, phenyl and cycloalkyl may be further substituted with from 1 to 3 substituents independently selected from hydroxyl, halo, C$_{1-4}$ alkoxy, —CF$_3$, and —OCF$_3$;

or a pharmaceutically acceptable salt, ester, prodrug, or solvate thereof.

In another embodiment, the disclosure relates to compounds of Formula I:

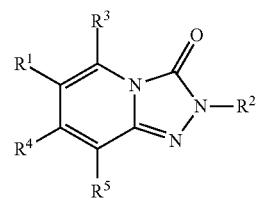

wherein:
R$^1$ is aryl or heteroaryl,
  wherein said aryl or heteroaryl are optionally substituted with one, two, or three substituents independently selected from the group consisting of hydroxyl, halo, —NO$_2$, CN, —SF$_5$, —Si(CH$_3$)$_3$, —O—CF$_3$, —O—R$^{20}$, —S—R$^{20}$, —C(O)—R$^{20}$, —N(R$^{20}$)(R$^{22}$), —C(O)—N(R$^{20}$)(R$^{22}$), N(R$^{20}$)—C(O)—R$^{22}$, —N(R$^{20}$)—S(O)$_2$—R$^{26}$, —S(O)$_2$—R$^{20}$, —S(O)$_2$—N(R$^{20}$)(R$^{22}$), C$_{1-3}$ alkoxy, C$_{1-4}$ alkyl, C$_{2-4}$ alkenyl, C$_{2-4}$ alkynyl, cycloalkyl, aryl, heteroaryl, and heterocyclyl, and
    wherein said C$_{1-3}$ alkoxy, C$_{1-4}$ alkyl, C$_{2-4}$ alkenyl, C$_{2-4}$ alkynyl, cycloalkyl, aryl, heteroaryl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

$R^2$ is hydrogen, $C_{1-15}$ alkyl, $C_{1-8}$ alkoxy, —C(O)—O—$R^{26}$, —C(O)—N($R^{26}$)($R^{28}$), —N($R^{20}$)—S(O)$_2$—$R^{20}$, cycloalkyl, aryl, heteroaryl, or heterocyclyl,
  wherein said $C_{1-15}$ alkyl is optionally substituted with one, two, or three substituents independently selected from hydroxyl, $C_{1-8}$ alkoxy, halo, —NO$_2$, O—CF$_3$, —O—CHF$_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
    wherein said $C_{1-8}$ alkoxy, $C_{2-4}$ alkenyl, $C_{2-4}$ alkynyl, aryl, heterocyclyl, heteroaryl, or cycloalkyl are optionally further substituted with one, two, or three substituents independently selected from hydroxyl, halo, —NO$_2$, —O—CF$_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
      wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from deuterium, hydroxyl, halo, —NO$_2$, —O—CF$_3$, —CF$_3$, —O—CHF$_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^3$ is selected from the group consisting of hydrogen, hydroxyl, halo, $C_{1-4}$ alkyl, $C_{1-3}$ alkoxy, —$R^{25}$—N($R^{20}$)($R^{22}$), —$R^{25}$—O—$R^{20}$, —$R^{25}$—C(O)—O—$R^{20}$, —$R^{25}$—C(O)—N($R^{20}$)($R^{22}$), —$R^{25}$—C(O)—O—N($R^{20}$)($R^{22}$), —$R^{25}$—N($R^{20}$)—C(O)—$R^{22}$, and —$R^{25}$—O—C(O)—N($R^{20}$)($R^{22}$), and
  wherein said $C_{1-4}$ alkyl is optionally substituted with one, two, or three substituents independently selected from hydroxyl, halo;
$R^4$ is selected from the group consisting of hydrogen, optionally substituted $C_{1-4}$ alkyl, aryl, —CF$_3$, -halo, and —O—$R^{24}$, and
  wherein said aryl is optionally further substituted with one, two, or three substituents independently selected from hydroxyl, halo, —NO$_2$, —O—CF$_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
    wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^5$ is selected from the group consisting of hydrogen, optionally substituted alkyl, amino, optionally substituted alkoxy, —CF$_3$, —O—CF$_3$, —CN, and —N($R^{20}$)C(O)—$R^{22}$;
$R^{20}$ and $R^{22}$ are in each instance independently selected from the group consisting of hydrogen, acyl, $C_{1-15}$ alkyl, $C_{2-15}$ alkenyl, $C_{2-15}$ alkynyl, cycloalkyl, heterocyclyl, aryl, and heteroaryl, and
  wherein said $C_{1-15}$ alkyl, $C_{2-15}$ alkenyl, $C_{2-15}$ alkynyl, cycloalkyl, heterocyclyl, aryl or heteroaryl are optionally substituted with one, two or three substituents independently selected from hydroxyl, halo, $C_{1-4}$ alkyl, mono- or dialkylamino, aminocarbonyl, —NO$_2$, —SO$_2$R$^{26}$, —CN, $C_{1-3}$ alkoxy, —CF$_3$, —OCF$_3$, aryl, cycloalkyl, and heteroaryl; or;
when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, aralkyl, aryl, aryloxy, aralkyloxy, mono- or dialkylamino, aminocarbonyl, —NO$_2$, —SO$_2$R$^{26}$, —CN, $C_{1-3}$ alkoxy, —CF$_3$, —OCF$_3$, and cycloalkyl;
$R^{25}$ is in each instance independently a bond or selected from $C_{1-6}$ alkylene optionally substituted with one or two $C_{1-3}$ alkyl groups; and
$R^{24}$, $R^{26}$, and $R^{28}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, $C_{1-4}$ alkoxy, —CF$_3$, and —OCF$_3$;
or a pharmaceutically acceptable salt, ester, prodrug, stereoisomer, solvate, or hydrate thereof,
with the proviso that the compound is not 1-(3,4-difluorobenzyl)-2-oxo-N-(3-(3-oxo-2,3-dihydro-[1,2,4]triazolo[4,3-a]pyridin-6-yl)benzyl)-1,2-dihydropyridine-3-carboxamide.

In some embodiments, $R^1$ is heteroaryl,
  wherein said heteroaryl is optionally substituted with one, two, or three substituents independently selected from the group consisting of hydroxyl, halo, —NO$_2$, CN, —SF$_5$, —Si(CH$_3$)$_3$, —O—CF$_3$, —O—$R^{20}$, —S—$R^{20}$, —C(O)—$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{26}$, —S(O)$_2$—$R^{20}$, —S(O)$_2$—N($R^{20}$)($R^{22}$), $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and
    wherein said $C_{1-3}$ alkoxy, $C_{1-4}$ alkyl, $C_{2-4}$ alkenyl, $C_{2-4}$ alkynyl, cycloalkyl, aryl, heteroaryl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$.

In some embodiments, $R^1$ is aryl,
  wherein said aryl is optionally substituted with one, two, or three substituents independently selected from the group consisting of hydroxyl, halo, —NO$_2$, CN, —SF$_5$, —Si(CH$_3$)$_3$, —O—CF$_3$, —O—$R^{20}$, —S—$R^{20}$, —C(O)—$R^{20}$, —N($R^{20}$)($R^{22}$), —C(O)—N($R^{20}$)($R^{22}$), —N($R^{20}$)—C(O)—$R^{20}$, —N($R^{20}$)—S(O)$_2$—$R^{26}$, —S(O)$_2$—$R^{20}$, —S(O)$_2$—N($R^{20}$)($R^{22}$), $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and
    wherein said $C_{1-3}$ alkoxy, $C_{1-4}$ alkyl, $C_{2-4}$ alkenyl, $C_{2-4}$ alkynyl, cycloalkyl, aryl, heteroaryl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$.

In some embodiments, $R^1$ is phenyl,
  wherein said phenyl is optionally substituted with one, two, or three substituents independently selected from the group consisting of hydroxyl, halo, —NO$_2$, CN, —SF$_5$, —Si(CH$_3$)$_3$, —O—CF$_3$, —O—$R^{20}$, —S—$R^{20}$, —C(O)—$R^{20}$, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{26}$, —S(O)$_2$—R$^{20}$, —S(O)$_2$—N(R$^{20}$)(R$^{22}$), C$_{1-3}$ alkoxy, C$_{1-4}$ alkyl, C$_{2-4}$ alkenyl, C$_{2-4}$ alkynyl, cycloalkyl, aryl, heteroaryl, and heterocyclyl, and wherein said C$_{1-3}$ alkoxy, C$_{1-4}$ alkyl, C$_{2-4}$ alkenyl, C$_{2-4}$ alkynyl, cycloalkyl, aryl, heteroaryl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In some embodiments, R$^2$ is hydrogen, C$_{1-15}$ alkyl, C$_{1-8}$ alkoxy, —C(O)—O—R$^{26}$, —C(O)—N(R$^{26}$)(R$^{28}$), —N(R$^{20}$)—S(O)$_2$—R$^{20}$, cycloalkyl, or heterocyclyl, wherein said C$_{1-15}$ alkyl is optionally substituted with one, two, or three substituents independently selected from hydroxyl, C$_{1-8}$ alkoxy, halo, —NO$_2$, O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-8}$ alkoxy, C$_{2-4}$ alkenyl, C$_{2-4}$ alkynyl, heterocyclyl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from deuterium, hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In some embodiments, R$^2$ is hydrogen, C$_{1-15}$ alkyl, C$_{1-8}$ alkoxy, —C(O)—O—R$^{26}$, —C(O)—N(R$^{26}$)(R$^{28}$), and —N(R$^{20}$)—S(O)$_2$—R$^{20}$, wherein said C$_{1-15}$ alkyl is optionally substituted with one, two, or three substituents independently selected from hydroxyl, C$_{1-8}$ alkoxy, halo, —NO$_2$, O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-8}$ alkoxy, C$_{2-4}$ alkenyl, C$_{2-4}$ alkynyl, heterocyclyl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from deuterium, hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In one embodiment, this disclosure relates to a compound of Formula I as described above, wherein at least one of R$^2$, R$^3$, R$^4$, and R$^5$ is not hydrogen.

In another embodiment, this disclosure relates to a compound of Formula II:

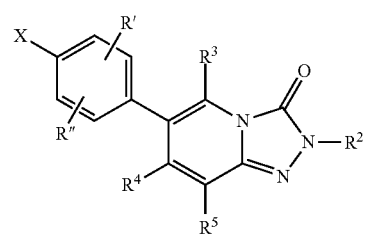

II wherein:

X is selected from the group consisting of hydroxyl, halo, —NO$_2$, CN, —SF$_5$, —Si(CH$_3$)$_3$, —O—CF$_3$, —O—R$^{20}$, —S—R$^{20}$, —C(O)—R$^{20}$, C(O)OH, —N(R$^{20}$)(R$^{22}$), —C(O)—N(R$^{20}$)(R$^{22}$), —N(R$^{20}$)—C(O)—R$^{22}$, —N(R$^{20}$)—S(O)$_2$—R$^{26}$, —S(O)$_2$—R$^{20}$, —S(O)$_2$—N(R$^{20}$)(R$^{22}$), C$_{1-3}$ alkoxy, C$_{1-4}$ alkyl, C$_{2-4}$ alkenyl, C$_{2-4}$ alkynyl, cycloalkyl, aryl, heteroaryl, and heterocyclyl, and wherein said C$_{1-3}$ alkoxy, C$_{1-4}$ alkyl, C$_{2-4}$ alkenyl, C$_{2-4}$ alkynyl, aryl, heteroaryl, cycloalkyl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R' and R'' are each independently selected from the group consisting of hydrogen, C$_{1-15}$ alkyl, C$_{1-4}$ alkoxy, hydroxyl, halo, —NO$_2$, —O—CF$_3$, cycloalkyl, aryl, heteroaryl, and heterocyclyl, and;

wherein said C$_{1-15}$ alkyl is optionally substituted with one, two, or three substituents independently selected from hydroxyl, C$_{1-3}$ alkoxy alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said alkoxy, C$_{2-4}$ alkenyl, C$_{2-4}$ alkynyl, cycloalkyl, aryl, heterocyclyl, or heteroaryl are optionally further substituted with one, two, or three substituents independently selected from deuterium, hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^2$ is selected from the group consisting of hydrogen, C$_{1-15}$ alkyl, C$_{1-4}$ alkoxy, —C(O)—O—R$^{26}$, —C(O)—N(R$^{26}$)(R$^{28}$), —N(R$^{20}$)—S(O)$_2$—R$^{20}$, cycloalkyl, aryl, heteroaryl, and heterocyclyl, and wherein said C$_{1-15}$ alkyl is optionally substituted with one, two, or three substituents independently selected from hydroxyl, C$_{1-4}$ alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-4}$ alkoxy, C$_{2-4}$ alkenyl, C$_{2-4}$ alkynyl, cycloalkyl, aryl, heterocyclyl, or heteroaryl are optionally further substituted with one, two, or three substituents independently selected from deuterium, hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, cycloalkyl, are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^3$ is selected from the group consisting of hydrogen, hydroxyl, halo, C$_{1-4}$ alkyl, C$_{1-3}$ alkoxy, —R$^{25}$—N(R)(R$^{22}$), —R$^{25}$—O—R$^{20}$, —R$^{25}$—C(O)—O—R$^{20}$, —R$^{25}$—C(O)—N(R)(R$^{22}$), —R$^{25}$—C(O)—O—N(R$^{20}$)(R$^{22}$), —R$^{25}$—N(R$^{20}$)—C(O)—R$^{22}$, and —R$^{25}$—O—C(O)—N(R$^{20}$)(R$^{22}$), and wherein said C$_{1-4}$ alkyl is optionally substituted with one, two, or three substituents independently selected from hydroxyl and halo;

R$^4$ is selected from the group consisting of hydrogen, optionally substituted alkyl, aryl, —CF$_3$, -halo, and —O—R$^{24}$, and wherein said aryl is optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^2$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, aralkyl, aryl, heterocyclyl, heteroaryl, cycloalkyl, are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^5$ is selected from the group consisting of hydrogen, optionally substituted alkyl, amino, optionally substituted alkoxy, —CF$_3$, —O—CF$_3$, —CN, and —N(R$^{20}$)C(O)—R$^{22}$;

R$^{20}$ and R$^{22}$ are in each instance independently selected from the group consisting of hydrogen, acyl, C$_{1-15}$ alkyl, C$_{2-15}$ alkenyl, C$_{2-15}$ alkynyl, cycloalkyl, heterocyclyl, aryl, and heteroaryl, and wherein the C$_{1-15}$ alkyl, C$_{2-15}$ alkenyl, C$_{2-15}$ alkynyl, heterocyclyl, aryl, and heteroaryl are optionally substituted with one, two, or three substituents independently selected from hydroxyl, halo, C$_{1-4}$ alkyl, mono- or dialkylamino, aminocarbonyl, —NO$_2$, —SO$_2$R$^{26}$, —CN, C$_{1-3}$ alkoxy, —CF$_3$, —OCF$_3$, aryl, cycloalkyl, and heteroaryl; or;

when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, aralkyl, aralkyloxy, mono- or dialkylamino, aminocarbonyl, —NO$_2$, —SO$_2$R$^{26}$, —CN, C$_{1-3}$ alkoxy, —CF$_3$, —OCF$_3$, aryl, and cycloalkyl;

R$^{25}$ is in each instance independently a bond or selected from C$_{1-6}$ alkylene optionally substituted with one or two C$_{1-3}$ alkyl groups; and R$^{24}$, R$^{26}$, and R$^{28}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, C$_{1-4}$ alkoxy, —CF$_3$, and —OCF$_3$, or a pharmaceutically acceptable salt, ester, prodrug, stereoisomer, solvate, or hydrate thereof.

In some embodiments, wherein X is C$_{1-3}$ alkoxy or C$_{1-4}$ alkyl, and wherein said C$_{1-4}$ alkyl is optionally substituted with one, two, or three substituents independently selected from hydroxyl, alkoxy, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-3}$ alkoxy is optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In some embodiments, X is OCF$_3$, and each of R' and R" is hydrogen. In some embodiments, X is CF$_3$ and each of R' and R" is hydrogen.

In another embodiment, this disclosure relates to a compound of Formula I as described above, wherein R$^2$ is hydrogen or C$_{1-15}$ alkyl, and wherein said C$_{1-15}$ alkyl is optionally substituted with one, two, or three substituents independently selected from hydroxyl, C$_{1-4}$ alkoxy alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-4}$ alkoxy, C$_{2-4}$ alkenyl, C$_{2-4}$ alkynyl, cycloalkyl, aryl, heterocyclyl, or heteroaryl are optionally further substituted with one, two, or three substituents independently selected from deuterium, hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In another embodiment, this disclosure relates to a compound of Formula III:

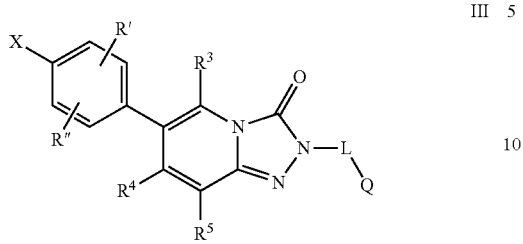

wherein:
X is selected from the group consisting of hydroxyl, halo, —$NO_2$, CN, —$SF_5$, —$Si(CH_3)_3$, —O—$CF_3$, —O—$R^{20}$, —S—$R^{20}$, —C(O)—$R^{20}$, C(O)OH, —N($R^{20}$)($R^{22}$), —C(O)—N($R^{20}$)($R^{22}$), —N($R^{20}$)—C(O)—$R^{22}$, —N($R^{20}$)—S(O)$_2$—$R^{26}$, —S(O)$_2$—$R^{20}$, —S(O)$_2$—N($R^{20}$)($R^{22}$), $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and
  wherein said alkoxy, $C_{1-4}$ alkyl, $C_{2-4}$ alkenyl, $C_{2-4}$ alkynyl, aryl, heteroaryl, cycloalkyl, or heterocyclyl are optionally substituted with one, two, or three substituents independently selected from hydroxyl, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;
R' and R" are each independently selected from the group consisting of hydrogen, $C_{1-15}$ alkyl, $C_{1-4}$ alkoxy, hydroxyl, halo, —$NO_2$, —O—$CF_3$, cycloalkyl, aryl, heteroaryl, and heterocyclyl, and;
  wherein said $C_{1-15}$ alkyl is optionally substituted with one, two, or three substituents independently selected from hydroxyl, alkoxy, halo, —$NO_2$, —O—$CF_3$, —O—$CHF_2$, alkenyl, alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
  wherein said alkoxy, alkenyl, alkynyl, cycloalkyl, aryl, heterocyclyl, or heteroaryl are optionally further substituted with one, two, or three substituents independently selected from deuterium, hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
  wherein said $C_{1-6}$ alkyl, $C_{1-4}$ alkoxy, aralkyl, aryl, heterocyclyl, heteroaryl, cycloalkyl, are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
L is selected from the group consisting of a bond and straight or branched $C_{1-6}$ alkylene,
  wherein said straight or branched $C_{1-6}$ alkylene is optionally further substituted with one, two, or three substituents independently selected from hydroxyl, alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
  wherein said alkoxy, $C_{2-4}$ alkenyl, $C_{2-4}$ alkynyl, cycloalkyl, aryl, heterocyclyl, or heteroaryl are optionally further substituted with one, two, or three substituents independently selected from hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
  wherein said $C_{1-6}$ alkyl, $C_{1-4}$ alkoxy, aralkyl, aryl, heterocyclyl, heteroaryl, cycloalkyl, are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
Q is selected from the group consisting of hydrogen, hydroxyl, $C_{1-4}$ alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and
  wherein said $C_{1-4}$ alkoxy, $C_{2-4}$ alkenyl, $C_{2-4}$ alkynyl, aryl, heterocyclyl, heteroaryl, or cycloalkyl are optionally further substituted with one, two, or three substituents independently selected from deuterium, hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
  wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;
$R^3$ is selected from the group consisting of hydrogen, hydroxyl, halo, $C_{1-4}$ alkyl, $C_{1-3}$ alkoxy, —$R^{25}$—N($R^{20}$)($R^{22}$), —$R^{25}$—O—$R^{20}$, —$R^{25}$—C(O)—O—$R^{20}$, —$R^{25}$—C(O)—N($R^{20}$)($R^{22}$), —$R^{25}$—C(O)—O—N($R^{20}$)($R^{22}$), —$R^{25}$—N($R^{20}$)—C(O)—$R^{22}$, and —$R^{25}$—O—C(O)—N($R^{20}$)($R^{22}$), and
  wherein said $C_{1-4}$ alkyl is optionally substituted with one, two, or three substituents independently selected from hydroxyl and halo;
$R^4$ is selected from the group consisting of hydrogen, optionally substituted alkyl, aryl, —$CF_3$, -halo, and —O—$R^{24}$, and
  wherein said aryl is optionally further substituted with one, two, or three substituents independently selected from hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and
  wherein said $C_{1-6}$ alkyl, $C_{1-4}$ alkoxy, aralkyl, aryl, heterocyclyl, heteroaryl, cycloalkyl, are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O_$R^{20}$;

$R^5$ is selected from the group consisting of hydrogen, optionally substituted alkyl, amino, optionally substituted alkoxy, —$CF_3$, —O—$CF_3$, —CN, and —N($R^{20}$)C(O)—$R^{22}$;

$R^{20}$ and $R^{22}$ are in each instance independently selected from the group consisting of hydrogen, acyl, $C_{1-15}$ alkyl, $C_{2-15}$ alkenyl, $C_{2-15}$ alkynyl, cycloalkyl, heterocyclyl, aryl, and heteroaryl, and wherein the $C_{1-15}$ alkyl, $C_{2-15}$ alkenyl, $C_{2-15}$ alkynyl, cycloalkyl, heterocyclyl, aryl, or heteroaryl are optionally substituted with one, two, or three substituents independently selected from hydroxyl, halo, $C_{1-4}$ alkyl, mono- or dialkylamino, aminocarbonyl, —$NO_2$, —$SO_2R^{26}$, —CN, $C_{1-3}$ alkoxy, —$CF_3$, —$OCF_3$, aryl, cycloalkyl, and heteroaryl; or when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, aralkyl, aralkyloxy, mono- or dialkylamino, aminocarbonyl, —$NO_2$, —$SO_2R^{26}$, —CN, $C_{1-3}$ alkoxy, —$CF_3$, —$OCF_3$, aryl, and cycloalkyl;

$R^{25}$ is in each instance independently a bond or selected from $C_{1-6}$ alkylene optionally substituted with one or two $C_{1-3}$ alkyl groups; and $R^{24}$ and $R^{26}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, $C_{1-4}$ alkoxy, —$CF_3$, and —$OCF_3$;

or a pharmaceutically acceptable salt, ester, prodrug, stereoisomer, solvate, or hydrate thereof.

In some embodiments, L is straight or branched $C_{1-6}$ alkylene, wherein L is straight or branched $C_{1-6}$ alkylene, wherein said straight or branched $C_{1-6}$ alkylene is optionally further substituted with one, two, or three substituents independently selected from hydroxyl, alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said alkoxy, $C_{2-4}$ alkenyl, $C_{2-4}$ alkynyl, cycloalkyl, aryl, heterocyclyl, or heteroaryl are optionally further substituted with one, two, or three substituents independently selected from hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

Q is selected from the group consisting of hydrogen, hydroxyl, $C_{1-4}$ alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said $C_{1-4}$ alkoxy, $C_{2-4}$ alkenyl, $C_{2-4}$ alkynyl, aryl, heterocyclyl, heteroaryl, or cycloalkyl are optionally further substituted with one, two, or three substituents independently selected from deuterium, hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$.

In some embodiments, $R^3$ is hydrogen or $C_{1-3}$ alkoxy. In another embodiment, $R^3$ is hydrogen. In some embodiments, $R^4$ is hydrogen or phenyl substituted with $OCF_3$. In some embodiments, wherein $R^5$ is hydrogen or alkyl. In some embodiments, each of R' and R" is hydrogen.

In another embodiment, this disclosure relates to a compound of Formula IV:

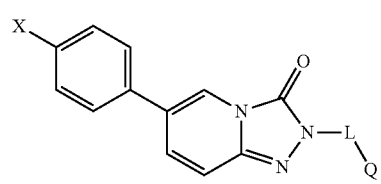

IV wherein:

X is selected from the group consisting of hydroxyl, halo, —$NO_2$, CN, —$SF_5$, —$Si(CH_3)_3$, —O—$CF_3$, —O—$R^{20}$, —S—$R^{20}$, —C(O)—$R^{20}$, C(O)OH, —N($R^{20}$)($R^{22}$), —C(O)—N($R^{20}$)($R^{22}$), —N($R^{20}$)—C(O)—$R^{20}$, —N($R^{20}$)—S(O)$_2$—$R^{26}$, —S(O)$_2$—$R^{20}$, —S(O)$_2$—N($R^{20}$)($R^{22}$), $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and wherein said $C_{1-3}$ alkoxy, $C_{1-4}$ alkyl, $C_{2-4}$ alkenyl, $C_{2-4}$ alkynyl, aryl, heteroaryl, cycloalkyl, or heterocyclyl are optionally substituted with one, two, or three substituents independently selected from hydroxyl, halo, —$NO_2$, —O—$CF_3$, —O—$CHF_2$, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$;

L is selected from the group consisting of a bond and straight or branched $C_{1-6}$ alkylene, and wherein said straight or branched $C_{1-6}$ alkylene is optionally further substituted with one, two, or three substituents independently selected from hydroxyl, alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said alkoxy, $C_{2-4}$ alkenyl, $C_{2-4}$ alkynyl, aryl, heterocyclyl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

Q is selected from the group consisting of hydrogen, hydroxyl, alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said alkoxy, C$_{2-4}$ alkenyl, C$_{2-4}$ alkynyl, aryl, heterocyclyl, heteroaryl, or cycloalkyl are optionally further substituted with one, two, or three substituents independently selected from deuterium, hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^{20}$ and R$^{22}$ are in each instance independently selected from the group consisting of hydrogen, acyl, C$_{1-15}$ alkyl, C$_{2-15}$ alkenyl, C$_{2-15}$ alkynyl, cycloalkyl, heterocyclyl, aryl, and heteroaryl, and wherein the C$_{1-15}$ alkyl, C$_{2-15}$ alkenyl, C$_{2-15}$ alkynyl, cycloalkyl, heterocyclyl, aryl, or heteroaryl are optionally substituted with one, two, or three substituents independently selected from hydroxyl, halo, C$_{1-4}$ alkyl, mono- or dialkylamino, aminocarbonyl, —NO$_2$, —SO$_2$R$^{26}$, —CN, C$_{1-3}$ alkoxy, —CF$_3$, —OCF$_3$, aryl, cycloalkyl, and heteroaryl; or;

when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, aralkyl, aryl, aryloxy, aralkyloxy, mono- or dialkylamino, aminocarbonyl, —NO$_2$, —SO$_2$R$^{26}$, —CN, C$_{1-3}$ alkoxy, —CF$_3$, —OCF$_3$, aryl, and cycloalkyl;

R$^{26}$ is in each instance independently selected from hydrogen, alkyl, aryl, or cycloalkyl, wherein the alkyl, aryl and cycloalkyl may be further substituted with from 1 to 3 substituents independently selected from hydroxyl, halo, C$_{1-4}$ alkoxy, —CF$_3$, and —OCF$_3$;

or a pharmaceutically acceptable salt, ester, prodrug, stereoisomer, solvate, or hydrate thereof.

In some embodiments, X is OCF$_3$. In other embodiments, X is CF$_3$.

In some embodiments, L is straight or branched C$_{1-6}$ alkylene, wherein said straight or branched C$_{1-6}$ alkylene is optionally further substituted with one, two, or three substituents independently selected from hydroxyl, alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said alkoxy, C$_{2-4}$ alkenyl, C$_{2-4}$ alkynyl, aryl, heterocyclyl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$; and Q is selected from the group consisting of hydrogen, C$_{2-4}$ alkenyl, C$_{2-4}$ alkynyl, aryl, heteroaryl, cycloalkyl, and —O—R$^{20}$, and wherein said C$_{2-4}$ alkenyl, C$_{2-4}$ alkynyl, aryl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

In some embodiments, Q is aryl or heteroaryl, and wherein said aryl or heteroaryl is optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

Some R$^1$ aryl and heteroaryl substituents are mono or bicyclic rings having 1 to 3 heteroatoms selected from O, N, and S. Exemplary R$^1$ moieties include, but are not limited to, the following:

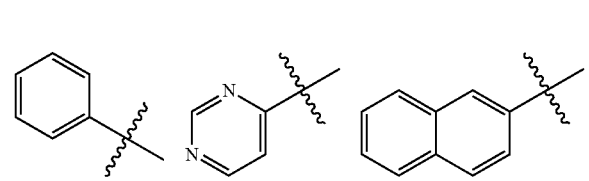

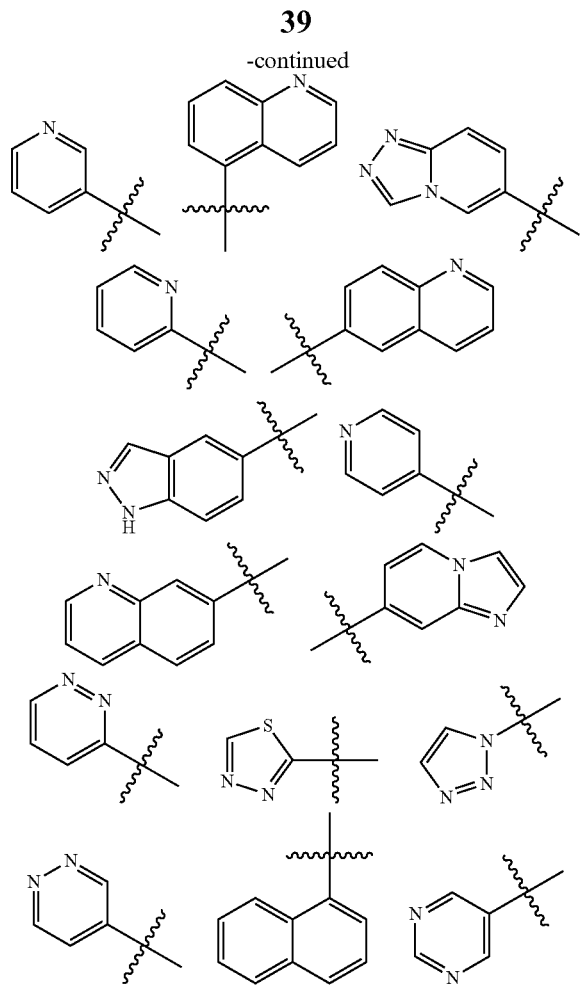

In many embodiments the R¹ moiety is further substituted with 1 to 3 substituents as defined above. Common substituents on the R¹ ring structures include, but are not limited to hydrogen; methyl, ethyl, propyl, isopropyl, tert-butyl, halo; amino, alkylamino, such as methylamino, dialkylamino such as dimethylamino, aminoalkyl, alkaminoalkyl, dialkylaminoalkyl, aryloxy, such as phenoxy, substituted phenoxy with 1, 2, or 3 substituents selected from alkyl, halo, nitro, and the like; halo substituted alkyl such as CF₃ and CHF₂; methoxy, ethoxy, propoxy, isopropoxy, tert-butoxy, methylthio, ethylthio, propylthio, halo substituted alkyoxy, such as trifluoromethoxy and difluoromethoxy, and trialkylsilyl, such as trimethylsilyl. Other substituents include, but are not limited to, the following:

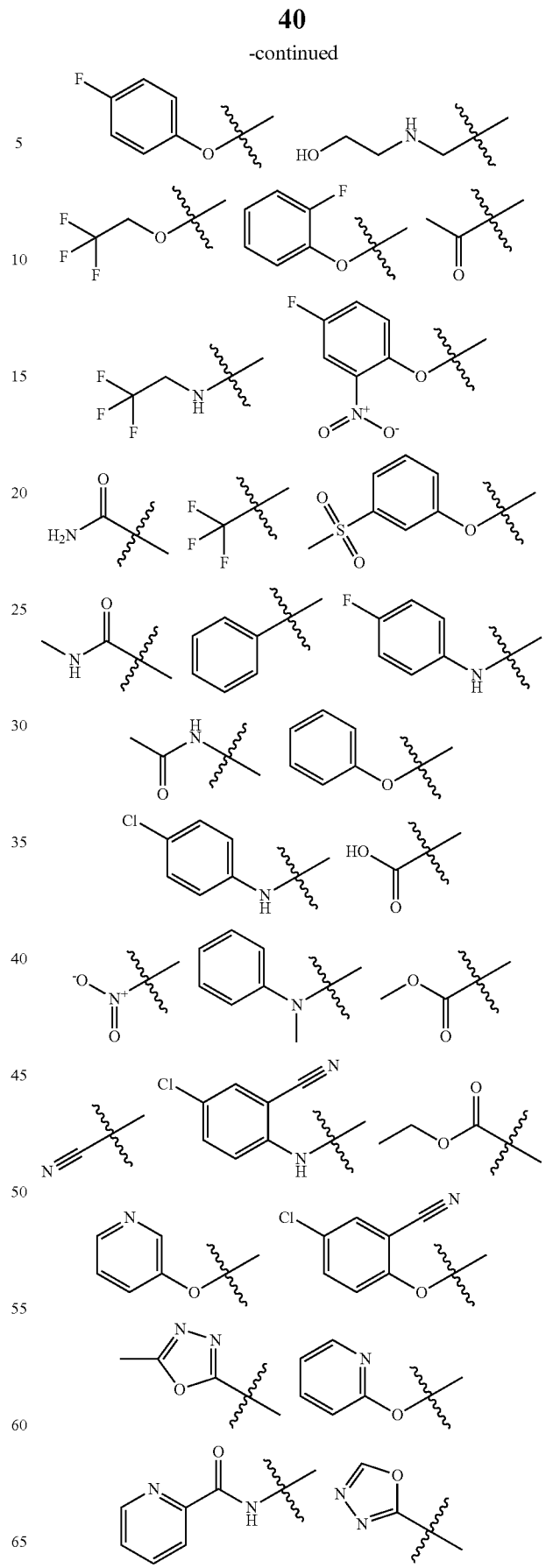

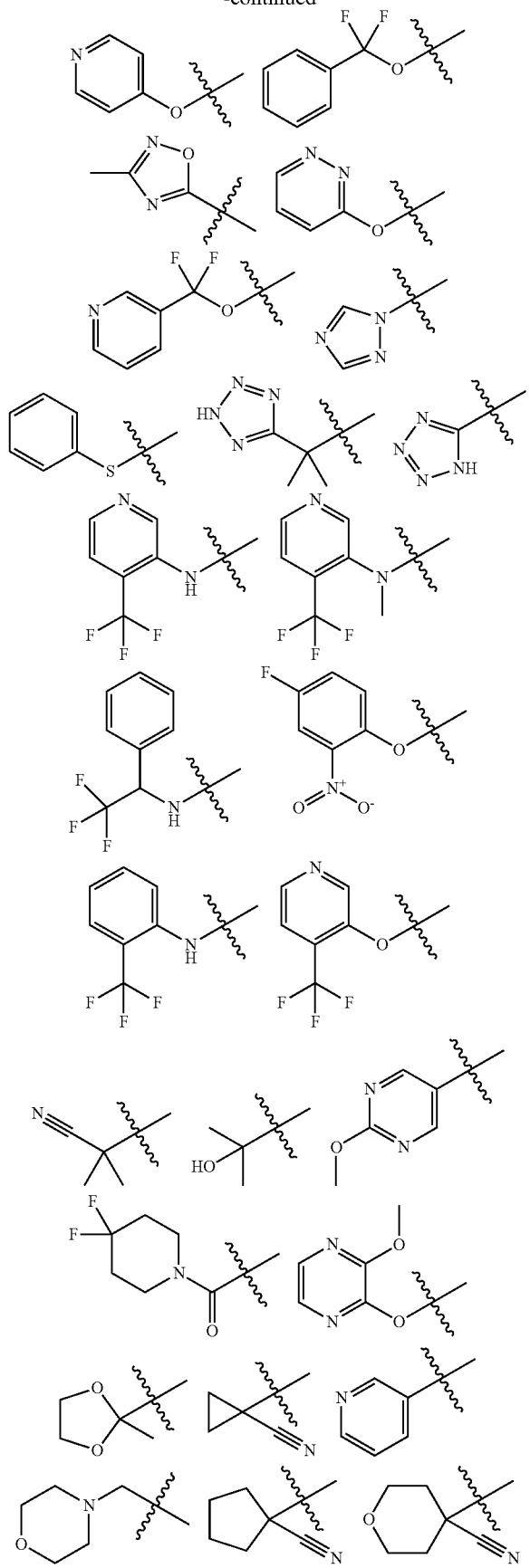
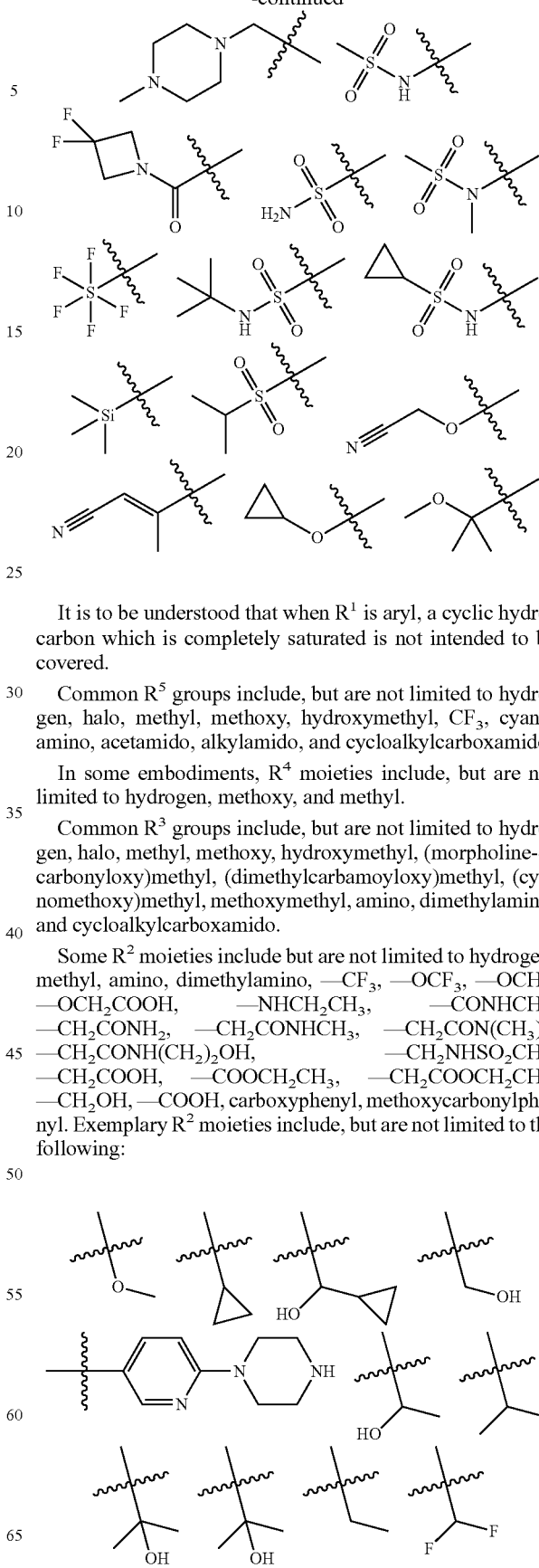

It is to be understood that when $R^1$ is aryl, a cyclic hydrocarbon which is completely saturated is not intended to be covered.

Common $R^5$ groups include, but are not limited to hydrogen, halo, methyl, methoxy, hydroxymethyl, $CF_3$, cyano, amino, acetamido, alkylamido, and cycloalkylcarboxamido.

In some embodiments, $R^4$ moieties include, but are not limited to hydrogen, methoxy, and methyl.

Common $R^3$ groups include, but are not limited to hydrogen, halo, methyl, methoxy, hydroxymethyl, (morpholine-4-carbonyloxy)methyl, (dimethylcarbamoyloxy)methyl, (cyanomethoxy)methyl, methoxymethyl, amino, dimethylamino, and cycloalkylcarboxamido.

Some $R^2$ moieties include but are not limited to hydrogen, methyl, amino, dimethylamino, —$CF_3$, —$OCF_3$, —$OCH_3$, —$OCH_2COOH$, —$NHCH_2CH_3$, —$CONHCH_3$, —$CH_2CONH_2$, —$CH_2CONHCH_3$, —$CH_2CON(CH_3)_2$, —$CH_2CONH(CH_2)_2OH$, —$CH_2NHSO_2CH_3$, —$CH_2COOH$, —$COOCH_2CH_3$, —$CH_2COOCH_2CH_3$, —$CH_2OH$, —$COOH$, carboxyphenyl, methoxycarbonylphenyl. Exemplary $R^2$ moieties include, but are not limited to the following:

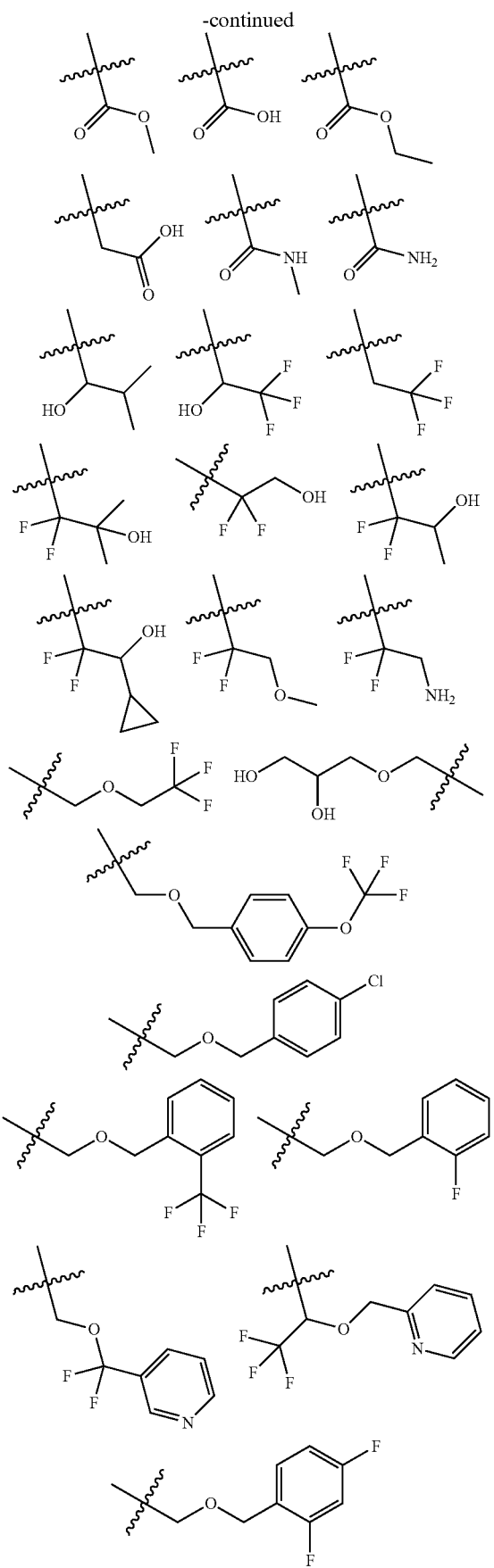
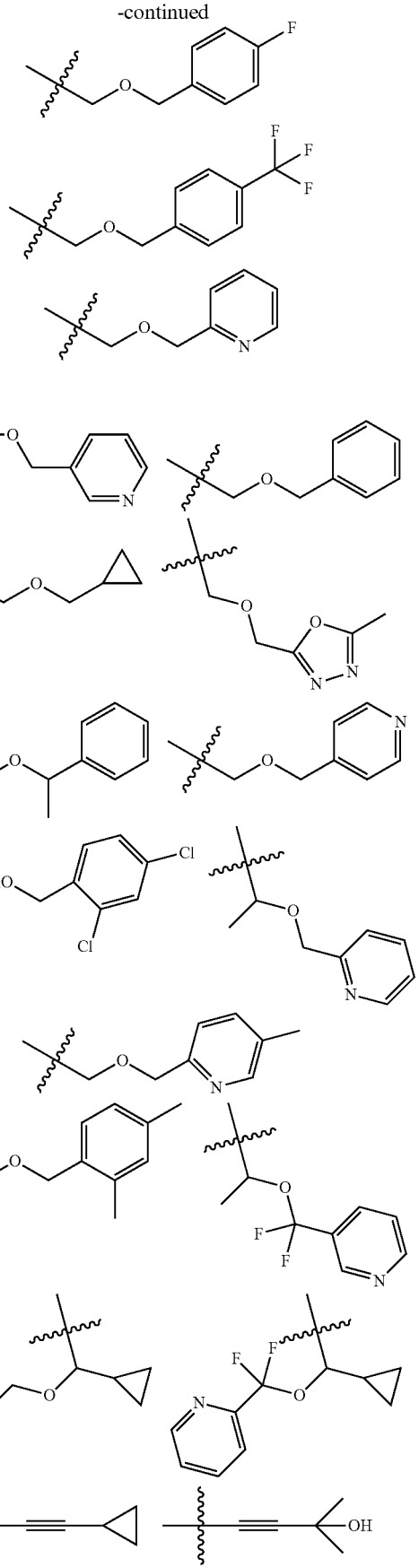

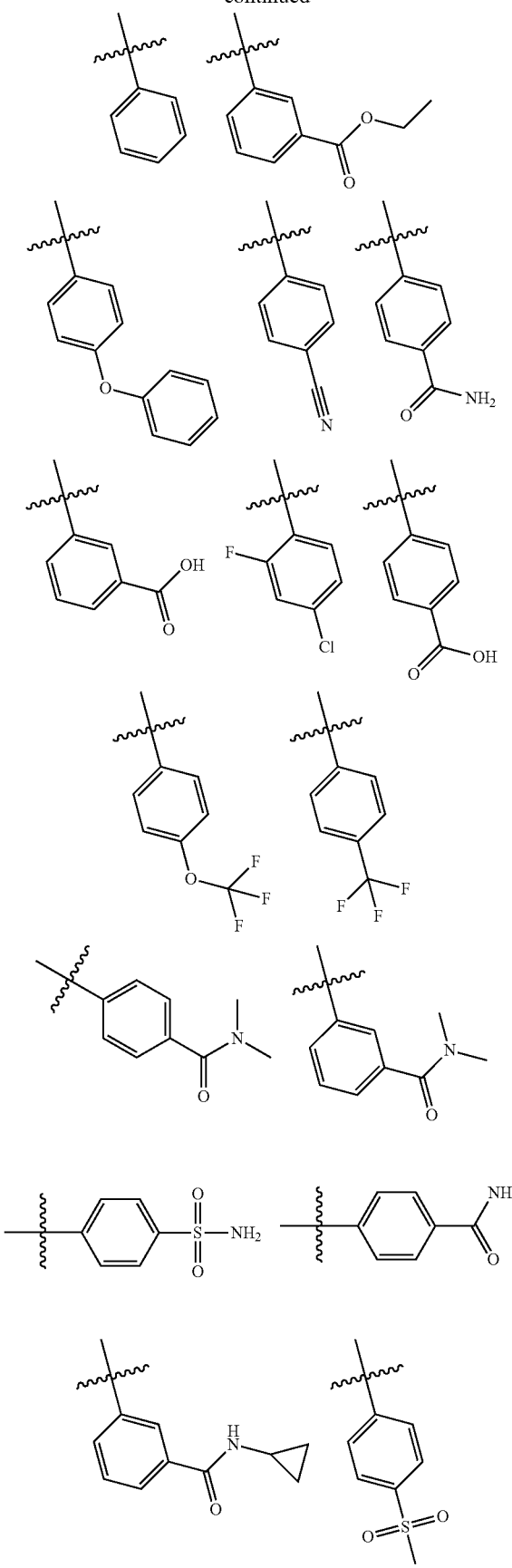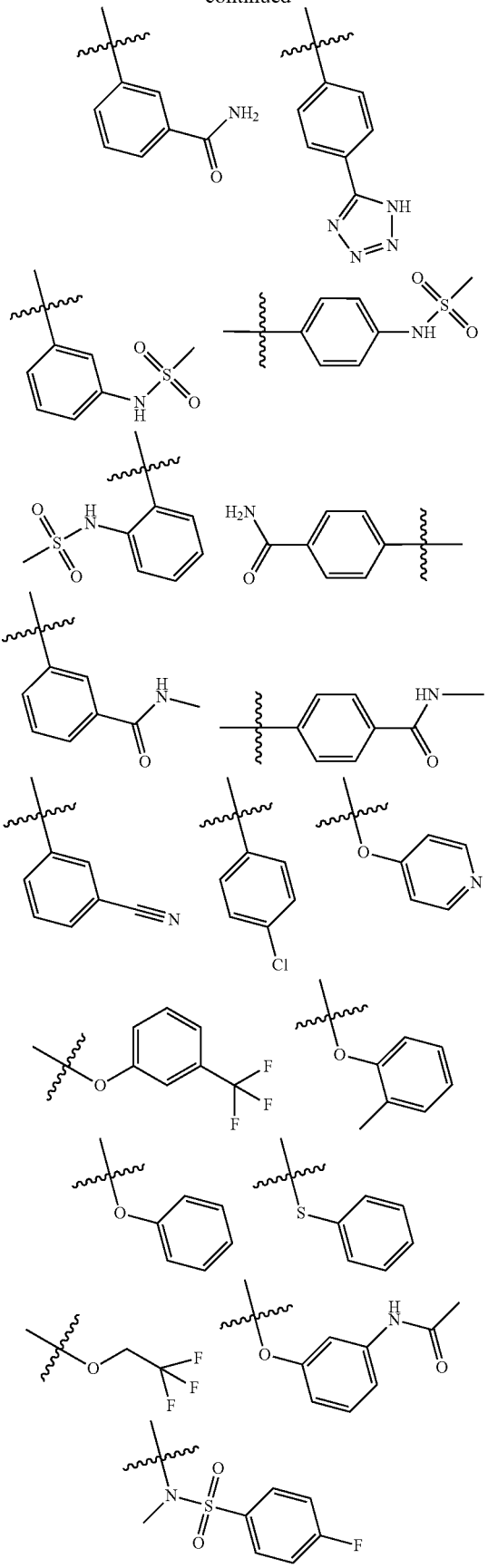

-continued
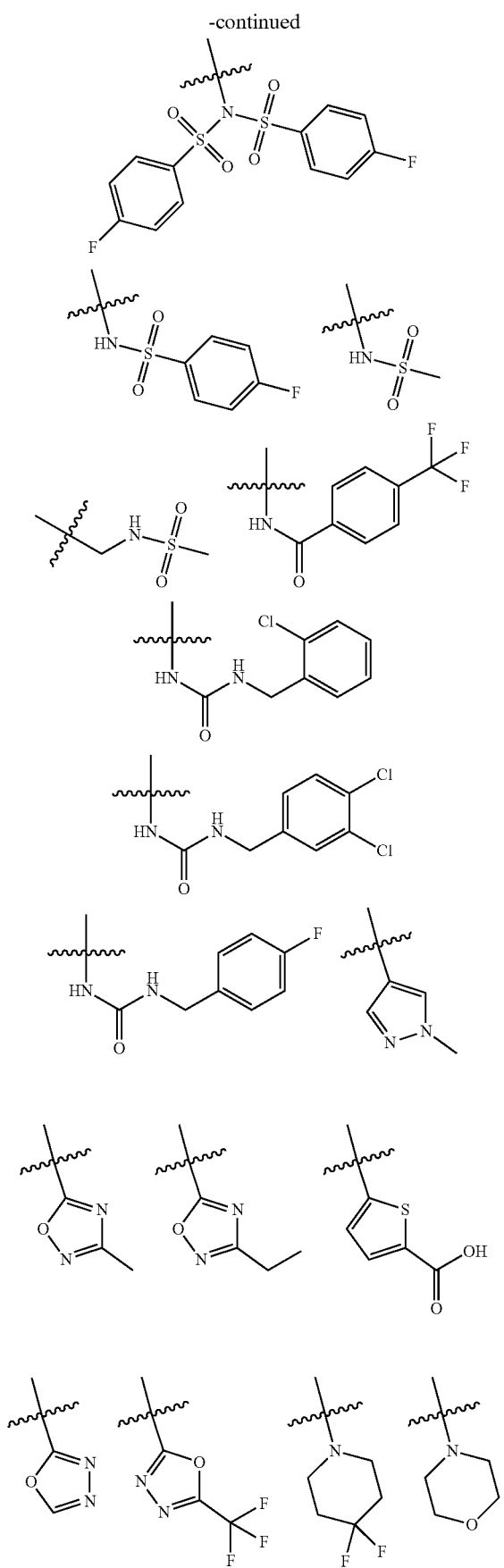
-continued
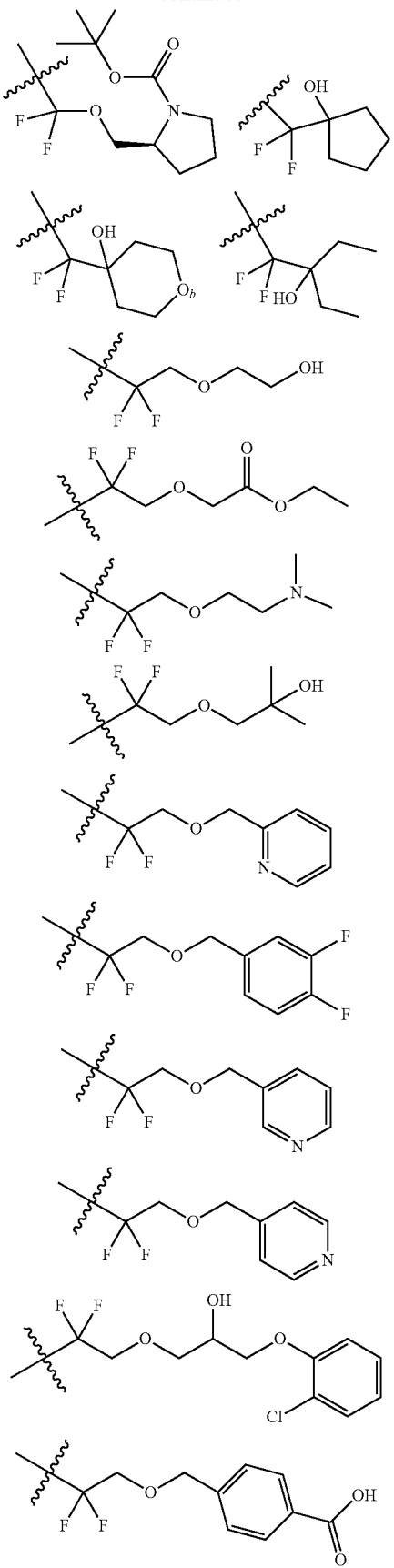

49
-continued
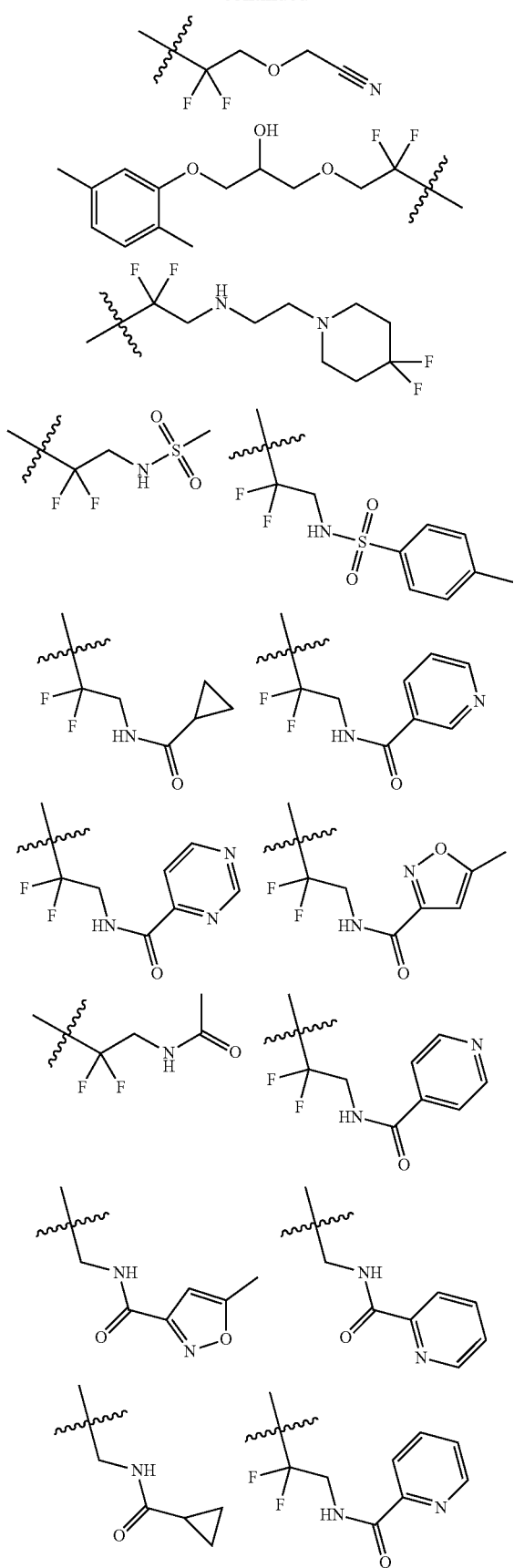
50
-continued
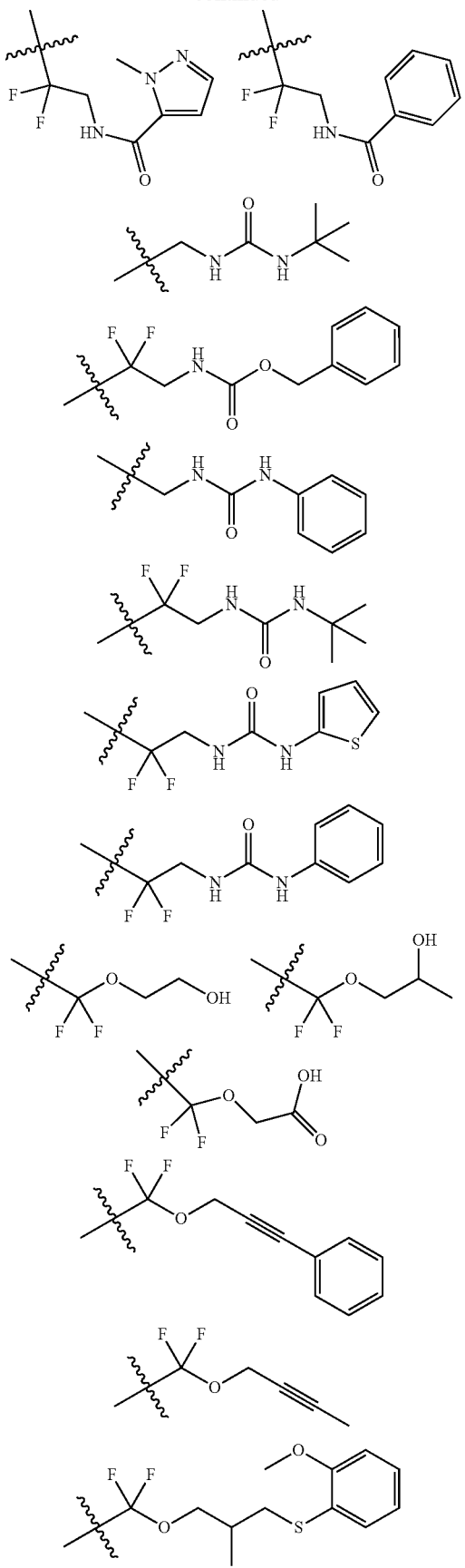

-continued
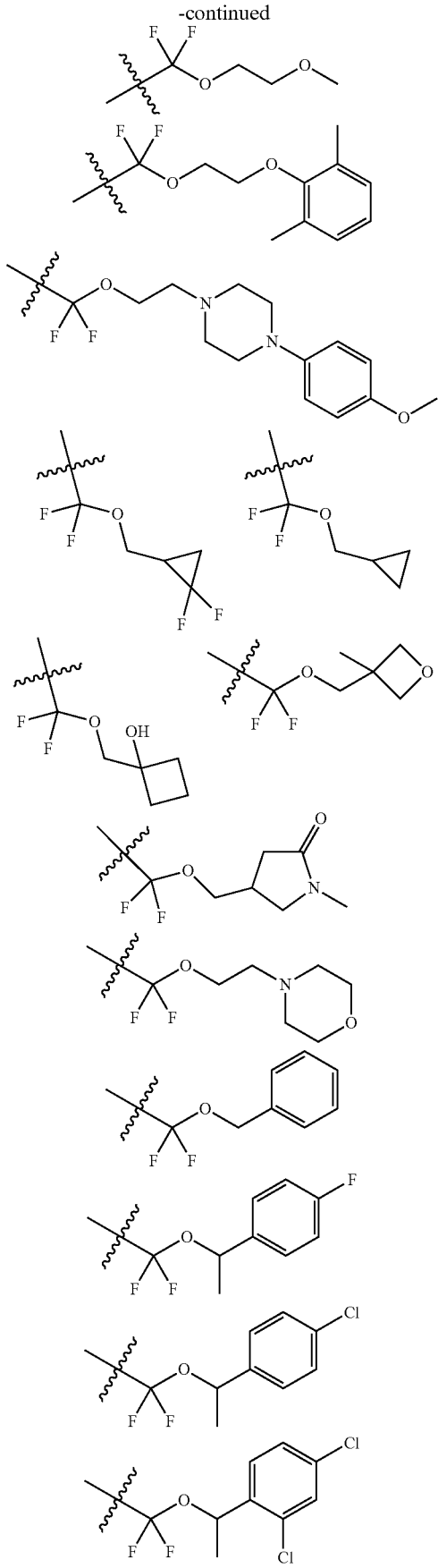
-continued
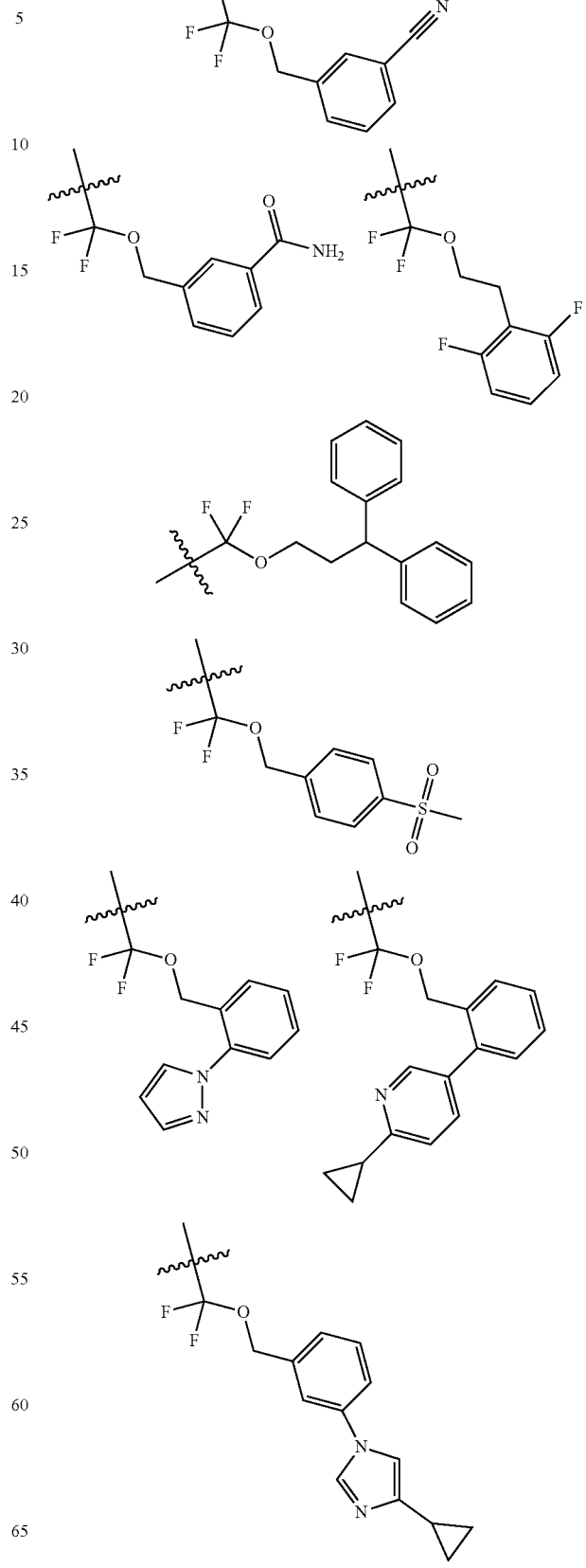

53
-continued
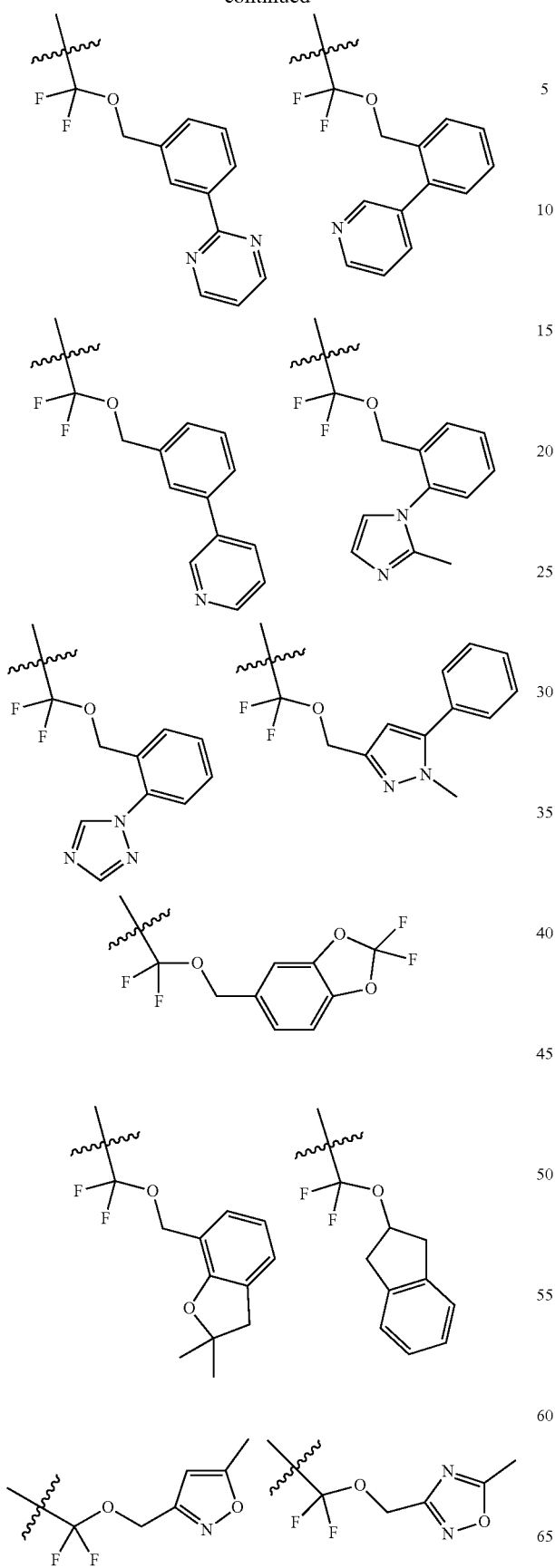
54
-continued
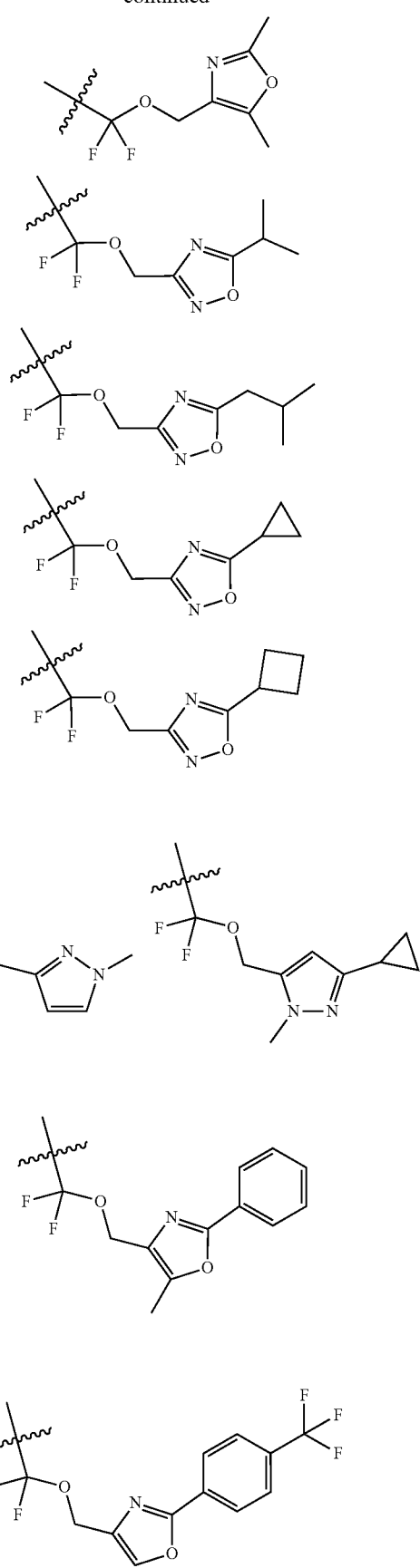

55
-continued
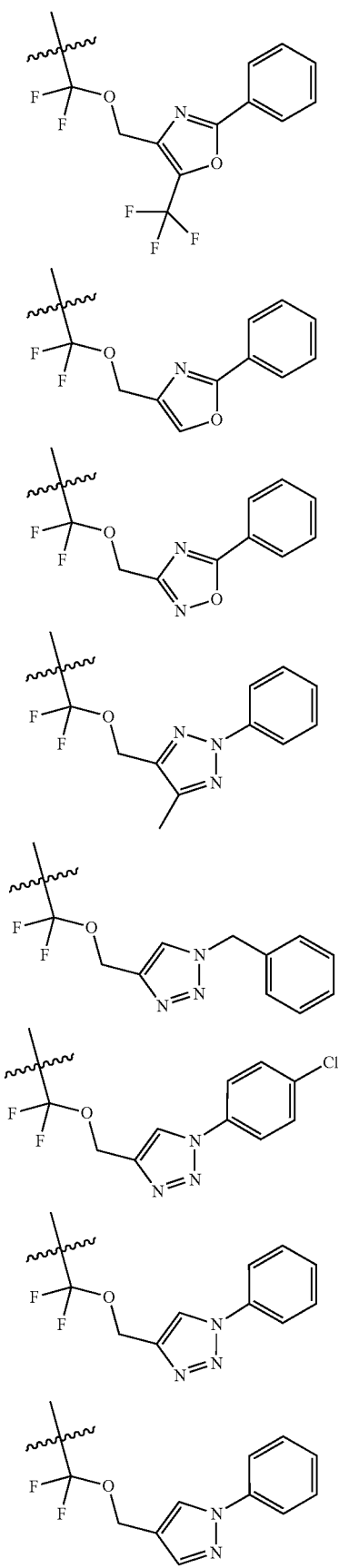
56
-continued
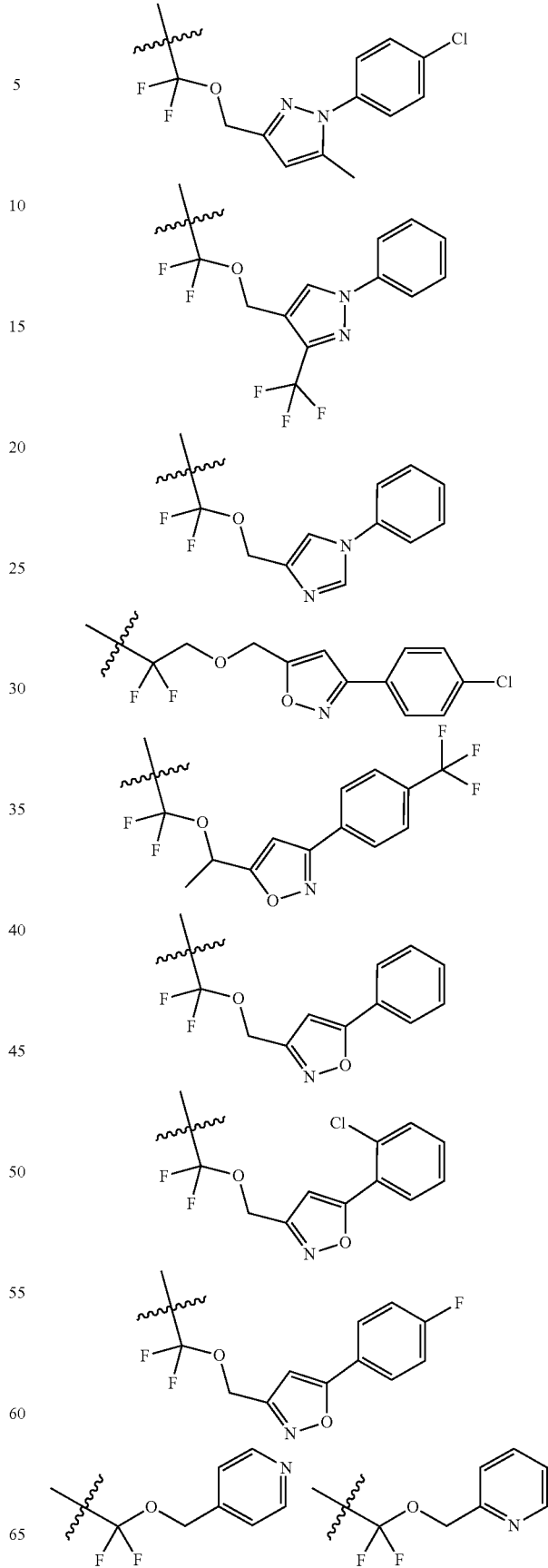

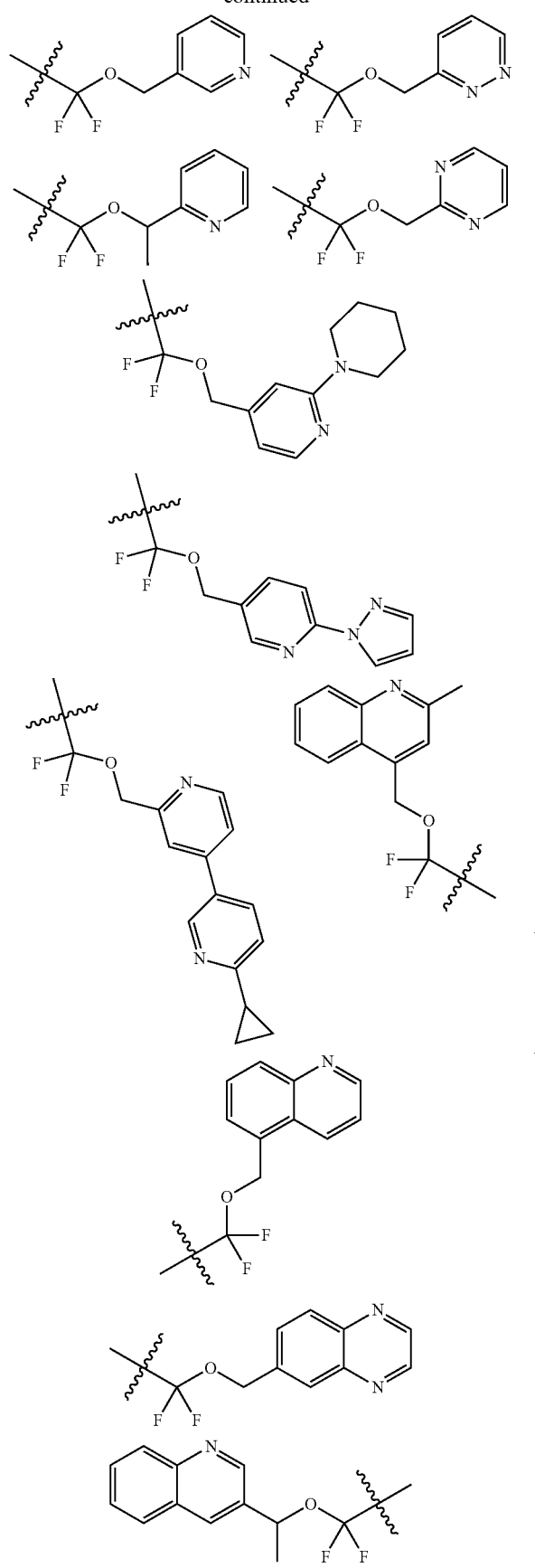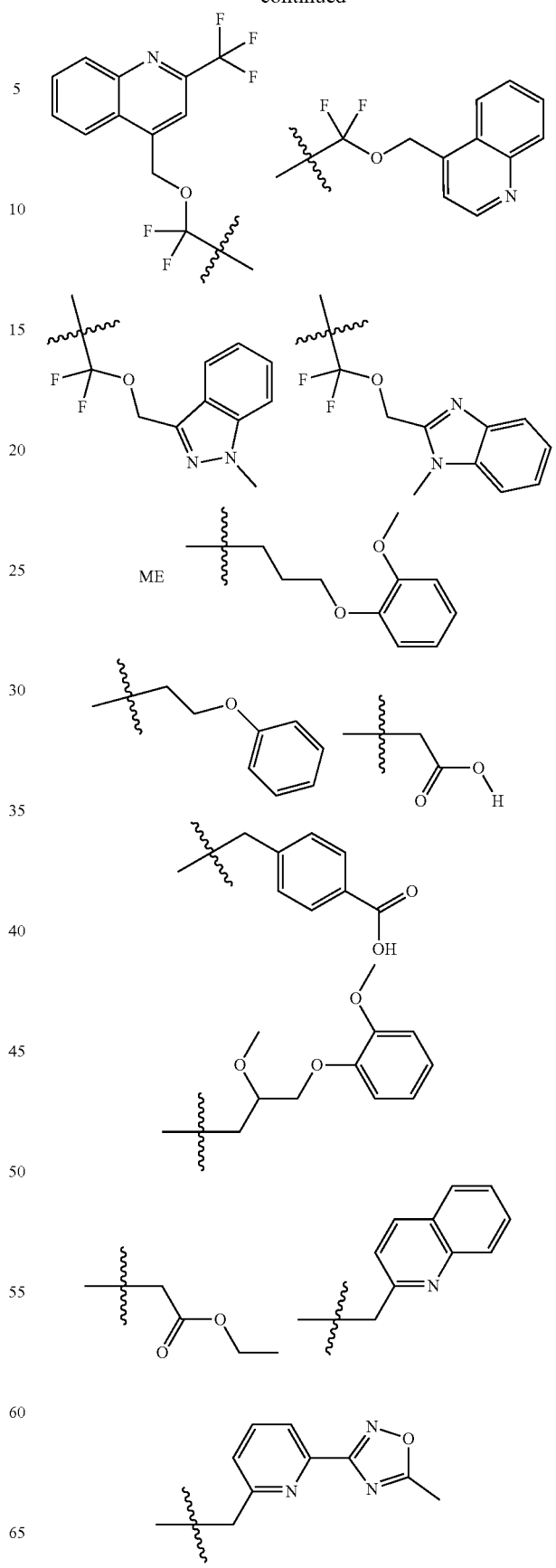

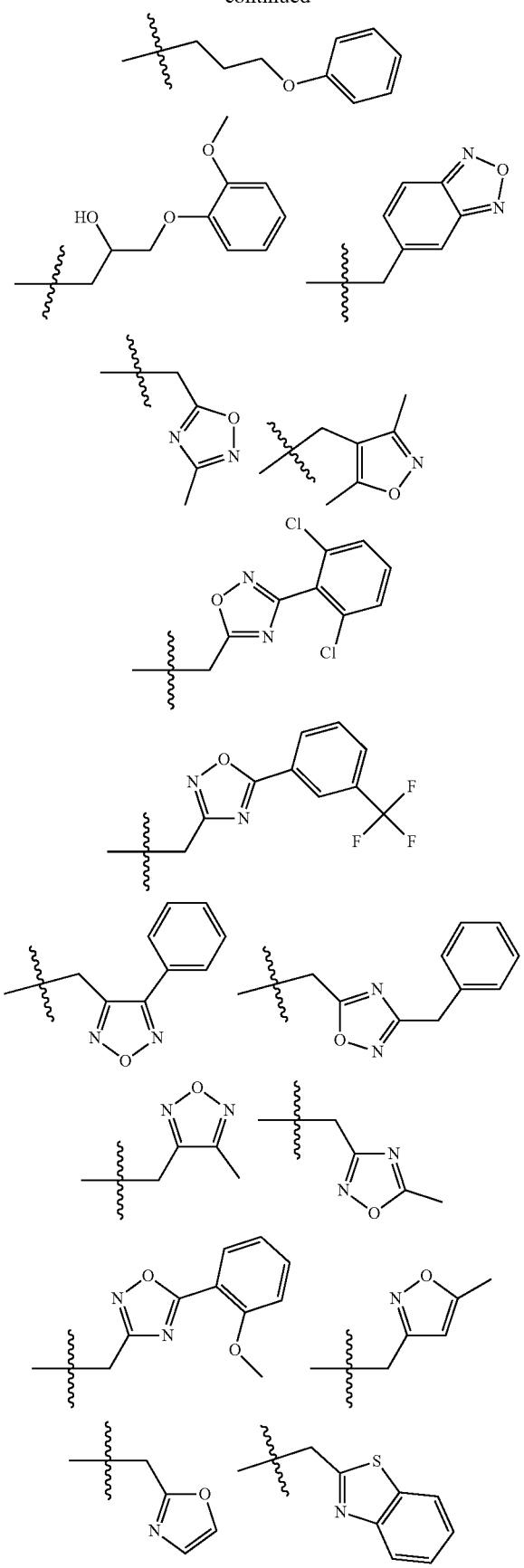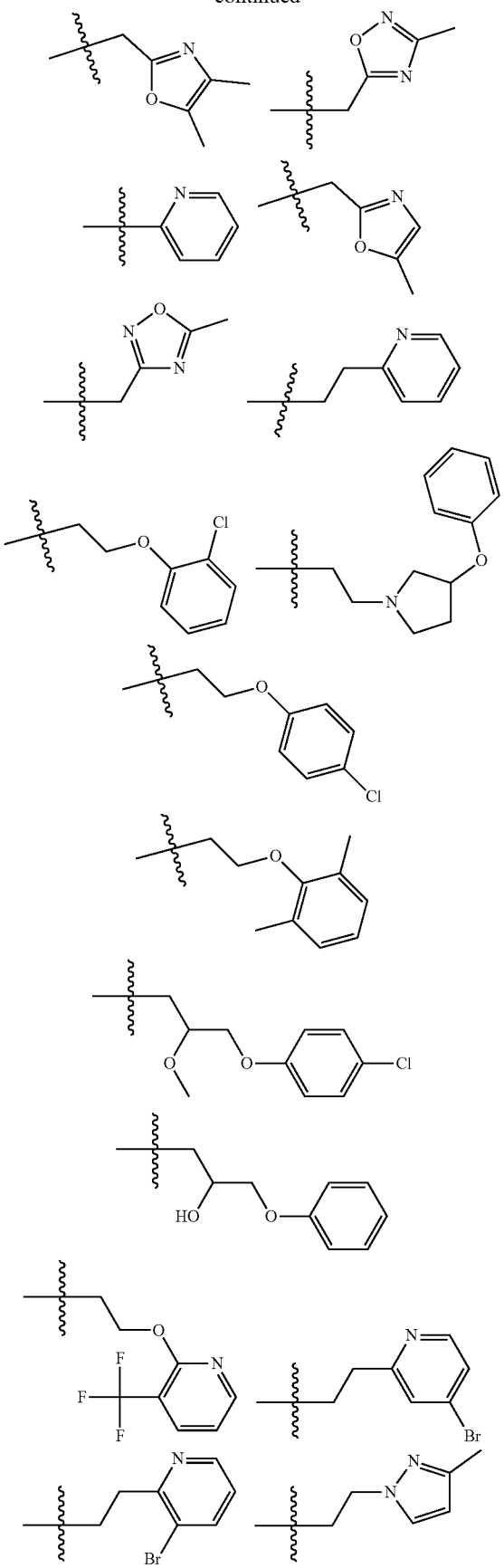

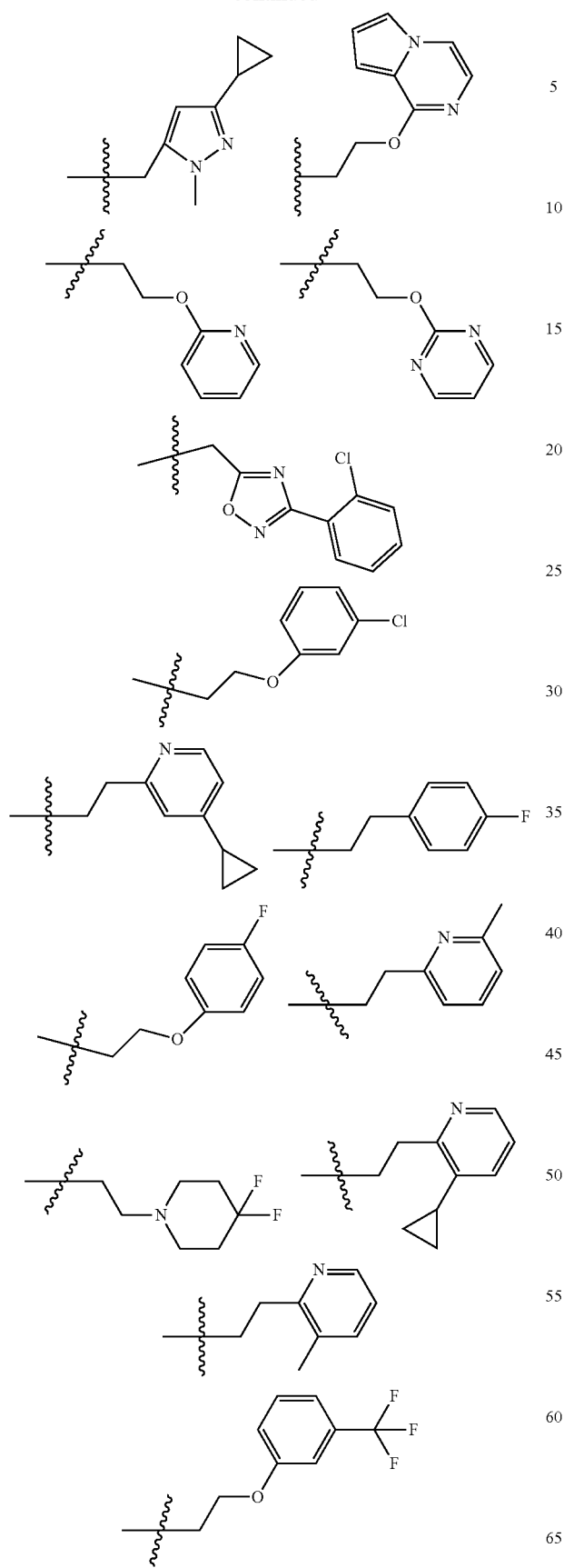
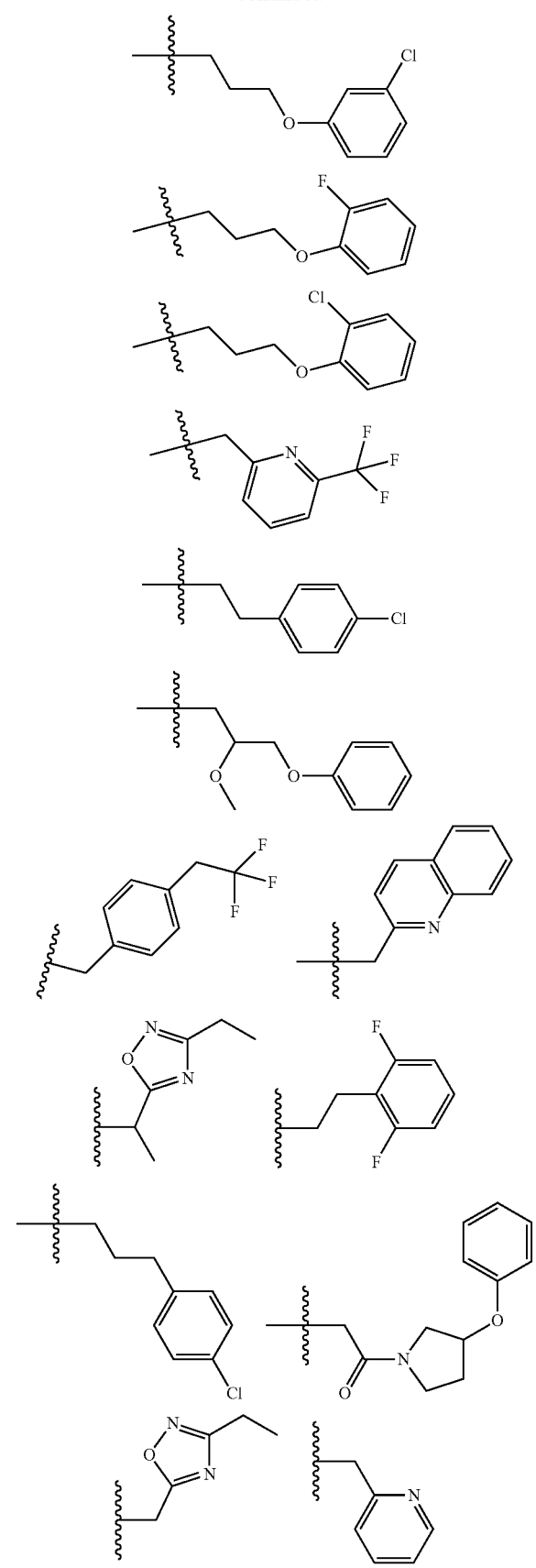

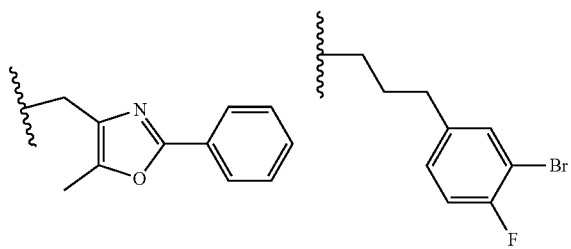
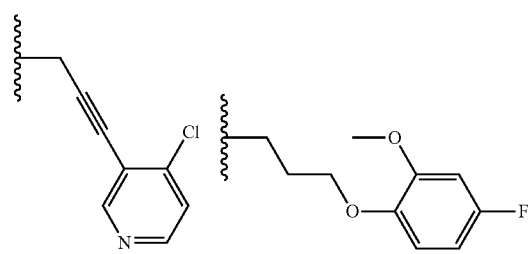
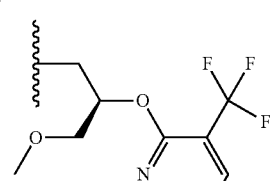
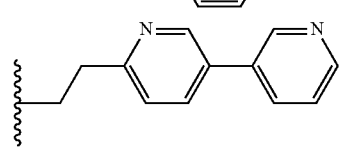
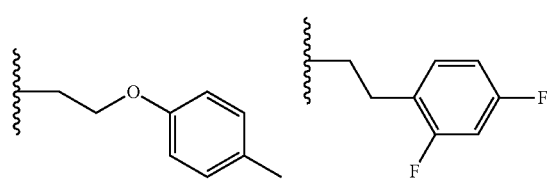
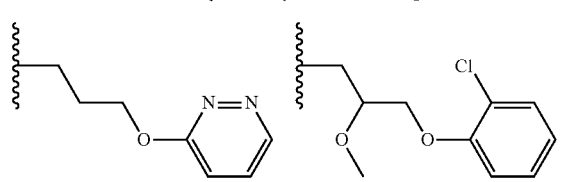
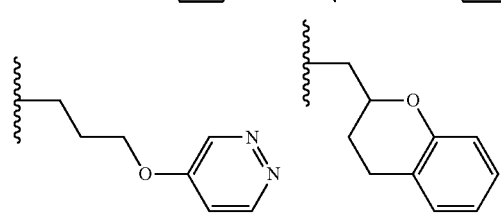
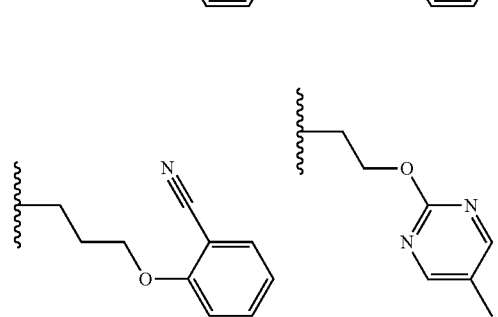
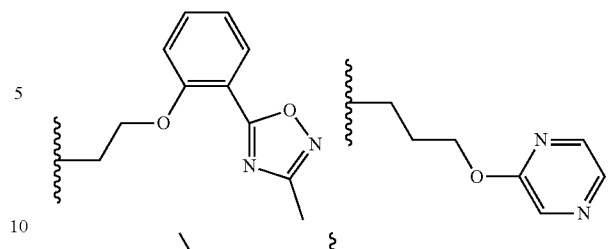
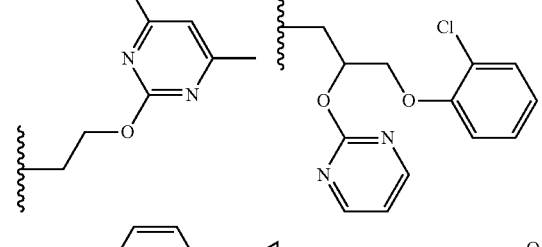
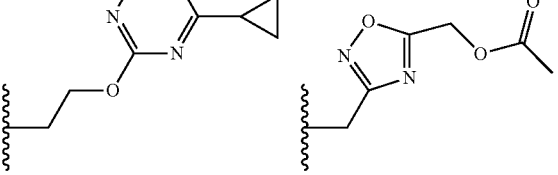
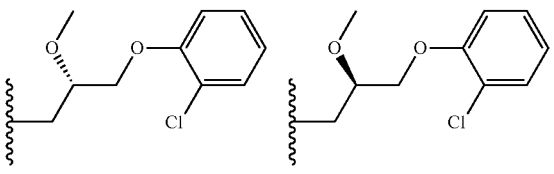
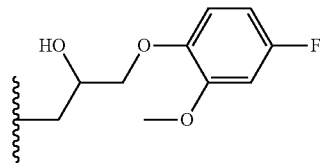
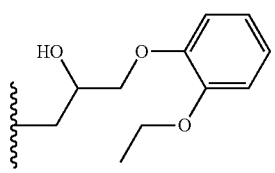
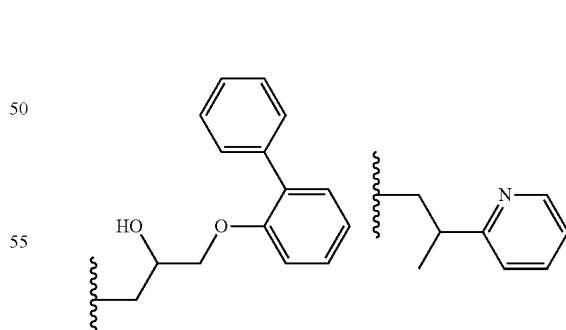
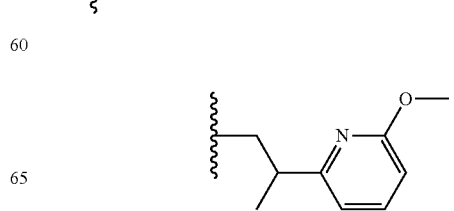

65
-continued
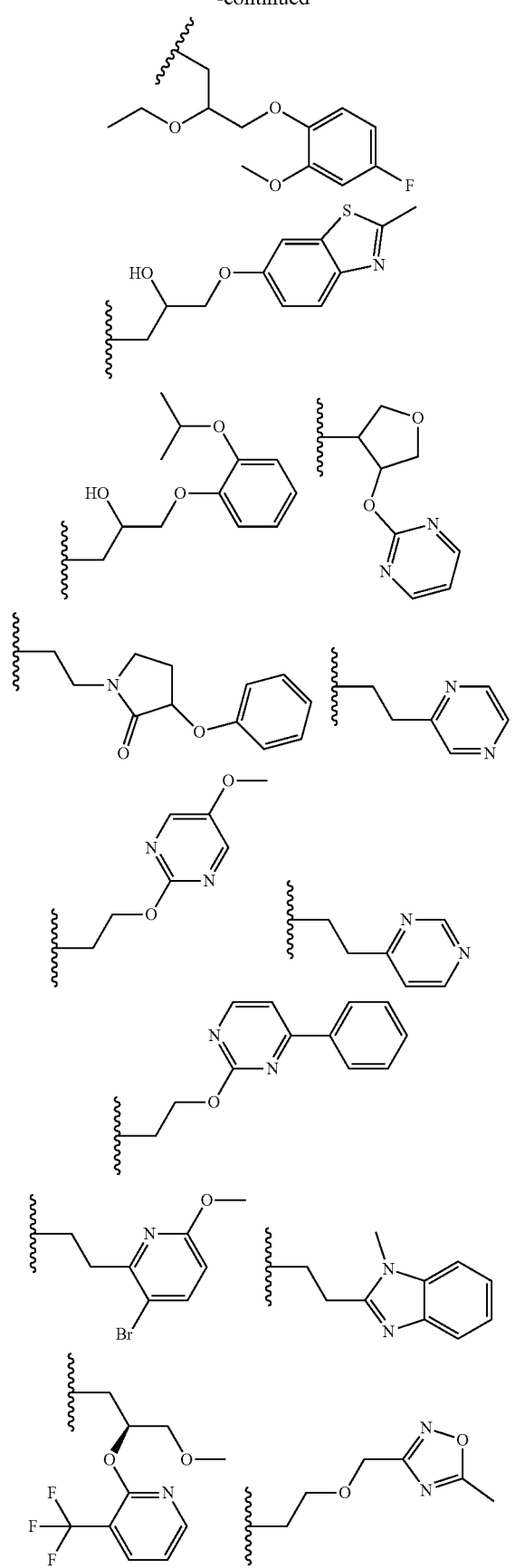
66
-continued
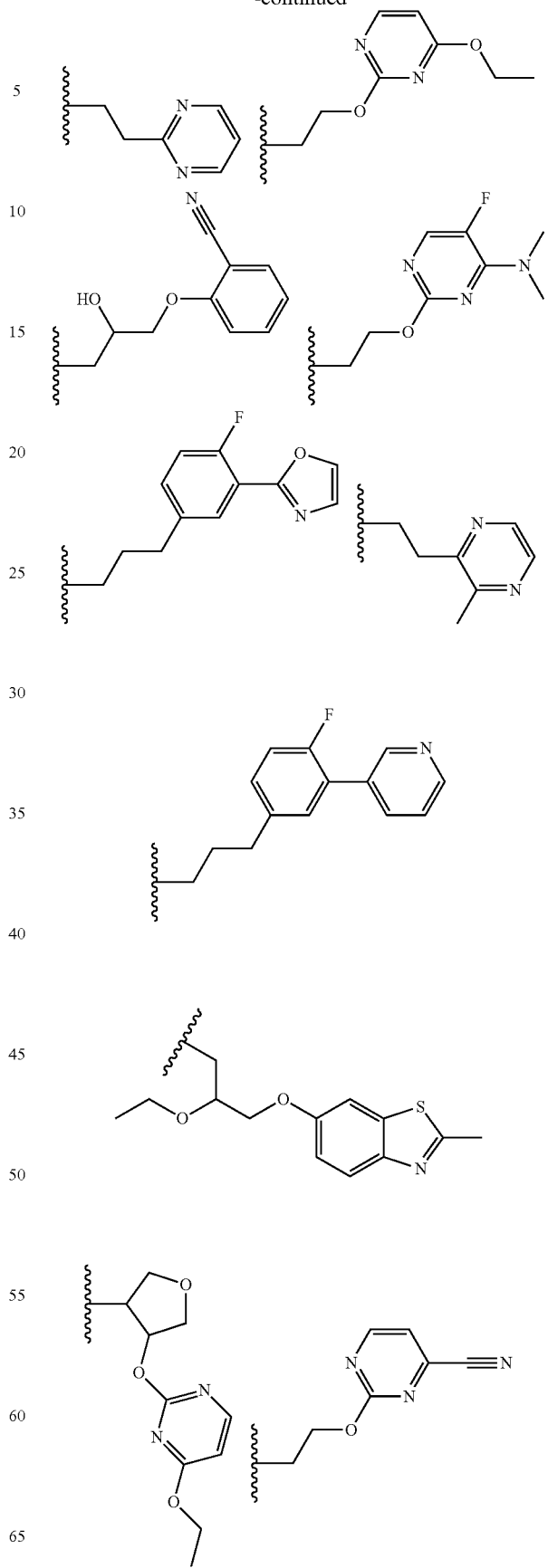

67
-continued
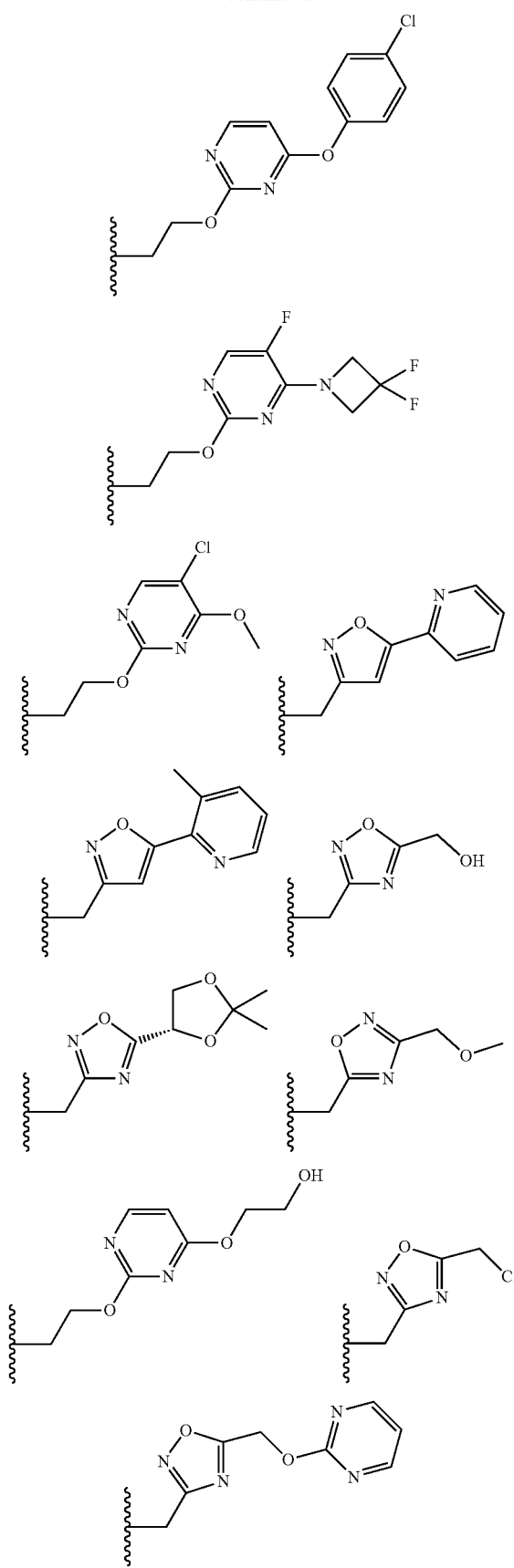
68
-continued
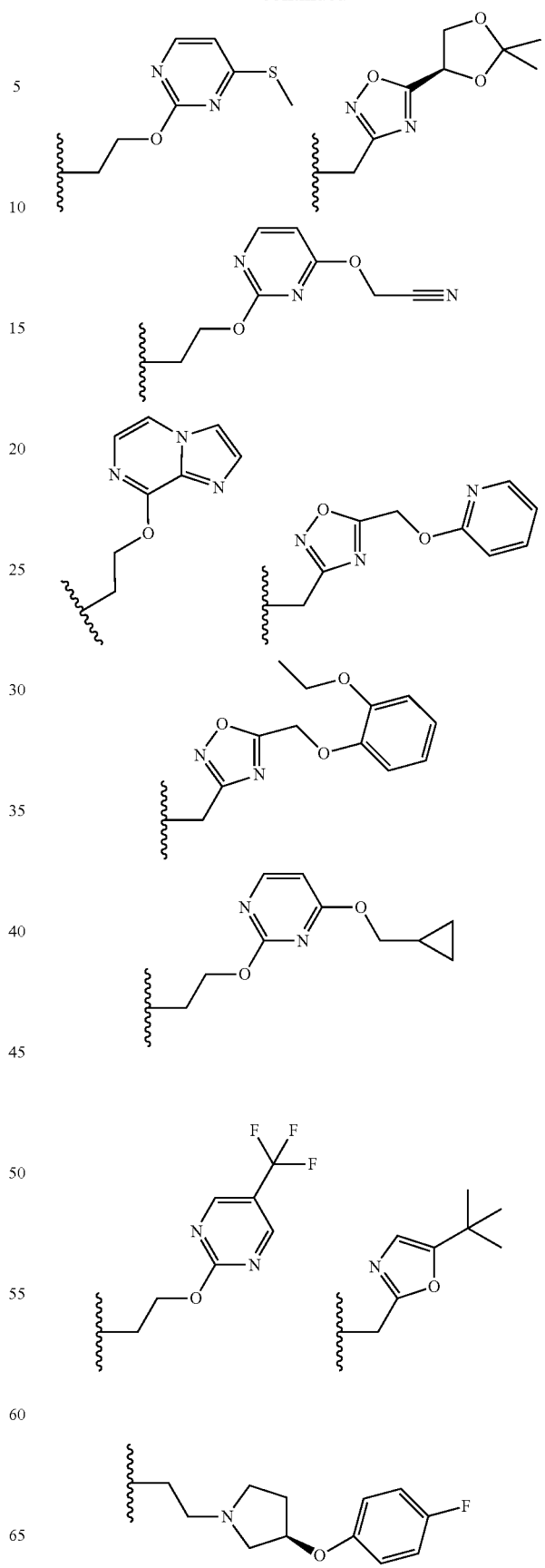

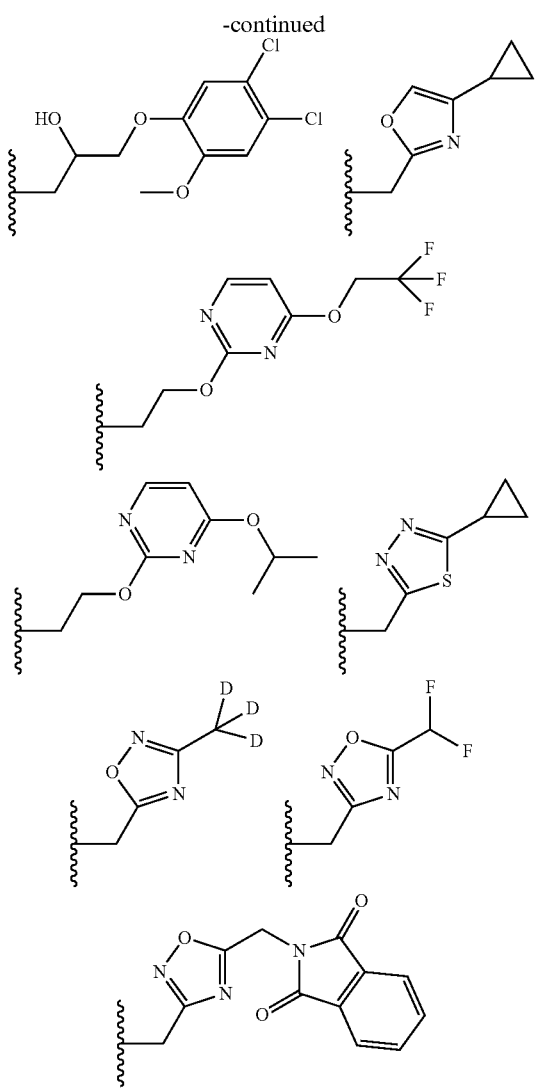

In another embodiment, this disclosure provides a compound selected from the group consisting of:

2-((3-methyl-1,2,4-oxadiazol-5-yl)methyl)-6-(4-(trifluoromethoxy)phenyl)-[1,2,4]triazolo[4,3-a]pyridin-3(2H)-one;
2-((4-methyl-1,2,5-oxadiazol-3-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethoxy)phenyl)-[1,2,4]triazolo[4,3-a]pyridin-3(2H)-one;
2-(2-hydroxy-3-(2-methoxyphenoxy)propyl)-6-(4-(trifluoromethoxy)phenyl)-[1,2,4]triazolo[4,3-a]pyridin-3(2H)-one;
2-((5-methylisoxazol-3-yl)methyl)-6-(4-(trifluoromethoxy)phenyl)-[1,2,4]triazolo[4,3-a]pyridin-3(2H)-one;
2-((3,5-dimethylisoxazol-4-yl)methyl)-6-(4-(trifluoromethoxy)phenyl)-[1,2,4]triazolo[4,3-a]pyridin-3(2H)-one;
6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one;
2-(3-(5-methyl-1,2,4-oxadiazol-3-yl)benzyl)-6-(4-(trifluoromethoxy)phenyl)-[1,2,4]triazolo[4,3-a]pyridin-3(2H)-one;
2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one;
2-(benzo[c][1,2,5]oxadiazol-5-ylmethyl)-6-(4-(trifluoromethoxy)phenyl)-[1,2,4]triazolo[4,3-a]pyridin-3(2H)-one;
2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one;
2-(4-(trifluoromethoxy)benzyl)-6-(4-(trifluoromethoxy)phenyl)-[1,2,4]triazolo[4,3-a]pyridin-3(2H)-one;
2-(quinolin-2-ylmethyl)-6-(4-(trifluoromethoxy)phenyl)-[1,2,4]triazolo[4,3-a]pyridin-3(2H)-one;
2-(1-(3-ethyl-1,2,4-oxadiazol-5-yl)ethyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethoxy)phenyl)-[1,2,4]triazolo[4,3-a]pyridin-3(2H)-one;
2-(pyridin-2-ylmethyl)-6-(4-(trifluoromethoxy)phenyl)-[1,2,4]triazolo[4,3-a]pyridin-3(2H)-one;
2-((4-phenyl-1,2,5-oxadiazol-3-yl)methyl)-6-(4-(trifluoromethoxy)phenyl)-[1,2,4]triazolo[4,3-a]pyridin-3(2H)-one;
2-((5-methyl-1,3,4-oxadiazol-2-yl)methyl)-6-(4-(trifluoromethoxy)phenyl)-[1,2,4]triazolo[4,3-a]pyridin-3(2H)-one;
2-(oxazol-2-ylmethyl)-6-(4-(trifluoromethoxy)phenyl)-[1,2,4]triazolo[4,3-a]pyridin-3(2H)-one;
2-(benzo[d]thiazol-2-ylmethyl)-6-(4-(trifluoromethoxy)phenyl)-[1,2,4]triazolo[4,3-a]pyridin-3(2H)-one;
2-((5-methyl-2-phenyloxazol-4-yl)methyl)-6-(4-(trifluoromethoxy)phenyl)-[1,2,4]triazolo[4,3-a]pyridin-3(2H)-one;
2-((4,5-dimethyloxazol-2-yl)methyl)-6-(4-(trifluoromethoxy)phenyl)-[1,2,4]triazolo[4,3-a]pyridin-3(2H)-one;
2-(2-methoxy-3-(2-methoxyphenoxy)propyl)-6-(4-(trifluoromethoxy)phenyl)-[1,2,4]triazolo[4,3-a]pyridin-3(2H)-one;
2-(3-phenoxypropyl)-6-(4-(trifluoromethoxy)phenyl)-[1,2,4]triazolo[4,3-a]pyridin-3(2H)-one;
2-((5-methyloxazol-2-yl)methyl)-6-(4-(trifluoromethoxy)phenyl)-[1,2,4]triazolo[4,3-a]pyridin-3(2H)-one;
2-((3-cyclopropyl-1-methyl-1H-pyrazol-5-yl)methyl)-6-(4-(trifluoromethoxy)phenyl)-[1,2,4]triazolo[4,3-a]pyridin-3(2H)-one;
2-((1,2,4-oxadiazol-3-yl)methyl)-6-(4-(trifluoromethoxy)phenyl)-[1,2,4]triazolo[4,3-a]pyridin-3(2H)-one;
2-(2-phenoxyethyl)-6-(4-(trifluoromethoxy)phenyl)-[1,2,4]triazolo[4,3-a]pyridin-3(2H)-one;
2-((3-benzyl-1,2,4-oxadiazol-5-yl)methyl)-6-(4-(trifluoromethoxy)phenyl)-[1,2,4]triazolo[4,3-a]pyridin-3(2H)-one;
5-methoxy-2-((3-methyl-1,2,4-oxadiazol-5-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(3-phenoxyphenyl)-[1,2,4]triazolo[4,3-a]pyridin-3(2H)-one;
6-(4-(4-chlorophenoxy)phenyl)-2-((5-methyl-1,2,4-oxadiazol-3-yl)methyl)-[1,2,4]triazolo[4,3-a]pyridin-3(2H)-one;
2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one;
2-(pyridin-2-yl)-6-(4-(trifluoromethoxy)phenyl)-[1,2,4]triazolo[4,3-a]pyridin-3(2H)-one;

2-(2-(1H-pyrazol-1-yl)ethyl)-6-(4-(trifluoromethoxy)phenyl)-[1,2,4]triazolo[4,3-a]pyridin-3(2H)-one;
2-(2-(pyridin-2-yl)ethyl)-6-(4-(trifluoromethoxy)phenyl)-[1,2,4]triazolo[4,3-a]pyridin-3(2H)-one;
2-(3-(2-methoxyphenoxy)propyl)-6-(4-(trifluoromethoxy)phenyl)-[1,2,4]triazolo[4,3-a]pyridin-3(2H)-one;
2-(3-(4-chlorophenoxy)-2-hydroxypropyl)-6-(4-(trifluoromethoxy)phenyl)-[1,2,4]triazolo[4,3-a]pyridin-3(2H)-one;
2-(2-(3-phenoxypyrrolidin-1-yl)ethyl)-6-(4-(trifluoromethoxy)phenyl)-[1,2,4]triazolo[4,3-a]pyridin-3(2H)-one;
2-(2-(4-chlorophenoxy)ethyl)-6-(4-(trifluoromethoxy)phenyl)-[1,2,4]triazolo[4,3-a]pyridin-3(2H)-one;
2-(2-(4-chloro-1H-pyrazol-1-yl)ethyl)-6-(4-(trifluoromethoxy)phenyl)-[1,2,4]triazolo[4,3-a]pyridin-3(2H)-one;
2-(2-(3-methyl-1H-pyrazol-1-yl)ethyl)-6-(4-(trifluoromethoxy)phenyl)-[1,2,4]triazolo[4,3-a]pyridin-3(2H)-one;
2-(2-hydroxy-3-phenoxypropyl)-6-(4-(trifluoromethoxy)phenyl)-[1,2,4]triazolo[4,3-a]pyridin-3(2H)-one;
2-(2-(2,6-dimethylphenoxy)ethyl)-6-(4-(trifluoromethoxy)phenyl)-[1,2,4]triazolo[4,3-a]pyridin-3(2H)-one;
2-(2-(4-phenyl-1H-imidazol-1-yl)ethyl)-6-(4-(trifluoromethoxy)phenyl)-[1,2,4]triazolo[4,3-a]pyridin-3(2H)-one;
2-(2-(2-chlorophenoxy)ethyl)-6-(4-(trifluoromethoxy)phenyl)-[1,2,4]triazolo[4,3-a]pyridin-3(2H)-one;
6-(4-(trifluoromethoxy)phenyl)-2-(2-(3-(trifluoromethyl)pyridin-2-yloxy)ethyl)-[1,2,4]triazolo[4,3-a]pyridin-3(2H)-one;
2-(2-(6-methylpyridin-2-yl)ethyl)-6-(4-(trifluoromethoxy)phenyl)-[1,2,4]triazolo[4,3-a]pyridin-3(2H)-one;
2-(2-(pyridin-2-yloxy)ethyl)-6-(4-(trifluoromethoxy)phenyl)-[1,2,4]triazolo[4,3-a]pyridin-3(2H)-one;
2-(2-(4,4-difluoropiperidin-1-yl)ethyl)-6-(4-(trifluoromethoxy)phenyl)-[1,2,4]triazolo[4,3-a]pyridin-3(2H)-one;
2-(3-(2-fluorophenoxy)propyl)-6-(4-(trifluoromethoxy)phenyl)-[1,2,4]triazolo[4,3-a]pyridin-3(2H)-one;
2-(3-(2-chlorophenoxy)propyl)-6-(4-(trifluoromethoxy)phenyl)-[1,2,4]triazolo[4,3-a]pyridin-3(2H)-one;
6-(4-chlorophenoxy)phenyl)-2-((3-methyl-1,2,4-oxadiazol-5-yl)methyl)-[1,2,4]triazolo[4,3-a]pyridin-3(2H)-one;
2-(2-(3-chlorophenoxy)ethyl)-6-(4-(trifluoromethoxy)phenyl)-[1,2,4]triazolo[4,3-a]pyridin-3(2H)-one;
2-(2-(4-fluorophenoxy)ethyl)-6-(4-(trifluoromethoxy)phenyl)-[1,2,4]triazolo[4,3-a]pyridin-3(2H)-one;
2-(2-(3-bromopyridin-2-yl)ethyl)-6-(4-(trifluoromethoxy)phenyl)-[1,2,4]triazolo[4,3-a]pyridin-3(2H)-one;
2-(2-(4-cyclopropylpyridin-2-yl)ethyl)-6-(4-(trifluoromethoxy)phenyl)-[1,2,4]triazolo[4,3-a]pyridin-3(2H)-one;
2-(2-(4-methylpyridin-2-yl)ethyl)-6-(4-(trifluoromethoxy)phenyl)-[1,2,4]triazolo[4,3-a]pyridin-3(2H)-one;
2-(4-fluorophenethyl)-6-(4-(trifluoromethoxy)phenyl)-[1,2,4]triazolo[4,3-a]pyridin-3(2H)-one;
2-(2-(3-cyclopropylpyridin-2-yl)ethyl)-6-(4-(trifluoromethoxy)phenyl)-[1,2,4]triazolo[4,3-a]pyridin-3(2H)-one;
2-(2-(3-methylpyridin-2-yl)ethyl)-6-(4-(trifluoromethoxy)phenyl)-[1,2,4]triazolo[4,3-a]pyridin-3(2H)-one;
6-(4-(trifluoromethoxy)phenyl)-2-((6-(trifluoromethyl)pyridin-2-yl)methyl)-[1,2,4]triazolo[4,3-a]pyridin-3(2H)-one;
2-(2,6-difluorophenethyl)-6-(4-(trifluoromethoxy)phenyl)-[1,2,4]triazolo[4,3-a]pyridin-3(2H)-one;
2-(3-(3-bromo-4-fluorophenyl)propyl)-6-(4-(trifluoromethoxy)phenyl)-[1,2,4]triazolo[4,3-a]pyridin-3(2H)-one;
6-(4-(trifluoromethoxy)phenyl)-2-(2-(6-(trifluoromethyl)pyridin-2-yloxy)ethyl)-[1,2,4]triazolo[4,3-a]pyridin-3(2H)-one;
6-(4-(trifluoromethoxy)phenyl)-2-(3-(2-(trifluoromethyl)phenoxy)propyl)-[1,2,4]triazolo[4,3-a]pyridin-3(2H)-one;
2-(3-(4-fluoro-2-methoxyphenoxy)propyl)-6-(4-(trifluoromethoxy)phenyl)-[1,2,4]triazolo[4,3-a]pyridin-3(2H)-one
2-(3-(4-chloropyridin-3-yl)prop-2-ynyl)-6-(4-(trifluoromethoxy)phenyl)-[1,2,4]triazolo[4,3-a]pyridin-3(2H)-one;
2-(2-(2-methoxyphenoxy)ethyl)-6-(4-(trifluoromethoxy)phenyl)-[1,2,4]triazolo[4,3-a]pyridin-3(2H)-one;
2-(3-(3-oxo-6-(4-(trifluoromethoxy)phenyl)-[1,2,4]triazolo[4,3-a]pyridin-2(3H)-yl)propoxy)benzonitrile;
6-(4-(trifluoromethoxy)phenyl)-2-(3-(2-(trifluoromethyl)phenoxy)propyl)-[1,2,4]triazolo[4,3-a]pyridin-3(2H)-one;
(R)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;
2-(2-(pyridin-3-yl)ethyl)-6-(4-(trifluoromethoxy)phenyl)-[1,2,4]triazolo[4,3-a]pyridin-3(2H)-one;
2-(2-(3,3'-bipyridin-6-yl)ethyl)-6-(4-(trifluoromethoxy)phenyl)-[1,2,4]triazolo[4,3-a]pyridin-3(2H)-one;
2-(2-(p-tolyloxy)ethyl)-6-(4-(trifluoromethoxy)phenyl)-[1,2,4]triazolo[4,3-a]pyridin-3(2H)-one;
2-(3-(4-fluorophenyl)propyl)-6-(4-(trifluoromethoxy)phenyl)-[1,2,4]triazolo[4,3-a]pyridin-3(2H)-one;
2-(chroman-2-ylmethyl)-6-(4-(trifluoromethoxy)phenyl)-[1,2,4]triazolo[4,3-a]pyridin-3(2H)-one;
2-(2,4-difluorophenethyl)-6-(4-(trifluoromethoxy)phenyl)-[1,2,4]triazolo[4,3-a]pyridin-3(2H)-one;
2-(3-(pyridazin-3-yloxy)propyl)-6-(4-(trifluoromethoxy)phenyl)-[1,2,4]triazolo[4,3-a]pyridin-3(2H)-one;
2-(3-(2-chlorophenoxy)-2-methoxypropyl)-6-(4-(trifluoromethoxy)phenyl)-[1,2,4]triazolo[4,3-a]pyridin-3(2H)-one
2-(2-(pyridazin-3-yloxy)ethyl)-6-(4-(trifluoromethoxy)phenyl)-[1,2,4]triazolo[4,3-a]pyridin-3(2H)-one
2-(2-(5-methylpyrimidin-2-yloxy)ethyl)-6-(4-(trifluoromethoxy)phenyl)-[1,2,4]triazolo[4,3-a]pyridin-3(2H)-one;
2-((3-methyl-1,2,4-oxadiazol-5-yl)methyl)-6-(4-(2,2,2-trifluoroethoxy)phenyl)-[1,2,4]triazolo[4,3-a]pyridin-3(2H)-one;
2-(2-(2-(3-methyl-1,2,4-oxadiazol-5-yl)phenoxy)ethyl)-6-(4-(trifluoromethoxy)phenyl)-[1,2,4]triazolo[4,3-a]pyridin-3(2H)-one;
2-(3-(pyrazin-2-yloxy)propyl)-6-(4-(trifluoromethoxy)phenyl)-[1,2,4]triazolo[4,3-a]pyridin-3(2H)-one;
2-(2-((5-methyl-1,2,4-oxadiazol-3-yl)methoxy)ethyl)-6-(4-(trifluoromethoxy)phenyl)-[1,2,4]triazolo[4,3-a]pyridin-3(2H)-one;
2-((3-methyl-1,2,4-oxadiazol-5-yl)methyl)-6-(2-methyl-4-(trifluoromethoxy)phenyl)-[1,2,4]triazolo[4,3-a]pyridin-3(2H)-one;
2-(2-(4,6-dimethylpyrimidin-2-yloxy)ethyl)-6-(4-(trifluoromethoxy)phenyl)-[1,2,4]triazolo[4,3-a]pyridin-3(2H)-one;

2-(3-(2-chlorophenoxy)-2-(pyrimidin-2-yloxy)propyl)-6-(4-(trifluoromethoxy)phenyl)-[1,2,4]triazolo[4,3-a]pyridin-3(2H)-one;

2-(2-(4-cyclopropylpyrimidin-2-yloxy)ethyl)-6-(4-(trifluoromethoxy)phenyl)-[1,2,4]triazolo[4,3-a]pyridin-3(2H)-one;

(S)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;

2-(2-(5-chloropyrimidin-2-yloxy)ethyl)-6-(4-(trifluoromethoxy)phenyl)-[1,2,4]triazolo[4,3-a]pyridin-3(2H)-one 6-(4-(4-fluorophenoxy)phenyl)-2-((3-methyl-1,2,4-oxadiazol-5-yl)methyl)-[1,2,4]triazolo[4,3-a]pyridin-3(2H)-one;

(3-((3-oxo-6-(4-(trifluoromethoxy)phenyl)-[1,2,4]triazolo[4,3-a]pyridin-2(3H)-yl)methyl)-1,2,4-oxadiazol-5-yl)methyl acetate;

(S)-2-(3-(2-chlorophenoxy)-2-methoxypropyl)-6-(4-(trifluoromethoxy)phenyl)-[1,2,4]triazolo[4,3-a]pyridin-3(2H)-one;

(R)-2-(3-(2-chlorophenoxy)-2-methoxypropyl)-6-(4-(trifluoromethoxy)phenyl)-[1,2,4]triazolo[4,3-a]pyridin-3(2H)-one;

2-(2-(1-methyl-1H-benzo[d]imidazol-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-hydroxypropyl)-6-(4-(trifluoromethoxy)phenyl)-[1,2,4]triazolo[4,3-a]pyridin-3(2H)-one;

2-(3-(2-ethoxyphenoxy)-2-hydroxypropyl)-6-(4-(trifluoromethoxy)phenyl)-[1,2,4]triazolo[4,3-a]pyridin-3(2H)-one;

2-(3-(biphenyl-2-yloxy)-2-hydroxypropyl)-6-(4-(trifluoromethoxy)phenyl)-[1,2,4]triazolo[4,3-a]pyridin-3(2H)-one;

2-(2-hydroxy-3-(3-oxo-6-(4-(trifluoromethoxy)phenyl)-[1,2,4]triazolo[4,3-a]pyridin-2(3H)-yl)propoxy)benzonitrile;

2-(2-(pyridin-2-yl)propyl)-6-(4-(trifluoromethoxy)phenyl)-[1,2,4]triazolo[4,3-a]pyridin-3(2H)-one;

2-(2-(6-methoxypyridin-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-methoxypropyl)-6-(4-(trifluoromethoxy)phenyl)-[1,2,4]triazolo[4,3-a]pyridin-3(2H)-one;

2-(2-ethoxy-3-(4-fluoro-2-methoxyphenoxy)propyl)-6-(4-(trifluoromethoxy)phenyl)-[1,2,4]triazolo[4,3-a]pyridin-3(2H)-one;

2-(2-(4-ethoxypyrimidin-2-yloxy)ethyl)-6-(4-(trifluoromethoxy)phenyl)-[1,2,4]triazolo[4,3-a]pyridin-3(2H)-one;

2-(2-hydroxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(2-hydroxy-3-(2-isopropoxyphenoxy)propyl)-6-(4-(trifluoromethoxy)phenyl)-[1,2,4]triazolo[4,3-a]pyridin-3(2H)-one;

2-(4-(pyrimidin-2-yloxy)tetrahydrofuran-3-yl)-6-(4-(trifluoromethoxy)phenyl)-[1,2,4]triazolo[4,3-a]pyridin-3(2H)-one;

2-((3-methyl-1,2,4-oxadiazol-5-yl)methyl)-6-(4-(trimethylsilyl)phenyl)-[1,2,4]triazolo[4,3-a]pyridin-3(2H)-one;

2-(2-(pyrimidin-2-yl)ethyl)-6-(4-(trifluoromethoxy)phenyl)-[1,2,4]triazolo[4,3-a]pyridin-3(2H)-one;

2-(2-(2-oxo-3-phenoxypyrrolidin-1-yl)ethyl)-6-(4-(trifluoromethoxy)phenyl)-[1,2,4]triazolo[4,3-a]pyridin-3(2H)-one;

2-(2-(pyrimidin-4-yl)ethyl)-6-(4-(trifluoromethoxy)phenyl)-[1,2,4]triazolo[4,3-a]pyridin-3(2H)-one;

2-(2-(pyrazin-2-yl)ethyl)-6-(4-(trifluoromethoxy)phenyl)-[1,2,4]triazolo[4,3-a]pyridin-3(2H)-one;

2-(2-(4-phenylpyrimidin-2-yloxy)ethyl)-6-(4-(trifluoromethoxy)phenyl)-[1,2,4]triazolo[4,3-a]pyridin-3(2H)-one;

2-(2-(5-methoxypyrimidin-2-yloxy)ethyl)-6-(4-(trifluoromethoxy)phenyl)-[1,2,4]triazolo[4,3-a]pyridin-3(2H)-one 2-(2-(3-methylpyrazin-2-yl)ethyl)-6-(4-(trifluoromethoxy)phenyl)-[1,2,4]triazolo[4,3-a]pyridin-3(2H)-one;

2-(2-(3-bromo-6-methoxypyridin-2-yl)ethyl)-6-(4-(trifluoromethoxy)phenyl)-[1,2,4]triazolo[4,3-a]pyridin-3(2H)-one;

2-(3-(4-fluoro-3-(oxazol-2-yl)phenyl)propyl)-6-(4-(trifluoromethoxy)phenyl)-[1,2,4]triazolo[4,3-a]pyridin-3(2H)-one;

6-(4-(4-chlorophenoxy)phenyl)-2-(2-(pyrimidin-2-yloxy)ethyl)-[1,2,4]triazolo[4,3-a]pyridin-3(2H)-one;

2-(3-(4-fluoro-3-(pyridin-3-yl)phenyl)propyl)-6-(4-(trifluoromethoxy)phenyl)-[1,2,4]triazolo[4,3-a]pyridin-3(2H)-one;

6-(4-(4-fluorophenoxy)phenyl)-2-(2-(pyrimidin-2-yloxy)ethyl)-[1,2,4]triazolo[4,3-a]pyridin-3(2H)-one;

2-(2-(pyrimidin-2-yloxy)ethyl)-6-(4-(trimethylsilyl)phenyl)-[1,2,4]triazolo[4,3-a]pyridin-3(2H)-one;

2-(2-ethoxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(4-(4-ethoxypyrimidin-2-yloxy)tetrahydrofuran-3-yl)-6-(4-(trifluoromethoxy)phenyl)-[1,2,4]triazolo[4,3-a]pyridin-3(2H)-one;

2-(2-(4-(dimethylamino)-5-fluoropyrimidin-2-yloxy)ethyl)-6-(4-(trifluoromethoxy)phenyl)-[1,2,4]triazolo[4,3-a]pyridin-3(2H)-one;

6-(3,5-difluoro-4-phenoxyphenyl)-2-((3-methyl-1,2,4-oxadiazol-5-yl)methyl)-[1,2,4]triazolo[4,3-a]pyridin-3(2H)-one;

2-((5-(methoxymethyl)-1,2,4-oxadiazol-3-yl)methyl)-6-(4-(trifluoromethoxy)phenyl)-[1,2,4]triazolo[4,3-a]pyridin-3(2H)-one;

2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidine-4-carbonitrile;

2-(2-(5-chloro-4-methoxypyrimidin-2-yloxy)ethyl)-6-(4-(trifluoromethoxy)phenyl)-[1,2,4]triazolo[4,3-a]pyridin-3(2H)-one;

6-(4-benzoylphenyl)-2-((3-methyl-1,2,4-oxadiazol-5-yl)methyl)-[1,2,4]triazolo[4,3-a]pyridin-3(2H)-one;

2-(2-(4-(4-chlorophenoxy)pyrimidin-2-yloxy)ethyl)-6-(4-(trifluoromethoxy)phenyl)-[1,2,4]triazolo[4,3-a]pyridin-3(2H)-one;

2-(2-(4-(3,3-difluoroazetidin-1-yl)-5-fluoropyrimidin-2-yloxy)ethyl)-6-(4-(trifluoromethoxy)phenyl)-[1,2,4]triazolo[4,3-a]pyridin-3(2H)-one;

6-(3,4-dichlorophenyl)-2-((3-methyl-1,2,4-oxadiazol-5-yl)methyl)-[1,2,4]triazolo[4,3-a]pyridin-3(2H)-one;

2-(2-(pyrrolo[1,2-a]pyrazin-1-yloxy)ethyl)-6-(4-(trifluoromethoxy)phenyl)-[1,2,4]triazolo[4,3-a]pyridin-3(2H)-one;

2-(3-(3-oxo-6-(4-(trifluoromethoxy)phenyl)-[1,2,4]triazolo[4,3-a]pyridin-2(3H)-yl)methyl)-1,2,4-oxadiazol-5-yl)methyl)isoindoline-1,3-dione 2-((3-methyl-1,2,4-oxadiazol-5-yl)methyl)-6-(4-(trifluoromethyl)phenyl)-[1,2,4]triazolo[4,3-a]pyridin-3(2H)-one;
2-(2-(5-fluoropyrimidin-2-yloxy)ethyl)-6-(4-(trifluoromethoxy)phenyl)-[1,2,4]triazolo[4,3-a]pyridin-3(2H)-one;
2-(2-(2-chloropyrimidin-5-yloxy)ethyl)-6-(4-(trifluoromethoxy)phenyl)-[1,2,4]triazolo[4,3-a]pyridin-3(2H)-one;
6-(4-(4-fluorophenoxy)phenyl)-2-((5-methyl-1,2,4-oxadiazol-3-yl)methyl)-[1,2,4]triazolo[4,3-a]pyridin-3(2H)-one;
2-(2-(isoquinolin-1-yloxy)ethyl)-6-(4-(trifluoromethoxy)phenyl)-[1,2,4]triazolo[4,3-a]pyridin-3(2H)-one;
2-((5-cyclopropyl-1,2,4-oxadiazol-3-yl)methyl)-6-(4-(trifluoromethoxy)phenyl)-[1,2,4]triazolo[4,3-a]pyridin-3(2H)-one;
6-(4-(4-fluorophenoxy)phenyl)-[1,2,4]triazolo[4,3-a]pyridin-3(2H)-one;
2-((5-(pyridin-2-yl)isoxazol-3-yl)methyl)-6-(4-(trifluoromethoxy)phenyl)-[1,2,4]triazolo[4,3-a]pyridin-3(2H)-one;
2-((5-(3-methylpyridin-2-yl)isoxazol-3-yl)methyl)-6-(4-(trifluoromethoxy)phenyl)-[1,2,4]triazolo[4,3-a]pyridin-3(2H)-one;
6-(4-(4-fluorophenoxy)phenyl)-2-((5-(hydroxymethyl)-1,2,4-oxadiazol-3-yl)methyl)-[1,2,4]triazolo[4,3-a]pyridin-3(2H)-one;
2-(1-(3-methyl-1,2,4-oxadiazol-5-yl)ethyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethyl)phenyl)-[1,2,4]triazolo[4,3-a]pyridin-3(2H)-one;
6-(4-chlorophenyl)-2-((3-methyl-1,2,4-oxadiazol-5-yl)methyl)-[1,2,4]triazolo[4,3-a]pyridin-3(2H)-one;
6-(3,4-difluorophenyl)-2-((3-methyl-1,2,4-oxadiazol-5-yl)methyl)-[1,2,4]triazolo[4,3-a]pyridin-3(2H)-one;
2-cinnamyl-6-(4-(trifluoromethoxy)phenyl)-[1,2,4]triazolo[4,3-a]pyridin-3(2H)-one;
(S)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one
2-(3-(methoxymethyl)-1,2,4-oxadiazol-5-yl)methyl)-6-(4-(trifluoromethoxy)phenyl)-[1,2,4]triazolo[4,3-a]pyridin-3(2H)-one;
2-((5-(difluoromethyl)-1,2,4-oxadiazol-3-yl)methyl)-6-(4-(trifluoromethoxy)phenyl)-[1,2,4]triazolo[4,3-a]pyridin-3(2H)-one;
6-(3-fluoro-4-(trifluoromethoxy)phenyl)-2-((3-methyl-1,2,4-oxadiazol-5-yl)methyl)-[1,2,4]triazolo[4,3-a]pyridin-3(2H)-one;
2-(2-(4-(2-hydroxyethoxy)pyrimidin-2-yloxy)ethyl)-6-(4-(trifluoromethoxy)phenyl)-[1,2,4]triazolo[4,3-a]pyridin-3(2H)-one;
2-((5-(chloromethyl)-1,2,4-oxadiazol-3-yl)methyl)-6-(4-(trifluoromethoxy)phenyl)-[1,2,4]triazolo[4,3-a]pyridin-3(2H)-one;
(R)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one
2-(2-(4-(methylthio)pyrimidin-2-yloxy)ethyl)-6-(4-(trifluoromethoxy)phenyl)-[1,2,4]triazolo[4,3-a]pyridin-3(2H)-one;
2-(2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidin-4-yloxy)acetonitrile;
6-(4-chloro-3-fluorophenyl)-2-((3-methyl-1,2,4-oxadiazol-5-yl)methyl)-[1,2,4]triazolo[4,3-a]pyridin-3(2H)-one;
2-((5-((pyrimidin-2-yloxy)methyl)-1,2,4-oxadiazol-3-yl)methyl)-6-(4-(trifluoromethoxy)phenyl)-[1,2,4]triazolo[4,3-a]pyridin-3(2H)-one;
2-((1-methyl-1H-pyrazol-4-yl)methyl)-6-(4-(trifluoromethoxy)phenyl)-[1,2,4]triazolo[4,3-a]pyridin-3(2H)-one;
2-((3-methylisoxazol-5-yl)methyl)-6-(4-(trifluoromethoxy)phenyl)-[1,2,4]triazolo[4,3-a]pyridin-3(2H)-one;
2-((1-methyl-1H-pyrazol-3-yl)methyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethoxy)phenyl)-[1,2,4]triazolo[4,3-a]pyridin-3(2H)-one;
2-((3-ethyl-1,2,4-oxadiazol-5-yl)methyl)-6-(4-(trifluoromethyl)phenyl)-[1,2,4]triazolo[4,3-a]pyridin-3(2H)-one;
2-((3-(methoxymethyl)-1,2,4-oxadiazol-5-yl)methyl)-6-(4-(trifluoromethyl)phenyl)-[1,2,4]triazolo[4,3-a]pyridin-3(2H)-one;
2-((3-trideuteromethyl-1,2,4-oxadiazol-5-yl)methyl)-6-(4-(trifluoromethoxy)phenyl)-[1,2,4]triazolo[4,3-a]pyridin-3(2H)-one;
2-((5-cyclopropyl-1,3,4-thiadiazol-2-yl)methyl)-6-(4-(trifluoromethoxy)phenyl)-[1,2,4]triazolo[4,3-a]pyridin-3(2H)-one;
6-(4-(trifluoromethyl)phenyl)-[1,2,4]triazolo[4,3-a]pyridin-3(2H)-one;
2-((5-methyloxazol-2-yl)methyl)-6-(4-(trifluoromethyl)phenyl)-[1,2,4]triazolo[4,3-a]pyridin-3(2H)-one;
2-((4,5-dimethyloxazol-2-yl)methyl)-6-(4-(trifluoromethyl)phenyl)-[1,2,4]triazolo[4,3-a]pyridin-3(2H)-one;
2-(2-(imidazo[1,2-a]pyrazin-8-yloxy)ethyl)-6-(4-(trifluoromethoxy)phenyl)-[1,2,4]triazolo[4,3-a]pyridin-3(2H)-one;
2-((5-((pyridin-2-yloxy)methyl)-1,2,4-oxadiazol-3-yl)methyl)-6-(4-(trifluoromethoxy)phenyl)-[1,2,4]triazolo[4,3-a]pyridin-3(2H)-one;
2-((5-((2-ethoxyphenoxy)methyl)-1,2,4-oxadiazol-3-yl)methyl)-6-(4-(trifluoromethoxy)phenyl)-[1,2,4]triazolo[4,3-a]pyridin-3(2H)-one;
2-(2-(4-isopropoxypyrimidin-2-yloxy)ethyl)-6-(4-(trifluoromethoxy)phenyl)-[1,2,4]triazolo[4,3-a]pyridin-3(2H)-one;
2-(2-(4-(2,2,2-trifluoroethoxy)pyrimidin-2-yloxy)ethyl)-6-(4-(trifluoromethoxy)phenyl)-[1,2,4]triazolo[4,3-a]pyridin-3(2H)-one;
2-(2-(4-(cyclopropylmethoxy)pyrimidin-2-yloxy)ethyl)-6-(4-(trifluoromethoxy)phenyl)-[1,2,4]triazolo[4,3-a]pyridin-3(2H)-one;
6-(4-(trifluoromethoxy)phenyl)-2-(2-(5-(trifluoromethyl)pyrimidin-2-yloxy)ethyl)-[1,2,4]triazolo[4,3-a]pyridin-3(2H)-one;
2-((2-cyclopropyloxazol-4-yl)methyl)-6-(4-(trifluoromethoxy)phenyl)-[1,2,4]triazolo[4,3-a]pyridin-3(2H)-one;
2-((5-cyclopropyl-1,3,4-oxadiazol-2-yl)methyl)-6-(4-(4-fluorophenoxy)phenyl)-[1,2,4]triazolo[4,3-a]pyridin-3(2H)-one;
2-((5-tert-butyloxazol-2-yl)methyl)-6-(4-(trifluoromethoxy)phenyl)-[1,2,4]triazolo[4,3-a]pyridin-3(2H)-one;
2-((5-tert-butyloxazol-2-yl)methyl)-6-(4-(trifluoromethyl)phenyl)-[1,2,4]triazolo[4,3-a]pyridin-3(2H)-one;
2-methyl-6-(4-(trifluoromethyl)phenyl)-[1,2,4]triazolo[4,3-a]pyridin-3(2H)-one;

(R)-2-(2-(3-(4-fluorophenoxy)pyrrolidin-1-yl)ethyl)-6-(4-(trifluoromethoxy)phenyl)-[1,2,4]triazolo[4,3-a]pyridin-3 (2H)-one;
5-methyl-6-(4-(trifluoromethoxy)phenyl)-[1,2,4]triazolo[4,3-a]pyridin-3(2H)-one;
5-methyl-2-((3-methyl-1,2,4-oxadiazol-5-yl)methyl)-6-(4-(trifluoromethoxy)phenyl)-[1,2,4]triazolo[4,3-a]pyridin-3 (2H)-one;
2-(2,2,2-trifluoroethyl)-6-(4-(trifluoromethoxy)phenyl)-[1,2,4]triazolo[4,3-a]pyridin-3(2H)-one;
2-isopropyl-6-(4-(trifluoromethoxy)phenyl)-[1,2,4]triazolo[4,3-a]pyridin-3(2H)-one;
2-((4-methyloxazol-2-yl)methyl)-6-(4-(trifluoromethoxy)phenyl)-[1,2,4]triazolo[4,3-a]pyridin-3(2H)-one;
2-((4-methyloxazol-2-yl)methyl)-6-(4-(trifluoromethyl)phenyl)-[1,2,4]triazolo[4,3-a]pyridin-3(2H)-one;
2-((4-cyclopropyloxazol-2-yl)methyl)-6-(4-(trifluoromethoxy)phenyl)-[1,2,4]triazolo[4,3-a]pyridin-3(2H)-one
2-((4-cyclopropyloxazol-2-yl)methyl)-6-(4-(trifluoromethyl)phenyl)-[1,2,4]triazolo[4,3-a]pyridin-3(2H)-one;
6-(4-chlorophenyl)-2-((5-methyloxazol-2-yl)methyl)-[1,2,4]triazolo[4,3-a]pyridin-3(2H)-one;
8-methyl-6-(4-(trifluoromethoxy)phenyl)-[1,2,4]triazolo[4,3-a]pyridin-3(2H)-one;
2-((2-methyloxazol-5-yl)methyl)-6-(4-(trifluoromethyl)phenyl)-[1,2,4]triazolo[4,3-a]pyridin-3(2H)-one;
2-(3-(4,5-dichloro-2-methoxyphenoxy)-2-hydroxypropyl)-6-(4-(trifluoromethyl)phenyl)-[1,2,4]triazolo[4,3-a]pyridin-3(2H)-one;
2-((5-cyclopropyloxazol-2-yl)methyl)-6-(4-(trifluoromethoxy)phenyl)-[1,2,4]triazolo[4,3-a]pyridin-3(2H)-one;
6-(4-(trifluoromethoxy)phenyl)-[1,2,4]triazolo[4,3-a]pyridin-3(2H)-one; and
2-methyl-6-(4-(trifluoromethoxy)phenyl)-[1,2,4]triazolo[4,3-a]pyridin-3(2H)-one,
or a pharmaceutically acceptable salt, ester, prodrug, stereoisomer, solvate, or hydrate thereof.

In another embodiment, the compounds of this disclosure include, but are not limited to:
6-(3,4-difluorophenyl)-[1,2,4]triazolo[4,3-a]pyridin-3(2H)-one;
6-(4-(trifluoromethoxy)phenyl)-[1,2,4]triazolo[4,3-a]pyridin-3(2H)-one;
2-methyl-6-(4-(trifluoromethoxy)phenyl)-[1,2,4]triazolo[4,3-a]pyridin-3(2H)-one;
2-(3-oxo-6-(4-(trifluoromethoxy)phenyl)-[1,2,4]triazolo[4,3-a]pyridin-2(3H)-yl)acetic acid;
4-((3-oxo-6-(4-(trifluoromethoxy)phenyl)-[1,2,4]triazolo[4,3-a]pyridin-2(3H)-yl)methyl)benzoic acid;
2-((3-methyl-1,2,4-oxadiazol-5-yl)methyl)-6-(4-(trifluoromethoxy)phenyl)-[1,2,4]triazolo[4,3-a]pyridin-3(2H)-one;
2-((4-methyl-1,2,5-oxadiazol-3-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethoxy)phenyl)-[1,2,4]triazolo[4,3-a]pyridin-3(2H)-one;
2-(2-hydroxy-3-(2-methoxyphenoxy)propyl)-6-(4-(trifluoromethoxy)phenyl)-[1,2,4]triazolo[4,3-a]pyridin-3(2H)-one;
2-((5-methylisoxazol-3-yl)methyl)-6-(4-(trifluoromethoxy)phenyl)-[1,2,4]triazolo[4,3-a]pyridin-3(2H)-one;
2-((3,5-dimethylisoxazol-4-yl)methyl)-6-(4-(trifluoromethoxy)phenyl)-[1,2,4]triazolo[4,3-a]pyridin-3(2H)-one;
6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one;
2-(3-(5-methyl-1,2,4-oxadiazol-3-yl)benzyl)-6-(4-(trifluoromethoxy)phenyl)-[1,2,4]triazolo[4,3-a]pyridin-3(2H)-one;
2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one;
2-(benzo[c][1,2,5]oxadiazol-5-ylmethyl)-6-(4-(trifluoromethoxy)phenyl)-[1,2,4]triazolo[4,3-a]pyridin-3(2H)-one;
2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one;
2-(quinolin-2-ylmethyl)-6-(4-(trifluoromethoxy)phenyl)-[1,2,4]triazolo[4,3-a]pyridin-3(2H)-one;
2-((4-phenyl-1,2,5-oxadiazol-3-yl)methyl)-6-(4-(trifluoromethoxy)phenyl)-[1,2,4]triazolo[4,3-a]pyridin-3(2H)-one;
2-(oxazol-2-ylmethyl)-6-(4-(trifluoromethoxy)phenyl)-[1,2,4]triazolo[4,3-a]pyridin-3(2H)-one;
2-(benzo[d]thiazol-2-ylmethyl)-6-(4-(trifluoromethoxy)phenyl)-[1,2,4]triazolo[4,3-a]pyridin-3(2H)-one;
2-((4,5-dimethyloxazol-2-yl)methyl)-6-(4-(trifluoromethoxy)phenyl)-[1,2,4]triazolo[4,3-a]pyridin-3(2H)-one;
2-(2-methoxy-3-(2-methoxyphenoxy)propyl)-6-(4-(trifluoromethoxy)phenyl)-[1,2,4]triazolo[4,3-a]pyridin-3(2H)-one;
2-(3-phenoxypropyl)-6-(4-(trifluoromethoxy)phenyl)-[1,2,4]triazolo[4,3-a]pyridin-3(2H)-one;
2-((5-methyloxazol-2-yl)methyl)-6-(4-(trifluoromethoxy)phenyl)-[1,2,4]triazolo[4,3-a]pyridin-3(2H)-one;
2-((3-cyclopropyl-1-methyl-1H-pyrazol-5-yl)methyl)-6-(4-(trifluoromethoxy)phenyl)-[1,2,4]triazolo[4,3-a]pyridin-3(2H)-one;
2-(2-phenoxyethyl)-6-(4-(trifluoromethoxy)phenyl)-[1,2,4]triazolo[4,3-a]pyridin-3(2H)-one;
2-((3-benzyl-1,2,4-oxadiazol-5-yl)methyl)-6-(4-(trifluoromethoxy)phenyl)-[1,2,4]triazolo[4,3-a]pyridin-3(2H)-one;
5-methoxy-2-((3-methyl-1,2,4-oxadiazol-5-yl)methyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(3-phenoxyphenyl)-[1,2,4]triazolo[4,3-a]pyridin-3(2H)-one;
6-(4-(4-chlorophenoxy)phenyl)-2-((5-methyl-1,2,4-oxadiazol-3-yl)methyl)-[1,2,4]triazolo[4,3-a]pyridin-3(2H)-one;
2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one;
2-(pyridin-2-yl)-6-(4-(trifluoromethoxy)phenyl)-[1,2,4]triazolo[4,3-a]pyridin-3(2H)-one;
2-(2-(pyridin-2-yl)ethyl)-6-(4-(trifluoromethoxy)phenyl)-[1,2,4]triazolo[4,3-a]pyridin-3(2H)-one;
2-(3-(2-methoxyphenoxy)propyl)-6-(4-(trifluoromethoxy)phenyl)-[1,2,4]triazolo[4,3-a]pyridin-3(2H)-one;
2-(2-(3-phenoxypyrrolidin-1-yl)ethyl)-6-(4-(trifluoromethoxy)phenyl)-[1,2,4]triazolo[4,3-a]pyridin-3(2H)-one;
2-(2-(4-chlorophenoxy)ethyl)-6-(4-(trifluoromethoxy)phenyl)-[1,2,4]triazolo[4,3-a]pyridin-3(2H)-one;

2-(2-(3-methyl-1H-pyrazol-1-yl)ethyl)-6-(4-(trifluoromethoxy)phenyl)-[1,2,4]triazolo[4,3-a]pyridin-3(2H)-one;

2-(2-hydroxy-3-phenoxypropyl)-6-(4-(trifluoromethoxy)phenyl)-[1,2,4]triazolo[4,3-a]pyridin-3(2H)-one;

2-(3-(4-chlorophenoxy)-2-methoxypropyl)-6-(4-(trifluoromethoxy)phenyl)-[1,2,4]triazolo[4,3-a]pyridin-3(2H)-one;

2-(2-(2,6-dimethylphenoxy)ethyl)-6-(4-(trifluoromethoxy)phenyl)-[1,2,4]triazolo[4,3-a]pyridin-3(2H)-one;

2-(2-(2-chlorophenoxy)ethyl)-6-(4-(trifluoromethoxy)phenyl)-[1,2,4]triazolo[4,3-a]pyridin-3(2H)-one;

6-(4-(trifluoromethoxy)phenyl)-2-(2-(3-(trifluoromethyl)pyridin-2-yloxy)ethyl)-[1,2,4]triazolo[4,3-a]pyridin-3(2H)-one;

2-(2-(6-methylpyridin-2-yl)ethyl)-6-(4-(trifluoromethoxy)phenyl)-[1,2,4]triazolo[4,3-a]pyridin-3(2H)-one;

2-(2-(4-bromopyridin-2-yl)ethyl)-6-(4-(trifluoromethoxy)phenyl)-[1,2,4]triazolo[4,3-a]pyridin-3(2H)-one;

2-(2-(pyridin-2-yloxy)ethyl)-6-(4-(trifluoromethoxy)phenyl)-[1,2,4]triazolo[4,3-a]pyridin-3(2H)-one;

2-(2-(pyrimidin-2-yloxy)ethyl)-6-(4-(trifluoromethoxy)phenyl)-[1,2,4]triazolo[4,3-a]pyridin-3(2H)-one;

2-(2-(4,4-difluoropiperidin-1-yl)ethyl)-6-(4-(trifluoromethoxy)phenyl)-[1,2,4]triazolo[4,3-a]pyridin-3(2H)-one;

2-(3-(2-fluorophenoxy)propyl)-6-(4-(trifluoromethoxy)phenyl)-[1,2,4]triazolo[4,3-a]pyridin-3(2H)-one;

2-(3-(2-chlorophenoxy)propyl)-6-(4-(trifluoromethoxy)phenyl)-[1,2,4]triazolo[4,3-a]pyridin-3(2H)-one;

6-(4-(4-chlorophenoxy)phenyl)-2-((3-methyl-1,2,4-oxadiazol-5-yl)methyl)-[1,2,4]triazolo[4,3-a]pyridin-3(2H)-one;

2-(2-(3-chlorophenoxy)ethyl)-6-(4-(trifluoromethoxy)phenyl)-[1,2,4]triazolo[4,3-a]pyridin-3(2H)-one;

2-(2-(4-fluorophenoxy)ethyl)-6-(4-(trifluoromethoxy)phenyl)-[1,2,4]triazolo[4,3-a]pyridin-3(2H)-one;

2-(2-(3-bromopyridin-2-yl)ethyl)-6-(4-(trifluoromethoxy)phenyl)-[1,2,4]triazolo[4,3-a]pyridin-3(2H)-one;

2-(2-(4-cyclopropylpyridin-2-yl)ethyl)-6-(4-(trifluoromethoxy)phenyl)-[1,2,4]triazolo[4,3-a]pyridin-3(2H)-one;

2-(4-fluorophenethyl)-6-(4-(trifluoromethoxy)phenyl)-[1,2,4]triazolo[4,3-a]pyridin-3(2H)-one;

2-(2-(3-cyclopropylpyridin-2-yl)ethyl)-6-(4-(trifluoromethoxy)phenyl)-[1,2,4]triazolo[4,3-a]pyridin-3(2H)-one;

2-(2-(3-methylpyridin-2-yl)ethyl)-6-(4-(trifluoromethoxy)phenyl)-[1,2,4]triazolo[4,3-a]pyridin-3(2H)-one;

6-(4-(trifluoromethoxy)phenyl)-2-(2-(3-(trifluoromethyl)phenoxy)ethyl)-[1,2,4]triazolo[4,3-a]pyridin-3(2H)-one;

2-(3-(3-chlorophenoxy)propyl)-6-(4-(trifluoromethoxy)phenyl)-[1,2,4]triazolo[4,3-a]pyridin-3(2H)-one;

2-(2-oxo-2-(3-phenoxypyrrolidin-1-yl)ethyl)-6-(4-(trifluoromethoxy)phenyl)-[1,2,4]triazolo[4,3-a]pyridin-3(2H)-one;

2-(2-methoxy-3-phenoxypropyl)-6-(4-(trifluoromethoxy)phenyl)-[1,2,4]triazolo[4,3-a]pyridin-3(2H)-one;

2-(4-chlorophenethyl)-6-(4-(trifluoromethoxy)phenyl)-[1,2,4]triazolo[4,3-a]pyridin-3(2H)-one;

6-(4-(trifluoromethoxy)phenyl)-2-((6-(trifluoromethyl)pyridin-2-yl)methyl)-[1,2,4]triazolo[4,3-a]pyridin-3(2H)-one; and 2-(3-(4-chlorophenyl)propyl)-6-(4-(trifluoromethoxy)phenyl)-[1,2,4]triazolo[4,3-a]pyridin-3(2H)-one, or a pharmaceutically acceptable salt, ester, prodrug, stereoisomer, solvate, or hydrate thereof.

FURTHER EMBODIMENTS

In some embodiments, the compounds provided by the present disclosure are effective in the treatment of conditions known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the disclosure may also possess a sufficient activity in modulating neuronal sodium channels, i.e., $Na_v$ 1.1, 1.2, 1.7, and/or 1.8, and may have appropriate pharmacokinetic properties such that they may active with regard to the central and/or peripheral nervous system. Consequently, some compounds of the disclosure may also be of use in the treatment of epilepsy or pain or itching of a neuropathic origin.

In some embodiments, the present disclosure is intended to encompass the compounds disclosed herein, and the pharmaceutically acceptable salts, pharmaceutically acceptable esters, tautomeric forms, polymorphs, solvates, and prodrugs of such compounds. In some embodiments, the present disclosure includes a pharmaceutically acceptable addition salt, a pharmaceutically acceptable ester, a hydrate of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula (I); such as a compound of Formula (I) named herein.

In one embodiment, this disclosure provides a method of treating a disease state in a mammal that is alleviable by treatment with an agent capable of reducing late sodium current, comprising administering to a mammal in need thereof a therapeutically effective dose of a compound of Formula I as described above. In another embodiment, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication. In another embodiment, the disease state is diabetes or diabetic peripheral neuropathy. In a further embodiment, the disease state results in one or more of neuropathic pain, epilepsy, seizures, or paralysis.

Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the general methods of preparation are vacuum-drying and freeze-drying techniques which yield a powder of the active ingredient plus any additional desired ingredient from a previously sterile-filtered solution thereof.

Oral administration is another route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from 1 mg to 2 g of a compound described herein, and for parenteral administration, in some embodiments, from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, in some embodiments, orally or nasally, from devices that deliver the formulation in an appropriate manner.

In one embodiment, this disclosure relates to a pharmaceutical composition comprising a pharmaceutically acceptable excipient or carrier and a therapeutically effective amount of the compound of Formula I as described above or a pharmaceutically acceptable salt, ester, prodrug, stereoisomer, or hydrate thereof.

Combination Therapy

Patients being treated by administration of the late sodium channel blockers of the disclosure often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastoalic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein 11b/111a inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the late sodium channel blocker ranolazine and amioarone and dronedarone. See U.S. Patent Application Publication No. 20100056536 and U.S. patent application Ser. No. 12/972,949, the entirety of which is incorporated herein.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, analgesics, antidepressants and anti-anxiety agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the $Na_V$ 1.7 and 1.8 sodium channels, combination with analgesics are particularly envisioned. See U.S. Patent Application Publication 2009/0203707.

Antidepressant and Anti-Anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Accordingly, one aspect of the disclosure provides for a composition comprising the late sodium channel blockers of the disclosure and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic affect.

Synthesis of Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, e.g. compounds having structures described by one or more of Formula I, may be accomplished as described in the following examples. If available, reagents may be purchased commercially, e.g. from Sigma Aldrich or other chemical suppliers.

General Syntheses

Embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are either obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, in some embodiments, nitrogen.

The term "q.s." means adding a quantity sufficient to achieve a stated function, e.g., to bring a solution to the desired volume (i.e., 100%).

The compounds of this disclosure can be prepared from readily available starting materials using, for example, the following general methods and procedures. It will be appreciated that where typical process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

Synthesis of the Compounds of Formula I

The compounds of Formula I are generally prepared by first providing the molecular core (1); which may be commercially obtained, for example 6-bromo-[1,2,4]triazolo[4,3-a]pyridine, 6-bromo-3-methyl-[1,2,4]triazolo[4,3-a]pyridine, 6-bromo-N-ethyl-[1,2,4]triazolo[4,3-a]pyridin-3-amine, and the like, or synthesized de novo, and then attaching the desired $R^1Q$ substituents using conditions known as Suzuki coupling. This is process is show below in Scheme I for a compound of Formula I.

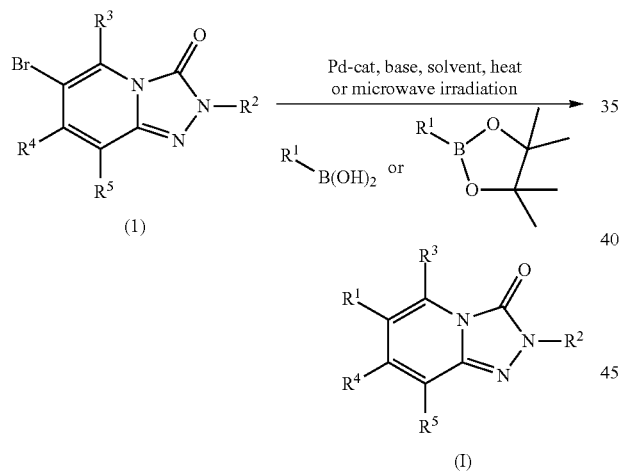

Scheme I (1)

(I)

In general, a halogenated compound of Formula (1), in this case a brominated compound, is reacted with an appropriately substituted boronic acid derivative of formula $R^1B(OH)_2$ in an inert solvent, for example aqueous N,N-dimethylformamide, in the presence of a mild base, for example potassium carbonate or sodium bicarbonate. The reaction is conducted in the presence of a metal catalyst with an appropriate ligand, for example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the product of Formula I is isolated by conventional means.

It will be appreciated that various R substituents can be modified or added either before or after the addition of the $R^1$ moiety. For example, in certain embodiments the $R^2$, $R^3$, $R^4$, or $R^5$ moieties may be coupled to the core before addition, of the $R^1$ substituents. Also, in the case where the $R^2$ substituent contains a heteroaryl ring, the ring may be synthesized and cyclized before or after addition of the $R^1$ portion.

It will also be appreciated that the addition of any substituent may result in the production of a number of isomeric products any or all of which may be isolated and purified using conventional techniques.

Optional Core Synthesis

When the compound of Formula I is synthesized de novo, the various components of the compounds are typically established by selecting the appropriate reactants for core synthesis. Additional modification to provide a desired $R^1$, $R^2$, $R^3$, $R^4$, or $R^5$, substituents may be subsequently carried out using conventional techniques.

In another embodiment, compounds of Formula I can be prepared as shown in Scheme II.

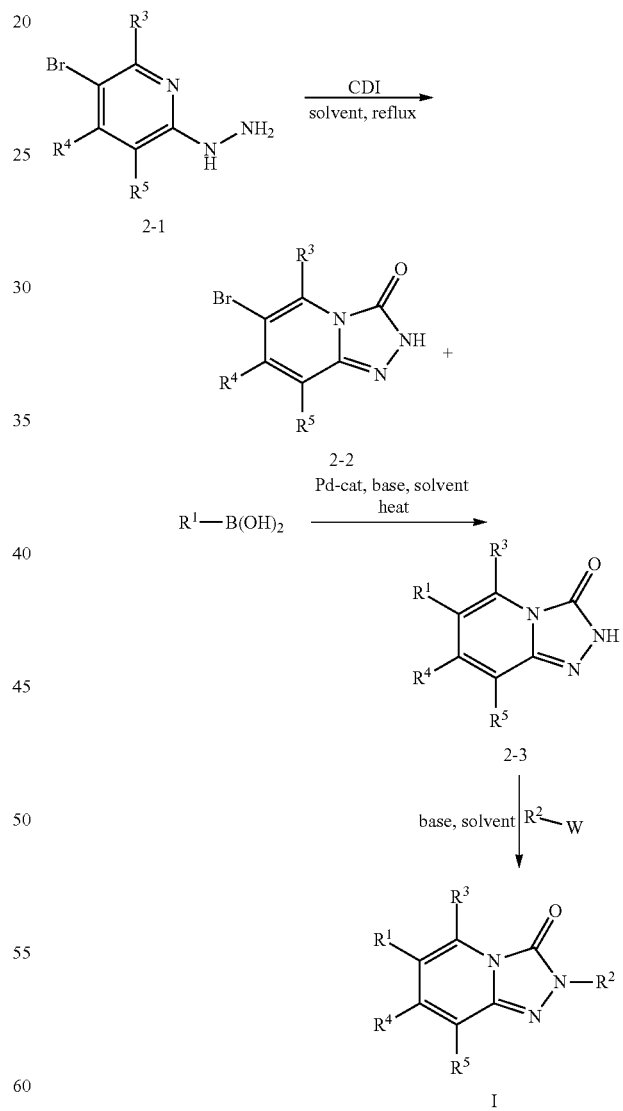

In general, a halogenated hydrazine compound, in this case a brominated compound 2-1, is cyclized using N,N'-Carbonyldiimidazole (CDI) or a similar agent to give compound 2-2 which is then reacted with an appropriately substituted boronic acid derivative of formula $R^1$—$B(OH)_2$ or a boronic ester thereof, in a solvent, for example aqueous toluene-isopropanol, in the presence of a mild base, for example potassium carbonate or sodium bicarbonate. The reaction is conducted in the presence of a metal catalyst with an appropriate ligand, for example dichlorobis(1,1'-Bis(diphenylphosphino)ferrocene)palladium(II), at a temperature of about 95° C., for 2 to 4 days. When the reaction is substantially complete, the product 2-3 is isolated by conventional means. Compound 2-3 is then alkylated by reacting with an alkyl halide (W is halo) in the presence of a mild base, for example potassium carbonate or sodium bicarbonate, in a solvent such as dimethylacetamide at a temperature of about 110° C., for about 1 to 5 hours. When the reaction is substantially complete, the product of Formula I is isolated by conventional means.

It will be appreciated that the $R^2$ substitutent can be modified or added either before (as shown in Scheme 1) or after the addition of the $R^1$ moiety (as shown in Scheme II).

Modification of $R^2$ Group

In another embodiment, the compounds containing a hydroxyl substituent in the $R^2$ group are synthesized as shown in Scheme III.

Scheme III

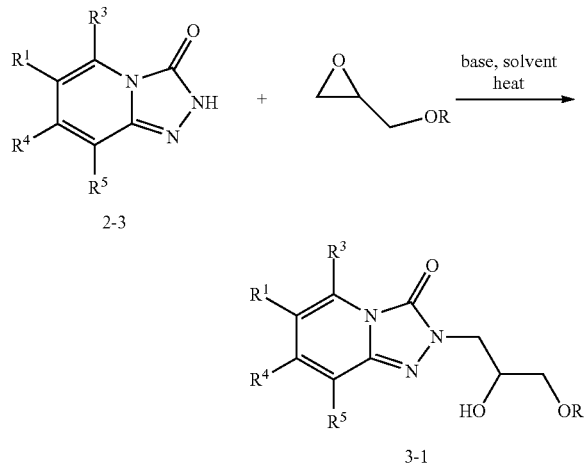

Compound 2-3 is reacted with an oxirane (R is alkyl, aryl, etc.) in the presence of a mild base, for example potassium carbonate or sodium bicarbonate, in a solvent such as dimethylacetamide at a temperature of about 140° C., for about 1 to 2 hours. When the reaction is substantially complete, compound 3-1 (a compound of Formula I), is isolated by conventional means. Alternatively, the hydroxyl group in compound 3-1 can be alkylated using an alkyl halide in the presence of a base such as sodium hydride in a solvent such as tetrahydrofuran to give the corresponding alkoxy compound.

In another embodiment, the compounds containing an aryloxy or heteroaryloxy substituent in the $R^2$ group are synthesized as shown in Scheme IV.

Scheme IV

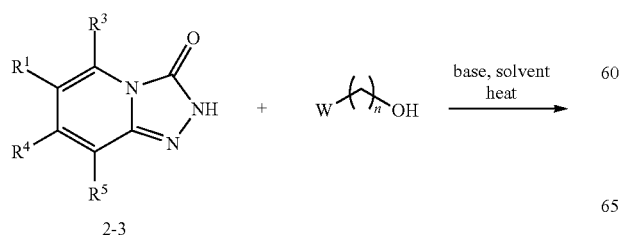

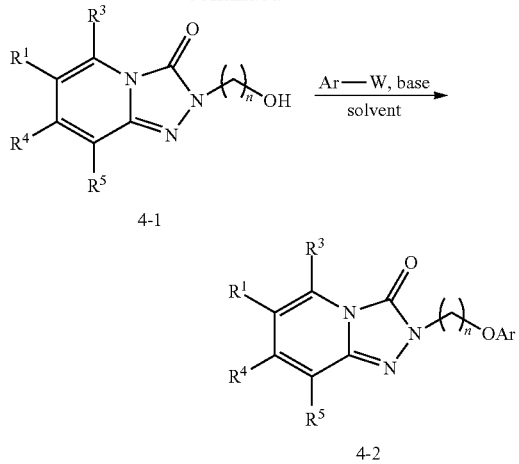

Compound 2-3 is alkylated with an alkyl halide containing a hydroxyl group in the presence of a mild base, for example potassium carbonate or sodium bicarbonate, in a solvent such as dimethylacetamide at a temperature of about 110° C., for about 1 to 5 hours. When the reaction is substantially complete, compound 4-1 is isolated by conventional means. Compound 4-1 is then treated with an aryl/heteroaryl halide (Ar is aryl or heteroaryl and W is halo) in the presence of a base such as sodium hydride in a solvent such as dimethylformamide to give compound 4-2 (a compound of Formula I) which is isolated by conventional means.

In another embodiment, the $R^2$ group can be introduced to prepare the compound of Formula I via Mitsunobu reaction as shown in Scheme V.

Scheme V

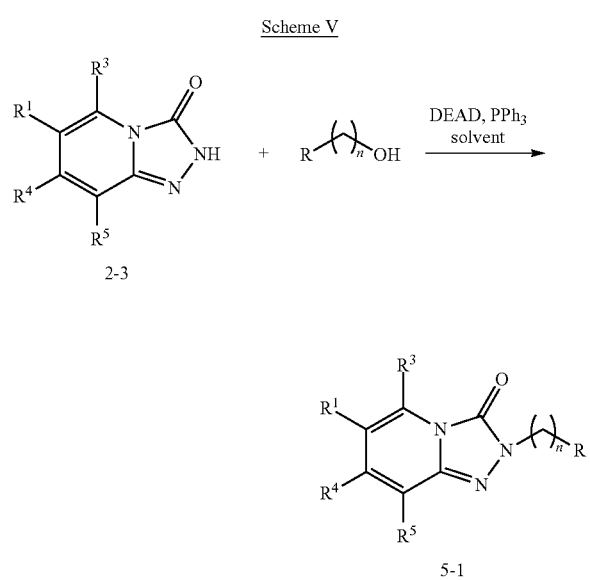

Compound 2.3 and triphenylphosphine ($PPh_3$) are dissolved in a solvent such as THF and this mixture is treated with an alcohol (R is alkyl, aryl and n=1-6) and diethyl azodicarboxylate (DEAD) at room temperature. After stirring for several hours, compound 5-1 (a compound of Formula I) is isolated by conventional means.

In another embodiment, the oxazol-2-ylmethyl group in R² can be introduced as shown in Scheme VI.

Scheme VI

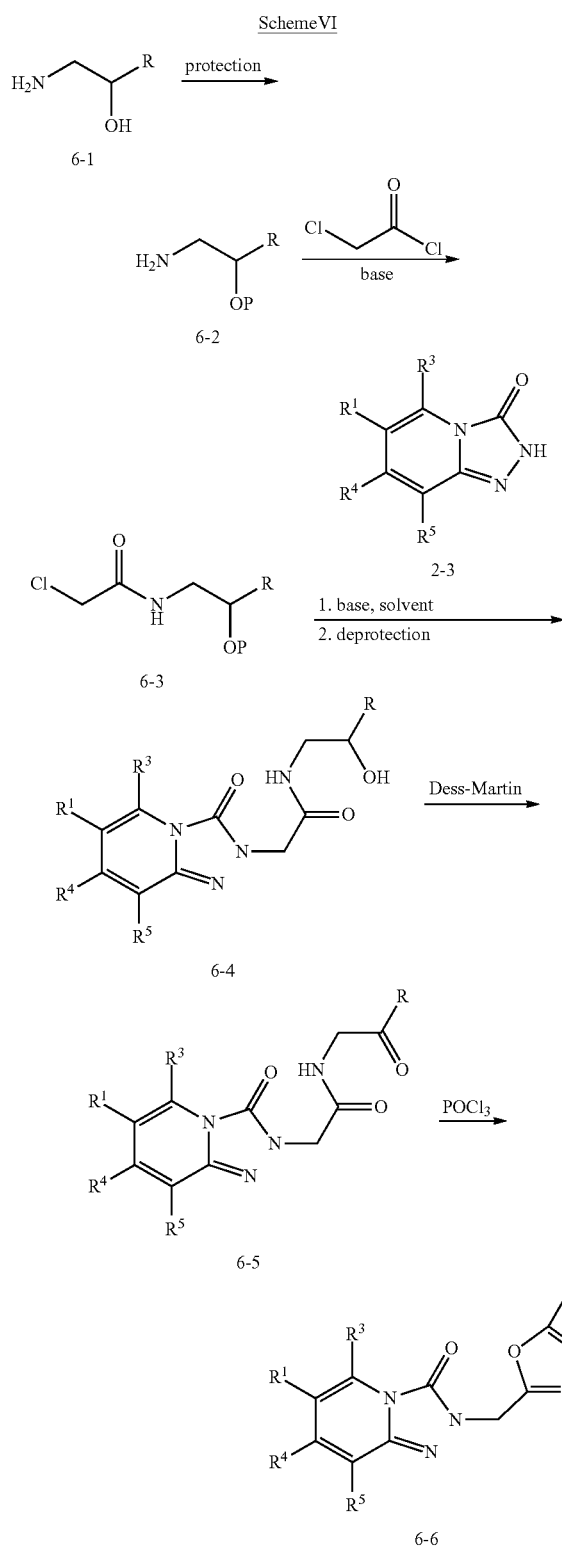

treated with chroloacetyl chloride in the presence of a base such as i-Pr₂NEt (diisopropylethylamine) in the presence of a solvent such as CH₂Cl₂ at 0° C. to give compound 6-3. Coupling of compound 6-3 with compound 2-3 in the presence of a mild base, for example potassium carbonate or sodium bicarbonate, in a solvent such as DMF followed by removal of the protecting group gives compound 6-4. Compound 6-4 is treated with Dess-Martin periodinane in a solvent such as THF at room temperature to give the desired ketone or aldehyde, compound 6-5. Intramolecular cyclization of compound 6-5 with POCl₃ at 70-100° C. for several hours gives the desired oxazole, compound 6-6 (a compound of Formula I).

In another embodiment, an aryl group in R² can be further substituted using Suzuki reaction as shown in Scheme VII.

Scheme VII

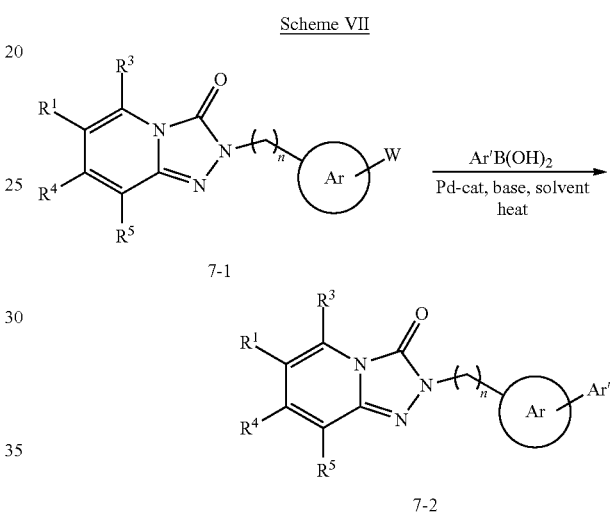

Compound 7-1 can be prepared as shown in Scheme V (Ar is aryl and W is halo) above and is then reacted with an appropriately substituted boronic acid derivative of formula Ar'—B(OH)₂ in a solvent, for example DMF, in the presence of a mild base, for example potassium carbonate or sodium bicarbonate. The reaction is conducted in the presence of a metal catalyst with an appropriate ligand, for example tetra (triphenylphosphine) palladium(IV), at a temperature of about 120-170° C. When the reaction is substantially complete, the product 7-2 (a compound of Formula I, Ar and Ar' are independently aryl) is isolated by conventional means.

In another embodiment, compounds of Formula I containing heteroaryl group as R² can be synthesized as shown in Scheme VIII.

Scheme VIII

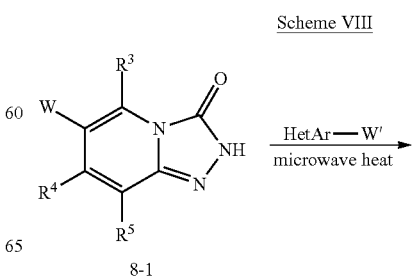

Hydroxy group in aminoalcohol 6-1 is protected with conventional protecting groups such as silyl groups to give compound 6-2 (P=protecting group). Compound 6-2 is then -continued

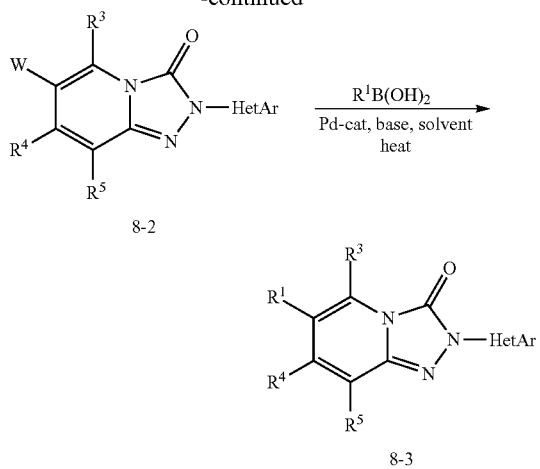

8-2

8-3

A mixture of compound 8-1 (W is halo) and a heteroaryl halide (HetAr is heteroaryl and W' is halo) is placed in a sealed microwave vial and heated to about 160° C. in a microwave reactor for about 1-3 hours. The product is isolated by conventional means to give compound 8-2 which on Suzuki conditions as described Scheme II gives compound 8-3 ((a compound of Formula I).

The following examples are included to demonstrate some embodiments of the disclosure. It should be appreciated by those of skill in the art that the techniques disclosed in the examples which follow represent techniques discovered by the inventor to function well in the practice of the disclosure, and thus can be considered to constitute the modes for its practice. However, those of skill in the art should, in light of the present disclosure, appreciate that many changes can be made in the specific embodiments which are disclosed and still obtain a like or similar result without departing from the spirit and scope of the disclosure. The compounds listed in Examples 108-196 were synthesized using the procedures described herein as well as using the methods known to one of skill in the art. As can be seen from Tables 2 and 3 in Example 207, those compounds were synthesized and tested for the biological activity.

It will also be appreciated that the addition of any substituent may result in the production of a number of isomeric products any or all of which may be isolated and purified using conventional techniques.

TABLE 1

List of abbreviations and acronyms

| Abbreviation | Meaning |
| --- | --- |
| ° C. | Degree Celcius |
| anal | Analytical |
| ATP | Adenosine-5'-triphosphate |
| ATX II | Anemonia sulcata toxin |
| ACN | Acetonitrile |
| BOC | tert-Butoxycarbonyl |
| CDI | 1,1'-Carbonyldiimidazole |
| CHO | Chinese hamster ovary |
| Cy | Cyclohexane |
| d | Doublet |
| dd | Doublet of doublets |
| DABAL-Me$_3$ | Bis(trimethylaluminum)-1,4-diazabicyclo[2.2.2]octane adduct |
| DEAD | Diethyl azodicarboxylate |
| DIEA | N,N-Diisopropylethylamine |
| DMF | Dimethylformamide |

TABLE 1-continued

List of abbreviations and acronyms

| Abbreviation | Meaning |
| --- | --- |
| DMSO | Dimethylsulfoxide |
| dppf | 1,1'-Bis(diphenylphosphino)ferrocene |
| dt | Doublet of triplets |
| ECF | Extracellular fluid |
| EDCI | 1-Ethyl-3-(3-dimethylaminopropyl)carbodiimide |
| EDTA | Ethylenediaminetetraacetic acid |
| EGTA | Ethylene glycol tetraacetic acid |
| equiv/eq | Equivalents |
| EtOAc | Ethyl acetate |
| EtOH | Ethanol |
| g | Grams |
| G418 | Geneticin |
| GTP | Guanosine-5'-triphosphate |
| HEPES | (4-(2-Hydroxyethyl)-1-piperazineethanesulfonic acid ) |
| hERG | human Ether-à-go-go Related Gene |
| HPLC | High-performance liquid chromatography |
| hrs/h | Hours |
| Hz | Hertz |
| IC$_{50}$ | The half maximal inhibitory concentration |
| IMR-32 | Human neuroblastoma cell line |
| IRES | Internal ribosome entry site |
| IU | International unit |
| J | Coupling constant |
| Kg | Kilogram |
| kHz | Kilohertz |
| L | Liter |
| LCMS/LC-MS | Liquid chromatography-mass spectrometry |
| M | Molar |
| m | Meter |
| m/z | mass-to-charge ratio |
| M+ | Mass peak |
| M + H | Mass peak plus hydrogen |
| M + Na | Mass peak plus sodium |
| Me | Methyl |
| mg | Milligram |
| MHz | Megahertz |
| min | Minute |
| ml/mL | Milliliter |
| mM | Millimolar |
| mm | Millimeter |
| mmol | Millimole |
| mOsmol | Milliosmole |
| MRM | Magnetic Resonance Microscopy |
| MS | Mass spectroscopy |
| ms | Millisecond |
| mV | Millivolt |
| MW/mw | Microwave |
| N | Normal |
| nmol | Nanomole |
| NMR | Nuclear magnetic resonance |
| pA | Picoamps |
| Ph | Phenyl |
| prep | Preparative |
| q.s. | Quantity sufficient to achieve a stated function |
| Rf | Retention factor |
| RT/rt/R.T | Room temperature |
| s | Second |
| s | Singlet |
| SEM | Standard error of the mean |
| t | Triplet |
| TB | Tonic Block |
| TEA | Triethylamine |
| TFA | Trifluoroacetic acid |
| THF | Tetrahydrofuran |
| TLC | Thin layer chromatography |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |
| μmol | Micromole |

EXAMPLES

Example 1

Preparation of a Compound of Formula I

A. Preparation of a Compound of Formula I in which R is 4-trifluoromethoxyphenyl (compound 1)

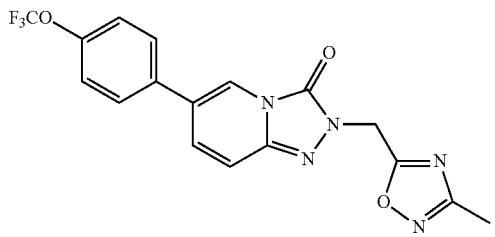

Step 1—Core Synthesis Preparation of 6-bromo-[1,2,4]triazolo[4,3-a]pyridin-3(2H)-one

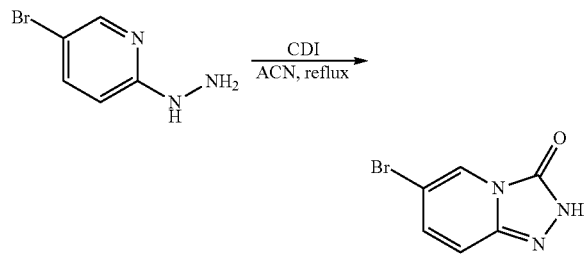

A suspension of 40 g 5-bromo-2-hydrazinylpyridine (212 mmol) and 38 g 1,1'-Carbonyldiimidazole (234 mmol) in 500 mL acetonitrile was refluxed for 2 h. The reaction was then cooled to room temperature overnight. The precipitate was collect by filtration. 6-Bromo-[1,2,4]triazolo[4,3-a]pyridin-3 (2H)-one as a light brown solid was collected. m/z (ESI)=213.9 [M+H]+. $^1$H NMR ($\delta$, d$_6$-DMSO, 400 MHz) 12.59 (s, 1H), 8.04 (dd, 1H), 7.21 (m, 2H).

Step 2—Addition of the R$^1$ Moiety

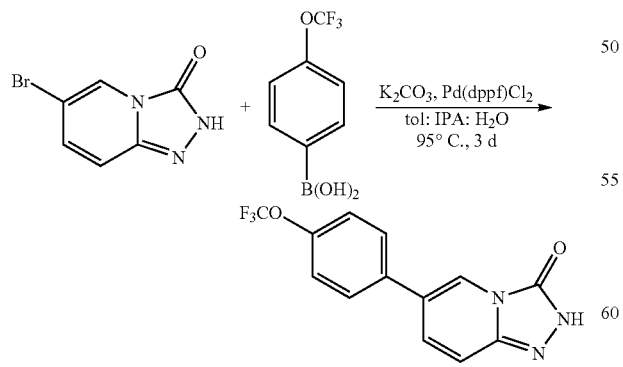

A mixture of 6.4 g 6-bromo-[1,2,4]triazolo[4,3-a]pyridin-3(2H)-one (31.3 mmol), 12.4 g 4-(trifluoromethoxy)phenyl boronic acid (60.0 mmol), 12.4 g potassium carbonate (90.0 mmol), and 1.1 g Pd(dppf)Cl$_2$ in 200 mL degassed 2:1:1 toluene:isopropanol:water was heated at 95° C. in sealed vessel. After 3 days, the aqueous layer was decanted and the organic concentrated. The residue was triturated with ethyl acetate to provide 6-(4-(trifluoromethoxy)phenyl)-[1,2,4]triazolo[4,3-a]pyridin-3(2H)-one as a dark grey solid. m/z (ESI)=226.2 [M+H]+. $^1$H NMR ($\delta$, d$_6$-DMSO, 400 MHz) 12.55 (s, 1H), 8.07 (s, 1H), 7.82 (d, 2H), 7.56 (dd, 1H), 7.43 (d, 2H), 7.33 (d, 1H)

Step 2—Addition of the R$^2$ Moiety

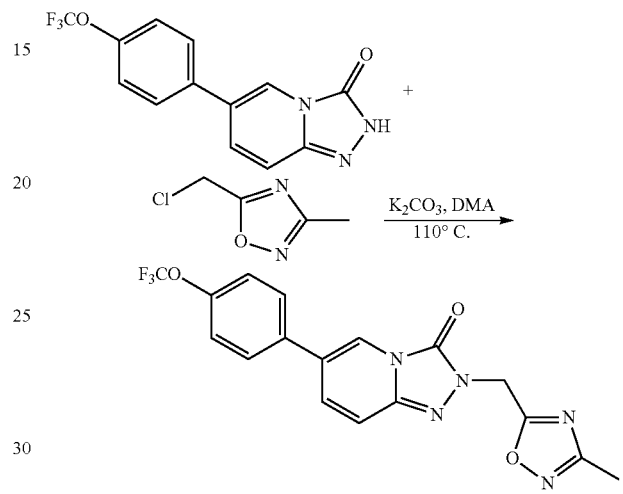

A mixture of 90 mg 6-(4-(trifluoromethoxy)phenyl)-[1,2,4]triazolo[4,3-a]pyridin-3(2H)-one (0.30 mmol), 40 mg 5-(chloromethyl)-3-methyl-1,2,4-oxadiazole (0.30 mmol) and 23 mg potassium carbonate (0.17 mmol) in 2 mL DMA was heated at 110° C. for 2 h. The reaction mixture was then filtered and the filtrate concentrated. The residue was column purified on 12 g silica, eluting with 36 mL 5% ethyl acetate in hexanes, then 5-50% over 60 mL, and then 50% 120 mL. 2-((3-methyl-1,2,4-oxadiazol-5-yl)methyl)-6-(4-(trifluoromethoxy)phenyl)-[1,2,4]triazolo[4,3-a]pyridin-3(2H)-one was isolated as a yellow solid. m/z (ESI)=392.0 [M+H]+. $^1$H NMR ($\delta$, d$_6$-DMSO, 400 MHz) 7.95 (dd, 1H) 7.54 (d, 2H), 7.40 (dd, 1H), 7.32 (d, 2H), 7.20 (dd, 1H) 5.43 (s, 2H), 2.40 (s, 3H)

Alternative Step 2—Addition of the R$^2$ Moiety Via Mitsunobu Reaction

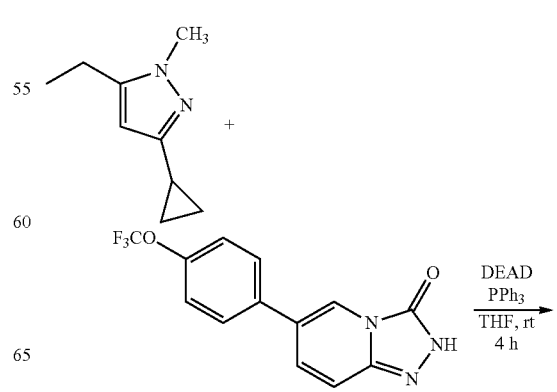

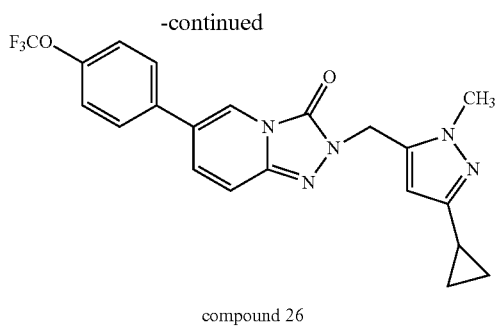

compound 26

6-(4-(Trifluoromethoxy)phenyl)-[1,2,4]triazolo[4,3-a]pyridin-3(2H)-one (50.0 mg, 0.169 mmol), (3-cyclopropyl-1-methyl-1H-pyrazol-5-yl)methanol (38.6 mg, 0.2535, 1.5 equiv.) and PPh$_3$ (60.5 mg, 0.2535 mmol, 1.5 equiv.) were placed in a 50 mL round bottomed flask under a nitrogen atmosphere. To the flask were added THF (3 mL) and diethyl azodicarboxylate (40% in toluene, 110.5 mg, 0.2535 mmol, 1.5 equiv.) at room temperature. The reaction mixture was stirred at the same temperature for 4 h. The reaction mixture was directly loaded onto prep-HPLC to give 2-((3-cyclopropyl-1-methyl-1H-pyrazol-5-yl)methyl)-6-(4-(trifluoromethoxy)phenyl)-[1,2,4]triazolo[4,3-a]pyridin-3(2H)-one as light yellow crystals. FTIR (ATR) 1710 cm$^{-1}$ (CO).

Alternative Step 2—Addition of the R² Moiety

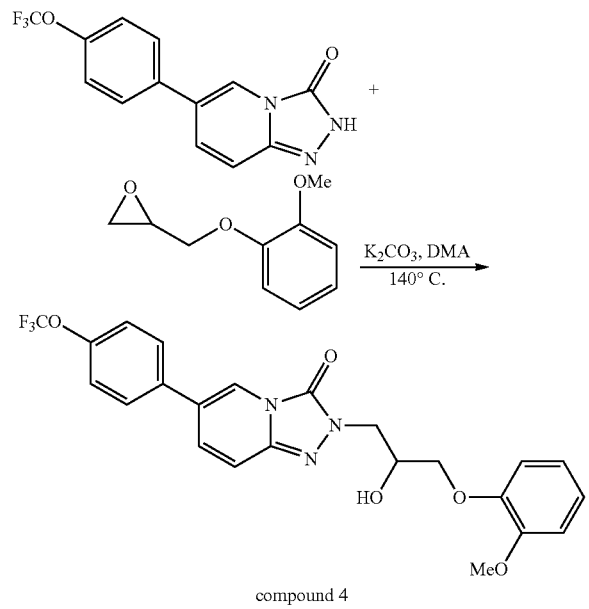

compound 4

A mixture of 100 mg 6-(4-(trifluoromethoxy)phenyl)-[1,2,4]triazolo[4,3-a]pyridin-3(2H)-one (0.34 mmol), 61 mg guaiacol glycidyl ether (0.34 mmol), and 93 mg potassium carbonate (0.68 mmol) in 2 mL DMA was heated at 140° C. for 1 h. The reaction mixture was then filtered and the filtrate concentrated. The residue was purified by reverse phase chromatography eluting with water with 0.1% TFA and acetonitrile with 0.1% TFA. 2-(2-hydroxy-3-(2-methoxyphenoxy)propyl)-6-(4-(trifluoromethoxy)phenyl)-[1,2,4]triazolo[4,3-a]pyridin-3(2H)-one was collected as an amber solid. m/z (ESI)=476.1 [M+H]$^+$. $^1$H NMR (δ, CDCl$_3$, 400 MHz) 7.96 (dd, 1H), 7.54 (d, 2H), 7.38 (dd, 1H), 7.31 (d, 2H), 7.21 (d, 1H), 6.97 (m, 2H), 6.91 (m, 2H), 4.47 (m, 1H), 4.31 (d, 2H), 4.14 (m, 2H), 3.85 (s, 3H), 3.49 (s, 1H).

Optional Step 3—Secondary Modification of the R² Moiety

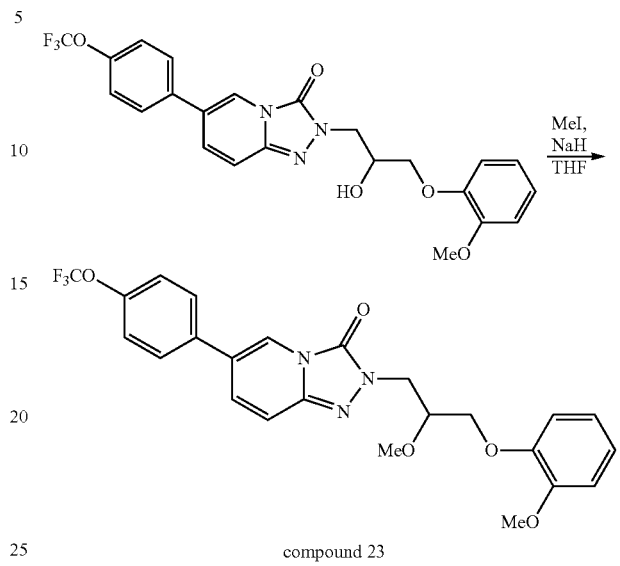

compound 23

To a solution of 2-(2-hydroxy-3-(2-methoxyphenoxy)propyl)-6-(4-(trifluoromethoxy)phenyl)-[1,2,4]triazolo[4,3-a]pyridin-3(2H)-one in 2 mL anhydrous tetrahydrofuran under N$_2$ was added 3 mg NaH, as 60% oil dispersion (79 nmol). The reaction was stirred for 30 min and then 5 μL MeI (79 nmol) was added. After 2 h, the reaction was concentrated and purified by preparative TLC eluting with 1:1 ethyl acetate: Hexanes. 2-(2-methoxy-3-(2-methoxyphenoxy)propyl)-6-(4-(trifluoromethoxy)phenyl)-[1,2,4]triazolo[4,3-a]pyridin-3(2H)-one was collected as an off-white solid. m/z (ESI)=490.1 [M+H]$^+$. $^1$H NMR (δ, CDCl$_3$, 300 MHz) 7.95 (dd, 1H), 7.55 (d, 2H), 7.40-7.24 (m, 3H), 7.20 (d, 1H), 7.06-6.81 (m, 4H), 4.31 (d, 2H), 4.25-4.07 (m, 3H), 3.83 (s, 3H), 3.53 (s, 3H).

B. Preparation of Compounds of Formula I varying R¹ and R²

Similarly, following the procedure of Example 1A above, but optionally substituting other boronic acids or pinacolate esters for 4-trifluoromethoxyphenylboronic acid and/or substituting other halogenated R² reactants, the following compounds of Formula I were prepared:

2-(quinolin-2-ylmethyl)-6-(4-(trifluoromethoxy)phenyl)-[1,2,4]triazolo[4,3-a]pyridin-3(2H)-one (Compound 13)

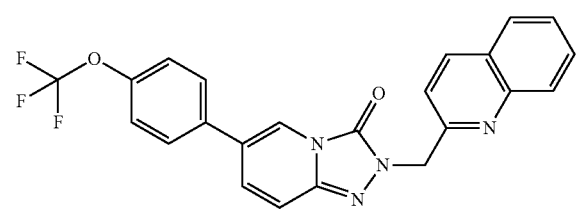 [SMILES: O=c1n(Cc2ccc3ccccc3n2)nc2ccc(-c3ccc(OC(F)(F)F)cc3)cn12]

LCMS (EI: 70 eV) 437 (M$^+$+1)

101

2-(quinolin-8-ylmethyl)-6-(4-(trifluoromethoxy)phenyl)-[1,2,4]triazolo[4,3-a]pyridin-3(2H)-one (Compound 202)

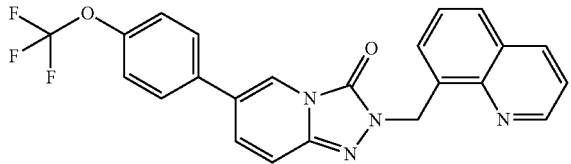 [SMILES: O=c1n(Cc2cccc3cccnc23)nc2ccc(-c3ccc(OC(F)(F)F)cc3)cn12]

LCMS (EI: 70 eV) 437 (M$^+$+1)

2-(pyridin-2-ylmethyl)-6-(4-(trifluoromethoxy)phenyl)-[1,2,4]triazolo[4,3-a]pyridin-3(2H)-one (Compound 16)

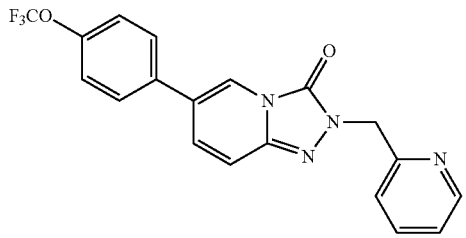 [SMILES: O=c1n(Cc2ccccn2)nc2ccc(-c3ccc(OC(F)(F)F)cc3)cn12]

LCMS (EI: 70 eV) 387 (M$^+$+1)

2-(pyrimidin-2-ylmethyl)-6-(4-(trifluoromethoxy)phenyl)-[1,2,4]triazolo[4,3-a]pyridin-3(2H)-one (Compound 203)

LCMS (EI: 70 eV) 388 (M$^+$+1)

2-(oxazol-2-ylmethyl)-6-(4-(trifluoromethoxy)phenyl)-[1,2,4]triazolo[4,3-a]pyridin-3(2H)-one (Compound 19)

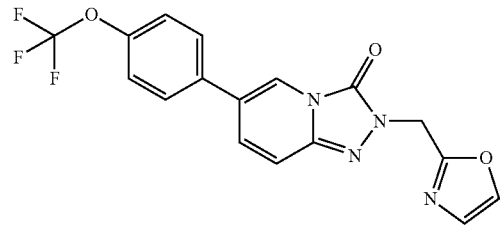 [SMILES: O=c1n(Cc2ncco2)nc2ccc(-c3ccc(OC(F)(F)F)cc3)cn12]

LCMS (EI: 70 eV) 399 (M$^+$+Na), 377 (M$^+$+1)

102

2-(2-morpholinoethyl)-6-(4-(trifluoromethoxy)phenyl)-[1,2,4]triazolo[4,3-a]pyridin-3(2H)-one (Compound 204)

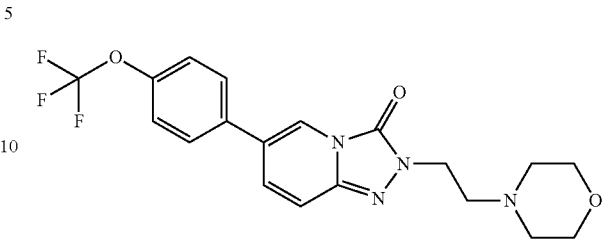

LCMS (EI: 70 eV) 409 (M$^+$+1)

C. Preparation of Compounds of Formula I Varying R$^1$, R$^2$, and R$^3$

Similarly, following the procedure of Example 1A above, but optionally substituting other boronic acids or pinacolate esters for 4-trifluoromethoxyphenylboronic acid and/or substituting other halogenated R$^2$ reactants, other compounds of Formula I may be prepared.

Similarly, following the procedure of Example 1 above, but optionally substituting other boronic acids or pinacolate esters for 4-trifluoromethoxyphenylboronic acid and/or substituting other commercial compounds for 5-(chloromethyl)-3-methyl-1,2,4-oxadiazole, the following Examples 2-44 were prepared.

Example 2

2-((2-methyloxazol-5-yl)methyl)-6-(4-(trifluoromethyl)phenyl)-[1,2,4]triazolo[4,3-a]pyridin-3(2H)-one (Compound 197)

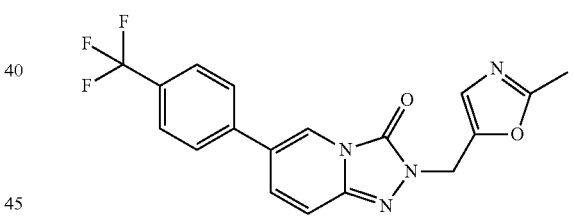

MS (ESI) 375.0 (base peak, M+H$^+$); 771.1 (2M+Na$^+$).

Example 3

6-(4-chlorophenyl)-2-((5-methyloxazol-2-yl)methyl)-[1,2,4]triazolo[4,3-a]pyridin-3(2H)-one (Compound 195)

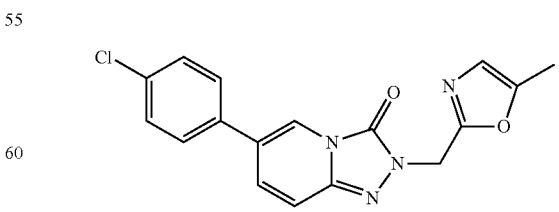

MS (ESI+) 341.0 (base peak, $^{35}$Cl-M+H$^+$); 343.0 ($^{37}$Cl-M+H$^+$); 703.1 ($^{35}$Cl$_2$-2M+Na$^+$); 705.1 ($^{35}$Cl$^{37}$Cl-2M+Na$^+$).
$^1$H NMR 7.91 (s, 1H); 7.44 (s, 4H); 7.38 (d, 1H); 7.20 (d, 1H); 6.72 (s, 1H); 5.28 (s, 2H); 2.29 (s, 3H).

Example 4

2-((4-methyloxazol-2-yl)methyl)-6-(4-(trifluoromethyl)phenyl)-[1,2,4]triazolo[4,3-a]pyridin-3(2H)-one (Compound 192)

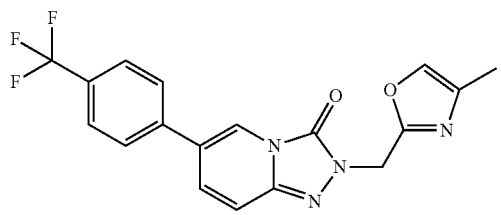 [SMILES: Cc1coc(Cn2nc3ccc(-c4ccc(C(F)(F)F)cc4)cn3c2=O)n1]

MS (ESI+) 375.0 (base peak, M+H$^+$); 771.2 (2M+Na$^+$). $^1$H NMR 8.02 (s, 1H); 7.73 (d, 2H); 7.63 (d, 2H); 7.40 (dd, 1H); 7.36 (s, 1H); 7.21 (d, 1H); 5.30 (s, 2H); 2.16 (s, 3H). $^{19}$F NMR −63.18 (s).

Example 5

2-((4-methyloxazol-2-yl)methyl)-6-(4-(trifluoromethoxy)phenyl)-[1,2,4]triazolo[4,3-a]pyridin-3(2H)-one (Compound 191)

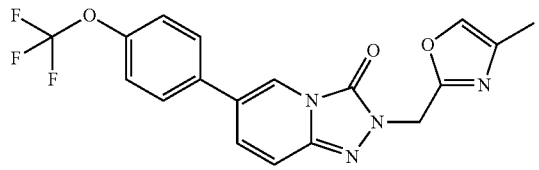 [SMILES: Cc1coc(Cn2nc3ccc(-c4ccc(OC(F)(F)F)cc4)cn3c2=O)n1]

MS (ESI+) 391.0 (base peak, M+H$^+$); 803.2 (2M+Na$^+$). $^1$H NMR 7.95 (s, 1H); 7.53 (d, 2H); 7.36 (m, 2H); 7.31 (d, 2H); 7.20 (d, 1H); 5.30 (s, 2H); 2.16 (s, 3H). $^{19}$F NMR −58.36 (s)

Example 6

2-isopropyl-6-(4-(trifluoromethoxy)phenyl)-[1,2,4]triazolo[4,3-a]pyridin-3(2H)-one (Compound 190)

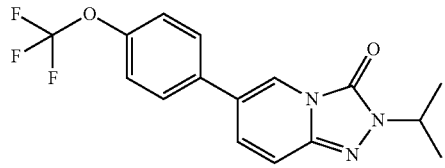 [SMILES: CC(C)n1nc2ccc(-c3ccc(OC(F)(F)F)cc3)cn2c1=O]

MS (ESI+) 338.0 (base peak, M+H$^+$); 697.2 (2M+Na$^+$).

Example 7

2-(2,2,2-trifluoroethyl)-6-(4-(trifluoromethoxy)phenyl)-[1,2,4]triazolo[4,3-a]pyridin-3(2H)-one (Compound 189)

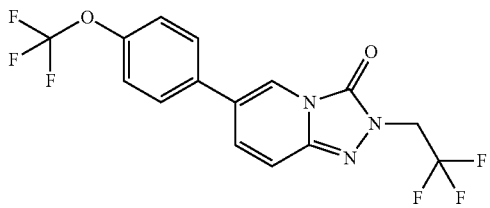 [SMILES: O=c1n(CC(F)(F)F)nc2ccc(-c3ccc(OC(F)(F)F)cc3)cn12]

MS (ESI+) 378.0 (base peak, M+H$^+$).

Example 8

2-methyl-6-(4-(trifluoromethyl)phenyl)-[1,2,4]triazolo[4,3-a]pyridin-3(2H)-one (Compound 185)

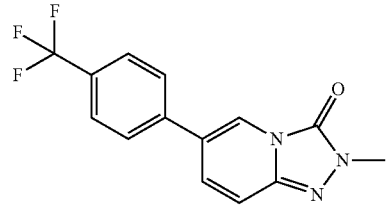 [SMILES: Cn1nc2ccc(-c3ccc(C(F)(F)F)cc3)cn2c1=O]

MS (ESI+) 294.1 (base peak, M+H$^+$); 609.1 (2M+Na$^+$).

Example 9

2-((5-tert-butyloxazol-2-yl)methyl)-6-(4-(trifluoromethyl)phenyl)-[1,2,4]triazolo[4,3-a]pyridin-3(2H)-one (Compound 184)

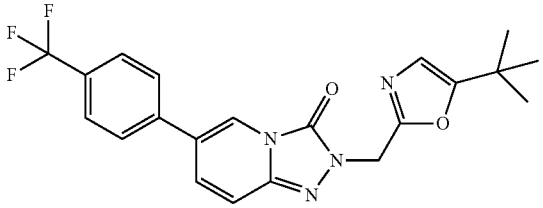 [SMILES: CC(C)(C)c1cnc(Cn2nc3ccc(-c4ccc(C(F)(F)F)cc4)cn3c2=O)o1]

MS (ESI+) 417.1 (base peak, M+H$^+$); 855.3 (2M+Na$^+$).

Example 10

2-((5-tert-butyloxazol-2-yl)methyl)-6-(4-(trifluoromethoxy)phenyl)-[1,2,4]triazolo[4,3-a]pyridin-3(2H)-one (Compound 183)

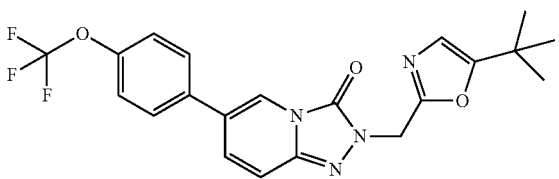 [SMILES: CC(C)(C)c1cnc(Cn2nc3ccc(-c4ccc(OC(F)(F)F)cc4)cn3c2=O)o1]

MS (ESI+) 433.1 (base peak, M+H$^+$); 887.3 (2M+Na$^+$).

Example 11

2-((5-cyclopropyl-1,3,4-oxadiazol-2-yl)methyl)-6-(4-(4-fluorophenoxy)phenyl)-[1,2,4]triazolo[4,3-a]pyridin-3(2H)-one (Compound 182)

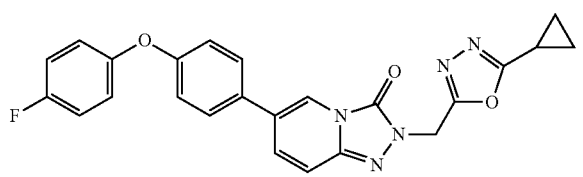 [SMILES: O=c1n(Cc2nnc(C3CC3)o2)nc2ccc(-c3ccc(Oc4ccc(F)cc4)cc3)cn12]

MS (ESI+) 444.1 (base peak, M+H$^+$); 909.3 (2M+Na$^+$).

Example 12

2-((4,5-dimethyloxazol-2-yl)methyl)-6-(4-(trifluoromethyl)phenyl)-[1,2,4]triazolo[4,3-a]pyridin-3(2H)-one (Compound 22)

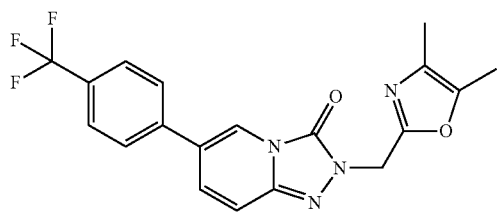 [SMILES: Cc1nc(Cn2nc3ccc(-c4ccc(C(F)(F)F)cc4)cn3c2=O)oc1C]

MS (ESI+) 389.1 (base peak, M+H$^+$); 799.2 (2M+Na$^+$).

Example 13

2-((5-methyloxazol-2-yl)methyl)-6-(4-(trifluoromethyl)phenyl)-[1,2,4]triazolo[4,3-a]pyridin-3(2H)-one (Compound 25)

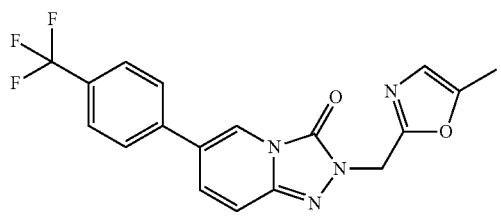 [SMILES: Cc1cnc(Cn2nc3ccc(-c4ccc(C(F)(F)F)cc4)cn3c2=O)o1]

MS (ESI+) 375.0 (base peak, M+H$^+$); 771.1 (2M+N$^+$). 8.02 (s, 1H); 7.72 (d, 2H); 7.63 (d, 2H); 7.40 (dd, 1H); 7.21 (d, 1H); 6.74 (s, 1H); 5.30 (s, 2H); 2.30 (s, 3H). $^{19}$F NMR −63.18 (s).

Example 14

6-(4-(trifluoromethyl)phenyl)-[1,2,4]triazolo[4,3-a]pyridin-3(2H)-one (Compound 171)

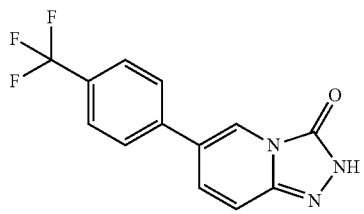 [SMILES: O=c1[nH]nc2ccc(-c3ccc(C(F)(F)F)cc3)cn12]

MS (ESI+) 280.0 (base peak, M+H$^+$); 581.1 (2M+Na$^+$).

Example 15

2-((5-cyclopropyl-1,3,4-thiadiazol-2-yl)methyl)-6-(4-(trifluoromethoxy)phenyl)-[1,2,4]triazolo[4,3-a]pyridin-3(2H)-one (Compound 170)

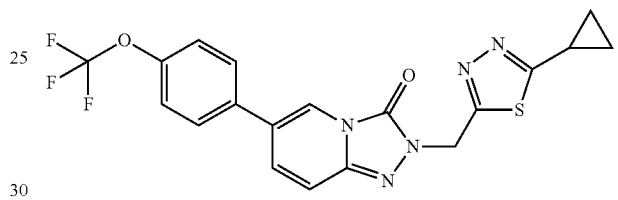

MS (ESI+) 434.0 (base peak, M+H$^+$); 889.1 (2M+Na$^+$).

Example 16

2-((3-trideuteromethyl-1,2,4-oxadiazol-5-yl)methyl)-6-(4-(trifluoromethoxy)phenyl)-[1,2,4]triazolo[4,3-a]pyridin-3(2H)-one (Compound 169)

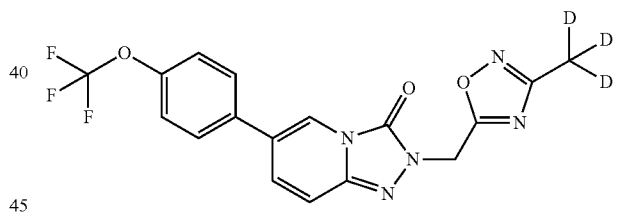

MS (ESI+) 395.0 (base peak, M+H$^+$); 811.1 (2M+Na$^+$). $^1$H NMR 7.95 (dd, 1H) 7.54 (d, 2H), 7.40 (dd, 1H), 7.32 (d, 2H), 7.20 (dd, 1H) 5.43 (s, 2H). $^{19}$F NMR −58.36 (s).

Example 17

2-((3-(methoxymethyl)-1,2,4-oxadiazol-5-yl)methyl)-6-(4-(trifluoromethyl)phenyl)-[1,2,4]triazolo[4,3-a]pyridin-3(2H)-one (Compound 168)

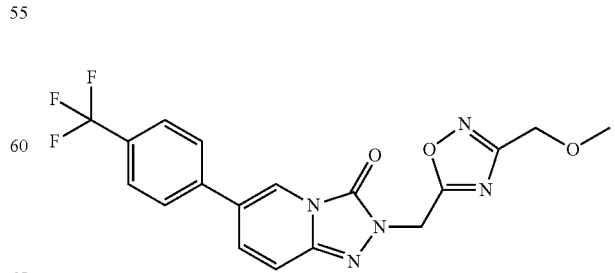

MS (ESI+) 405.4 (base peak, M+H$^+$); 427.4 (M+Na$^+$); 832.2 (2M+Na$^+$).

Example 18

2-((3-ethyl-1,2,4-oxadiazol-5-yl)methyl)-6-(4-(trifluoromethyl)phenyl)-[1,2,4]triazolo[4,3-a]pyridin-3(2H)-one (Compound 167)

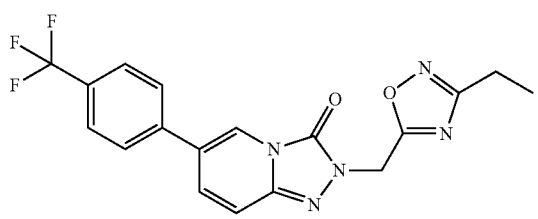 [SMILES: CCc1noc(Cn2nc3ccc(-c4ccc(C(F)(F)F)cc4)cn3c2=O)n1]

MS (ESI+) 389.5 (base peak, M+H$^+$); 411.4 (M+Na$^+$); 800.2 (2M+Na$^+$). $^1$H NMR 8.02 (s, 1H); 7.73 (d, 2H); 7.63 (d, 2H); 7.42 (dd, 1H); 7.22 (d, 1H); 5.44 (s, 2H); 2.77 (q, 2H); 1.31 (t, 3H). $^{19}$F NMR −63.19 (s).

Example 19

2-((3-ethyl-1,2,4-oxadiazol-5-yl)methyl)-6-(4-(trifluoromethoxy)phenyl)-[1,2,4]triazolo[4,3-a]pyridin-3(2H)-one (Compound 166)

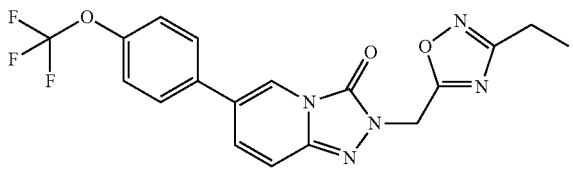 [SMILES: CCc1noc(Cn2nc3ccc(-c4ccc(OC(F)(F)F)cc4)cn3c2=O)n1]

MS (ESI+) 406.0 (base peak, M+H$^+$); 428.0 (M+Na$^+$); 833.1 (2M+Na$^+$).

Example 20

2-((1-methyl-1H-pyrazol-3-yl)methyl)-6-(4-(trifluoromethoxy)phenyl)-[1,2,4]triazolo[4,3-a]pyridin-3(2H)-one (Compound 165)

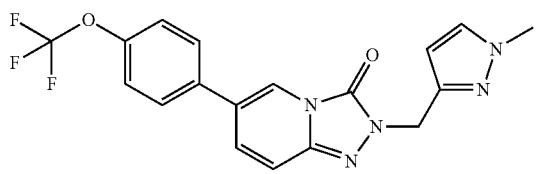 [SMILES: Cn1ccc(Cn2nc3ccc(-c4ccc(OC(F)(F)F)cc4)cn3c2=O)n1]

MS (ESI+) 390.1 (base peak, M+H$^+$); 801.2 (2M+Na$^+$).

Example 21

2-((3-methylisoxazol-5-yl)methyl)-6-(4-(trifluoromethoxy)phenyl)-[1,2,4]triazolo[4,3-a]pyridin-3(2H)-one (Compound 164)

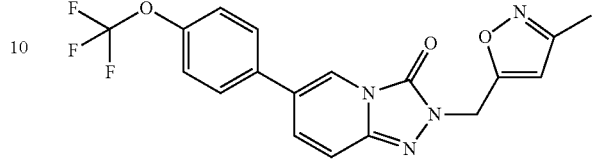

MS (ESI+) 391.0 (base peak, M+H$^+$); 413.0 (M+Na$^+$); 803.1 (2M+Na$^+$).

Example 22

2-((1-methyl-1H-pyrazol-4-yl)methyl)-6-(4-(trifluoromethoxy)phenyl)-[1,2,4]triazolo[4,3-a]pyridin-3(2H)-one (Compound 163)

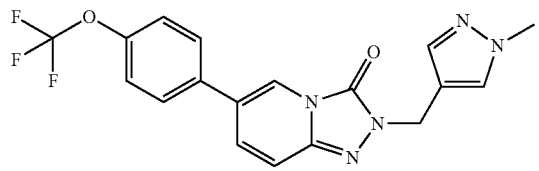 [SMILES: Cn1cc(Cn2nc3ccc(-c4ccc(OC(F)(F)F)cc4)cn3c2=O)cn1]

MS (ESI+) 390.1 (base peak, M+H$^+$); 801.2 (2M+Na$^+$).

Example 23

6-(3-fluoro-4-(trifluoromethoxy)phenyl)-2-((3-methyl-1,2,4-oxadiazol-5-yl)methyl)-[1,2,4]triazolo[4,3-a]pyridin-3(2H)-one (Compound 155)

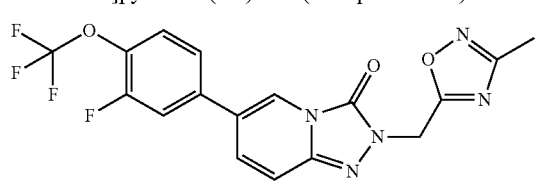

MS (ESI+) 410.0 (base peak, M+H$^+$); 432.0 (M+Na$^+$); 841.0 (2M+Na$^+$).

Example 24

2-((5-(difluoromethyl)-1,2,4-oxadiazol-3-yl)methyl)-6-(4-(trifluoromethoxy)phenyl)-[1,2,4]triazolo[4,3-a]pyridin-3(2H)-one (Compound 154)

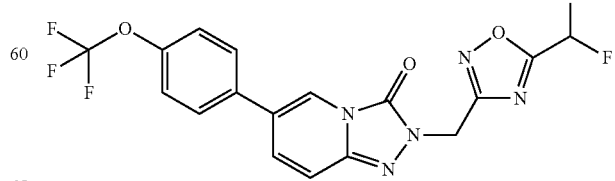

MS (ESI+) 428.0 (base peak, M+H$^+$); 450.0 (M+Na$^+$); 877.1 (2M+Na$^+$).

Example 25

2-((3-(methoxymethyl)-1,2,4-oxadiazol-5-yl)methyl)-6-(4-(trifluoromethoxy)phenyl)-[1,2,4]triazolo[4,3-a]pyridin-3(2H)-one (Compound 153)

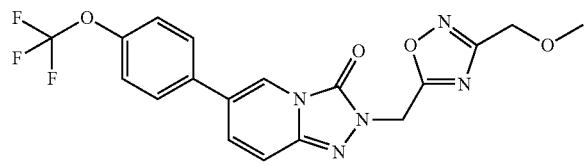 [SMILES: COCc1noc(Cn2nc3ccc(-c4ccc(OC(F)(F)F)cc4)cn3c2=O)n1]

MS (ESI+) 422.0 (base peak, M+H⁺); 444.0 (M+Na⁺); 865.1 (2M+Na⁺).

Example 26

2-cinnamyl-6-(4-(trifluoromethoxy)phenyl)-[1,2,4]triazolo[4,3-a]pyridin-3(2H)-one (Compound 151)

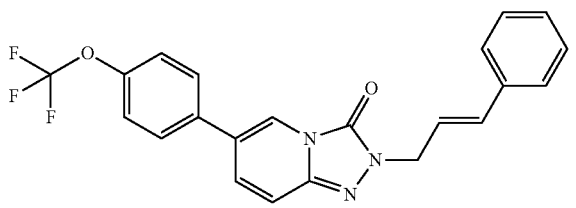 [SMILES: O=c1n(C/C=C/c2ccccc2)nc2ccc(-c3ccc(OC(F)(F)F)cc3)cn12]

MS (ESI+) 412.0 (base peak, M+H⁺); 434.0 (M+Na⁺); 845.2 (2M+Na⁺).

Example 27

6-(3,4-difluorophenyl)-2-((3-methyl-1,2,4-oxadiazol-5-yl)methyl)-[1,2,4]triazolo[4,3-a]pyridin-3(2H)-one (Compound 150)

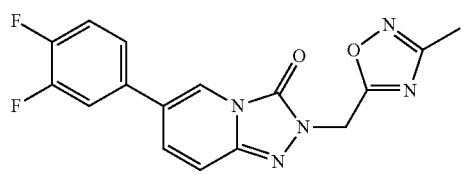 [SMILES: Cc1noc(Cn2nc3ccc(-c4ccc(F)c(F)c4)cn3c2=O)n1]

$^1$H NMR 7.93 (s, 1H); 7.40-7.20 (m, 5H); 5.43 (s, 2H); 2.40 (s, 3H). $^{19}$F NMR −136.20-136.41 (m, 1F); −137.86−−138.02 (m, 1F).

Example 28

6-(4-chlorophenyl)-2-((3-methyl-1,2,4-oxadiazol-5-yl)methyl)-[1,2,4]triazolo[4,3-a]pyridin-3(2H)-one (Compound 149)

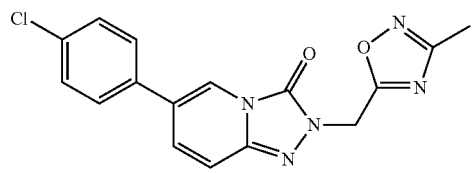 [SMILES: Cc1noc(Cn2nc3ccc(-c4ccc(Cl)cc4)cn3c2=O)n1]

MS (ESI+) 342.0 ($^{35}$Cl-M+H⁺); 344.0 ($^{37}$Cl-M+H⁺); 364.0 ($^{35}$Cl-M+Na⁺); 365.9 ($^{37}$Cl-M+H⁺); 705.1 ($^{35}$Cl$_2$-2M+Na⁺); 707.1 ($^{35}$Cl$^{37}$Cl-2M+Na⁺).

Example 29

2-((5-methyl-1,2,4-oxadiazol-3-yl)methyl)-6-(4-(trifluoromethyl)phenyl)-[1,2,4]triazolo[4,3-a]pyridin-3(2H)-one (Compound 148)

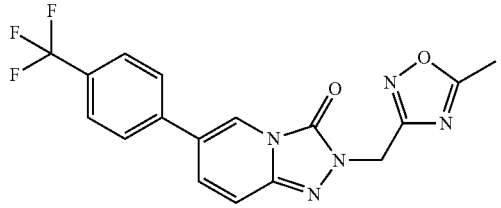 [SMILES: Cc1nc(Cn2nc3ccc(-c4ccc(C(F)(F)F)cc4)cn3c2=O)no1]

MS (ESI+) 376.0 (base peak, M+H⁺); 773.1 (2M+Na⁺).

Example 30

2-(1-(3-methyl-1,2,4-oxadiazol-5-yl)ethyl)-6-(4-(trifluoromethoxy)phenyl)-[1,2,4]triazolo[4,3-a]pyridin-3(2H)-one (Compound 147)

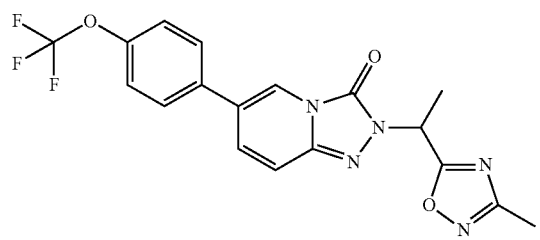 [SMILES: Cc1noc(C(C)n2nc3ccc(-c4ccc(OC(F)(F)F)cc4)cn3c2=O)n1]

MS (ESI+) 406.1 (base peak, M+H⁺); 428.0 (M+Na⁺); 833.1 (2M+Na⁺).

Example 31

6-(4-(4-fluorophenoxy)phenyl)-[1,2,4]triazolo[4,3-a]pyridin-3(2H)-one (Compound 143)

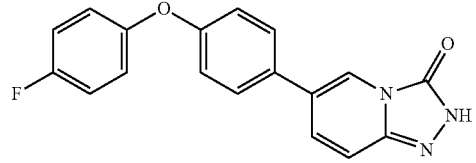 [SMILES: O=c1[nH]nc2ccc(-c3ccc(Oc4ccc(F)cc4)cc3)cn12]

MS (ESI+) 322.0 (base peak, M+H⁺); 665.1 (2M+Na⁺). $^1$H NMR 12.51 (s, 1H); 7.97 (s, 1H); 7.70 (d, 2H); 7.54 (d, 1H); 7.27 (d, 1H); 7.23 (d, 2H); 7.12 (d, 2H); 7.03 (d, 2H). $^{19}$F NMR −119.84 (m).

Example 32

2-((5-cyclopropyl-1,2,4-oxadiazol-3-yl)methyl)-6-(4-(trifluoromethoxy)phenyl)-[1,2,4]triazolo[4,3-a]pyridin-3(2H)-one (Compound 142)

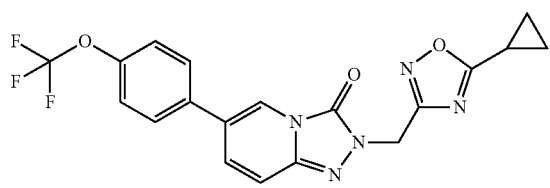 [SMILES: O=c1n(Cc2noc(C3CC3)n2)nc2ccc(-c3ccc(OC(F)(F)F)cc3)cn12]

$^1$H NMR 7.96 (s, 1H); 7.77 (d, 2H); 7.38 (d, 1H); 7.32 (d, 2H); 7.20 (d, 1H); 5.27 (s, 2H); 2.19 (m, 1H); 1.22 (m, 4H).

Example 33

6-(4-(4-fluorophenoxy)phenyl)-2-((5-methyl-1,2,4-oxadiazol-3-yl)methyl)-[1,2,4]triazolo[4,3-a]pyridin-3(2H)-one (Compound 140)

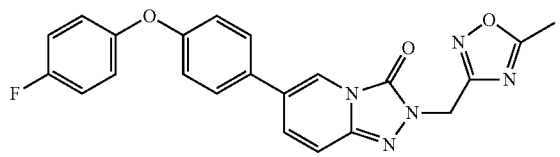 [SMILES: Cc1nc(Cn2nc3ccc(-c4ccc(Oc5ccc(F)cc5)cc4)cn3c2=O)no1]

MS (ESI+) 418.1 (base peak, M+H$^+$).

Example 34

2-((3-methyl-1,2,4-oxadiazol-5-yl)methyl)-6-(4-(trifluoromethyl)phenyl)-[1,2,4]triazolo[4,3-a]pyridin-3(2H)-one (Compound 137)

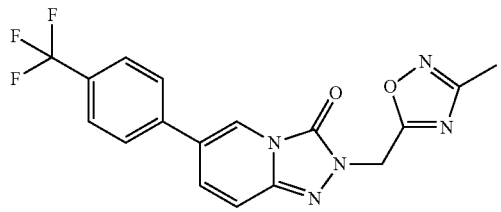 [SMILES: Cc1noc(Cn2nc3ccc(-c4ccc(C(F)(F)F)cc4)cn3c2=O)n1]

$^1$H NMR 8.02 (s, 1H); 7.74 (d, 2H); 7.63 (d, 2H); 7.42 (dd, 1H); 7.22 (d, 1H); 5.44 (s, 2H); 2.40 (s, 3H). $^{19}$F NMR −63.20 (s).

Example 35

6-(3,4-dichlorophenyl)-2-((3-methyl-1,2,4-oxadiazol-5-yl)methyl)-[1,2,4]triazolo[4,3-a]pyridin-3(2H)-one (Compound 134)

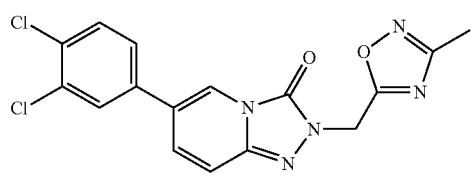 [SMILES: Cc1noc(Cn2nc3ccc(-c4ccc(Cl)c(Cl)c4)cn3c2=O)n1]

MS (ESI+) 346.0 ($^{35}$Cl$_2$-M+H$^+$); 348.0 ($^{35}$Cl$^{37}$Cl-2M+Na$^+$); 773.0 ($^{35}$Cl$_4$-M+Na$^+$); 775.0 (base peak, $^{35}$Cl$_3$$^{37}$Cl-2M+Na$^+$); 776.9 ($^{35}$Cl$_2$$^{37}$Cl$_2$-2M+Na$^+$).

Example 36

6-(4-benzoylphenyl)-2-((3-methyl-1,2,4-oxadiazol-5-yl)methyl)-[1,2,4]triazolo[4,3-a]pyridin-3(2H)-one (Compound 131)

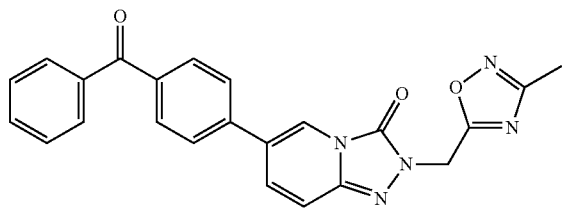 [SMILES: Cc1noc(Cn2nc3ccc(-c4ccc(C(=O)c5ccccc5)cc4)cn3c2=O)n1]

$^1$H NMR 8.05 (s, 1H); 7.87 (d, 2H); 7.82 (d, 2H); 7.70-7.60 (m, 3H); 7.60-7.48 (m, 3H); 7.22 (d, 1H); 5.44 (s, 2H); 2.40 (s, 3H).

Example 37

2-((5-(methoxymethyl)-1,2,4-oxadiazol-3-yl)methyl)-6-(4-(trifluoromethoxy)phenyl)-[1,2,4]triazolo[4,3-a]pyridin-3(2H)-one (Compound 128)

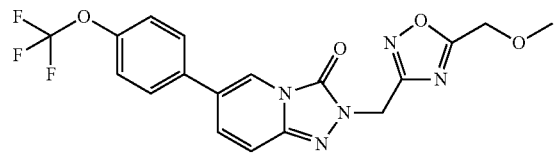 [SMILES: COCc1nc(Cn2nc3ccc(-c4ccc(OC(F)(F)F)cc4)cn3c2=O)no1]

MS (ESI+) 422.1 (base peak, M+H$^+$); 444.0 (M+Na$^+$); 865.1 (2M+Na$^+$).

Example 38

6-(3,5-difluoro-4-phenoxyphenyl)-2-((3-methyl-1,2,4-oxadiazol-5-yl)methyl)-[1,2,4]triazolo[4,3-a]pyridin-3(2H)-one (Compound 127)

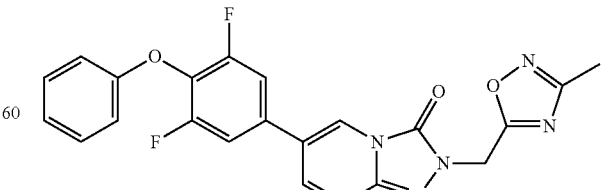

MS (ESI+) 436.1 (base peak, M+H$^+$); 458.0 (M+Na$^+$); 893.1 (2M+Na$^+$).

Example 39

2-((3-methyl-1,2,4-oxadiazol-5-yl)methyl)-6-(4-(trimethylsilyl)phenyl)-[1,2,4]triazolo[4,3-a]pyridin-3(2H)-one (Compound 110)

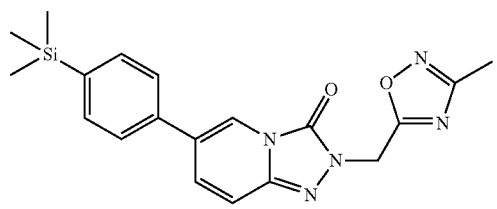

MS (ESI+) 380.1 (base peak, M+H$^+$); 402.1 (M+Na$^+$); 781.2 (2M+Na$^+$).

Example 40

6-(4-(4-fluorophenoxy)phenyl)-2-((3-methyl-1,2,4-oxadiazol-5-yl)methyl)-[1,2,4]triazolo[4,3-a]pyridin-3(2H)-one (Compound 93)

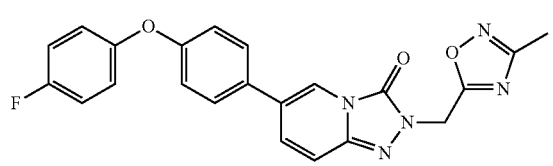 [SMILES: Cc1noc(Cn2nc3ccc(-c4ccc(Oc5ccc(F)cc5)cc4)cn3c2=O)n1]

MS (ESI+) 418.1 (base peak, M+H$^+$); 440.1 (M+Na$^+$); 857.2 (2M+Na$^+$). $^1$H NMR 7.92 (s, 1H); 7.47 (d, 2H); 7.41 (d, 1H); 7.20 (d, 1H); 7.08-7.00 (m, 6H); 5.43 (s, 2H); 2.40 (s, 2H). $^{19}$F NMR –119.64 (m).

Example 41

2-((3-methyl-1,2,4-oxadiazol-5-yl)methyl)-6-(2-methyl-4-(trifluoromethoxy)phenyl)-[1,2,4]triazolo[4,3-a]pyridin-3(2H)-one (Compound 87)

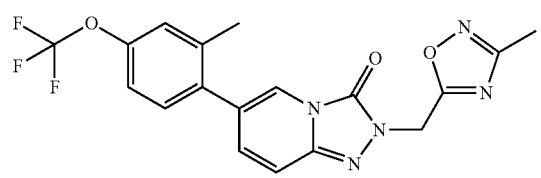 [SMILES: Cc1noc(Cn2nc3ccc(-c4ccc(OC(F)(F)F)cc4C)cn3c2=O)n1]

MS (ESI+) 406.2 (base peak, M+H$^+$).

Example 42

2-(chroman-2-ylmethyl)-6-(4-(trifluoromethoxy)phenyl)-[1,2,4]triazolo[4,3-a]pyridin-3(2H)-one (Compound 77)

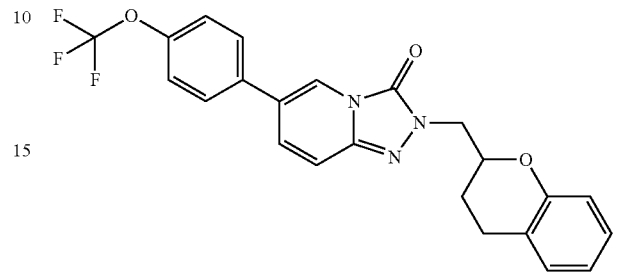

MS (ESI+) 442.1 (base peak, M+H$^+$); 905.2 (2M+Na$^+$).

Example 43

2-(2-(p-tolyloxy)ethyl)-6-(4-(trifluoromethoxy)phenyl)-[1,2,4]triazolo[4,3-a]pyridin-3(2H)-one (Compound 75)

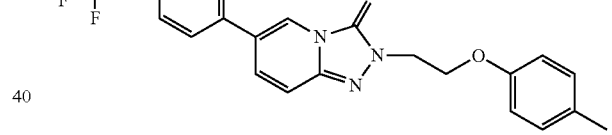

MS (ESI+) 430.1 (base peak, M+H$^+$); 452.0 (M+Na$^+$); 881.2 (2M+Na$^+$).

Example 44

2-(3-(3-oxo-6-(4-(trifluoromethoxy)phenyl)-[1,2,4]triazolo[4,3-a]pyridin-2(3H)-yl)propoxy)benzonitrile (Compound 70)

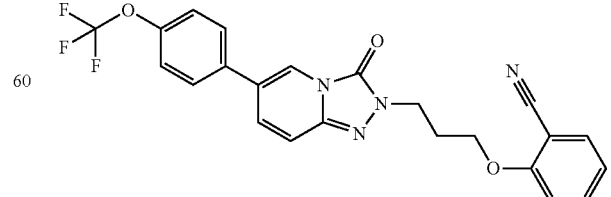

MS (ESI+) 455.1 (base peak, M+H$^+$); 931.2 (2M+Na$^+$).

Similarly, following the procedures above, but optionally substituting other substituted hydrazinopyridine derivatives for 5-bromo-2-hydrazinylpyridine, the following Examples 45-47 were prepared.

Example 45

8-methyl-6-(4-(trifluoromethoxy)phenyl)-[1,2,4]triazolo[4,3-a]pyridin-3(2H)-one (Compound 196)

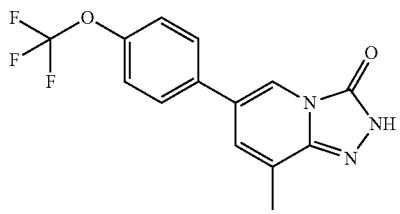 [SMILES: Cc1cc(-c2ccc(OC(F)(F)F)cc2)cn2c(=O)[nH]nc12]

MS (ESI+) 310.0 (base peak, M+H⁺); 332.0 (M+Na⁺); 641.1 (2M+Na⁺). 1H NMR 12.52 (s, 1H); 7.96 (s, 1H); 7.81 (d, 2H); 7.43-7.40 (m, 3H); 2.30 (s, 3H). $^{19}$F NMR −57.28 (s).

Example 46

5-methyl-2-((3-methyl-1,2,4-oxadiazol-5-yl)methyl)-6-(4-(trifluoromethoxy)phenyl)-[1,2,4]triazolo[4,3-a]pyridin-3(2H)-one (Compound 188)

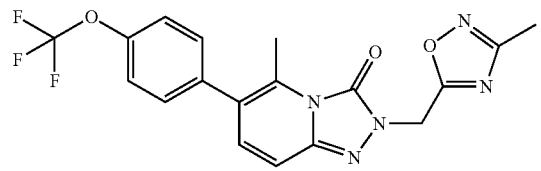 [SMILES: Cc1noc(Cn2nc3ccc(-c4ccc(OC(F)(F)F)cc4)c(C)n3c2=O)n1]

MS (ESI+) 406.1 (base peak, M+H⁺); 428.0 (M+Na⁺); 833.2 (2M+Na⁺).

Example 47

5-methyl-6-(4-(trifluoromethoxy)phenyl)-[1,2,4]triazolo[4,3-a]pyridin-3(2H)-one (Compound 187)

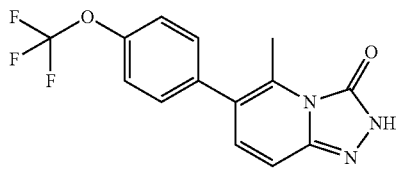 [SMILES: Cc1c(-c2ccc(OC(F)(F)F)cc2)ccc2n[nH]c(=O)n12]

¹H NMR 12.36 (s, 1H); 7.49-7.42 (m, 4H); 7.03-6.98 (m, 2H); 2.62 (s, 3H). $^{19}$F NMR −57.26 (s).

Example 48

6-(4-(trifluoromethoxy)phenyl)-2-(2-(5-(trifluoromethyl)pyrimidin-2-yloxy)ethyl)-[1,2,4]triazolo[4,3-a]pyridin-3(2H)-one (Compound 180)

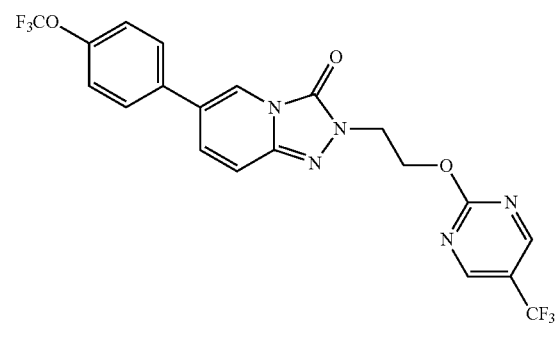 [SMILES: O=c1n(CCOc2ncc(C(F)(F)F)cn2)nc2ccc(-c3ccc(OC(F)(F)F)cc3)cn12]

Alternative Step 2—Addition of the R² Moiety

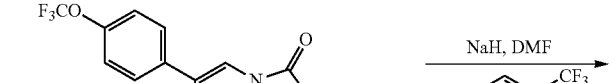

6-(4-(trifluoromethoxy)phenyl)-[1,2,4]triazolo[4,3-a]pyridin-3(2H)-one (825 mg) from Example 1 above was dissolved in DMA (10 mL), 2-bromoethanol (1.0 g) and potassium carbonate (235 mg) were added. Heated overnight at 110° C. Filtered, concentrated, and purified by chromatography (ethyl acetate/hexanes). 2-(2-hydroxyethyl)-6-(4-(trifluoromethoxy)phenyl)-[1,2,4]triazolo[4,3-a]pyridin-3(2H)-one was obtained as white solid (830 mg). m/z (ESI)=340.0 (base peak, M+H⁺); 701.1 (2M+Na⁺). 2-(2-hydroxyethyl)-6-(4-(trifluoromethoxy)phenyl)-[1,2,4]triazolo[4,3-a]pyridin-3(2H)-one (50 mg) was dissolved in dry DMF and the NaH suspension (12 mg, 60% in oil) was added, followed shortly by 2-chloro-5-trifluoromethylpyridine (54 mg). Concentrated and purified on silica using ethyl acetate/hexanes gradient to obtain compound 180 as a white solid (71 mg). m/z (ESI)=486.1 (base peak, M+H⁺); 508.1 (M+Na⁺); 993.2 (2M+Na⁺). ¹H NMR (δ, CDCl₃, 400 MHz) 8.75 (s, 2H); 7.98 (d, 1H); 7.53 (d, 2H); 7.40-7.30 (m, 3H); 7.18 (d, 1H); 4.90 (t, 2H); 4.49 (t, 2H). ¹⁹F NMR (δ, CDCl₃, 376 MHz) −58.36 (s, 1F); −61.99 (s, 1F).

Similarly, following the procedures above, but optionally substituting other reactive electrophiles for 2-chloro-4-trifluoromethylpyrimidine, and other bromoalcohols for 2-bromoethanol, the following Examples 49-71 were prepared.

Example 49

2-(2-(4-(cyclopropylmethoxy)pyrimidin-2-yloxy)ethyl)-6-(4-(trifluoromethoxy)phenyl)-[1,2,4]triazolo[4,3-a]pyridin-3(2H)-one (Compound 179)

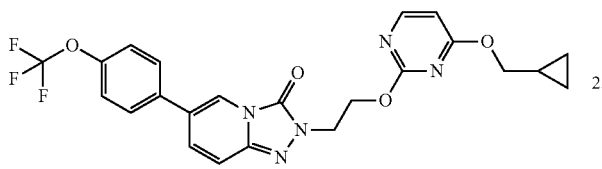

MS (ESI+) 488.1 (base peak, M+H⁺); 997.3 (2M+Na⁺).

Example 50

2-(2-(4-(2,2,2-trifluoroethoxy)pyrimidin-2-yloxy)ethyl)-6-(4-(trifluoromethoxy)phenyl)-[1,2,4]triazolo[4,3-a]pyridin-3(2H)-one (Compound 178)

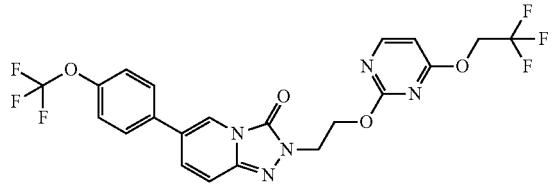 [SMILES: O=c1n(CCOc2nccc(OCC(F)(F)F)n2)nc2ccc(-c3ccc(OC(F)(F)F)cc3)cn12]

MS (ESI+) 516.1 (base peak, M+H⁺); 538.1 (M+Na⁺); 1053.2 (2M+Na⁺).

Example 51

2-(2-(4-isopropoxypyrimidin-2-yloxy)ethyl)-6-(4-(trifluoromethoxy)phenyl)-[1,2,4]triazolo[4,3-a]pyridin-3(2H)-one (Compound 177)

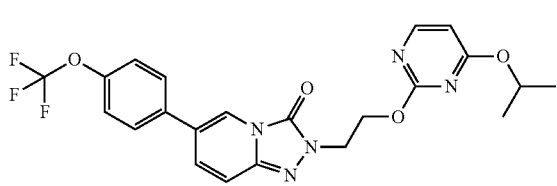 [SMILES: CC(C)Oc1ccnc(OCCn2nc3ccc(-c4ccc(OC(F)(F)F)cc4)cn3c2=O)n1]

MS (ESI+) 476.1 (base peak, M+H⁺); 973.3 (2M+Na⁺).

Example 52

2-(2-(imidazo[1,2-a]pyrazin-8-yloxy)ethyl)-6-(4-(trifluoromethoxy)phenyl)-[1,2,4]triazolo[4,3-a]pyridin-3(2H)-one (Compound 174)

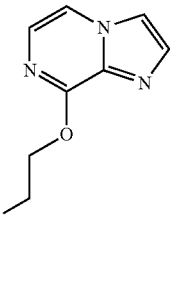

MS (ESI+) 457.1 (base peak, M+H⁺); 935.2 (2M+Na⁺).

Example 53

2-(2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidin-4-yloxy)acetonitrile (Compound 160)

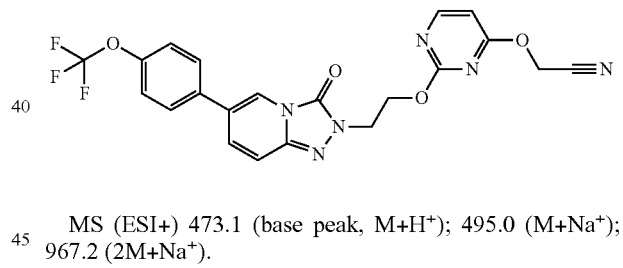

MS (ESI+) 473.1 (base peak, M+H⁺); 495.0 (M+Na⁺); 967.2 (2M+Na⁺).

Example 54

2-(2-(4-(methylthio)pyrimidin-2-yloxy)ethyl)-6-(4-(trifluoromethoxy)phenyl)-[1,2,4]triazolo[4,3-a]pyridin-3(2H)-one (Compound 159)

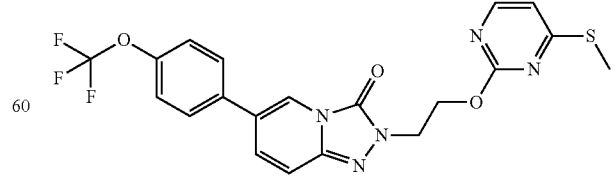

MS (ESI+) 464.0 (base peak, M+H⁺); 949.1 (2M+Na⁺). ¹H NMR 8.11 (d, 1H); 7.91 (s, 1H); 7.53 (d, 2H); 7.38-7.28 (m, 3H); 7.19 (d, 1H); 6.81 (d, 1H); 4.82 (t, 2H); 4.66 (t, 2H).

Example 55

2-(2-(isoquinolin-1-yloxy)ethyl)-6-(4-(trifluoromethoxy)phenyl)-[1,2,4]triazolo[4,3-a]pyridin-3(2H)-one (Compound 141)

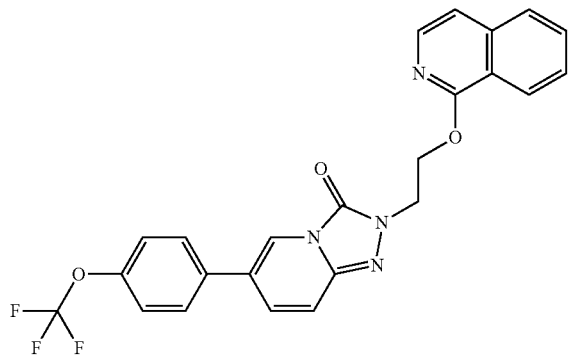 [SMILES: O=c1n(CCOc2nccc3ccccc23)nc2ccc(-c3ccc(OC(F)(F)F)cc3)cn12]

MS (ESI+) 467.1 (base peak, M+H$^+$); 489.0 (M+Na$^+$); 955.2 (2M+Na$^+$). $^1$H NMR 8.22 (d, 1H); 7.94 (s, 1H); 7.65 (d, 2H); 7.61 (t, 1H); 7.51 (d, 2H); 7.32-7.27 (m, 2H); 7.20 (d, 1H); 7.18 (d, 1H); 4.91 (t, 2H); 4.55 (t, 2H). $^{19}$F NMR −58.39 (s).

Example 56

2-(2-(4-(dimethylamino)-5-fluoropyrimidin-2-yloxy)ethyl)-6-(4-(trifluoromethoxy)phenyl)-[1,2,4]triazolo[4,3-a]pyridin-3(2H)-one (Compound 126)

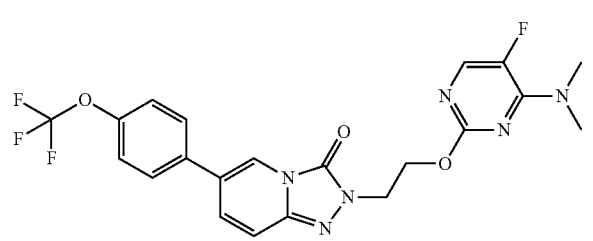 [SMILES: CN(C)c1nc(OCCn2nc3ccc(-c4ccc(OC(F)(F)F)cc4)cn3c2=O)ncc1F]

MS (ESI+) 479.1 (base peak, M+H$^+$); 979.2 (2M+Na$^+$). $^1$H NMR 7.92 (s, 1H); 7.80 (d, 1H); 7.53 (d, 2H); 7.34 (dd, 1H); 7.31 (d, 2H); 7.19 (d, 2H); 4.69 (t, 2H); 4.43 (t, 2H); 3.21 (s, 3H); 3.20 (s, 3H). $^{19}$F NMR −58.36 (s, 3F), −158.51 (br s, 1F).

Example 57

6-(4-(4-chlorophenoxy)phenyl)-2-(2-(pyrimidin-2-yloxy)ethyl)-[1,2,4]triazolo[4,3-a]pyridin-3(2H)-one (Compound 120)

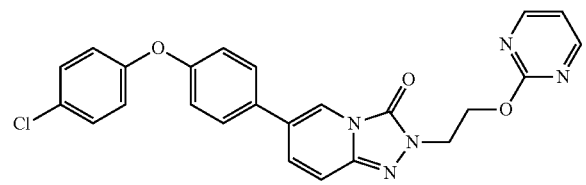 [SMILES: O=c1n(CCOc2ncccn2)nc2ccc(-c3ccc(Oc4ccc(Cl)cc4)cc3)cn12]

MS (ESI+) 460.1 (base peak, $^{35}$Cl-M+H$^+$); 462.0 ($^{37}$Cl-M+H$^+$); 941.1 ($^{35}$Cl$_2$-2M+Na$^+$).

Example 58

6-(4-(4-fluorophenoxy)phenyl)-2-(2-(pyrimidin-2-yloxy)ethyl)-[1,2,4]triazolo[4,3-a]pyridin-3(2H)-one (Compound 122)

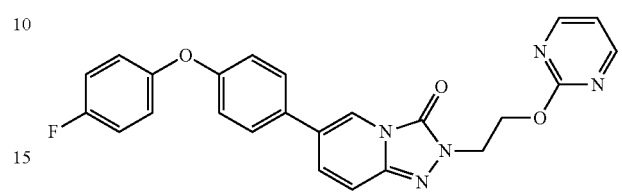

MS (ESI+) 444.0 (base peak, M+H$^+$); 908.9 (2M+Na$^+$).

Example 59

2-(2-(pyrimidin-2-yloxy)ethyl)-6-(4-(trimethylsilyl)phenyl)-[1,2,4]triazolo[4,3-a]pyridin-3(2H)-one (Compound 123)

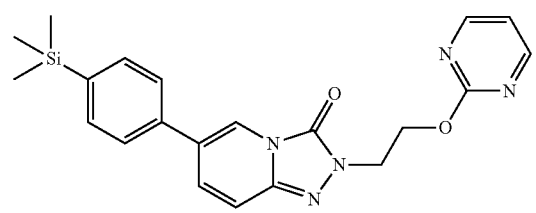 [SMILES: C[Si](C)(C)c1ccc(-c2ccc3nn(CCOc4ncccn4)c(=O)n3c2)cc1]

MS (ESI+) 406.0 (base peak, M+H$^+$); 832.9 (2M+Na$^+$). $^1$H NMR 8.50 (d, 2H); 7.99 (s, 1H); 7.80 (d, 2H); 7.50 (d, 2H); 7.39 (d, 1H); 7.18 (d, 1H); 6.96 (t, 1H); 4.81 (t, 2H); 4.47 (t, 2H); 0.29 (s, 9H).

Example 60

2-(2-(5-methoxypyrimidin-2-yloxy)ethyl)-6-(4-(trifluoromethoxy)phenyl)-[1,2,4]triazolo[4,3-a]pyridin-3(2H)-one (Compound 116)

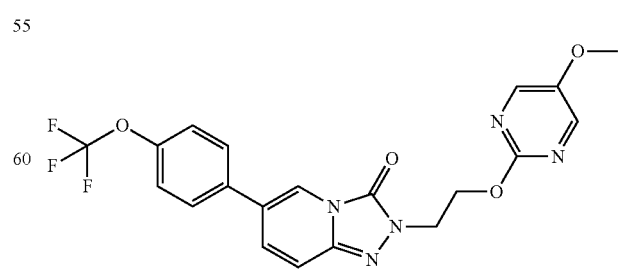

MS (ESI+) 448.1 (base peak, M+H$^+$); 917.1 (2M+Na$^+$).

Example 61

2-(2-(4-phenylpyrimidin-2-yloxy)ethyl)-6-(4-(trifluoromethoxy)phenyl)-[1,2,4]triazolo[4,3-a]pyridin-3(2H)-one (Compound 115)

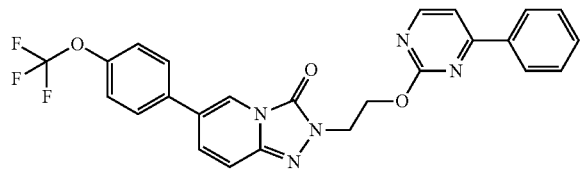 [SMILES: O=c1n(CCOc2nccc(-c3ccccc3)n2)nc2ccc(-c3ccc(OC(F)(F)F)cc3)cn12]

MS (ESI+) 494.1 (base peak, M+H$^+$); 1009.2 (2M+Na$^+$).

Example 62

2-(2-(4-ethoxypyrimidin-2-yloxy)ethyl)-6-(4-(trifluoromethoxy)phenyl)-[1,2,4]triazolo[4,3-a]pyridin-3(2H)-one (Compound 106)

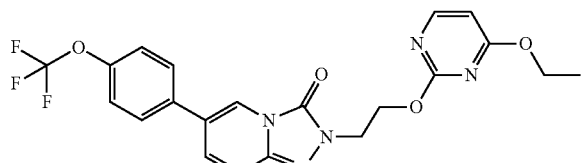

MS (ESI+) 462.1 (base peak, M+H$^+$); 945.2 (2M+Na$^+$).

Example 63

2-(2-(5-chloropyrimidin-2-yloxy)ethyl)-6-(4-(trifluoromethoxy)phenyl)-[1,2,4]triazolo[4,3-a]pyridin-3(2H)-one (Compound 92)

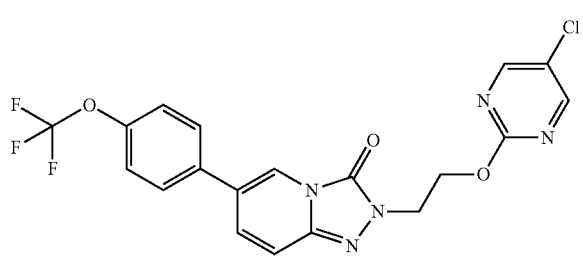 [SMILES: O=c1n(CCOc2ncc(Cl)cn2)nc2ccc(-c3ccc(OC(F)(F)F)cc3)cn12]

MS (ESI+) 452.0 (base peak, $^{35}$Cl-M+H$^+$); 454.0 ($^{37}$Cl-M+H$^+$); 925.0 ($^{35}$Cl$_2$-2M+Na$^+$).

Example 64

2-(2-(4-cyclopropylpyrimidin-2-yloxy)ethyl)-6-(4-(trifluoromethoxy)phenyl)-[1,2,4]triazolo[4,3-a]pyridin-3(2H)-one (Compound 90)

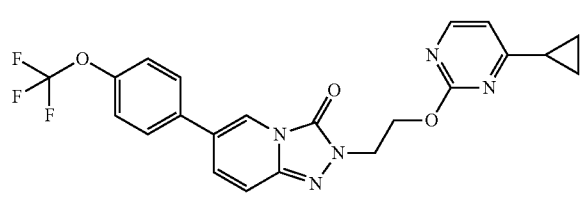 [SMILES: O=c1n(CCOc2nccc(C3CC3)n2)nc2ccc(-c3ccc(OC(F)(F)F)cc3)cn12]

MS (ESI+) 458.1 (base peak, M+H$^+$); 937.2 (2M+Na$^+$). $^1$H NMR 8.25 (d, 1H); 7.90 (s, 1H); 7.52 (d, 2H); 7.34-7.29 (m, 3H); 7.17 (d, 1H); 6.81 (d, 1H); 4.75 (t, 2H); 4.43 (t, 2H); 1.97 (m, 1H); 1.18 (m, 2H); 1.08 (m, 2H). $^{19}$F NMR −58.36 (s)

Example 65

2-(2-(4,6-dimethylpyrimidin-2-yloxy)ethyl)-6-(4-(trifluoromethoxy)phenyl)-[1,2,4]triazolo[4,3-a]pyridin-3(2H)-one (Compound 88)

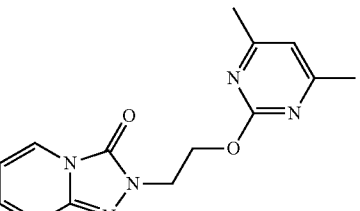

MS (ESI+) 446.1 (base peak, M+H$^+$); 913.2 (2M+Na$^+$).

Example 66

2-(3-(pyrazin-2-yloxy)propyl)-6-(4-(trifluoromethoxy)phenyl)-[1,2,4]triazolo[4,3-a]pyridin-3(2H)-one (Compound 85)

MS (ESI+) 418.0 (base peak, M+H); 440.0 (M+Na$^+$). $^1$H NMR 8.22 (s, 1H); 8.11 (s, 1H); 8.05 (s, 1H); 7.94 (s, 1H); 7.53 (d, 2H); 7.39-7.24 (m, 3H); 7.19 (d, 1H); 4.77 (t, 2H); 4.44 (t, 2H); 2.39 (quintet, 1H). $^{19}$F NMR −58.36 (s).

Example 67

2-(2-(5-methylpyrimidin-2-yloxy)ethyl)-6-(4-(trifluoromethoxy)phenyl)-[1,2,4]triazolo[4,3-a]pyridin-3(2H)-one (Compound 82)

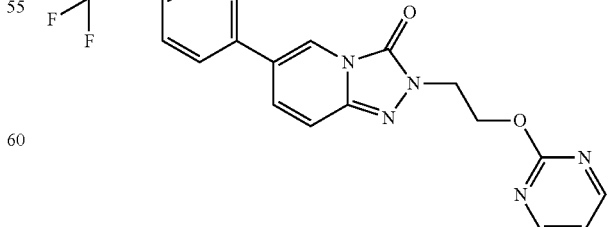

MS (ESI+) 432.1 (base peak, M+H$^+$); 885.2 (2M+Na$^+$).

Example 68

2-(2-(pyridazin-3-yloxy)ethyl)-6-(4-(trifluoromethoxy)phenyl)-[1,2,4]triazolo[4,3-a]pyridin-3(2H)-one (Compound 81)

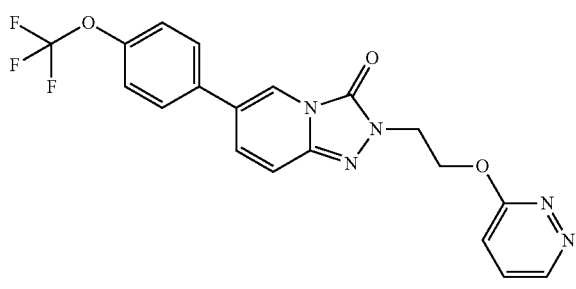 [SMILES: O=c1n(CCOc2cccnn2)nc2ccc(-c3ccc(OC(F)(F)F)cc3)cn12]

MS (ESI+) 418.0 (base peak, M+H⁺); 857.1 (2M+Na⁺).

Example 69

2-(3-(pyridazin-3-yloxy)propyl)-6-(4-(trifluoromethoxy)phenyl)-[1,2,4]triazolo[4,3-a]pyridin-3(2H)-one (Compound 79)

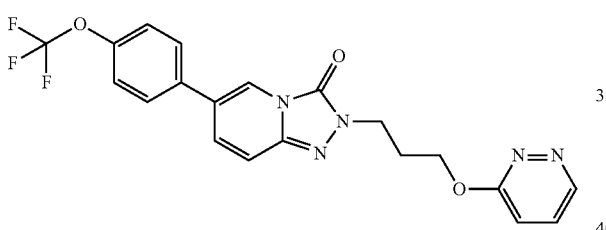

MS (ESI+) 432.1 (base peak, M+H⁺); 885.2 (2M+Na⁺). $^1$H NMR 8.82 (d, 1H); 7.92 (s, 1H); 7.53 (d, 2H); 7.40 (dd, 1H); 7.57 (d, 2H); 7.38 (d, 1H); 7.35 (d, 2H); 7.18 (d, 1H); 7.02 (d, 1H); 4.61 (t, 2H); 4.25 (t, 2H); 2.41 (quintet, 1H).

Example 70

6-(4-(trifluoromethoxy)phenyl)-2-(3-(2-(trifluoromethyl)phenoxy)propyl)-[1,2,4]triazolo[4,3-a]pyridin-3(2H)-one (Compound 71)

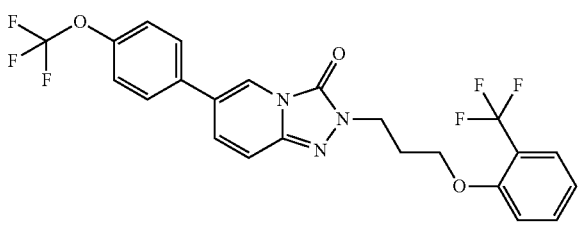 [SMILES: O=c1n(CCCOc2ccccc2C(F)(F)F)nc2ccc(-c3ccc(OC(F)(F)F)cc3)cn12]

MS (ESI+) 499.1 (base peak, M+H⁺); 1019.2 (2M+Na⁺). $^1$H NMR 8.28 (dd, 1H); 7.93 (d, 1H); 7.86 (dd, 2H); 7.57 (d, 2H); 7.36-7.30 (m, 3H); 7.20 (d, 1H); 6.96 (dd, 1H); 4.53 (t, 2H); 4.24 (t, 2H); 2.39 (quintet, 1H). $^{19}$F NMR −58.36 (s, 1F), −64.37 (s, 1F).

Example 71

6-(4-(trifluoromethoxy)phenyl)-2-(2-(6-(trifluoromethyl)pyridin-2-yloxy)ethyl)-[1,2,4]triazolo[4,3-a]pyridin-3(2H)-one (Compound 72)

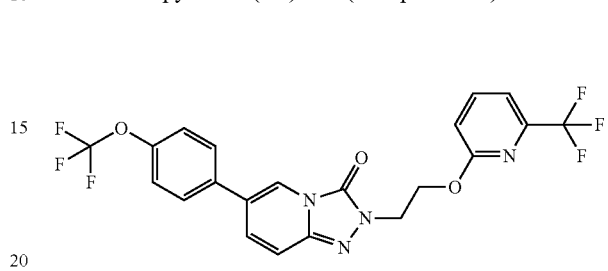

MS (ESI+) 485.0 (base peak, M+H⁺); 991.1 (2M+Na⁺).

Using the procedure described in Example 1, the following Examples 72-88 were prepared.

Example 72

2-(2-(1H-pyrazol-1-yl)ethyl)-6-(4-(trifluoromethoxy)phenyl)-[1,2,4]triazolo[4,3-a]pyridin-3(2H)-one (Compound 35)

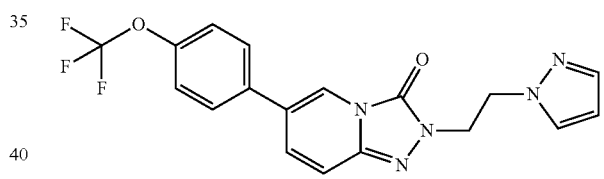

$C_{18}H_{14}F_3N_5O_2$, m/z (ESI)=390.1 [M+H]⁺.

Example 73

2-(2-(pyridin-2-yl)ethyl)-6-(4-(trifluoromethoxy)phenyl)-[1,2,4]triazolo[4,3-a]pyridin-3(2H)-one (Compound 36)

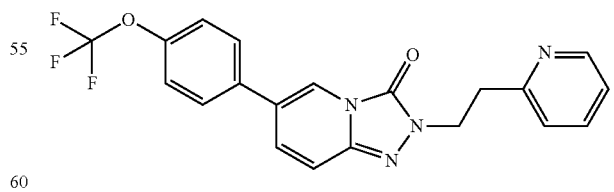

$C_{20}H_{15}F_3N_4O_2$, m/z (ESI)=401.0 [M+H]⁺. $^1$H NMR (δ, d₆-DMSO, 400 MHz) 8.40-8.46 (m, 1H), 8.09 (t, J=1.6 Hz, 1H), 7.83 (dt, J=1.6, 8.8 Hz, 2H), 7.66 (dt, J=2.0, 6.4 Hz, 1H), 7.60 (dd, J=1.6, 9.6 Hz, 1H), 7.43 (d, J=8.0 Hz, 2H), 7.35 (dd, J=0.8, 9.6 Hz, 1H), 7.25 (d, J=8.0 Hz, 1H), 7.19-7.22 (m, 1H), 4.28 (t, J=8.0 Hz, 2H), 3.21 (t, J=8.0 Hz, 2H).

Example 74

2-(2-(4-chloro-1H-pyrazol-1-yl)ethyl)-6-(4-(trifluoromethoxy)phenyl)-[1,2,4]triazolo[4,3-a]pyridin-3(2H)-one (Compound 41)

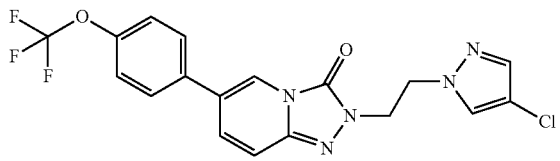 [SMILES: O=c1n(CCn2cc(Cl)cn2)nc2ccc(-c3ccc(OC(F)(F)F)cc3)cn12]

$C_{18}H_{13}ClF_3N_5O_2$, m/z (ESI)=424.1 [M+H]$^+$.

Example 75

2-(2-(3-methyl-1H-pyrazol-1-yl)ethyl)-6-(4-(trifluoromethoxy)phenyl)-[1,2,4]triazolo[4,3-a]pyridin-3(2H)-one (Compound 42)

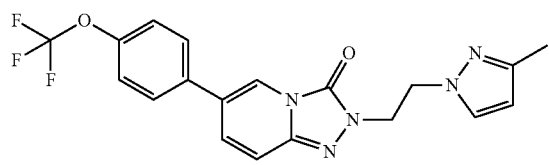 [SMILES: Cc1ccn(CCn2nc3ccc(-c4ccc(OC(F)(F)F)cc4)cn3c2=O)n1]

$C_{19}H_{16}F_3N_5O_2$, m/z (ESI)=404.1 [M+H]$^+$.

Example 76

6-(4-(trifluoromethoxy)phenyl)-2-((6-(trifluoromethyl)pyridin-2-yl)methyl)-[1,2,4]triazolo[4,3-a]pyridin-3(2H)-one (Compound 62)

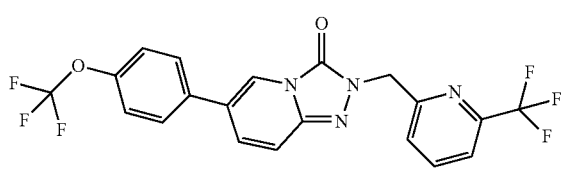 [SMILES: O=c1n(Cc2cccc(C(F)(F)F)n2)nc2ccc(-c3ccc(OC(F)(F)F)cc3)cn12]

$C_{20}H_{12}F_6N_4O_2$, m/z (ESI)=455.1 [M+H]$^+$.

Example 77

2-(2-(pyridin-3-yl)ethyl)-6-(4-(trifluoromethoxy)phenyl)-[1,2,4]triazolo[4,3-a]pyridin-3(2H)-one (Compound 73)

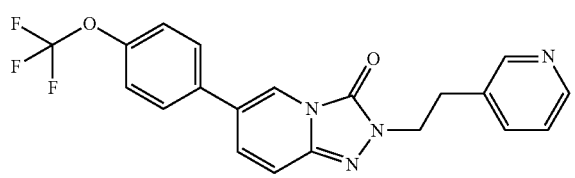 [SMILES: O=c1n(CCc2cccnc2)nc2ccc(-c3ccc(OC(F)(F)F)cc3)cn12]

$C_{20}H_{15}F_3N_4O_2$, m/z (ESI)=401.1 [M+H]$^+$.

Example 78

2-(2-(1-methyl-1H-benzo[d]imidazol-2-yl)ethyl)-6-(4-(trifluoromethoxy)phenyl)-[1,2,4]triazolo[4,3-a]pyridin-3(2H)-one (Compound 97)

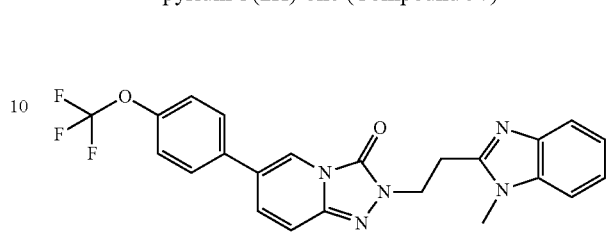

$C_{23}H_{18}F_3N_5O_2$, m/z (ESI)=454.1 [M+H]$^+$.

Using the procedure described in alternative step 2 of Example 1, the following Examples 79-89 were prepared.

Example 79

2-(2-(6-methylpyridin-2-yl)ethyl)-6-(4-(trifluoromethoxy)phenyl)-[1,2,4]triazolo[4,3-a]pyridin-3(2H)-one (Compound 48)

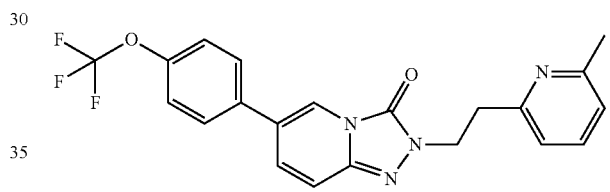

$C_{21}H_{17}F_3N_4O_2$, m/z (ESI)=415.1 [M+H]$^+$. $^1$H NMR (δ, d$_6$-DMSO, 400 MHz) 8.11 (s, 1H), 7.82-7.85 (m, 2H), 7.60 (dd, J=2.0, 10.0 Hz, 1H), 7.55 (t, J=7.6 Hz, 1H), 7.43 (d, J=8.0 Hz, 1H), 7.36 (dd, J=1.2, 10.0 Hz, 1H), 7.05 (t, J=8.4 Hz, 2H), 4.24 (t, J=7.2 Hz, 2H), 3.15 (t, J=7.2 Hz, 2H), 2.38 (s, 3H).

Example 80

2-(2-(3-bromopyridin-2-yl)ethyl)-6-(4-(trifluoromethoxy)phenyl)-[1,2,4]triazolo[4,3-a]pyridin-3(2H)-one (Compound 56)

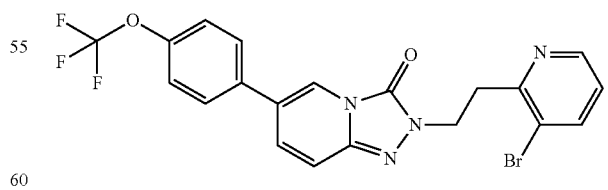

$C_{20}H_{14}BrF_3N_4O_2$, m/z (ESI)=481.0 [M+H]$^+$. $^1$H NMR (δ, d$_6$-DMSO, 400 MHz) 8.47 (dd, J=1.2, 4.4 Hz, 1H), 8.10 (s, 1H), 8.02 (dd, J=1.6, 7.6 Hz, 1H), 7.84 (d, J=8.8 Hz, 2H), 7.60 (dd, J=2.0, 10.0 Hz, 1H), 7.43 (d, J=8.0 Hz, 2H), 7.35 (d, J=9.6 Hz, 1H), 7.22 (dd, J=4.0, 7.6 Hz, 1H), 4.32 (t, J=6.8 Hz, 2H), 3.37 (t, J=6.8 Hz, 2H).

Example 81

2-(3-(4-chloropyridin-3-yl)prop-2-ynyl)-6-(4-(trifluoromethoxy)phenyl)-[1,2,4]triazolo[4,3-a]pyridin-3(2H)-one 9 (Compound 68)

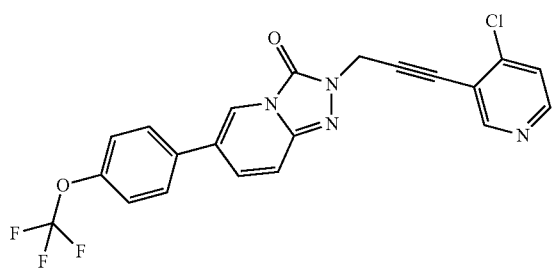 [SMILES: O=c1n(CC#Cc2cnccc2Cl)nc2ccc(-c3ccc(OC(F)(F)F)cc3)cn12]

$C_{21}H_{12}ClF_3N_4O_2$, m/z (ESI)=445.0 [M+H]$^+$.

Example 82

2-(2-(pyridin-2-yl)propyl)-6-(4-(trifluoromethoxy)phenyl)-[1,2,4]triazolo[4,3-a]pyridin-3(2H)-one (Compound 102)

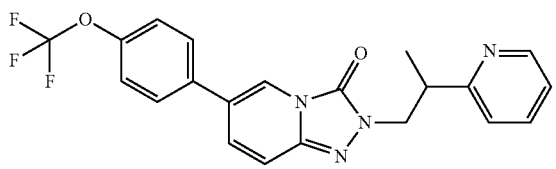 [SMILES: CC(Cn1nc2ccc(-c3ccc(OC(F)(F)F)cc3)cn2c1=O)c1ccccn1]

$C_{21}F_{17}F_3N_4O_2$, m/z (ESI)=415.1 [M+H]$^+$. $^1$H NMR (δ, d$_6$-DMSO, 400 MHz) 8.49-8.51 (m, 1H), 8.09 (s, 1H), 7.82 (dt, J=2.0, 8.8 Hz, 2H), 7.67 (ddd, J=2.0, 9.2, 17.2 Hz, 1H), 7.59 (dd, J=2.0, 9.6 Hz, 1H), 7.43 (d, J=7.6 Hz, 2H), 7.34 (dd, J=0.8, 9.6 Hz, 1H), 7.27 (d, J=7.6 Hz, 1H), 7.19-7.22 (m, 1H), 4.11-4.21 (m, 2H), 3.50 (q, J=7.2 Hz, 1H), 1.21 (d, J=6.4 Hz, 3H).

Example 83

2-(2-(6-methoxypyridin-2-yl)ethyl)-6-(4-(trifluoromethoxy)phenyl)-[1,2,4]triazolo[4,3-a]pyridin-3(2H)-one (Compound 103)

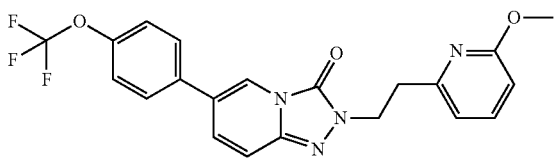 [SMILES: COc1cccc(CCn2nc3ccc(-c4ccc(OC(F)(F)F)cc4)cn3c2=O)n1]

$C_{21}H_{17}F_3N_4O_3$, m/z (ESI)=431.2 [M+H]$^+$. $^1$H NMR (δ, d$_6$-DMSO, 400 MHz) 8.09 (s, 1H), 7.81-7.85 (m, 2H), 7.60 (dd, J=1.6, 9.6 Hz, 1H), 7.56 (dd, J=7.6, 8.4 Hz, 1H), 7.43 (d, J=8.0 Hz, 2H), 7.36 (d, J=9.6 Hz, 1H), 6.82 (d, J=7.2 Hz, 1H), 6.60 (d, J=8.0 Hz, 1H), 4.28 (t, J=6.8 Hz, 2H), 3.75 (s, 3H), 3.14 (t, J=6.8 Hz, 2H).

Example 84

2-(2-(pyrimidin-2-yl)ethyl)-6-(4-(trifluoromethoxy)phenyl)-[1,2,4]triazolo[4,3-a]pyridin-3(2H)-one (Compound III)

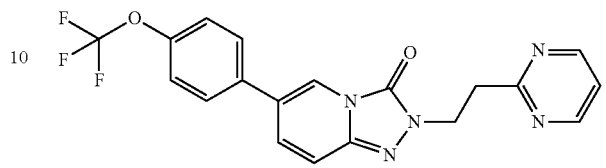

$C_{19}H_{14}F_3N_5O_2$, m/z (ESI)=402.0 [M+H]$^+$.

Example 85

2-(2-(pyrimidin-4-yl)ethyl)-6-(4-(trifluoromethoxy)phenyl)-[1,2,4]triazolo[4,3-a]pyridin-3(2H)-one (Compound 113)

$C_{19}H_{14}F_3N_5O_2$, m/z (ESI)=402.0 [M+H]$^+$.

Example 86

2-(2-(pyrazin-2-yl)ethyl)-6-(4-(trifluoromethoxy)phenyl)-[1,2,4]triazolo[4,3-a]pyridin-3(2H)-one (Compound 114)

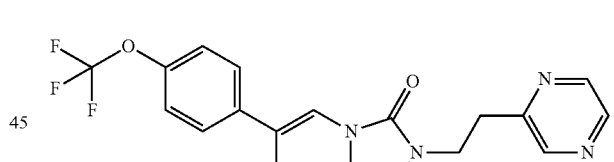

$C_{19}H_{14}F_3N_5O_2$, m/z (ESI)=402.0 [M+H]$^+$.

Example 87

2-(2-(3-methylpyrazin-2-yl)ethyl)-6-(4-(trifluoromethoxy)phenyl)-[1,2,4]triazolo[4,3-a]pyridin-3(2H)-one (Compound 117)

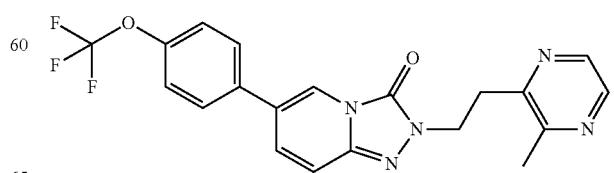

$C_{20}H_{16}F_3N_5O_2$, m/z (ESI)=416.1 [M+H]$^+$.

Example 88

2-(2-(3-bromo-6-methoxypyridin-2-yl)ethyl)-6-(4-(trifluoromethoxy)phenyl)-[1,2,4]triazolo[4,3-a]pyridin-3(2H)-one (Compound 118)

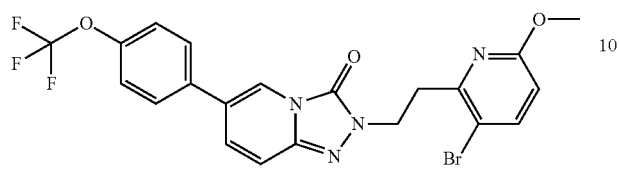

$C_{21}H_{16}BrF_3N_4O_3$, m/z (ESI)=509.1 [M+H]⁺. ¹H NMR (δ, d₆-DMSO, 400 MHz) 8.10 (s, 1H), 7.80-7.85 (m, 3H), 7.60 (dd, J=2.0, 9.6 Hz, 1H), 7.43 (d, J=8.4 Hz, 2H), 7.35 (d, J=9.6 Hz, 1H), 6.43 (d, J=8.4 Hz, 1H), 4.33 (t, J=6.8 Hz, 2H), 3.72 (s, 3H), 3.26-3.30 (m, 2H).

Example 89

2-(pyridin-2-yl)-6-(4-(trifluoromethoxy)phenyl)-[1,2,4]triazolo[4,3-a]pyridin-3(2H)-one (Compound 34)

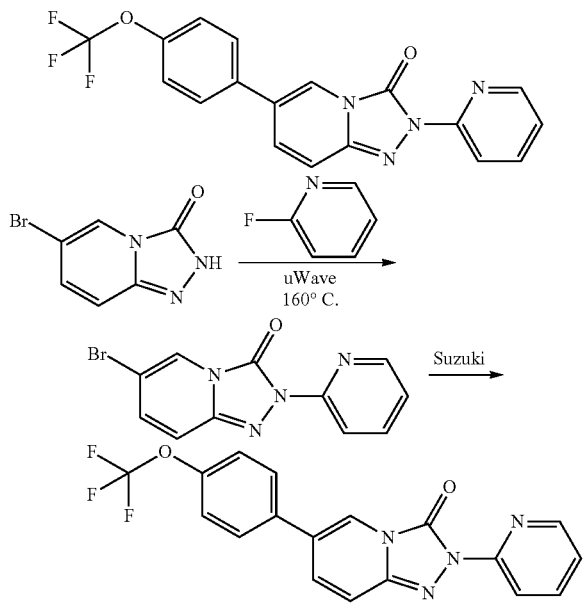

A mixture of 6-bromo-[1,2,4]triazolo[4,3-a]pyridin-3(2H)-one (100 mg, 0.467 mmol), K₂CO₃ (129 mg, 0.94 mmol), and 2-fluoropyridine (1 mL) was placed in a sealed microwave vial and heated to 160° C. in a microwave reactor for 90 minutes. The reaction was cooled, diluted with water/EtOAC and the layers were separated. The organic layer was washed with NaHCO₃ and brine. The organics were dried (MgSO₄), filtered, concentrated and purified by flash chromatography (R$_f$=0.23, 1:2 hexanes:EtOAc) to afford 70 mg (51% y) 6-bromo-2-(pyridin-2-yl)-[1,2,4]triazolo[4,3-a]pyridin-3(2H)-one, which was used directly in the next reaction (M+1=292.1). Compound 34 was synthesized according to the procedure disclosed in Example 1, however the reaction was done in 24 hours (28% y). $C_{18}H_{11}F_3N_4O_2$, m/z (ESI)=373.2 [M+H]⁺. ¹H NMR (δ, d₆-DMSO, 400 MHz) 8.54-8.57 (m, 1H), 8.22 (t, J=1.2 Hz, 2H), 7.98-8.07 (m, 2H), 7.88 (dt, J=2.0, 8.4 Hz, 2H), 7.72 (dd, J=2.0, 9.6 Hz, 1H), 7.43-7.47 (m, 3H), 7.36-7.40 (m, 1H)

Example 90

2-(2-(4-phenyl-1H-imidazol-1-yl)ethyl)-6-(4-(trifluoromethoxy)phenyl)-[1,2,4]triazolo[4,3-a]pyridin-3(2H)-one (Compound 45)

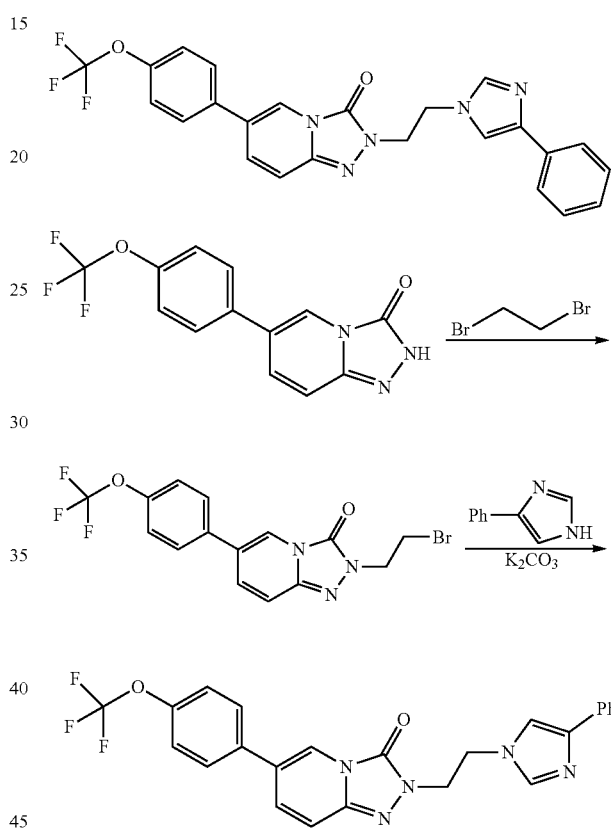

6-(4-(trifluoromethoxy)phenyl)-[1,2,4]triazolo[4,3-a]pyridin-3(2H)-one (synthesized according to Example 1, 500 mg, 1.69 mmol) was dissolved in 5 ml DMF and 1,2 dibromoethane (1.0 mL, 11.8 mmol) was added. The reaction was heated to 95° C. overnight. The reaction was cooled, diluted with water/EtOAC and the layers were separated. The organic layer was washed with NaHCO₃. The organics were dried (MgSO₄), filtered, concentrated and purified by flash chromatography (R$_f$=0.46, 1:1 hexanes:EtOAc) to afford 2-(2-bromoethyl)-6-(4-(trifluoromethoxy)phenyl)-[1,2,4]triazolo[4,3-a]pyridin-3(2H)-one. To a solution of 2-(2-bromoethyl)-6-(4-(trifluoromethoxy)phenyl)-[1,2,4]triazolo[4,3-a]pyridin-3(2H)-one (50 mg, 0.124 mmol) in 1 mL DMF was added K₂CO₃ (51 mg, 0.372 mmol) and 4-phenyl-1H-imidazole (36 mg, 0.249 mmol) and the reaction was heated to 85° C. for 24-72 hours until the SM was consumed. The reaction was concentrated and purified by reverse phase HPLC to afford compound 100 (24 mg, 41%). GS-490257. $C_{24}H_{18}F_3N_5O_2$, m/z (ESI)=466.2 [M+H]⁺.

Example 91

2-(2-(4-cyclopropylpyridin-2-yl)ethyl)-6-(4-(trifluoromethoxy)phenyl)-[1,2,4]triazolo[4,3-a]pyridin-3(2H)-one (Compound 57)

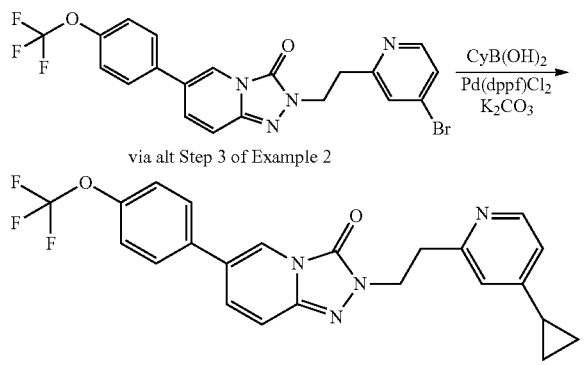

via alt Step 3 of Example 2

A mixture of 2-(2-(4-bromopyridin-2-yl)ethyl)-6-(4-(trifluoromethoxy)phenyl)-[1,2,4]triazolo[4,3-a]pyridin-3(2H)-one (synthesized according to Example 1, 40 mg, 0.084 mmol), cyclopropyl boronic acid (22 mg, 0.25 mmol), dppf (Pd)Cl$_2$ (9.0 mg, 0.013 mmol), potassium carbonate (46 mg, 0.33 mmol) in degassed dioxane (1 mL) was heated at 100° C. for 3 hours. The reaction was concentrated and the residue was purified by reverse phase HPLC to provide compound 57 as a white powder (30 mg, 81% yield). $C_{23}H_{19}F_3N_4O_2$, m/z (ESI)=441.1 [M+H]$^+$.

Using the procedure described in Example 91, the following Examples 92-94 were prepared.

Example 92

2-(2-(4-methylpyridin-2-yl)ethyl)-6-(4-(trifluoromethoxy)phenyl)-[1,2,4]triazolo[4,3-a]pyridin-3(2H)-one (Compound 58)

Methyl boronic acid was used in place of cyclopropyl boronic acid. $C_{21}H_{17}F_3N_4O_2$, m/z (ESI)=415.1 [M+H]$^+$.

Example 93

2-(2-(3-cyclopropylpyridin-2-yl)ethyl)-6-(4-(trifluoromethoxy)phenyl)-[1,2,4]triazolo[4,3-a]pyridin-3(2H)-one (Compound 60)

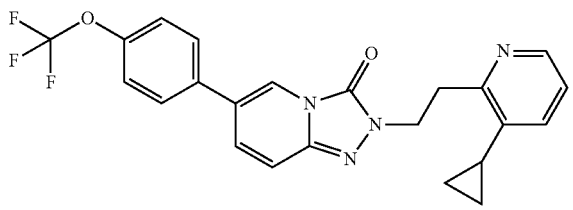

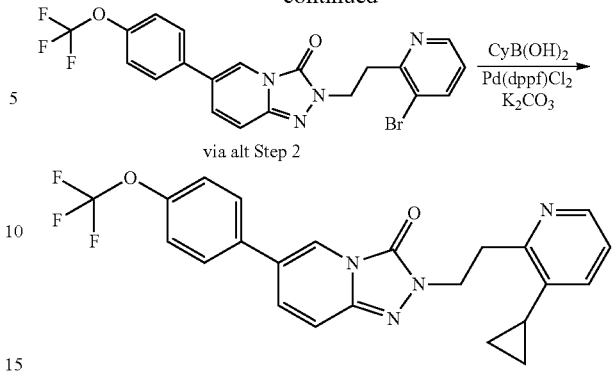

via alt Step 2

$C_{23}H_{19}F_3N_4O_2 \cdot HCO_2H$, m/z (ESI)=441.2 [M+H]$^+$. $^1$H NMR (δ, d$_6$-DMSO, 400 MHz) 8.27-8.30 (m, 1H), 8.25 (s, 1H, formate salt), 8.11 (s, 1H), 7.84 (d, J=8.8 Hz, 2H), 7.60 (dd, J=1.6, 10.0 Hz, 1H), 7.43 (d, J=8.0 Hz, 2H), 7.36 (d, J=10.0 Hz, 1H), 7.32 (d, J=8.0 Hz, 1H), 7.14 (dd, J=4.8, 7.6 Hz, 1H), 4.35 (t, J=7.2 Hz, 2H), 3.40 (t, J=7.2 Hz, 2H), 1.93-1.98 (m, 1H), 0.87-0.92 (m, 2H), 0.60-0.63 (m, 2H).

Example 94

2-(2-(3-methylpyridin-2-yl)ethyl)-6-(4-(trifluoromethoxy)phenyl)-[1,2,4]triazolo[4,3-a]pyridin-3(2H)-one (Compound 61)

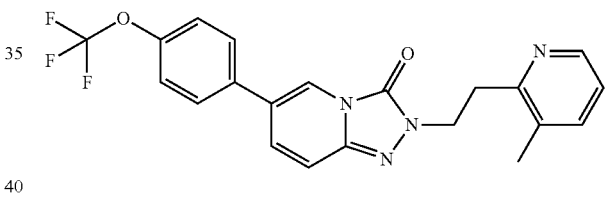

Methyl boronic acid was used in place of cyclopropyl boronic acid. $C_{21}H_{17}F_3N_4O_2 \cdot HCO_2H$, m/z (ESI)=415.1 [M+H]$^+$. $^1$H NMR (δ, d$_6$-DMSO, 400 MHz) 8.40 (s, 1H, formate salt), 8.31 (d, J=4.4 Hz, 1H), 8.12 (s, 1H), 7.84 (d, J=8.4 Hz, 2H), 7.61 (dd, J=2.0, 10.0 Hz, 1H), 7.53 (d, J=8.0 Hz, 1H), 7.44 (d, J=8.0 Hz, 2H), 7.36 (d, J=10.0 Hz, 1H), 7.14 (dd, J=5.2, 7.6 Hz, 1H), 4.31 (t, J=7.6 Hz, 2H), 3.21 (t, J=7.6 Hz, 2H), 2.26 (s, 3H).

Example 95

2-((3-methyl-1,2,4-oxadiazol-5-yl)methyl)-6-(4-(2,2,2-trifluoroethoxy)phenyl)-[1,2,4]triazolo[4,3-a]pyridin-3(2H)-one (Compound 83)

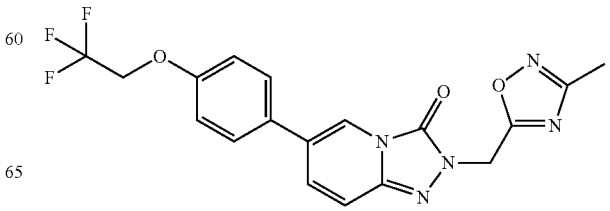

133

-continued

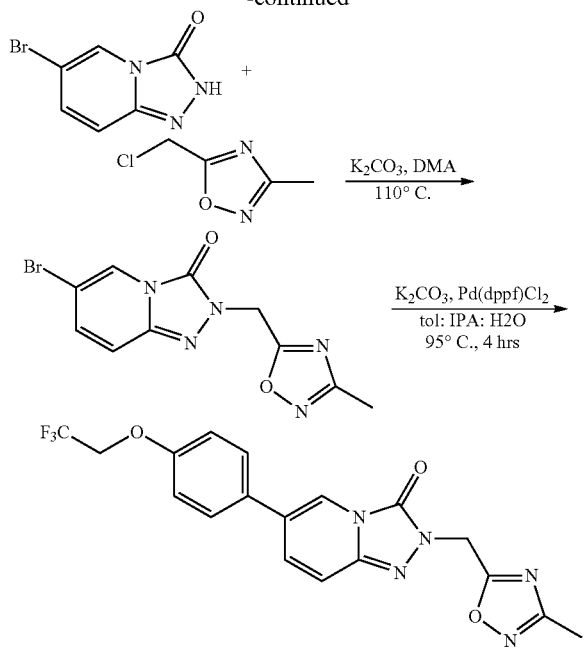

This compound was synthesized using the same experimental conditions as Example 1, but the order of steps are reversed. As a consequence of the triazolone having already undergone alkylation, the subsequent Suzuki reaction usually occurs much faster. $C_{18}H_{14}F_3N_5O_3$, m/z (ESI)=406.0 [M+H]$^+$.

Example 96

2-(3-(4,5-dichloro-2-methoxyphenoxy)-2-hydroxypropyl)-6-(4-(trifluoromethyl)phenyl)-[1,2,4]triazolo[4,3-a]pyridin-3(2H)-one (Compound 198)

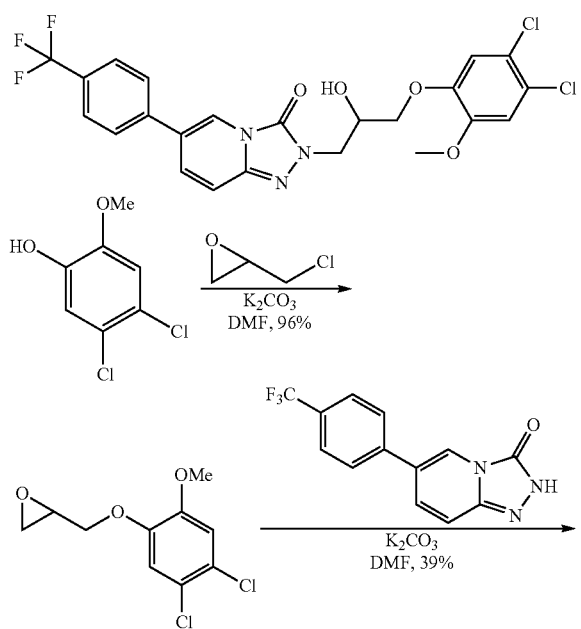

134

-continued

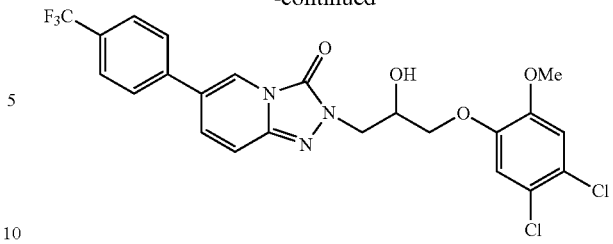

4,5-dichloro-2-methoxyphenol (200.0 mg, 1.036 mmol), epichlorohydrin (958.6 mg, 10.36 mmol, 10 equiv.) and $K_2CO_3$ (1.43 g, 10.36 mmol, 10 equiv.) were placed in a 50 mL round bottomed flask under a nitrogen atmosphere. To the flask were added DMF (3 mL) at ambient temperature. The mixture was heated at 70° C. for 16 hour. To the mixture was added water (30 mL). And then the whole was extracted with EtOAc (30 mL×3). Combined organic layers were washed with brine and dried over $Na_2SO_4$. The solvent was removed under a reduced pressure. Crude product (2-((4,5-dichloro-2-methoxyphenoxy)methyl)oxirane, 248.7 mg, 0.998 mmol, 96.4%) was used for the subsequent step without further purification. 6-(4-(trifluoromethyl)phenyl)-[1,2,4]triazolo[4,3-a]pyridin-3(2H)-one (47.2 mg, 0.169 mmol), 2-((4,5-dichloro-2-methoxyphenoxy)methyl)oxirane (50.5 mg, 0.2028 mmol, 1.2 equiv.) and $K_2CO_3$ (46.8 mg, 0.339 mmol, 2.0 equiv.) were placed in a 50 mL round bottomed flask under a nitrogen atmosphere. To the flask were added DMF (3 mL) at ambient temperature. The mixture was heated at 80° C. for 1 hour. The mixture was filtered through Celite and the filtrate was injected to preparative HPLC to give compound 198 as a colorless oil (24.3 mg, 0.0460 mmol, 27.2%). LCMS (EI: 70 eV) 552 (M$^+$+2+Na), 551 (M$^+$+1+Na), 550 (M$^+$+Na), 530 (M$^+$+2), 529 (M$^+$+1), 528 (M$^+$).

Example 97

2-((2-cyclopropyloxazol-4-yl)methyl)-6-(4-(trifluoromethoxy)phenyl)-[1,2,4]triazolo[4,3-a]pyridin-3(2H)-one (Compound 181)

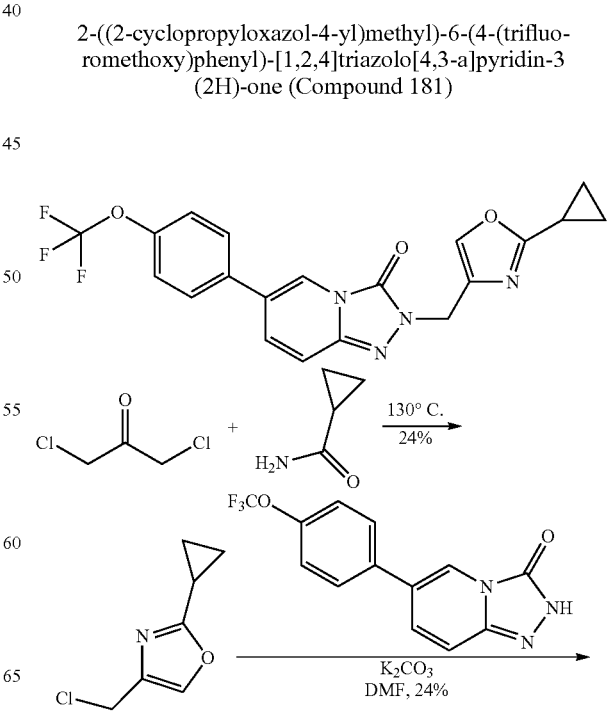

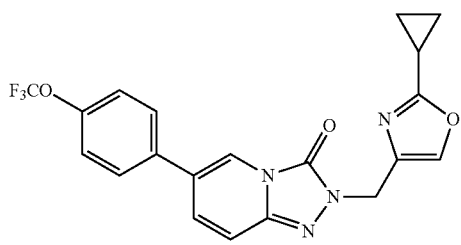

Dichloroacetone (1.0 g, 7.876 mmol) and acetamide (670.2 mg, 7.876 mmol, 1 equiv.) were placed in a 50 mL round bottomed flask. The mixture was heated at 130° C. for 1 h. The mixture was dissolved in DMF and loaded onto silica-gel column chromatography ($SiO_2$=25 g, AcOEt:hexane=1:3) for purification. The chromatography gave the desired oxazole as a colorless oil (4-(chloromethyl)-2-cyclopropyloxazole, 297.9 mg, 1.890 mmol, 24.0%). 6-(4-(trifluoromethoxy)phenyl)-[1,2,4]triazolo[4,3-a]pyridin-3(2H)-one (50.0 mg, 0.169 mmol), 4-(chloromethyl)-2-cyclopropyloxazole (40.0 mg, 0.2535 mmol, 1.5 equiv.), $K_2CO_3$ (46.7 mg, 0.338 mmol, 2 equiv.) and NaI (25.3 mg, 0.169 mmol, 1.0 equiv.) were placed in a 50 mL round bottomed flask. The mixture was heated at 80° C. for 1 h. The mixture was filtered through a piece of cotton and then injected into preparative HPLC. The purification gave compound 194 as a colorless crystals (17.2 mg, 0.0413 mmol, 24.4%). LCMS (EI: 70 eV) 417 ($M^+$+1)

Example 98

2-((5-methyloxazol-2-yl)methyl)-6-(4-(trifluoromethyl)phenyl)-[1,2,4]triazolo[4,3-a]pyridin-3(2H)-one (Compound 172)

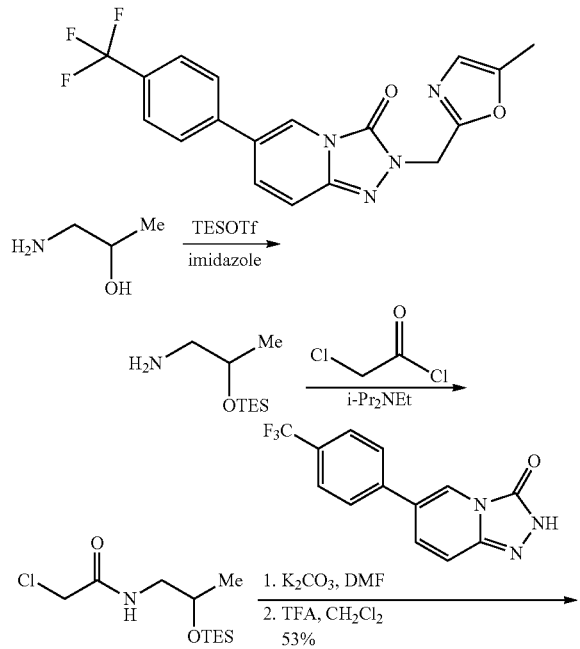

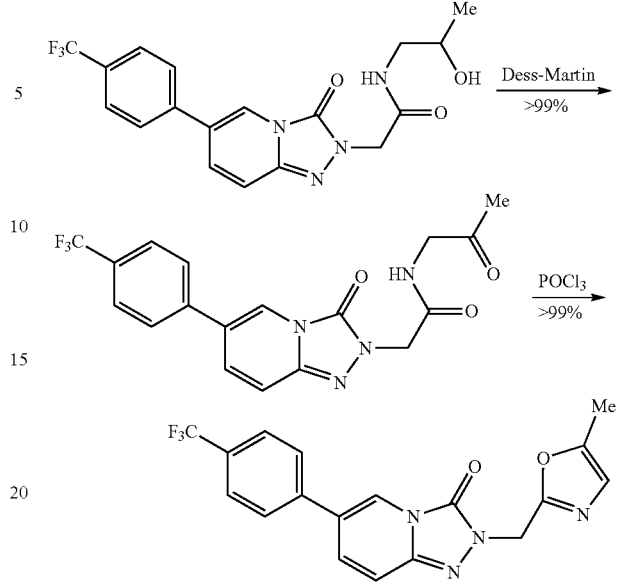

In a 50 mL round bottomed flask, 1-methyl-2-aminoethanol (500.0 mg, 6.66 mmol) and imidazole (498.8 mg, 7.326 mmol, 1.1 equiv.) were dissolved in THF (3 mL). The mixture was cooled down to −78° C. and then TESOTf (1.76 g, 6.66 mmol, 1.0 equiv.) was added at the same temperature. The mixture was allowed to warm to room temperature. After stirring for 1 h, water (30 mL) was added to the mixture and the whole was extracted with EtOAc (30 mL×3). Combined organic layers were washed with brine (30 mL) and dried over $Na_2SO_4$. The solvent was removed under a reduced pressure to give the O-silylated aminoalcohol as a colorless oil (2-(triethylsilyloxy)propan-1-amine, 2.34 g). Obtained product was immediately used for the subsequent step.

2-(Triethylsilyloxy)propan-1-amine (6.66 mmol) and i-$Pr_2$NEt (2.58 g, 19.98 mmol, 3.0 equiv.) were dissolved in $CH_2Cl_2$ (10 mL) in a 50 mL round bottomed flask. To the mixture was added a solution of chroloacetyl chloride (1.5 g, 13.32 mmol, 2.0 equiv.) in $CH_2Cl_2$ (5 mL) at 0° C. After stirring for 20 min, water (30 mL) was added to the mixture and the whole was extracted with EtOAc (30 mL×3). Combined organic layers were washed with brine (30 mL) and dried over $Na_2SO_4$. The solvent was removed under a reduced pressure to give a crude product as a brown oil (8.39 g). The crude product was purified by a column chromatography ($SiO_2$=80 g, EtOAc/hexane=1:7 to 1:3, Rf=0.35). The fractions containing the desired product were concentrated by rotary evaporator to give the desired product as a light brown oil (2-chloro-N-(2-(triethylsilyloxy)propyl)acetamide, 859.4 mg).

6-(4-(Trifluoromethyl)phenyl)-[1,2,4]triazolo[4,3-a]pyridin-3(2H)-one (99.0 mg, 0.355 mmol) and $K_2CO_3$ (98.1 mg, 0.71 mmol, 2.0 equiv.) were placed in a 50 mL round bottomed flank. To the mixture was added a solution of 2-chloro-N-(2-(triethylsilyloxy)propyl)acetamide (94.4 mg, 0.355 mg, 1.0 equiv.) in DMF (3 mL) at room temperature. The mixture was stirred at room temperature for 1 h and then 80° C. for 1 h. To the mixture was added water (30 mL) and the whole was extracted with EtOAc (30 mL×3). Combined organic layers were washed with brine (30 mL) and dried over $Na_2SO_4$. The solvent was removed under a reduced pressure to give a crude product as a brown oil and solid (252.0 mg). The crude product was then treated with TFA (0.5 mL) in $CH_2Cl_2$ (5 mL) at room temperature for 1 h. The solvent and the reagent were removed under a reduced pressure. To obtained mixture was added $CH_2Cl_2$ (5 mL) to form a suspension. The suspension was filtered through a glass filter. The crystals on the filter was collected (N-(2-hydroxypropyl)-2-(3-oxo-6-(4-(trifluoromethyl)phenyl)-[1,2,4]triazolo[4,3-a]pyridin-2(3H)-yl)acetamide, light brown powder, 73.6 mg, 0.187 mmol, 52.6%). LCMS (EI: 70 eV) 417 (M$^+$+Na), 395 (M$^+$+1).

N-(2-Hydroxypropyl)-2-(3-oxo-6-(4-(trifluoromethyl)phenyl)-[1,2,4]triazolo[4,3-a]pyridin-2(3H)-yl)acetamide (30.0 mg, 0.0761 mmol) was treated with Dess-Martin periodinane (64.6 mg, 0.1522 mmol, 2.0 equiv.) in THF (2 mL) at room temperature in a 50 mL round bottomed flask. After stirring for 1 h, water (30 mL) was added and the whole was extracted with EtOAc (30 mL×3). Combined organic layers were washed with sat. Na$_2$S$_2$O$_3$ aq. solution (30 mL), sat. NaHCO$_3$ aq. solution (30 mL) and brine (30 mL) successively. The organic layer was dried over Na$_2$SO$_4$. The solvent was removed under a reduced pressure to give the desired product as colorless crystals (2-(3-oxo-6-(4-(trifluoromethyl)phenyl)-[1,2,4]triazolo[4,3-a]pyridin-2(3H)-yl)-N-(2-oxopropyl)acetamide, 30.3 mg, 0.077 mmol, >99%). LCMS (EI: 70 eV) 415 (M$^+$+Na), 393 (M$^+$+1).

2-(3-oxo-6-(4-(trifluoromethyl)phenyl)-[1,2,4]triazolo[4,3-a]pyridin-2(3H)-yl)-N-(2-oxopropyl)acetamide was dissolved in POCl$_3$ (3 mL) in a 50 mL round bottomed flask. The mixture was heated at 70-90° C. for 2 h and then 100° C. for 15 h. After removal of POCl$_3$ under a reduced pressure, obtained residue was quenched with sat. NaHCO$_3$ aq. solution (30 mL). The whole was extracted with EtOAc (30 mL×3). Combined organic layers were washed with brine (30 mL) and dried over Na$_2$SO$_4$. The solvent was removed under a reduced pressure to give compound 172 as pink crystals, 30.3 mg, 0.0756 mmol, >99%). LCMS (EI: 70 eV) 397 (M$^+$+Na), 375 (M$^+$+1).

The following Examples 99-101 were prepared using the procedures described herein.

Example 99

2-((4-cyclopropyloxazol-2-yl)methyl)-6-(4-(trifluoromethyl)phenyl)-[1,2,4]triazolo[4,3-a]pyridin-3(2H)-one (Compound 194)

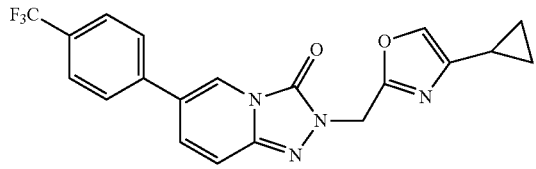 [SMILES: O=c1n(Cc2nc(C3CC3)co2)nc2ccc(-c3ccc(C(F)(F)F)cc3)cn12]

LCMS (EI: 70 eV) 423 (M$^+$+Na), 401 (M$^+$+1).

Example 100

2-((4-cyclopropyloxazol-2-yl)methyl)-6-(4-(trifluoromethoxy)phenyl)-[1,2,4]triazolo[4,3-a]pyridin-3(2H)-one (Compound 193)

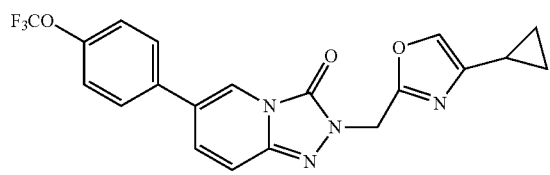 [SMILES: O=c1n(Cc2nc(C3CC3)co2)nc2ccc(-c3ccc(OC(F)(F)F)cc3)cn12]

LCMS (EI: 70 eV) 440 (M$^+$+Na), 417 (M$^+$+1).

Example 101

2-((4-cyclopropyloxazol-2-yl)methyl)-6-(4-(trifluoromethoxy)phenyl)-[1,2,4]triazolo[4,3-a]pyridin-3(2H)-one (Compound 199)

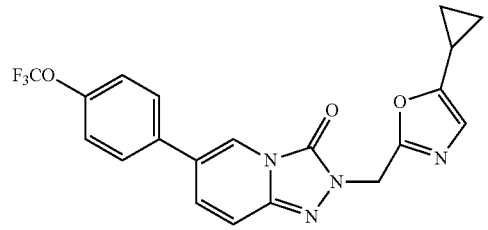 [SMILES: O=c1n(Cc2ncc(C3CC3)o2)nc2ccc(-c3ccc(OC(F)(F)F)cc3)cn12]

LCMS (EI: 70 eV) 440 (M$^+$+Na), 417 (M$^+$+1).

Example 102

(2-(2,6-difluorophenethyl)-6-(4-(trifluoromethoxy)phenyl)-[1,2,4]triazolo[4,3-a]pyridin-3(2H)-one (Compound 63)

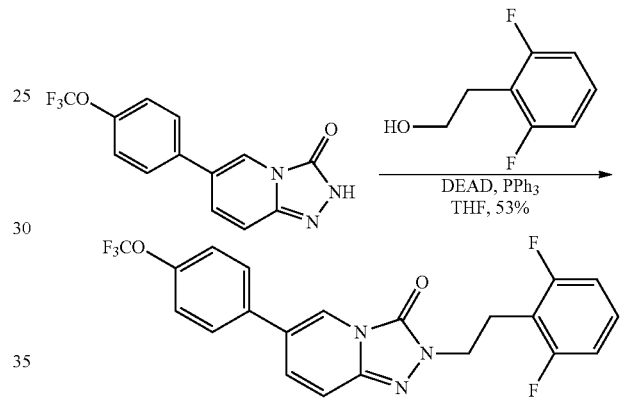

6-(4-(Trifluoromethoxy)phenyl)-[1,2,4]triazolo[4,3-a]pyridin-3(2H)-one (50.0 mg, 0.169 mmol), 2-(2,6-difluorophenyl)ethanol (40.1 mg, 0.2535 mmol, 1.5 equiv.) and PPh$_3$ (66.5 mg, 0.2535 mmol, 1.5 equiv.) were dissolved in THF (3 mL) under nitrogen atmosphere in a 50 mL round bottomed flask. This mixture was treated with diethyl azodicarboxylate (40% toluene solution, d=0.956, 0.12 mL, 0.2535 mmol, 1.5 equiv.) at room temperature. After stirring for 5 h, the mixture was directly loaded onto preparative HPLC. The HPLC purification gave compound 63 as colorless crystals (38.6 mg, 0.0887 mmol, 52.5%). LCMS (EI: 70 eV) 458 (M$^+$+Na), 436 (M$^+$+1). FTIR (ATR) 1701 (O=C).

Example 103

2-(2,4-difluorophenethyl)-6-(4-(trifluoromethoxy)phenyl)-[1,2,4]triazolo-[4,3-a]pyridin-3(2H)-one (Compound 78)

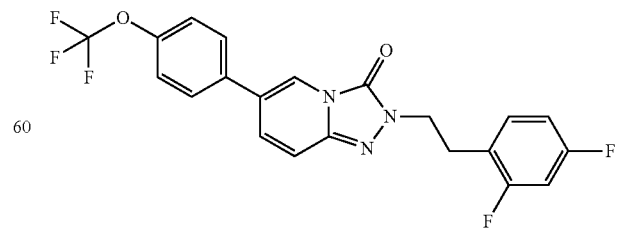

LCMS (EI: 70 eV) 436 (M$^+$+1), 458 (M$^+$+Na). FTIR (ATR) 1717 (C=O).

Example 104

2-(3-(4-fluorophenyl)propyl)-6-(4-(trifluoromethoxy)phenyl)[1,2,4]triazolo-[4,3-a]pyridin-3(2H)-one (Compound 76)

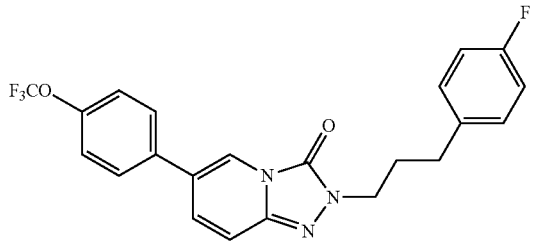 [SMILES: O=c1n(CCCc2ccc(F)cc2)nc2ccc(-c3ccc(OC(F)(F)F)cc3)cn12]

LCMS (EI: 70 eV) 431 (M$^+$+1), 453 (M$^+$+Na). FTIR (ATR) 1713 (C=O).

Example 105

2-(3-(3-bromo-4-fluorophenyl)propyl)-6-(4-(trifluoromethoxy)phenyl)-[1,2,4]triazolo[4,3-a]pyridin-3(2H)-one (Compound 64)

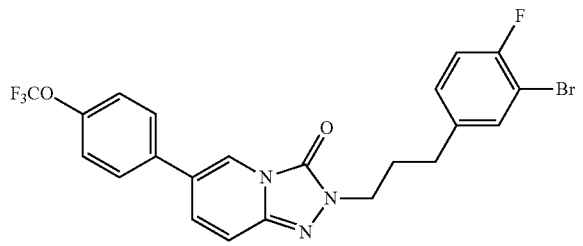 [SMILES: O=c1n(CCCc2ccc(F)c(Br)c2)nc2ccc(-c3ccc(OC(F)(F)F)cc3)cn12]

LCMS (EI: 70 eV) 510 (M+), 512 (M++2), 532 (M++Na−1), 534 (M++Na+1). FTIR (ATR) 1707 (C=O).

Example 106

2-(3-(4-fluoro-3-(pyridin-3-yl)phenyl)propyl)-6-(4-(trifluoromethoxy)phenyl)-[1,2,4]triazolo[4,3-a]pyridin-3(2H)-one (Compound 121)

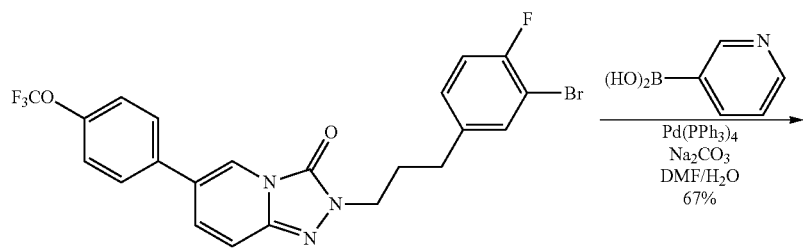

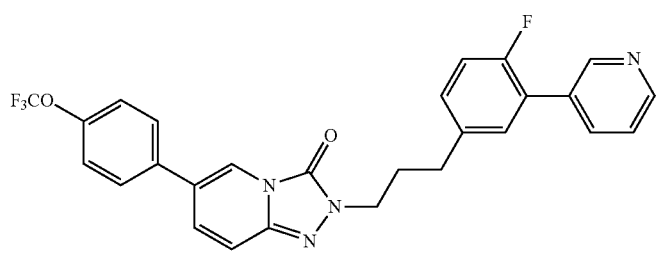

Compound 64 (70.0 mg, 0.137 mmol), 3-pyridineboronic acid (25.3 mg, 0.2055 mmol, 1.5 equiv.) and Pd(PPh$_3$)$_4$ (7.9 mg, 0.00685 mmol, 0.05 equiv.) were placed in a 2-5 mL Smith process vial. Under a nitrogen atmosphere, DMF (4 mL) and 2M-Na$_2$CO$_3$ (1 mL) were added to the mixture. The reaction mixture was heated at 160° C. for 10 min using microwave reactor (Biotage, Optimizer). After heating, the mixture was filtered through Celite (3 g) using EtOAc (70 mL). Obtained filtrate was washed with brine (30 mL) and dried over Na$_2$SO$_4$. The solvent was removed under a reduced pressure to give a crude product. The crude product was purified by a column chromatography (SiO$_2$=25 g, EtOAc/hexane=1:1 to straight EtOAc). The fractions containing the desired product were concentrated by rotary evaporator to give compound 121 as a colorless oil (46.7 mg, 0.0918 mmol, 67.0%). LCMS (EI: 70 eV) 509 (M$^+$+1), 531 (M$^+$+Na). FTIR (ATR) 1703 (C=O).

Example 107

2-(3-(4-fluoro-3-(oxazol-2-yl)phenyl)propyl)-6-(4-(trifluoromethoxy)-phenyl)[1,2,4]triazolo[4,3-a]pyridin-3(2H)-one (Compound 119)

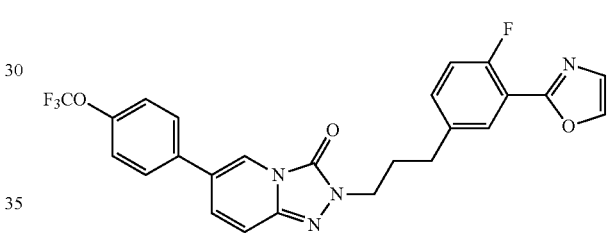

LCMS (EI: 70 eV) 499 (M$^+$+1), 531 (M$^+$+Na).

The following Examples 108-196 were synthesized using the procedures described herein.

Example 108

2-((4-methyl-1,2,5-oxadiazol-3-yl)methyl)-6-(4-(trifluoromethoxy)phenyl)-[1,2,4]triazolo[4,3-a]pyridin-3(2H)-one (Compound 2)

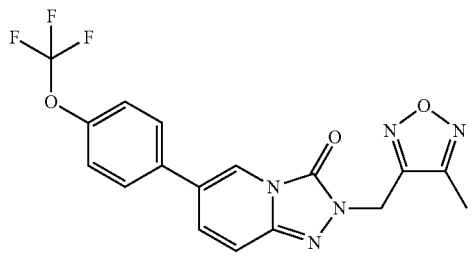 [SMILES: Cc1nonc1Cn1nc2ccc(-c3ccc(OC(F)(F)F)cc3)cn2c1=O]

Example 109

2-((5-methyl-1,2,4-oxadiazol-3-yl)methyl)-6-(4-(trifluoromethoxy)phenyl)-[1,2,4]triazolo[4,3-a]pyridin-3(2H)-one (Compound 3)

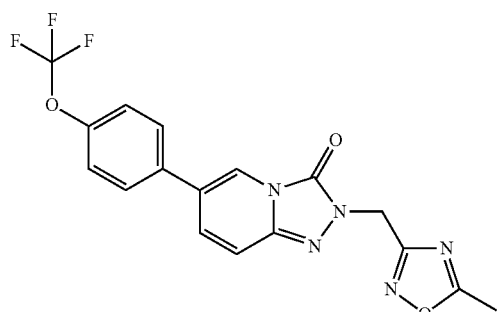

Example 110

2-((5-methylisoxazol-3-yl)methyl)-6-(4-(trifluoromethoxy)phenyl)-[1,2,4]triazolo[4,3-a]pyridin-3(2H)-one (Compound 5)

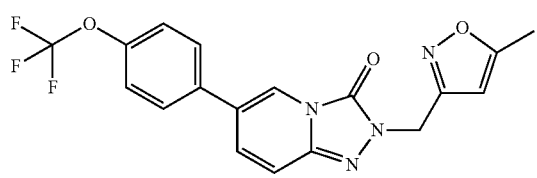 [SMILES: Cc1cc(Cn2nc3ccc(-c4ccc(OC(F)(F)F)cc4)cn3c2=O)no1]

Example 111

2-((3,5-dimethylisoxazol-4-yl)methyl)-6-(4-(trifluoromethoxy)phenyl)-[1,2,4]triazolo[4,3-a]pyridin-3(2H)-one (Compound 6)

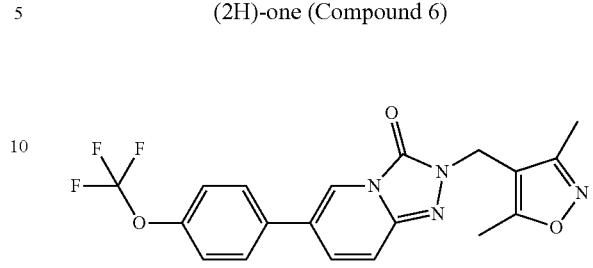

Example 112

6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one (Compound 7)

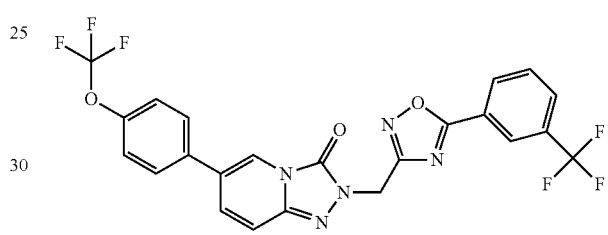

Example 113

2-(3-(5-methyl-1,2,4-oxadiazol-3-yl)benzyl)-6-(4-(trifluoromethoxy)phenyl)-[1,2,4]triazolo[4,3-a]pyridin-3(2H)-one (Compound 8)

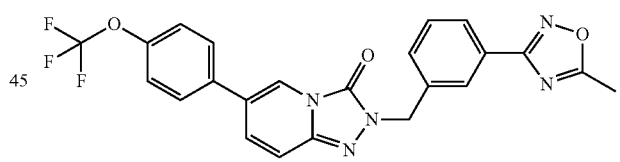

Example 114

2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one (Compound 9)

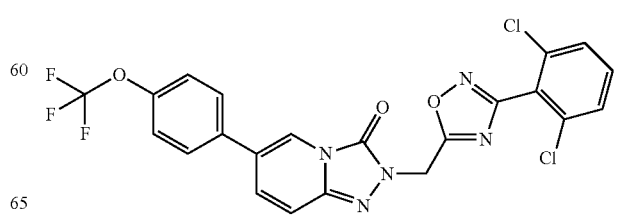

Example 115

2-(benzo[c][1,2,5]oxadiazol-5-ylmethyl)-6-(4-(trifluoromethoxy)phenyl)-[1,2,4]triazolo[4,3-a]pyridin-3(2H)-one (Compound 10)

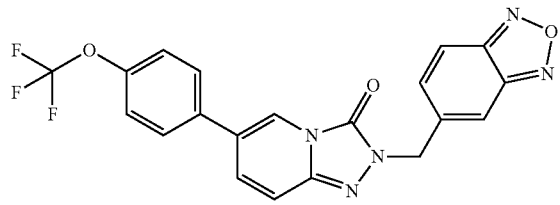 [SMILES: O=c1n(Cc2ccc3nonc3c2)nc2ccc(-c3ccc(OC(F)(F)F)cc3)cn12]

Example 116

2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one (Compound 11)

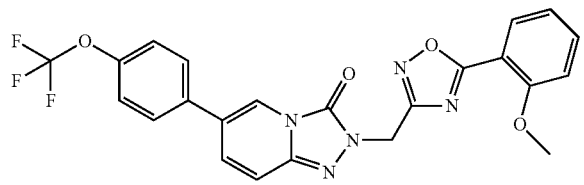 [SMILES: COc1ccccc1-c1nc(Cn2nc3ccc(-c4ccc(OC(F)(F)F)cc4)cn3c2=O)no1]

Example 117

2-(4-(trifluoromethoxy)benzyl)-6-(4-(trifluoromethoxy)phenyl)-[1,2,4]triazolo[4,3-a]pyridin-3(2H)-one (Compound 12)

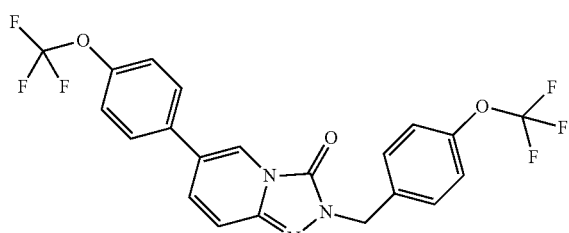

Example 118

2-(quinolin-2-ylmethyl)-6-(4-(trifluoromethoxy)phenyl)-[1,2,4]triazolo[4,3-a]pyridin-3(2H)-one (Compound 13)

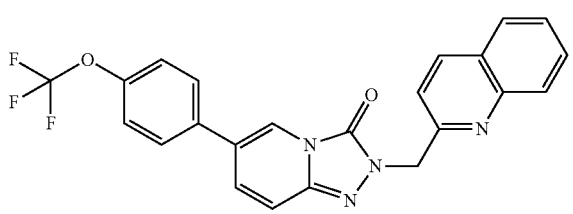 [SMILES: O=c1n(Cc2ccc3ccccc3n2)nc2ccc(-c3ccc(OC(F)(F)F)cc3)cn12]

Example 119

2-(1-(3-ethyl-1,2,4-oxadiazol-5-yl)ethyl)-6-(4-(trifluoromethoxy)phenyl)-[1,2,4]triazolo[4,3-a]pyridin-3(2H)-one (Compound 14)

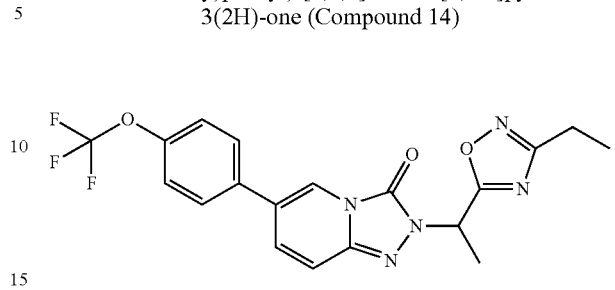

Example 120

2-((3-ethyl-1,2,4-oxadiazol-5-yl)methyl)-6-(4-(trifluoromethoxy)phenyl)-[1,2,4]triazolo[4,3-a]pyridin-3(2H)-one (Compound 15)

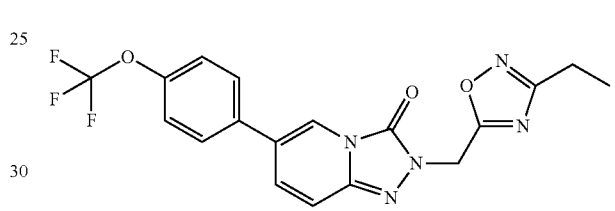

Example 121

2-((4-phenyl-1,2,5-oxadiazol-3-yl)methyl)-6-(4-(trifluoromethoxy)phenyl)-[1,2,4]triazolo[4,3-a]pyridin-3(2H)-one (Compound 17)

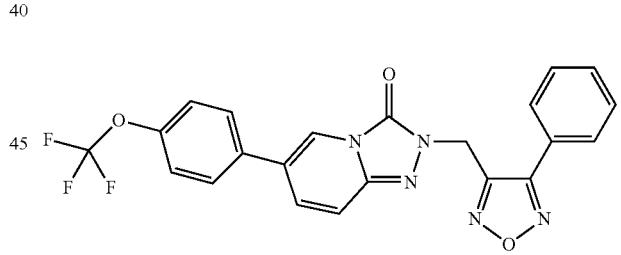

Example 122

2-((5-methyl-1,3,4-oxadiazol-2-yl)methyl)-6-(4-(trifluoromethoxy)phenyl)-[1,2,4]triazolo[4,3-a]pyridin-3(2H)-one (Compound 18)

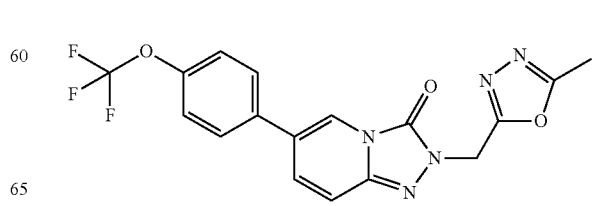

Example 123

2-(benzo[d]thiazol-2-ylmethyl)-6-(4-(trifluoromethoxy)phenyl)-[1,2,4]triazolo[4,3-a]pyridin-3(2H)-one (Compound 20)

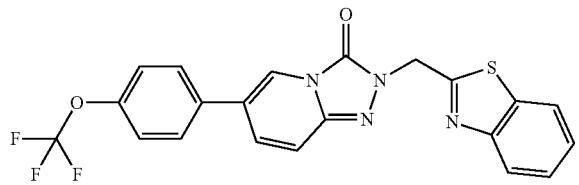 [SMILES: O=c1n(Cc2nc3ccccc3s2)nc2ccc(-c3ccc(OC(F)(F)F)cc3)cn12]

Example 124

2-((5-methyl-2-phenyloxazol-4-yl)methyl)-6-(4-(trifluoromethoxy)phenyl)-[1,2,4]triazolo[4,3-a]pyridin-3(2H)-one (Compound 21)

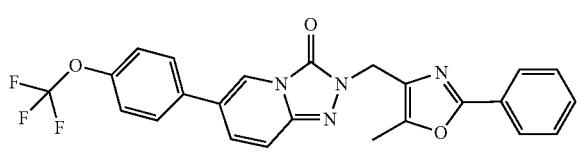 [SMILES: Cc1oc(-c2ccccc2)nc1Cn1nc2ccc(-c3ccc(OC(F)(F)F)cc3)cn2c1=O]

Example 125

2-(3-phenoxypropyl)-6-(4-(trifluoromethoxy)phenyl)-[1,2,4]triazolo[4,3-a]pyridin-3(2H)-one (Compound 24)

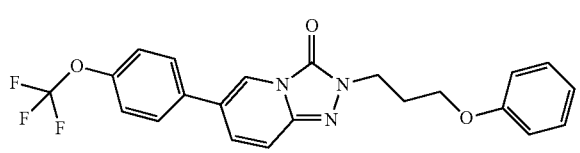 [SMILES: O=c1n(CCCOc2ccccc2)nc2ccc(-c3ccc(OC(F)(F)F)cc3)cn12]

Example 126

2-((1,2,4-oxadiazol-3-yl)methyl)-6-(4-(trifluoromethoxy)phenyl)-[1,2,4]triazolo[4,3-a]pyridin-3(2H)-one (Compound 27)

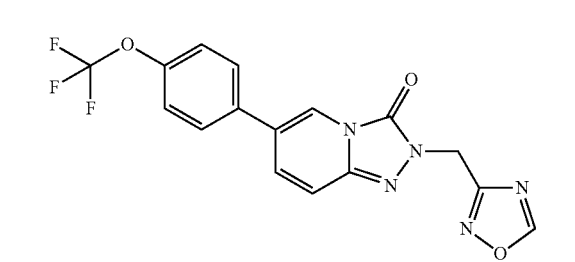 [SMILES: O=c1n(Cc2ncon2)nc2ccc(-c3ccc(OC(F)(F)F)cc3)cn12]

Example 127

2-(2-phenoxyethyl)-6-(4-(trifluoromethoxy)phenyl)[1,2,4]triazolo[4,3-a]pyridin-3(2H)-one (Compound 28)

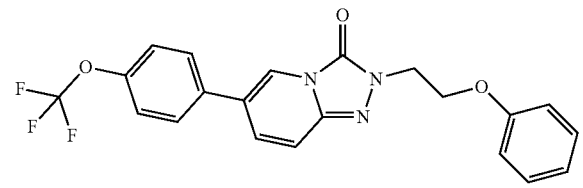 [SMILES: O=c1n(CCOc2ccccc2)nc2ccc(-c3ccc(OC(F)(F)F)cc3)cn12]

Example 128

2-((3-benzyl-1,2,4-oxadiazol-5-yl)methyl)-6-(4-(trifluoromethoxy)phenyl)-[1,2,4]triazolo[4,3-a]pyridin-3(2H)-one (Compound 29)

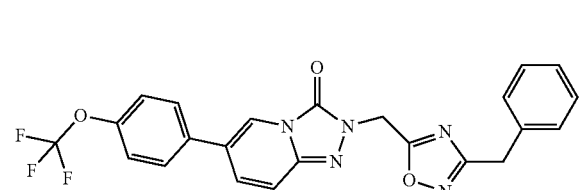

Example 129

5-methoxy-2-((3-methyl-1,2,4-oxadiazol-5-yl)methyl)-6-(4-(trifluoromethoxy)phenyl)-[1,2,4]triazolo[4,3-a]pyridin-3(2H)-one (Compound 30)

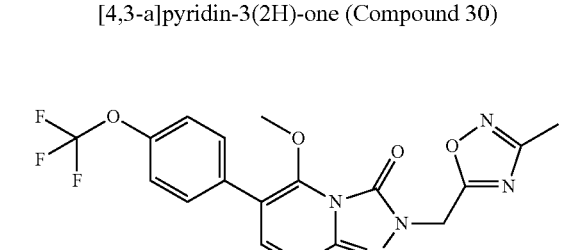

Example 130

2-((5-methyl-1,2,4-oxadiazol-3-yl)methyl)-6-(3-phenoxyphenyl)-[1,2,4]triazolo[4,3-a]pyridin-3(2H)-one (Compound 31)

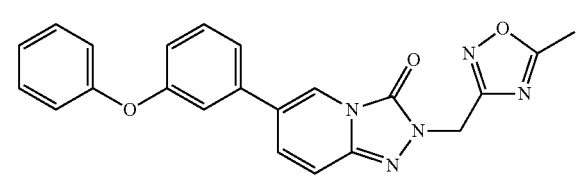 [SMILES: Cc1nc(Cn2nc3ccc(-c4cccc(Oc5ccccc5)c4)cn3c2=O)no1]

Example 131

6-(4-(4-chlorophenoxy)phenyl)-2-((5-methyl-1,2,4-oxadiazol-3-yl)methyl)-[1,2,4]triazolo[4,3-a]pyridin-3(2H)-one (Compound 32)

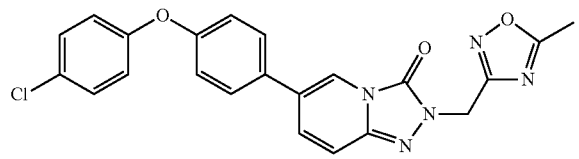 [SMILES: Cc1nc(Cn2nc3ccc(-c4ccc(Oc5ccc(Cl)cc5)cc4)cn3c2=O)no1]

Example 132

2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one (Compound 33)

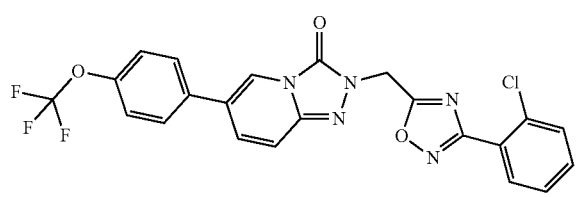 [SMILES: O=c1n(Cc2nc(-c3ccccc3Cl)no2)nc2ccc(-c3ccc(OC(F)(F)F)cc3)cn12]

Example 133

2-(3-(2-methoxyphenoxy)propyl)-6-(4-(trifluoromethoxy)phenyl)-[1,2,4]triazolo[4,3-a]pyridin-3(2H)-one (Compound 37)

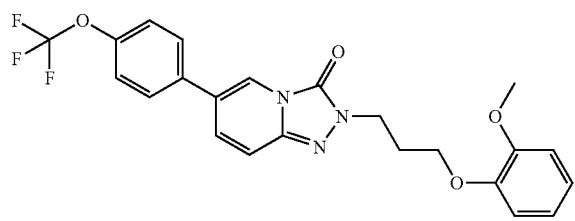 [SMILES: COc1ccccc1OCCCn1nc2ccc(-c3ccc(OC(F)(F)F)cc3)cn2c1=O]

Example 134

2-(3-(4-chlorophenoxy)-2-hydroxypropyl)-6-(4-(trifluoromethoxy)phenyl)-[1,2,4]triazolo[4,3-a]pyridin-3(2H)-one (Compound 38)

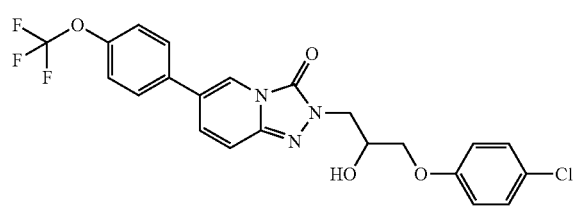 [SMILES: O=c1n(CC(O)COc2ccc(Cl)cc2)nc2ccc(-c3ccc(OC(F)(F)F)cc3)cn12]

Example 135

2-(2-(3-phenoxypyrrolidin-1-yl)ethyl)-6-(4-(trifluoromethoxy)phenyl)-[1,2,4]triazolo[4,3-a]pyridin-3(2H)-one (Compound 39)

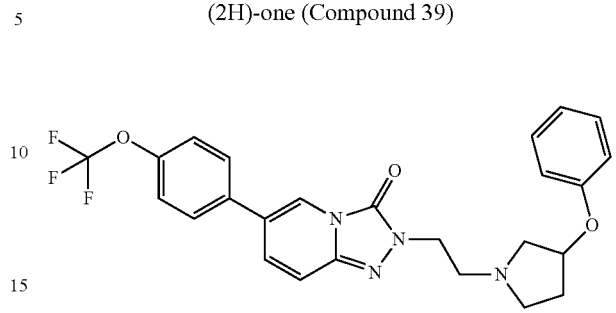

Example 136

2-(2-(4-chlorophenoxy)ethyl)-6-(4-(trifluoromethoxy)phenyl)-[1,2,4]triazolo[4,3-a]pyridin-3(2H)-one (Compound 40)

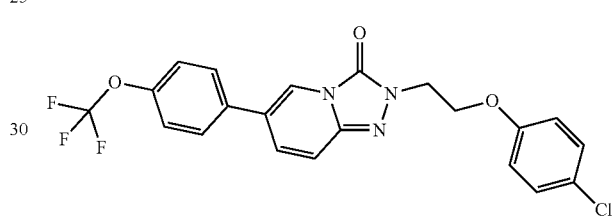

Example 137

2-(2-hydroxy-3-phenoxypropyl)-6-(4-(trifluoromethoxy)phenyl)-[1,2,4]triazolo[4,3-a]pyridin-3(2H)-one (Compound 43)

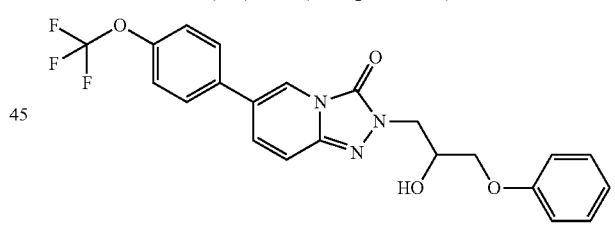

Example 138

2-(2-(2,6-dimethylphenoxy)ethyl)-6-(4-(trifluoromethoxy)phenyl)-[1,2,4]triazolo[4,3-a]pyridin-3(2H)-one (Compound 44)

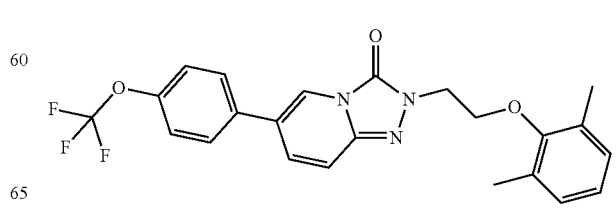

Example 139

2-(2-(2-chlorophenoxy)ethyl)-6-(4-(trifluoromethoxy)phenyl)-[1,2,4]triazolo[4,3-a]pyridin-3(2H)-one (Compound 46)

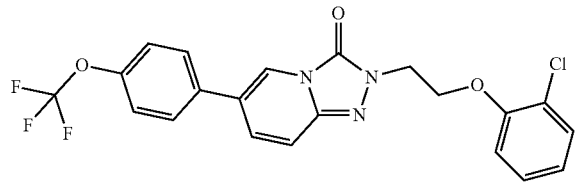 [SMILES: O=c1n(CCOc2ccccc2Cl)nc2ccc(-c3ccc(OC(F)(F)F)cc3)cn12]

Example 140

6-(4-(trifluoromethoxy)phenyl)-2-(2-(3-(trifluoromethyl)pyridin-2-yloxy)ethyl)-[1,2,4]triazolo[4,3-a]pyridin-3(2H)-one (Compound 47)

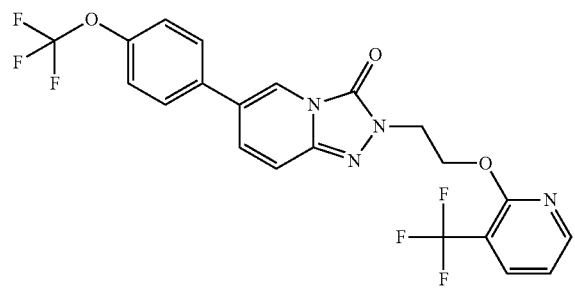 [SMILES: O=c1n(CCOc2ncccc2C(F)(F)F)nc2ccc(-c3ccc(OC(F)(F)F)cc3)cn12]

Example 141

2-(2-(pyridin-2-yloxy)ethyl)-6-(4-(trifluoromethoxy)phenyl)-[1,2,4]triazolo[4,3-a]pyridin-3(2H)-one (Compound 49)

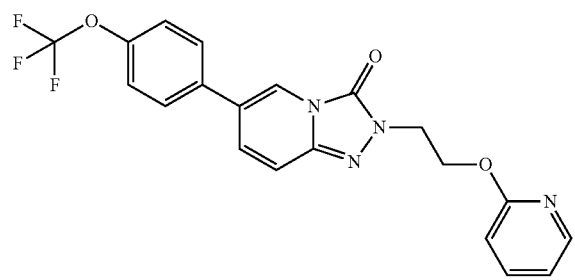 [SMILES: O=c1n(CCOc2ccccn2)nc2ccc(-c3ccc(OC(F)(F)F)cc3)cn12]

Example 142

2-(2-(4,4-difluoropiperidin-1-yl)ethyl)-6-(4-(trifluoromethoxy)phenyl)-[1,2,4]triazolo[4,3-a]pyridin-3(2H)-one (Compound 50)

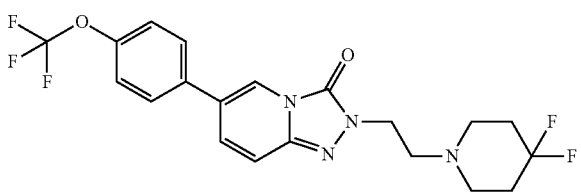 [SMILES: O=c1n(CCN2CCC(F)(F)CC2)nc2ccc(-c3ccc(OC(F)(F)F)cc3)cn12]

Example 143

2-(3-(2-fluorophenoxy)propyl)-6-(4-(trifluoromethoxy)phenyl)-[1,2,4]triazolo[4,3-a]pyridin-3(2H)-one (Compound 51)

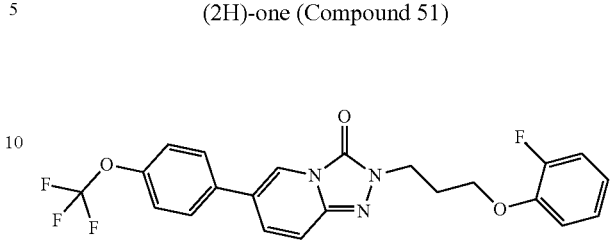

Example 144

2-(3-(2-chlorophenoxy)propyl)-6-(4-(trifluoromethoxy)phenyl)-[1,2,4]triazolo[4,3-a]pyridin-3(2H)-one (Compound 52)

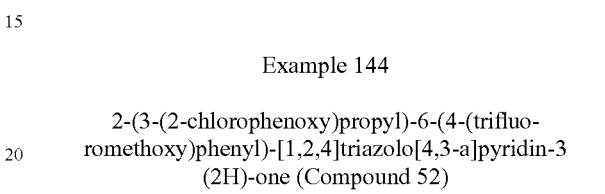

Example 145

6-(4-(4-chlorophenoxy)phenyl)-2-((3-methyl-1,2,4-oxadiazol-5-yl)methyl)-[1,2,4]triazolo[4,3-a]pyridin-3(2H)-one (Compound 53)

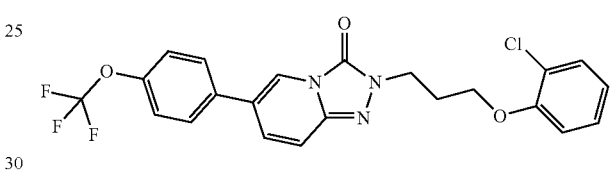

Example 146

2-(2-(3-chlorophenoxy)ethyl)-6-(4-(trifluoromethoxy)phenyl)-[1,2,4]triazolo[4,3-a]pyridin-3(2H)-one (Compound 54)

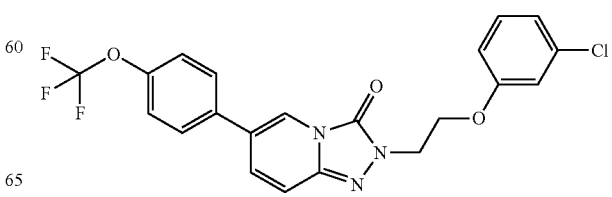

Example 147

2-(2-(4-fluorophenoxy)ethyl)-6-(4-(trifluoromethoxy)phenyl)-[1,2,4]triazolo[4,3-a]pyridin-3(2H)-one (Compound 55)

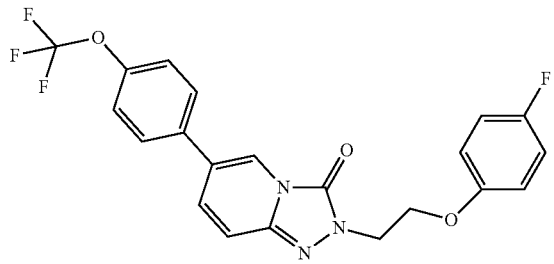 [SMILES: O=c1n(CCOc2ccc(F)cc2)nc2ccc(-c3ccc(OC(F)(F)F)cc3)cn12]

Example 148

2-(4-fluorophenethyl)-6-(4-(trifluoromethoxy)phenyl)-[1,2,4]triazolo[4,3-a]pyridin-3(2H)-one (Compound 59)

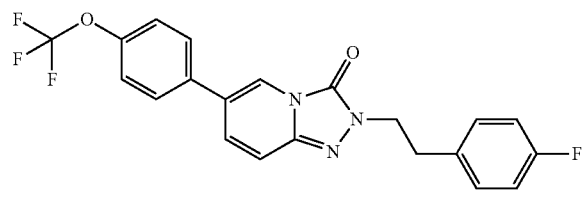 [SMILES: O=c1n(CCc2ccc(F)cc2)nc2ccc(-c3ccc(OC(F)(F)F)cc3)cn12]

Example 149

6-(4-(trifluoromethoxy)phenyl)-2-(2-(6-(trifluoromethyl)pyridin-2-yloxy)ethyl)-[1,2,4]triazolo[4,3-a]pyridin-3(2H)-one (Compound 65)

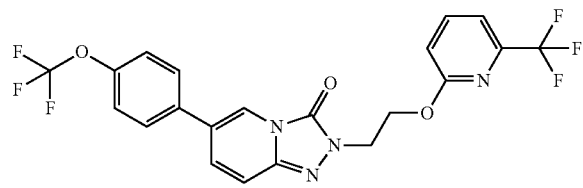 [SMILES: O=c1n(CCOc2cccc(C(F)(F)F)n2)nc2ccc(-c3ccc(OC(F)(F)F)cc3)cn12]

Example 150

6-(4-(trifluoromethoxy)phenyl)-2-(3-(2-(trifluoromethyl)phenoxy)propyl)-[1,2,4]triazolo[4,3-a]pyridin-3(2H)-one (Compound 66)

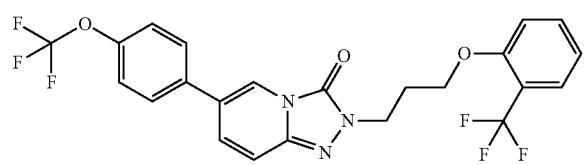 [SMILES: O=c1n(CCCOc2ccccc2C(F)(F)F)nc2ccc(-c3ccc(OC(F)(F)F)cc3)cn12]

Example 151

2-(3-(4-fluoro-2-methoxyphenoxy)propyl)-6-(4-(trifluoromethoxy)phenyl)-[1,2,4]triazolo[4,3-a]pyridin-3(2H)-one (Compound 67)

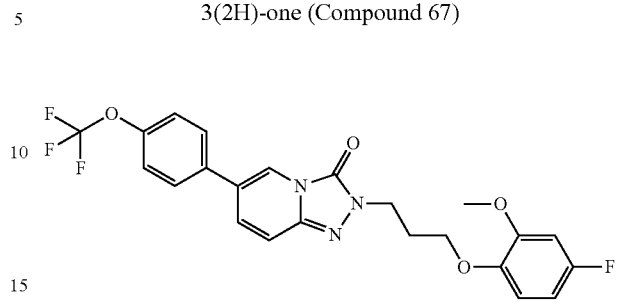

Example 152

=2-(2-(2-methoxyphenoxy)ethyl)-6-(4-(trifluoromethoxy)phenyl)-[1,2,4]triazolo[4,3-a]pyridin-3(2H)-one (Compound 69)

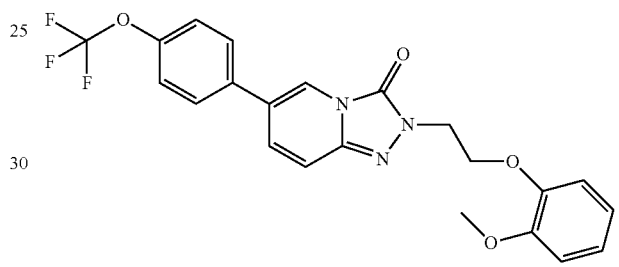

Example 153

2-(2-(3,3'-bipyridin-6-yl)ethyl)-6-(4-(trifluoromethoxy)phenyl)-[1,2,4]triazolo[4,3-a]pyridin-3(2H)-one (Compound 74)

Example 154

2-(3-(2-chlorophenoxy)-2-methoxypropyl)-6-(4-(trifluoromethoxy)phenyl)-[1,2,4]triazolo[4,3-a]pyridin-3(2H)-one (Compound 80)

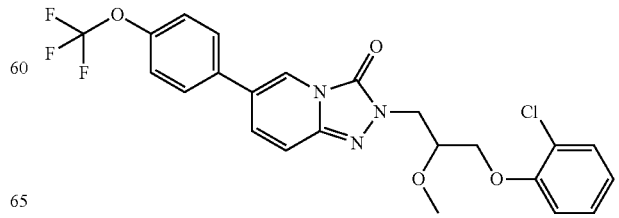

Example 155

2-(2-(2-(3-methyl-1,2,4-oxadiazol-5-yl)phenoxy)ethyl)-6-(4-(trifluoromethoxy)phenyl)-[1,2,4]triazolo[4,3-a]pyridin-3(2H)-one (Compound 84)

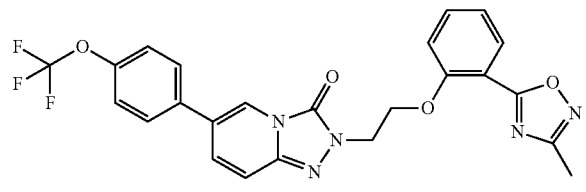 [SMILES: Cc1noc(-c2ccccc2OCCn2nc3ccc(-c4ccc(OC(F)(F)F)cc4)cn3c2=O)n1]

Example 156

2-(2-((5-methyl-1,2,4-oxadiazol-3-yl)methoxy)ethyl)-6-(4-(trifluoromethoxy)phenyl)-[1,2,4]triazolo[4,3-a]pyridin-3(2H)-one (Compound 86)

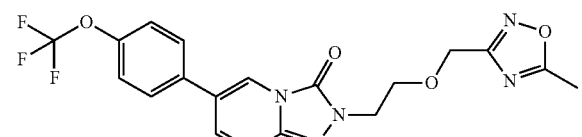

Example 157

2-(3-(2-chlorophenoxy)-2-(pyrimidin-2-yloxy)propyl)-6-(4-(trifluoromethoxy)phenyl)-[1,2,4]triazolo[4,3-a]pyridin-3(2H)-one (Compound 89)

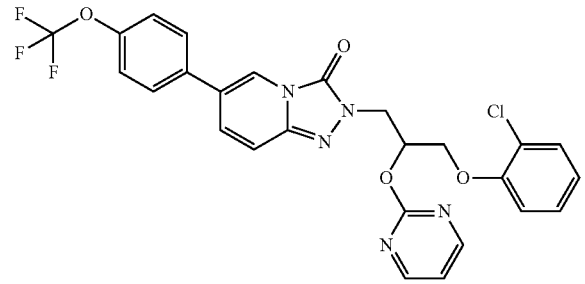 [SMILES: O=c1n(CC(COc2ccccc2Cl)Oc2ncccn2)nc2ccc(-c3ccc(OC(F)(F)F)cc3)cn12]

Example 158

(S)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one (Compound 91)

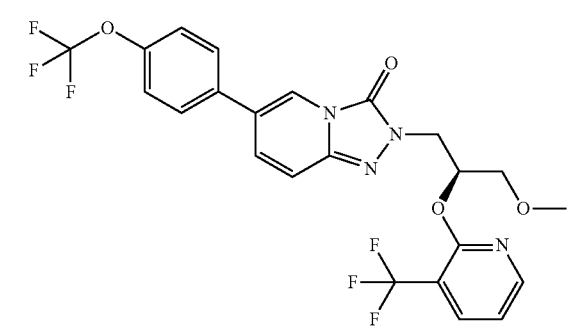 [SMILES: COC[C@H](Cn1nc2ccc(-c3ccc(OC(F)(F)F)cc3)cn2c1=O)Oc1ncccc1C(F)(F)F]

Example 159

(3-((3-oxo-6-(4-(trifluoromethoxy)phenyl)-[1,2,4]triazolo[4,3-a]pyridin-2(3H)-yl)methyl)-1,2,4-oxadiazol-5-yl)methyl acetate (Compound 94)

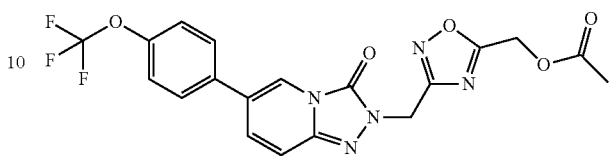

Example 160

(S)-2-(3-(2-chlorophenoxy)-2-methoxypropyl)-6-(4-(trifluoromethoxy)phenyl)-[1,2,4]triazolo[4,3-a]pyridin-3(2H)-one (Compound 95)

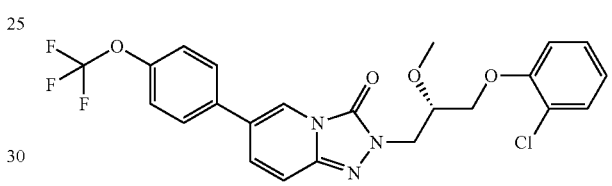

Example 161

(R)-2-(3-(2-chlorophenoxy)-2-methoxypropyl)-6-(4-(trifluoromethoxy)phenyl)-[1,2,4]triazolo[4,3-a]pyridin-3(2H)-one (Compound 96)

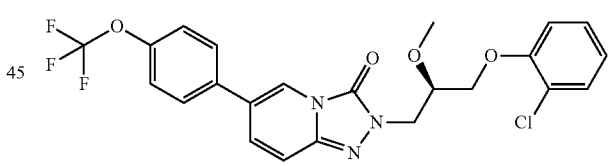

Example 162

2-(3-(4-fluoro-2-methoxyphenoxy)-2-hydroxypropyl)-6-(4-(trifluoromethoxy)phenyl)-[1,2,4]triazolo[4,3-a]pyridin-3(2H)-one (Compound 98)

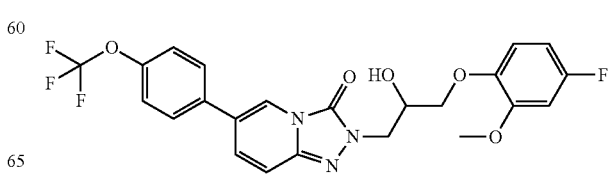

Example 163

2-(3-(2-ethoxyphenoxy)-2-hydroxypropyl)-6-(4-(trifluoromethoxy)phenyl)-[1,2,4]triazolo[4,3-a]pyridin-3(2H)-one (Compound 99)

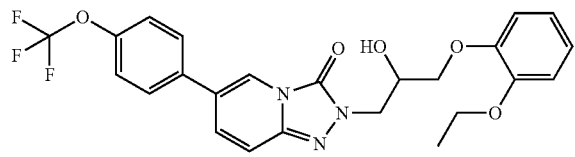 [SMILES: CCOc1ccccc1OCC(O)Cn1nc2ccc(-c3ccc(OC(F)(F)F)cc3)cn2c1=O]

Example 164

2-(3-(biphenyl-2-yloxy)-2-hydroxypropyl)-6-(4-(trifluoromethoxy)phenyl)-[1,2,4]triazolo[4,3-a]pyridin-3(2H)-one (Compound 100)

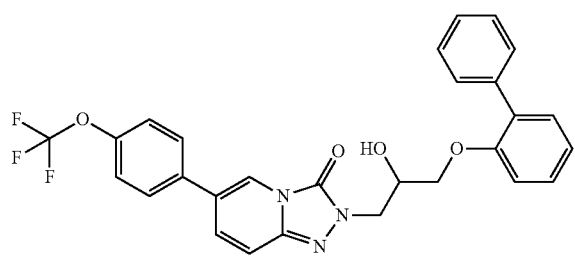 [SMILES: O=c1n(CC(O)COc2ccccc2-c2ccccc2)nc2ccc(-c3ccc(OC(F)(F)F)cc3)cn12]

Example 165

2-(2-hydroxy-3-(3-oxo-6-(4-(trifluoromethoxy)phenyl)-[1,2,4]triazolo[4,3-a]pyridin-2(3H)-yl)propoxy)benzonitrile (Compound 101)

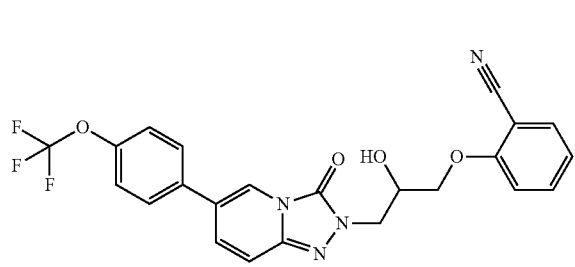 [SMILES: N#Cc1ccccc1OCC(O)Cn1nc2ccc(-c3ccc(OC(F)(F)F)cc3)cn2c1=O]

Example 166

2-(3-(4-fluoro-2-methoxyphenoxy)-2-methoxypropyl)-6-(4-(trifluoromethoxy)phenyl)-[1,2,4]triazolo[4,3-a]pyridin-3(2H)-one (Compound 104)

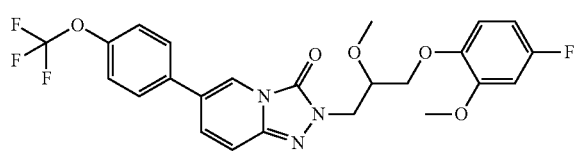 [SMILES: COc1cc(F)ccc1OCC(Cn1nc2ccc(-c3ccc(OC(F)(F)F)cc3)cn2c1=O)OC]

Example 167

2-(2-ethoxy-3-(4-fluoro-2-methoxyphenoxy)propyl)-6-(4-(trifluoromethoxy)phenyl)-[1,2,4]triazolo[4,3-a]pyridin-3(2H)-one (Compound 105)

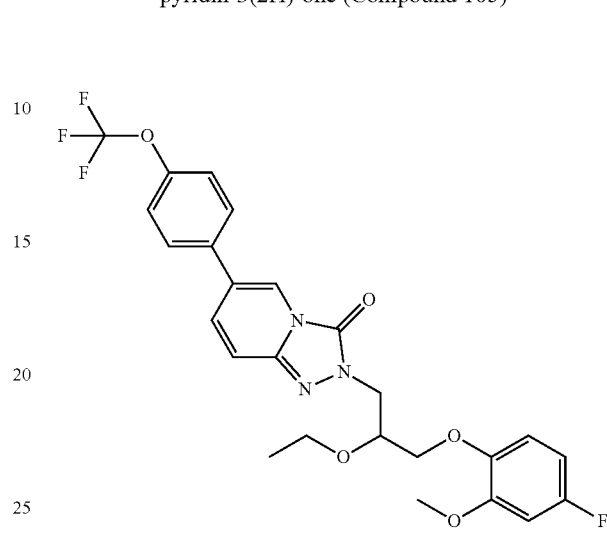

Example 168

2-(2-hydroxy-3-(2-methylbenzo[d]thiazol-6-yloxy)propyl)-6-(4-(trifluoromethoxy)phenyl)-[1,2,4]triazolo[4,3-a]pyridin-3(2H)-one (Compound 107)

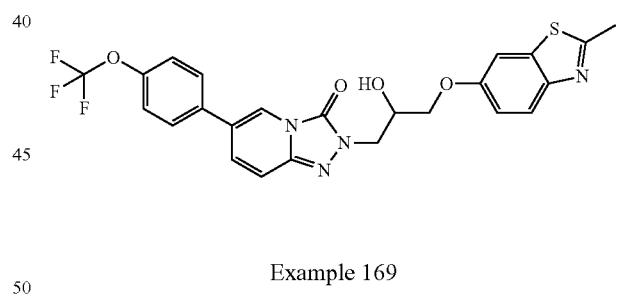

Example 169

2-(2-hydroxy-3-(2-isopropoxyphenoxy)propyl)-6-(4-(trifluoromethoxy)phenyl)-[1,2,4]triazolo[4,3-a]pyridin-3(2H)-one (Compound 108)

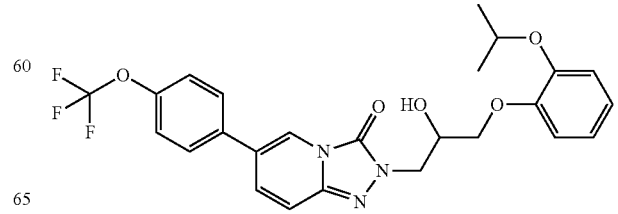

Example 170

2-(4-(pyrimidin-2-yloxy)tetrahydrofuran-3-yl)-6-(4-(trifluoromethoxy)phenyl)-[1,2,4]triazolo[4,3-a]pyridin-3(2H)-one (Compound 109)

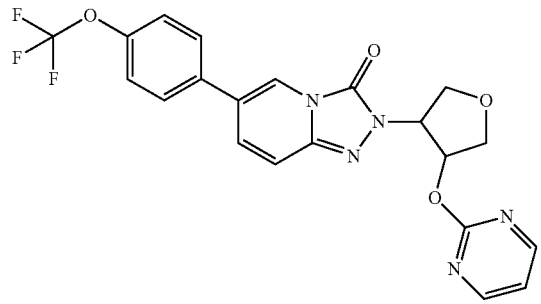 [SMILES: O=c1n(C2COCC2Oc2ncccn2)nc2ccc(-c3ccc(OC(F)(F)F)cc3)cn12]

Example 171

2-(2-(2-oxo-3-phenoxypyrrolidin-1-yl)ethyl)-6-(4-(trifluoromethoxy)phenyl)-[1,2,4]triazolo[4,3-a]pyridin-3(2H)-one (Compound 112)

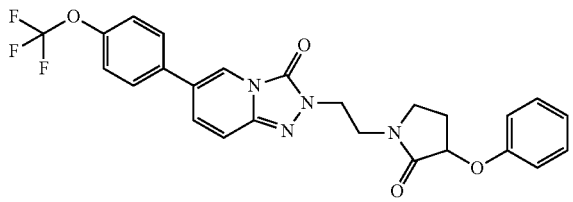 [SMILES: O=C1C(Oc2ccccc2)CCN1CCn1nc2ccc(-c3ccc(OC(F)(F)F)cc3)cn2c1=O]

Example 172

2-(2-ethoxy-3-(2-methylbenzo[d]thiazol-6-yloxy)propyl)-6-(4-(trifluoromethoxy)phenyl)-[1,2,4]triazolo[4,3-a]pyridin-3(2H)-one (Compound 124)

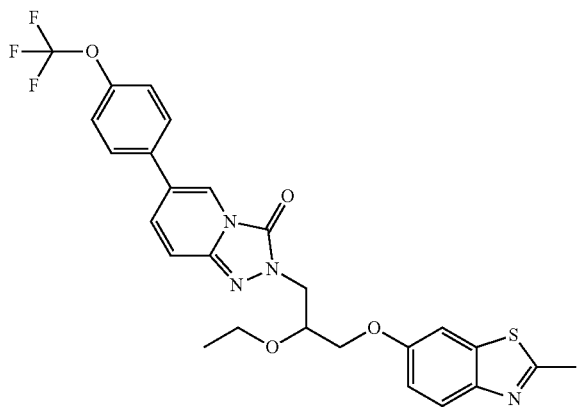 [SMILES: CCOC(COc1ccc2nc(C)sc2c1)Cn1nc2ccc(-c3ccc(OC(F)(F)F)cc3)cn2c1=O]

Example 173

2-(4-(4-ethoxypyrimidin-2-yloxy)tetrahydrofuran-3-yl)-6-(4-(trifluoromethoxy)phenyl)-[1,2,4]triazolo[4,3-a]pyridin-3(2H)-one (Compound 125)

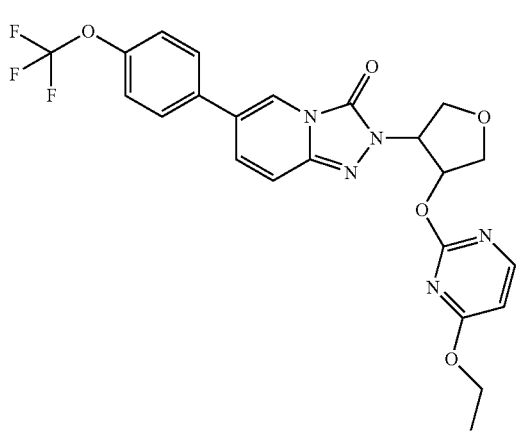 [SMILES: CCOc1ccnc(OC2COCC2n2nc3ccc(-c4ccc(OC(F)(F)F)cc4)cn3c2=O)n1]

Example 174

2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidine-4-carbonitrile (Compound 129)

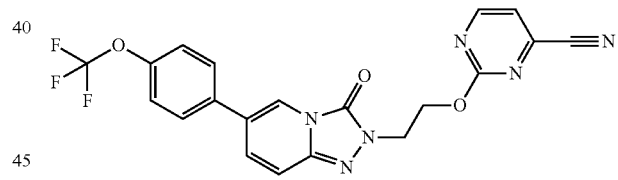

Example 175

2-(2-(5-chloro-4-methoxypyrimidin-2-yloxy)ethyl)-6-(4-(trifluoromethoxy)phenyl)-[1,2,4]triazolo[4,3-a]pyridin-3(2H)-one (Compound 130)

Example 176

2-(2-(4-(4-chlorophenoxy)pyrimidin-2-yloxy)ethyl)-6-(4-(trifluoromethoxy)phenyl)-[1,2,4]triazolo[4,3-a]pyridin-3(2H)-one (Compound 132)

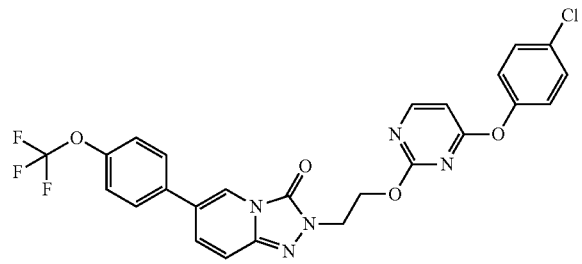 [SMILES: O=c1n(CCOc2nccc(Oc3ccc(Cl)cc3)n2)nc2ccc(-c3ccc(OC(F)(F)F)cc3)cn12]

Example 177

2-(2-(4-(3,3-difluoroazetidin-1-yl)-5-fluoropyrimidin-2-yloxy)ethyl)-6-(4-(trifluoromethoxy)phenyl)-[1,2,4]triazolo[4,3-a]pyridin-3(2H)-one (Compound 133)

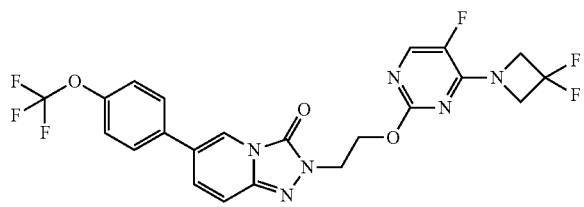 [SMILES: O=c1n(CCOc2ncc(F)c(N3CC(F)(F)C3)n2)nc2ccc(-c3ccc(OC(F)(F)F)cc3)cn12]

Example 178

2-(2-(pyrrolo[1,2-a]pyrazin-1-yloxy)ethyl)-6-(4-(trifluoromethoxy)phenyl)-[1,2,4]triazolo[4,3-a]pyridin-3(2H)-one (Compound 135)

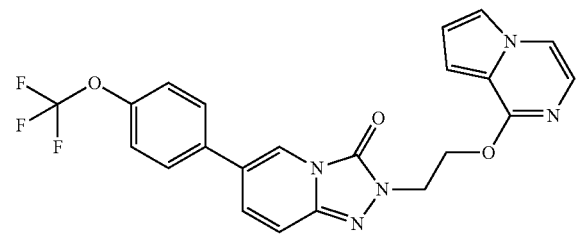 [SMILES: O=c1n(CCOc2nccn3cccc23)nc2ccc(-c3ccc(OC(F)(F)F)cc3)cn12]

Example 179

2-((3-((3-oxo-6-(4-(trifluoromethoxy)phenyl)-[1,2,4]triazolo[4,3-a]pyridin-2(3H)-yl)methyl)-1,2,4-oxadiazol-5-yl)methyl)isoindoline-1,3-dione (Compound 136)

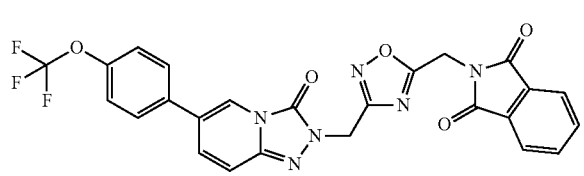 [SMILES: O=C1c2ccccc2C(=O)N1Cc1nc(Cn2nc3ccc(-c4ccc(OC(F)(F)F)cc4)cn3c2=O)no1]

Example 180

2-(2-(5-fluoropyrimidin-2-yloxy)ethyl)-6-(4-(trifluoromethoxy)phenyl)-[1,2,4]triazolo[4,3-a]pyridin-3(2H)-one (Compound 138)

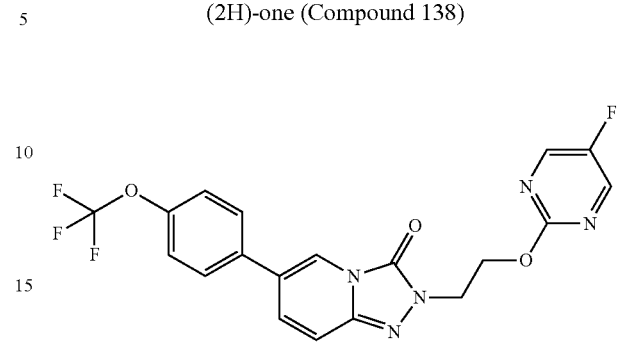

Example 181

2-(2-(2-chloropyrimidin-5-yloxy)ethyl)-6-(4-(trifluoromethoxy)phenyl)-[1,2,4]triazolo[4,3-a]pyridin-3(2H)-one (Compound 139)

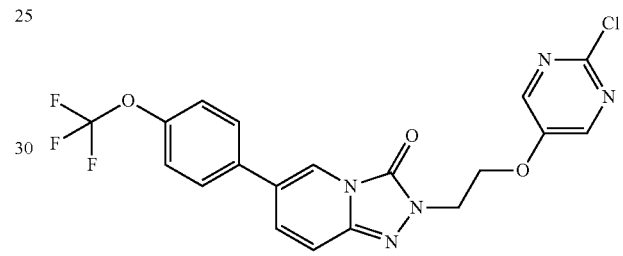

Example 182

2-((5-(pyridin-2-yl)isoxazol-3-yl)methyl)-6-(4-(trifluoromethoxy)phenyl)-[1,2,4]triazolo[4,3-a]pyridin-3(2H)-one (Compound 144)

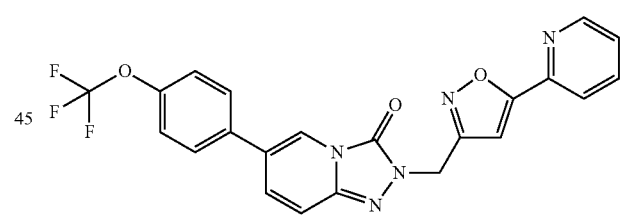

Example 183

2-((5-(3-methylpyridin-2-yl)isoxazol-3-yl)methyl)-6-(4-(trifluoromethoxy)phenyl)-[1,2,4]triazolo[4,3-a]pyridin-3(2H)-one (Compound 145)

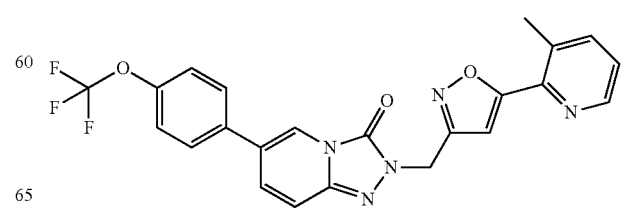

Example 184

6-(4-(4-fluorophenoxy)phenyl)-2-((5-(hydroxymethyl)-1,2,4-oxadiazol-3-yl)methyl)-[1,2,4]triazolo[4,3-a]pyridin-3(2H)-one (Compound 146)

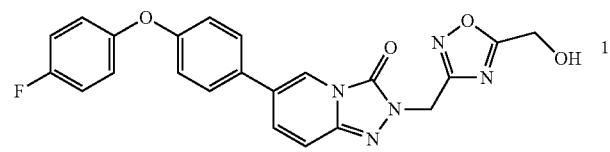

Example 185

(S)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one (Compound 152)

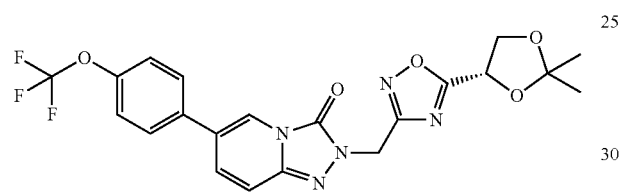

Example 186

2-(2-(4-(2-hydroxyethoxy)pyrimidin-2-yloxy)ethyl)-6-(4-(trifluoromethoxy)phenyl)-[1,2,4]triazolo[4,3-a]pyridin-3(2H)-one (Compound 156)

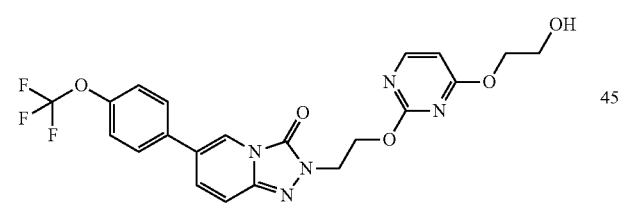

Example 187

2-((5-(chloromethyl)-1,2,4-oxadiazol-3-yl)methyl)-6-(4-(trifluoromethoxy)phenyl)-[1,2,4]triazolo[4,3-a]pyridin-3(2H)-one (Compound 157)

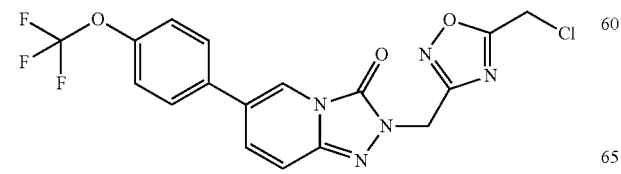

Example 188

(R)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one (Compound 158)

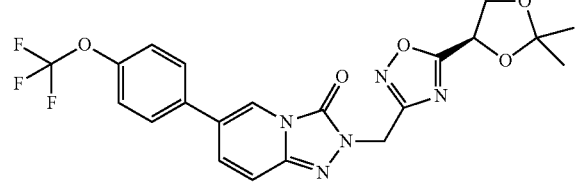

Example 189

6-(4-chloro-3-fluorophenyl)-2-((3-methyl-1,2,4-oxadiazol-5-yl)methyl)-[1,2,4]triazolo[4,3-a]pyridin-3(2H)-one (Compound 161)

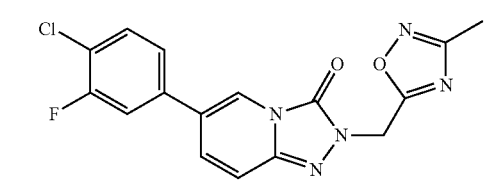 [SMILES: Cc1noc(Cn2nc3ccc(-c4ccc(Cl)c(F)c4)cn3c2=O)n1]

Example 190

2-((5-((pyrimidin-2-yloxy)methyl)-1,2,4-oxadiazol-3-yl)methyl)-6-(4-(trifluoromethoxy)phenyl)-[1,2,4]triazolo[4,3-a]pyridin-3(2H)-one (Compound 162)

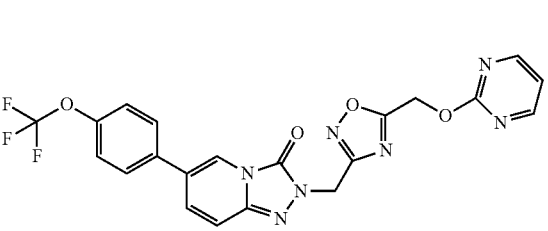 [SMILES: O=c1n(Cc2noc(COc3ncccn3)n2)nc2ccc(-c3ccc(OC(F)(F)F)cc3)cn12]

Example 191

2-((4,5-dimethyloxazol-2-yl)methyl)-6-(4-(trifluoromethyl)phenyl)-[1,2,4]triazolo[4,3-a]pyridin-3(2H)-one (Compound 173)

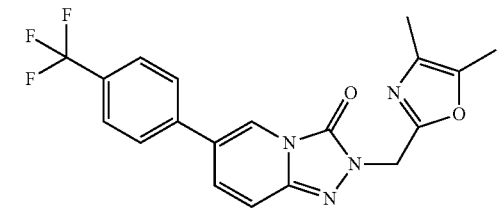 [SMILES: Cc1nc(Cn2nc3ccc(-c4ccc(C(F)(F)F)cc4)cn3c2=O)oc1C]

Example 192

2-((5-((pyridin-2-yloxy)methyl)-1,2,4-oxadiazol-3-yl)methyl)-6-(4-(trifluoromethoxy)phenyl)-[1,2,4]triazolo[4,3-a]pyridin-3(2H)-one (Compound 175)

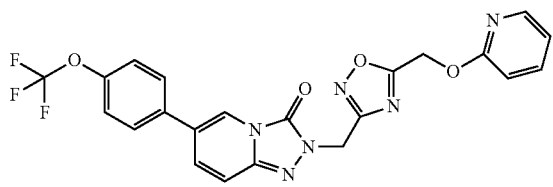

Example 193

2-((5-((2-ethoxyphenoxy)methyl)-1,2,4-oxadiazol-3-yl)methyl)-6-(4-(trifluoromethoxy)phenyl)-[1,2,4]triazolo[4,3-a]pyridin-3(2H)-one (Compound 176)

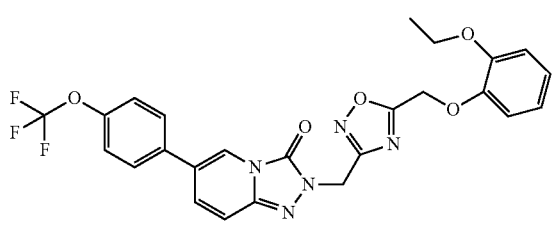 [SMILES: CCOc1ccccc1OCc1nc(Cn2nc3ccc(-c4ccc(OC(F)(F)F)cc4)cn3c2=O)no1]

Example 194

(R)-2-(2-(3-(4-fluorophenoxy)pyrrolidin-1-yl)ethyl)-6-(4-(trifluoromethoxy)phenyl)-[1,2,4]triazolo[4,3-a]pyridin-3(2H)-one (Compound 186)

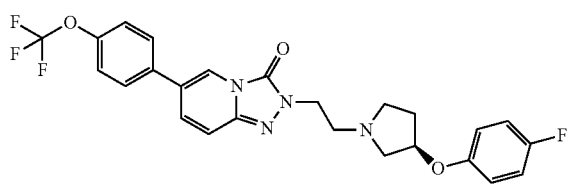 [SMILES: O=c1n(CCN2CC[C@@H](Oc3ccc(F)cc3)C2)nc2ccc(-c3ccc(OC(F)(F)F)cc3)cn12]

Example 195

6-(4-(trifluoromethoxy)phenyl)-[1,2,4]triazolo[4,3-a]pyridin-3(2H)-one (Compound 200)

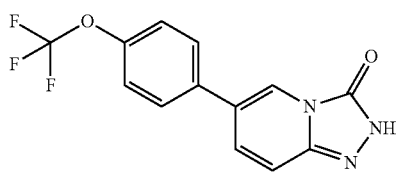 [SMILES: O=c1[nH]nc2ccc(-c3ccc(OC(F)(F)F)cc3)cn12]

Example 196

2-methyl-6-(4-(trifluoromethoxy)phenyl)-[1,2,4]triazolo[4,3-a]pyridin-3(2H)-one (Compound 201)

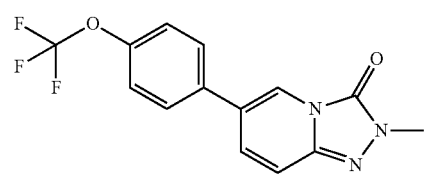 [SMILES: Cn1nc2ccc(-c3ccc(OC(F)(F)F)cc3)cn2c1=O]

Example 197

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 198

A tablet Formula (I)s prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 199

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 200

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 201

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 202

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 203

A subcutaneous formulation may be prepared as follows:

| Ingredient | Quantity |
| --- | --- |
| Active Ingredient | 5.0 mg |
| Corn Oil | 1.0 mL |

Example 204

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5-6) |
| water (distilled, sterile) | q.s. to 1.0 ml |
| Nitrogen Gas, NF | q.s. |

Example 205

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Example 206

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. In some embodiments, aqueous solutions of strong bases are solutions of alkali metal hydroxides, such as sodium or potassium hydroxide, typically sodium hydroxide, in water (optionally containing up to 25% of water-miscible solvents such as lower alcohols).

The resulting tablets may be coated with an optional film-forming agent, for identification, taste-masking purposes and to improve ease of swallowing. In some embodiments, the film forming agent will be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

In some embodiments, the compressed tablets have a hardness sufficient to withstand 8 Kp compression. The tablet size will depend primarily upon the amount of compound in the tablet. The tablets will include from 300 to 1100 mg of compound free base. In some embodiments, the tablets will include amounts of compound free base ranging from 400-600 mg, 650-850 mg, and 900-1100 mg.

In order to influence the dissolution rate, the time during which the compound containing powder is wet mixed is controlled. In some embodiments, the total powder mix time, i.e. the time during which the powder is exposed to sodium hydroxide solution, will range from 1 to 10 minutes and in some embodiments, from 2 to 5 minutes. Following granulation, the particles are removed from the granulator and placed in a fluid bed dryer for drying at about 60° C.

Example 207

Activity testing is conducted in the Examples below using methods described herein and those well known in the art.

Sodium Current Screening Assays

The late sodium current (Late INa) and peak sodium current (Peak INa) assays are performed on an automated electrophysiology platform, PatchXpress 7000A (MDS Analytical Technologies, Sunnyvale, Calif.), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 µg/ml Geneticin in the culture medium. Cells isolated for use on PatchXpress are incubated for 5 minutes in Versene 1× and then for 2 minutes in 0.0125% Trypsin-EDTA (both at 37° C.) to ensure that 80-90% of the cells are single and not part of a cell cluster. Experiments are carried out at 24-27° C.

For both the Late INa and Peak INa assays, series resistance compensation is set to 50% and whole-cell compensation is performed automatically. Currents are low-pass filtered at 10 kHz and digitized at 31.25 kHz. Currents through open sodium channels are automatically recorded and stored in the DataXpress2 database (MDS Analytical Technologies, Sunnyvale, Calif.). Analysis is performed using DataXpress2 analysis software and data are compiled in Excel.

Compound stocks are routinely made in glass vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM CaCl$_2$, 0.75 mM MgCl$_2$, and 5 mM HEPES with pH adjusted to 7.4 using NaOH. The extracellular solution for screening Peak INa is composed of: 20 mM NaCl, 120 mM N-methyl-D glucamine, 4 mM KCl, 1.8 mM CaCl$_2$, 0.75 mM MgCl$_2$, and 5 mM HEPES with pH adjusted to 7.4 using HCl. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 10 µM in glass vials and then transferred to glass well plates before robotic addition to the cells. The 0Na extracellular solution used at the end of each experiment for the Late INa and Peak INa assays to measure baseline current contains: 140 mM N-methyl-D-glucamine; 4 mM KCl; 1.8 mM CaCl$_2$; 0.75 mM MgCl$_2$; 5 mM HEPES and pH was adjusted to 7.4 with HCl.

Late INa Screening Assay

For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical Na$_v$1.5 sodium currents activate rapidly to a peak negative current and then inactivate nearly completely within 3-4 ms.

All compounds are tested to determine their activity in blocking the late sodium current. Late INa current is generated by adding 10 µM Tefluthrin (pyrethroid) to the extracellular solution while recording Na currents. For some experiments, 50 nM ATX II (sea anemone toxin), another late INa activator, was used to generate the late component. Both activators generate late components that are large enough that block of the late component by compounds can be measured easily. For the purposes of the screening, late INa is defined as the mean current between 225 ms and 250 ms after stepping to −20 mV to activate Na channels. After establishing the whole cell recording configuration, late INa activators are added to each well 4 times over a 16-17 minute period so that the late component of the Na current reaches a stable value. Compounds are then added (typically at 10 µM), in the presence of late INa activator, with 3 additions over the course of 7 or 8 minutes. Measurements are made typically at the end of exposure to the third compound addition. Measurements are made at the end of exposure to the third compound addition and values are normalized to the current level when all Na$^+$ is removed from the extracellular solution after two additions of 0Na-ECF. Results are reported as percent block of late INa Peak INa Screening Assay Compounds were also evaluated for their effect in several other assays, including their effect on Peak INa. After screening compounds against late INa, selected compounds are evaluated for their effect in several other assays, including their effect on peak INa. One goal of this program is to avoid significant block of peak INa. Since the peak INa in our cells can be very large, introducing artifacts in the recording, the concentration of Na$^+$ in the bath is reduced to 20 mM and a nonpermeant cation is added to compensate for the Na$^+$ that was removed to maintain the osmolarity and ionic strength of the solution (see solution details above). All measurements are normalized to the current level when all Na$^+$ is removed from the extracellular solution, after two additions of 0Na-ECF.

In some cases we measured the effect of compound on peak INa using data from the late INa assay. But often peak currents were too large to make this possible, requiring that we perform a separate assay to evaluate the effect on peak INa.

For the original peak INa assay, we activate the channel every 10 seconds by depolarizing the cell membrane to −20 mV for 250 ms from a holding potential of −120 mV. After establishing the whole cell recording configuration, the recorded currents are allowed to stabilize for 6-7 minutes. Compound is added at 10 µM with three additions over an 8-9 minute period. Analysis of peak INa generally requires correction for rundown before determining the % block of peak current by the tested compound.

A new Peak INa screening assay was developed to allow assessment of the effect of compounds on peak INa at both low and high stimulation frequencies. The goal is to find compounds that are highly selective for block of late INa but do not block peak INa. A low stimulation frequency of 0.1 Hz is used to determine the effect of compound when the channel spends most of the time in the resting (closed) state and provides information about Tonic Block (TB). A higher stimulation frequency (3 Hz) is used to measure block of the channel when it spends more time in the activated and inactivated states, and provides a measure of Use-Dependent Block (UDB). The −100 mV holding potential and the 3 Hz stimulation frequency were chosen so that our benchmark compound would have a small but detectable effect under experimental conditions, allowing for direct comparison of new compounds with the benchmark.

For the new peak INa assay, $Na^+$ channels are activated by depolarizing the cell membrane to 0 mV for 20 ms from a holding potential of −100 mV. After establishing the whole cell recording configuration, channels are stimulated to open with low frequency stimulation (0.1 Hz) for 7 minutes so that we can monitor the recording and assess the extent to which the recording has stabilized. After this stabilization period the stimulation frequency is increased to 3 Hz for 2 minutes, and then returned to 0.1 Hz. Since 3 Hz stimulation causes a small decrease in the peak current even in the absence of compound, we use this internal control for each cell, when no compound is present, to correct the results from 3 Hz stimulation when compound is present. Following 3 Hz stimulation under control conditions, the cell is allowed to recover for 200 seconds before compound is added. Compound (10 µM) is added 3 times at 60 second intervals, while stimulating the channels to open at 0.1 Hz to monitor the progression of block. After the $3^{rd}$ compound addition, a 320 second wait period is imposed to allow for equilibration before the second period of 3 Hz stimulation begins. TB is measured before the second period of 3 Hz stimulation. Both TB and UDB are analyzed by incorporating rundown correction for the peak INa and UDB is calculated by compensating for the small use-dependent effect of the stimulation protocol on peak INa in the absence of compound.

hERG Screening Assay

Compounds were screened to test their activity in blocking the hERG potassium channel. The hERG channel is heterologously expressed in a CHO (Chinese Hamster Ovary) cell line. Cells are maintained with standard tissue culture procedures and stable channel expression is maintained with 500 µg/ml G418 in the culture medium. Cells are harvested for testing on the PatchXpress automated patch clamp with Accumax (Innovative Cell Technologies, San Diego, Calif.) to isolate single cells.

The following solutions are used for electrophysiological recordings. The external solution contains: 2 mM $CaCl_2$; 2 mM $MgCl_2$; 4 mM KCl; 150 mM NaCl; 10 mM Glucose; 10 mM HEPES (pH 7.4 with 1M NaOH, osmolarity). The internal solution contains: 140 mM KCl, 10 mM $MgCl_2$, 6 mM EGTA, 5 mM HEPES, 5 mM ATP (pH adjusted to 7.25 with KOH).

hERG channels are activated when the voltage is stepped to +20 mV from the −80 mV holding potential. During a 5 second step at +20 mV, the channels activate and then largely inactivate, so the currents are relatively small. Upon returning to −50 mV from +20 mV, hERG currents transiently become much larger as inactivation is rapidly removed and then the channel closes. The first step to −50 mV for 300 ms is used as a baseline for measuring the peak amplitude during the step to −50 mV after channel activation. The peak current at −50 mV is measured both under control conditions and after addition of compound.

All compounds are prepared as 10 mM DMSO stocks in glass vials. Stock solutions are mixed by vigorous vortexing and sonication for about 2 minutes at room temperature. For testing, compounds are diluted in glass vials using an intermediate dilution step in pure DMSO and then further diluted to working concentrations in external solution. Dilutions are prepared no longer than 20 minutes before use.

After achieving the whole-cell configuration, cells are monitored for 90 seconds to assess stability and washed with external solution for 66 seconds. The voltage protocol described above is then applied to the cells every 12 seconds and throughout the whole procedure. Only cells with stable recording parameters and meeting specified health criteria are allowed to enter the compound addition procedure.

External solution containing 0.1% DMSO (vehicle) is applied to the cells first to establish the control peak current amplitude. After allowing the current to stabilize for 3 to 5 minutes, 1 µM and then 10 µM test compounds are applied. Each compound concentration is added 4 times and cells are kept in test solution until the effect of the compound reaches steady state or for a maximum of 12 minutes. After addition of test compound, a positive control (1 µM Cisapride) is added and must block >95% of the current for the experiment to be considered valid. Washout in the external solution compartment is performed until the recovery of the current reaches steady state. Data are analyzed using DataXpress, Clampfit (Molecular Devices, Inc., Sunnyvale) and Origin 7 (Originlab Corp.)

L-Type Calcium Channel Activity Well-Plate Assay

Cell Culture: IMR-32 (human neuroblastoma) cells were obtained from The American Type Culture Collection. The cells were maintained in MEM supplemented with 10% fetal bovine serum, 2 mM of L-glutamine, 100 IU/ml of penicillin, 50 µg/ml of streptomycin, 1% of sodium pyruvate, 1% of sodium bicarbonate and 1% of non-essential amino acid. The cells were cultured at 37° C. in a humidified 5% $CO_2$/95% air incubator. Culture medium was changed every two days and cells were recultivated when they reached 70-80% confluent.

Assay: IMR-32 cells were seeded on a Microtest 96-well Assay Plate (BD FALCON™) at a density of 200,000 cells/well in 200 µl culture medium for overnight. The culture medium was removed, and replaced by 120 µl Ca-4 dye (MDS Analytical Technologies, Sunnyvale, Calif.) in HBSS (1× Hank's Balanced Salt solution plus 20 mM HEPES, pH 7.4) containing 2 mM probenecid. Cells were then incubated for 1 hour at 37° C. in incubator. Testing compounds were diluted from 5 µM-50 µM in HBSS, and 40 µl were added in cells before assay. L-type calcium channel activities (Max Min) were measured after addition of 40 µl of 1 µM (−) Bay K 8644 plus 50 mM KCl (final concentration) using FlexStation (Molecular Devices) immediately after addition of testing compounds. The inhibition of L-type calcium channel activity by compounds was then calculated.

Compounds were tested and found to be effective using the described assay methods at a concentration of 1 µM and 10 µM in the late INa and Peak INa assays, and at 1 µM and 10 µM for the hERG and L-type calcium channel assays. The assay results demonstrated that the compounds tested showed activity as modulators of late sodium current, for example by inhibiting (or reducing) the late sodium current.

Compounds were tested using the described assay methods. Data are obtained obtained by testing the listed compounds at 10 µM and 1 µM concentrations in the late INa assay, and at 1 µM and 10 µM for the hERG and L-type calcium channel assays. Data are shown in Table 2 below for those compounds that inhibit Late INa by at least 10% at the 1 µM concentration.

TABLE 2

Late INa Assay results

| No. | Name | Late INa 1 µM |
|---|---|---|
| 1. | 2-((3-methyl-1,2,4-oxadiazol-5-yl)methyl)-6-(4-(trifluoromethoxy)phenyl)-[1,2,4]triazolo[4,3-a]pyridin-3(2H)-one; | 27.4926 |
| 2. | 2-((4-methyl-1,2,5-oxadiazol-3-yl)methyl)-6-(4-(trifluoromethoxy)phenyl)-[1,2,4]triazolo[4,3-a]pyridin-3(2H)-one; | 41.3107 |
| 3. | 2-((5-methyl-1,2,4-oxadiazol-3-yl)methyl)-6-(4-(trifluoromethoxy)phenyl)-[1,2,4]triazolo[4,3-a]pyridin-3(2H)-one; | 29.2706 |
| 4. | 2-(2-hydroxy-3-(2-methoxyphenoxy)propyl)-6-(4-(trifluoromethoxy)phenyl)-[1,2,4]triazolo[4,3-a]pyridin-3(2H)-one; | 20.8324 |
| 5. | 2-((5-methylisoxazol-3-yl)methyl)-6-(4-(trifluoromethoxy)phenyl)-[1,2,4]triazolo[4,3-a]pyridin-3(2H)-one; | 28.3468 |
| 6. | 2-((3,5-dimethylisoxazol-4-yl)methyl)-6-(4-(trifluoromethoxy)phenyl)-[1,2,4]triazolo[4,3-a]pyridin-3(2H)-one; | 15.22 |
| 7. | 6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one; | 24.4883 |
| 8. | 2-(3-(5-methyl-1,2,4-oxadiazol-3-yl)benzyl)-6-(4-(trifluoromethoxy)phenyl)-[1,2,4]triazolo[4,3-a]pyridin-3(2H)-one; | 16.2849 |
| 9. | 2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one; | 29.8408 |
| 10. | 2-(benzo[c][1,2,5]oxadiazol-5-ylmethyl)-6-(4-(trifluoromethoxy)phenyl)-[1,2,4]triazolo[4,3-a]pyridin-3(2H)-one; | 16.8658 |
| 11. | 2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one; | 22.0027 |
| 12. | 2-(4-(trifluoromethoxy)benzyl)-6-(4-(trifluoromethoxy)phenyl)-[1,2,4]triazolo[4,3-a]pyridin-3(2H)-one; | 11.1423 |
| 13. | 2-(quinolin-2-ylmethyl)-6-(4-(trifluoromethoxy)phenyl)-[1,2,4]triazolo[4,3-a]pyridin-3(2H)-one; | 24.606 |
| 14. | 2-(1-(3-ethyl-1,2,4-oxadiazol-5-yl)ethyl)-6-(4-(trifluoromethoxy)phenyl)-[1,2,4]triazolo[4,3-a]pyridin-3(2H)-one; | 11.9819 |
| 15. | 2-((3-ethyl-1,2,4-oxadiazol-5-yl)methyl)-6-(4-(trifluoromethoxy)phenyl)-[1,2,4]triazolo[4,3-a]pyridin-3(2H)-one; | 13.5253 |
| 16. | 2-(pyridin-2-ylmethyl)-6-(4-(trifluoromethoxy)phenyl)-[1,2,4]triazolo[4,3-a]pyridin-3(2H)-one; | 11.5042 |
| 17. | 2-((4-phenyl-1,2,5-oxadiazol-3-yl)methyl)-6-(4-(trifluoromethoxy)phenyl)-[1,2,4]triazolo[4,3-a]pyridin-3(2H)-one; | 18.4092 |
| 18. | 2-((5-methyl-1,3,4-oxadiazol-2-yl)methyl)-6-(4-(trifluoromethoxy)phenyl)-[1,2,4]triazolo[4,3-a]pyridin-3(2H)-one; | 11.5167 |
| 19. | 2-(oxazol-2-ylmethyl)-6-(4-(trifluoromethoxy)phenyl)-[1,2,4]triazolo[4,3-a]pyridin-3(2H)-one; | 18.1054 |
| 20. | 2-(benzo[d]thiazol-2-ylmethyl)-6-(4-(trifluoromethoxy)phenyl)-[1,2,4]triazolo[4,3-a]pyridin-3(2H)-one; | 17.4367 |
| 21. | 2-((5-methyl-2-phenyloxazol-4-yl)methyl)-6-(4-(trifluoromethoxy)phenyl)-[1,2,4]triazolo[4,3-a]pyridin-3(2H)-one; | 11.0036 |
| 22. | 2-((4,5-dimethyloxazol-2-yl)methyl)-6-(4-(trifluoromethoxy)phenyl)-[1,2,4]triazolo[4,3-a]pyridin-3(2H)-one; | 29.4152 |
| 23. | 2-(2-methoxy-3-(2-methoxyphenoxy)propyl)-6-(4-(trifluoromethoxy)phenyl)-[1,2,4]triazolo[4,3-a]pyridin-3(2H)-one; | 55.0886 |
| 24. | 2-(3-phenoxypropyl)-6-(4-(trifluoromethoxy)phenyl)-[1,2,4]triazolo[4,3-a]pyridin-3(2H)-one; | 25.0109 |
| 25. | 2-((5-methyloxazol-2-yl)methyl)-6-(4-(trifluoromethoxy)phenyl)-[1,2,4]triazolo[4,3-a]pyridin-3(2H)-one; | 30.2998 |
| 26. | 2-((3-cyclopropyl-1-methyl-1H-pyrazol-5-yl)methyl)-6-(4-(trifluoromethoxy)phenyl)-[1,2,4]triazolo[4,3-a]pyridin-3(2H)-one; | 19.285 |
| 27. | 2-((1,2,4-oxadiazol-3-yl)methyl)-6-(4-(trifluoromethoxy)phenyl)-[1,2,4]triazolo[4,3-a]pyridin-3(2H)-one; | 11.2187 |
| 28. | 2-(2-phenoxyethyl)-6-(4-(trifluoromethoxy)phenyl)-[1,2,4]triazolo[4,3-a]pyridin-3(2H)-one; | 46.3013 |
| 29. | 2-((3-benzyl-1,2,4-oxadiazol-5-yl)methyl)-6-(4-(trifluoromethoxy)phenyl)-[1,2,4]triazolo[4,3-a]pyridin-3(2H)-one; | 27.1643 |
| 30. | 5-methoxy-2-((3-methyl-1,2,4-oxadiazol-5-yl)methyl)-6-(4-(trifluoromethoxy)phenyl)-[1,2,4]triazolo[4,3-a]pyridin-3(2H)-one; | 18.2013 |
| 31. | 2-((5-methyl-1,2,4-oxadiazol-3-yl)methyl)-6-(3-phenoxyphenyl)-[1,2,4]triazolo[4,3-a]pyridin-3(2H)-one; | 24.3518 |
| 32. | 6-(4-(4-chlorophenoxy)phenyl)-2-((5-methyl-1,2,4-oxadiazol-3-yl)methyl)-[1,2,4]triazolo[4,3-a]pyridin-3(2H)-one; | 68.4737 |

TABLE 2-continued

Late INa Assay results

| No. | Name | Late INa 1 μM |
|---|---|---|
| 33. | 2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one; | 20.4663 |
| 34. | 2-(pyridin-2-yl)-6-(4-(trifluoromethoxy)phenyl)-[1,2,4]triazolo[4,3-a]pyridin-3(2H)-one; | 26.0109 |
| 35. | 2-(2-(1H-pyrazol-1-yl)ethyl)-6-(4-(trifluoromethoxy)phenyl)-[1,2,4]triazolo[4,3-a]pyridin-3(2H)-one; | 12.2358 |
| 36. | 2-(2-(pyridin-2-yl)ethyl)-6-(4-(trifluoromethoxy)phenyl)-[1,2,4]triazolo[4,3-a]pyridin-3(2H)-one; | 48.3966 |
| 37. | 2-(3-(2-methoxyphenoxy)propyl)-6-(4-(trifluoromethoxy)phenyl)-[1,2,4]triazolo[4,3-a]pyridin-3(2H)-one; | 34.546 |
| 38. | 2-(3-(4-chlorophenoxy)-2-hydroxypropyl)-6-(4-(trifluoromethoxy)phenyl)-[1,2,4]triazolo[4,3-a]pyridin-3(2H)-one; | 10.8406 |
| 39. | 2-(2-(3-phenoxypyrrolidin-1-yl)ethyl)-6-(4-(trifluoromethoxy)phenyl)-[1,2,4]triazolo[4,3-a]pyridin-3(2H)-one; | 45.4051 |
| 40. | 2-(2-(4-chlorophenoxy)ethyl)-6-(4-(trifluoromethoxy)phenyl)-[1,2,4]triazolo[4,3-a]pyridin-3(2H)-one; | 34.2725 |
| 41. | 2-(2-(4-chloro-1H-pyrazol-1-yl)ethyl)-6-(4-(trifluoromethoxy)phenyl)-[1,2,4]triazolo[4,3-a]pyridin-3(2H)-one; | 12.2348 |
| 42. | 2-(2-(3-methyl-1H-pyrazol-1-yl)ethyl)-6-(4-(trifluoromethoxy)phenyl)-[1,2,4]triazolo[4,3-a]pyridin-3(2H)-one; | 18.874 |
| 43. | 2-hydroxy-3-phenoxypropyl)-6-(4-(trifluoromethoxy)phenyl)-[1,2,4]triazolo[4,3-a]pyridin-3(2H)-one; | 19.2769 |
| 44. | 2-(2-(2,6-dimethylphenoxy)ethyl)-6-(4-(trifluoromethoxy)phenyl)-[1,2,4]triazolo[4,3-a]pyridin-3(2H)-one; | 43.0789 |
| 45. | 2-(2-(4-phenyl-1H-imidazol-1-yl)ethyl)-6-(4-(trifluoromethoxy)phenyl)-[1,2,4]triazolo[4,3-a]pyridin-3(2H)-one; | 11.7826 |
| 46. | 2-(2-(2-chlorophenoxy)ethyl)-6-(4-(trifluoromethoxy)phenyl)-[1,2,4]triazolo[4,3-a]pyridin-3(2H)-one; | 43.2338 |
| 47. | 6-(4-(trifluoromethoxy)phenyl)-2-(2-(3-(trifluoromethyl)pyridin-2-yloxy)ethyl)-[1,2,4]triazolo[4,3-a]pyridin-3(2H)-one; | 43.6421 |
| 48. | 2-(2-(6-methylpyridin-2-yl)ethyl)-6-(4-(trifluoromethoxy)phenyl)-[1,2,4]triazolo[4,3-a]pyridin-3(2H)-one; | 34.9249 |
| 49. | 2-(2-(pyridin-2-yloxy)ethyl)-6-(4-(trifluoromethoxy)phenyl)-[1,2,4]triazolo[4,3-a]pyridin-3(2H)-one; | 29.9253 |
| 50. | 2-(2-(4,4-difluoropiperidin-1-yl)ethyl)-6-(4-(trifluoromethoxy)phenyl)-[1,2,4]triazolo[4,3-a]pyridin-3(2H)-one; | 14.1515 |
| 51. | 2-(3-(2-fluorophenoxy)propyl)-6-(4-(trifluoromethoxy)phenyl)-[1,2,4]triazolo[4,3-a]pyridin-3(2H)-one; | 25.6438 |
| 52. | 2-(3-(2-chlorophenoxy)propyl)-6-(4-(trifluoromethoxy)phenyl)-[1,2,4]triazolo[4,3-a]pyridin-3(2H)-one; | 33.3316 |
| 53. | 6-(4-(4-chlorophenoxy)phenyl)-2-((3-methyl-1,2,4-oxadiazol-5-yl)methyl)-[1,2,4]triazolo[4,3-a]pyridin-3(2H)-one; | 55.8815 |
| 54. | 2-(2-(3-chlorophenoxy)ethyl)-6-(4-(trifluoromethoxy)phenyl)-[1,2,4]triazolo[4,3-a]pyridin-3(2H)-one; | 20.2003 |
| 55. | 2-(2-(4-fluorophenoxy)ethyl)-6-(4-(trifluoromethoxy)phenyl)-[1,2,4]triazolo[4,3-a]pyridin-3(2H)-one; | 24.2631 |
| 56. | 2-(2-(3-bromopyridin-2-yl)ethyl)-6-(4-(trifluoromethoxy)phenyl)-[1,2,4]triazolo[4,3-a]pyridin-3(2H)-one; | 39.7828 |
| 57. | 2-(2-(4-cyclopropylpyridin-2-yl)ethyl)-6-(4-(trifluoromethoxy)phenyl)-[1,2,4]triazolo[4,3-a]pyridin-3(2H)-one; | 20.7 |
| 58. | 2-(2-(4-methylpyridin-2-yl)ethyl)-6-(4-(trifluoromethoxy)phenyl)-[1,2,4]triazolo[4,3-a]pyridin-3(2H)-one; | 14.8908 |
| 59. | 2-(4-fluorophenethyl)-6-(4-(trifluoromethoxy)phenyl)-[1,2,4]triazolo[4,3-a]pyridin-3(2H)-one; | 27.0505 |
| 60. | 2-(2-(3-cyclopropylpyridin-2-yl)ethyl)-6-(4-(trifluoromethoxy)phenyl)-[1,2,4]triazolo[4,3-a]pyridin-3(2H)-one; | 34.0592 |
| 61. | 2-(2-(3-methylpyridin-2-yl)ethyl)-6-(4-(trifluoromethoxy)phenyl)-[1,2,4]triazolo[4,3-a]pyridin-3(2H)-one; | 41.5137 |
| 62. | 6-(4-(trifluoromethoxy)phenyl)-2-((6-(trifluoromethyl)pyridin-2-yl)methyl)-[1,2,4]triazolo[4,3-a]pyridin-3(2H)-one; | 21.6 |
| 63. | 2-(2,6-difluorophenethyl)-6-(4-(trifluoromethoxy)phenyl)-[1,2,4]triazolo[4,3-a]pyridin-3(2H)-one; | 46.8866 |
| 64. | 2-(3-(3-bromo-4-fluorophenyl)propyl)-6-(4-(trifluoromethoxy)phenyl)-[1,2,4]triazolo[4,3-a]pyridin-3(2H)-one; | 16.71 |
| 65. | 6-(4-(trifluoromethoxy)phenyl)-2-(2-(6-(trifluoromethyl)pyridin-2-yloxy)ethyl)-[1,2,4]triazolo[4,3-a]pyridin-3(2H)-one; | 21.1403 |
| 66. | 6-(4-(trifluoromethoxy)phenyl)-2-(3-(2-(trifluoromethyl)phenoxy)propyl)-[1,2,4]triazolo[4,3-a]pyridin-3(2H)-one; | 14.6604 |
| 67. | 2-(3-(4-fluoro-2-methoxyphenoxy)propyl)-6-(4-(trifluoromethoxy)phenyl)-[1,2,4]triazolo[4,3-a]pyridin-3(2H)-one | 19.181 |
| 68. | 2-(3-(4-chloropyridin-3-yl)prop-2-ynyl)-6-(4-(trifluoromethoxy)phenyl)-[1,2,4]triazolo[4,3-a]pyridin-3(2H)-one; | 11.1201 |

TABLE 2-continued

Late INa Assay results

| No. | Name | Late INa 1 μM |
|---|---|---|
| 69. | 2-(2-(2-methoxyphenoxy)ethyl)-6-(4-(trifluoromethoxy)phenyl)-[1,2,4]triazolo[4,3-a]pyridin-3(2H)-one; | 32.512 |
| 70. | 2-(3-(3-oxo-6-(4-(trifluoromethoxy)phenyl)-[1,2,4]triazolo[4,3-a]pyridin-2(3H)-yl)propoxy)benzonitrile; | 29.8771 |
| 71. | 6-(4-(trifluoromethoxy)phenyl)-2-(3-(2-(trifluoromethyl)phenoxy)propyl)-[1,2,4]triazolo[4,3-a]pyridin-3(2H)-one; | 26.0692 |
| 72. | (R)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one; | 41.8779 |
| 73. | 2-(2-(pyridin-3-yl)ethyl)-6-(4-(trifluoromethoxy)phenyl)-[1,2,4]triazolo[4,3-a]pyridin-3(2H)-one; | 10.383 |
| 74. | 2-(2-(3,3'-bipyridin-6-yl)ethyl)-6-(4-(trifluoromethoxy)phenyl)-[1,2,4]triazolo[4,3-a]pyridin-3(2H)-one; | 11.127 |
| 75. | 2-(2-(p-tolyloxy)ethyl)-6-(4-(trifluoromethoxy)phenyl)-[1,2,4]triazolo[4,3-a]pyridin-3(2H)-one; | 25.684 |
| 76. | 2-(3-(4-fluorophenyl)propyl)-6-(4-(trifluoromethoxy)phenyl)-[1,2,4]triazolo[4,3-a]pyridin-3(2H)-one; | 19.0357 |
| 77. | 2-(chroman-2-ylmethyl)-6-(4-(trifluoromethoxy)phenyl)-[1,2,4]triazolo[4,3-a]pyridin-3(2H)-one; | 32.1188 |
| 78. | 2-(2,4-difluorophenethyl)-6-(4-(trifluoromethoxy)phenyl)-[1,2,4]triazolo[4,3-a]pyridin-3(2H)-one; | 36.6993 |
| 79. | 2-(3-(pyridazin-3-yloxy)propyl)-6-(4-(trifluoromethoxy)phenyl)-[1,2,4]triazolo[4,3-a]pyridin-3(2H)-one; | 11.7081 |
| 80. | 2-(3-(2-chlorophenoxy)-2-methoxypropyl)-6-(4-(trifluoromethoxy)phenyl)-[1,2,4]triazolo[4,3-a]pyridin-3(2H)-one | 33.3906 |
| 81. | 2-(2-(pyridazin-3-yloxy)ethyl)-6-(4-(trifluoromethoxy)phenyl)-[1,2,4]triazolo[4,3-a]pyridin-3(2H)-one | 10.9591 |
| 82. | 2-(2-(5-methylpyrimidin-2-yloxy)ethyl)-6-(4-(trifluoromethoxy)phenyl)-[1,2,4]triazolo[4,3-a]pyridin-3(2H)-one; | 32.5156 |
| 83. | 2-((3-methyl-1,2,4-oxadiazol-5-yl)methyl)-6-(4-(2,2,2-trifluoroethoxy)phenyl)-[1,2,4]triazolo[4,3-a]pyridin-3(2H)-one; | 10.7427 |
| 84. | 2-(2-(2-(3-methyl-1,2,4-oxadiazol-5-yl)phenoxy)ethyl)-6-(4-(trifluoromethoxy)phenyl)-[1,2,4]triazolo[4,3-a]pyridin-3(2H)-one; | 34.274 |
| 85. | 2-(3-(pyrazin-2-yloxy)propyl)-6-(4-(trifluoromethoxy)phenyl)-[1,2,4]triazolo[4,3-a]pyridin-3(2H)-one; | 12.2393 |
| 86. | 2-(2-((5-methyl-1,2,4-oxadiazol-3-yl)methoxy)ethyl)-6-(4-(trifluoromethoxy)phenyl)-[1,2,4]triazolo[4,3-a]pyridin-3(2H)-one; | 17.4537 |
| 87. | 2-((3-methyl-1,2,4-oxadiazol-5-yl)methyl)-6-(2-methyl-4-(trifluoromethoxy)phenyl)-[1,2,4]triazolo[4,3-a]pyridin-3(2H)-one; | 21.3128 |
| 88. | 2-(2-(4,6-dimethylpyrimidin-2-yloxy)ethyl)-6-(4-(trifluoromethoxy)phenyl)-[1,2,4]triazolo[4,3-a]pyridin-3(2H)-one; | 20.752 |
| 89. | 2-(3-(2-chlorophenoxy)-2-(pyrimidin-2-yloxy)propyl)-6-(4-(trifluoromethoxy)phenyl)-[1,2,4]triazolo[4,3-a]pyridin-3(2H)-one; | 16.0092 |
| 90. | 2-(2-(4-cyclopropylpyrimidin-2-yloxy)ethyl)-6-(4-(trifluoromethoxy)phenyl)-[1,2,4]triazolo[4,3-a]pyridin-3(2H)-one; | 36.2522 |
| 91. | (S)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one; | 58.3263 |
| 92. | 2-(2-(5-chloropyrimidin-2-yloxy)ethyl)-6-(4-(trifluoromethoxy)phenyl)-[1,2,4]triazolo[4,3-a]pyridin-3(2H)-one | 35.2602 |
| 93. | 6-(4-(4-fluorophenoxy)phenyl)-2-((3-methyl-1,2,4-oxadiazol-5-yl)methyl)-[1,2,4]triazolo[4,3-a]pyridin-3(2H)-one; | 71.2637 |
| 94. | (3-((3-oxo-6-(4-(trifluoromethoxy)phenyl)-[1,2,4]triazolo[4,3-a]pyridin-2(3H)-yl)methyl)-1,2,4-oxadiazol-5-yl)methyl acetate; | 28.2375 |
| 95. | (S)-2-(3-(2-chlorophenoxy)-2-methoxypropyl)-6-(4-(trifluoromethoxy)phenyl)-[1,2,4]triazolo[4,3-a]pyridin-3(2H)-one; | 42.5175 |
| 96. | (R)-2-(3-(2-chlorophenoxy)-2-methoxypropyl)-6-(4-(trifluoromethoxy)phenyl)-[1,2,4]triazolo[4,3-a]pyridin-3(2H)-one; | 46.11 |
| 97. | 2-(2-(1-methyl-1H-benzo[d]imidazol-2-yl)ethyl)-6-(4-(trifluoromethoxy)phenyl)-[1,2,4]triazolo[4,3-a]pyridin-3(2H)-one; | 15.9545 |
| 98. | 2-(3-(4-fluoro-2-methoxyphenoxy)-2-hydroxypropyl)-6-(4-(trifluoromethoxy)phenyl)-[1,2,4]triazolo[4,3-a]pyridin-3(2H)-one; | 23.2121 |
| 99. | 2-(3-(2-ethoxyphenoxy)-2-hydroxypropyl)-6-(4-(trifluoromethoxy)phenyl)-[1,2,4]triazolo[4,3-a]pyridin-3(2H)-one; | 36.5416 |
| 100. | 2-(3-(biphenyl-2-yloxy)-2-hydroxypropyl)-6-(4-(trifluoromethoxy)phenyl)-[1,2,4]triazolo[4,3-a]pyridin-3(2H)-one; | 17.9635 |
| 101. | 2-(2-hydroxy-3-(3-oxo-6-(4-(trifluoromethoxy)phenyl)-[1,2,4]triazolo[4,3-a]pyridin-2(3H)-yl)propoxy)benzonitrile; | 11.6837 |
| 102. | 2-(2-(pyridin-2-yl)propyl)-6-(4-(trifluoromethoxy)phenyl)-[1,2,4]triazolo[4,3-a]pyridin-3(2H)-one; | 36.2033 |
| 103. | 2-(2-(6-methoxypyridin-2-yl)ethyl)-6-(4-(trifluoromethoxy)phenyl)-[1,2,4]triazolo[4,3-a]pyridin-3(2H)-one; | 49.6619 |

TABLE 2-continued

Late INa Assay results

| No. | Name | Late INa 1 μM |
|---|---|---|
| 104. | 2-(3-(4-fluoro-2-methoxyphenoxy)-2-methoxypropyl)-6-(4-(trifluoromethoxy)phenyl)-[1,2,4]triazolo[4,3-a]pyridin-3(2H)-one; | 41.4787 |
| 105. | 2-(2-ethoxy-3-(4-fluoro-2-methoxyphenoxy)propyl)-6-(4-(trifluoromethoxy)phenyl)-[1,2,4]triazolo[4,3-a]pyridin-3(2H)-one; | 45.016 |
| 106. | 2-(2-(4-ethoxypyrimidin-2-yloxy)ethyl)-6-(4-(trifluoromethoxy)phenyl)-[1,2,4]triazolo[4,3-a]pyridin-3(2H)-one; | 47.1789 |
| 107. | 2-(2-hydroxy-3-(2-methylbenzo[d]thiazol-6-yloxy)propyl)-6-(4-(trifluoromethoxy)phenyl)-[1,2,4]triazolo[4,3-a]pyridin-3(2H)-one; | 22.4131 |
| 108. | 2-(2-hydroxy-3-(2-isopropoxyphenoxy)propyl)-6-(4-(trifluoromethoxy)phenyl)-[1,2,4]triazolo[4,3-a]pyridin-3(2H)-one; | 41.5295 |
| 109. | 2-(4-(pyrimidin-2-yloxy)tetrahydrofuran-3-yl)-6-(4-(trifluoromethoxy)phenyl)-[1,2,4]triazolo[4,3-a]pyridin-3(2H)-one; | 12.9149 |
| 110. | 2-((3-methyl-1,2,4-oxadiazol-5-yl)methyl)-6-(4-(trimethylsilyl)phenyl)-[1,2,4]triazolo[4,3-a]pyridin-3(2H)-one; | 44.3346 |
| 111. | 2-(2-(pyrimidin-2-yl)ethyl)-6-(4-(trifluoromethoxy)phenyl)-[1,2,4]triazolo[4,3-a]pyridin-3(2H)-one; | 18.5967 |
| 112. | 2-(2-(2-oxo-3-phenoxypyrrolidin-1-yl)ethyl)-6-(4-(trifluoromethoxy)phenyl)-[1,2,4]triazolo[4,3-a]pyridin-3(2H)-one; | 11.1418 |
| 113. | 2-(2-(pyrimidin-4-yl)ethyl)-6-(4-(trifluoromethoxy)phenyl)-[1,2,4]triazolo[4,3-a]pyridin-3(2H)-one; | 17.8222 |
| 114. | 2-(2-(pyrazin-2-yl)ethyl)-6-(4-(trifluoromethoxy)phenyl)-[1,2,4]triazolo[4,3-a]pyridin-3(2H)-one; | 14.4366 |
| 115. | 2-(2-(4-phenylpyrimidin-2-yloxy)ethyl)-6-(4-(trifluoromethoxy)phenyl)-[1,2,4]triazolo[4,3-a]pyridin-3(2H)-one; | 22.8879 |
| 116. | 2-(2-(5-methoxypyrimidin-2-yloxy)ethyl)-6-(4-(trifluoromethoxy)phenyl)-[1,2,4]triazolo[4,3-a]pyridin-3(2H)-one; | 31.3385 |
| 117. | 2-(2-(3-methylpyrazin-2-yl)ethyl)-6-(4-(trifluoromethoxy)phenyl)-[1,2,4]triazolo[4,3-a]pyridin-3(2H)-one; | 18.2437 |
| 118. | 2-(2-(3-bromo-6-methoxypyridin-2-yl)ethyl)-6-(4-(trifluoromethoxy)phenyl)-[1,2,4]triazolo[4,3-a]pyridin-3(2H)-one; | 47.8823 |
| 119. | 2-(3-(4-fluoro-3-(oxazol-2-yl)phenyl)propyl)-6-(4-(trifluoromethoxy)phenyl)-[1,2,4]triazolo[4,3-a]pyridin-3(2H)-one; | 21.9669 |
| 120. | 6-(4-(4-chlorophenoxy)phenyl)-2-(2-(pyrimidin-2-yloxy)ethyl)-[1,2,4]triazolo[4,3-a]pyridin-3(2H)-one; | 73.8868 |
| 121. | 2-(3-(4-fluoro-3-(pyridin-3-yl)phenyl)propyl)-6-(4-(trifluoromethoxy)phenyl)-[1,2,4]triazolo[4,3-a]pyridin-3(2H)-one; | 13.0775 |
| 122. | 6-(4-(4-fluorophenoxy)phenyl)-2-(2-(pyrimidin-2-yloxy)ethyl)-[1,2,4]triazolo[4,3-a]pyridin-3(2H)-one; | 58.5091 |
| 123. | 2-(2-(pyrimidin-2-yloxy)ethyl)-6-(4-(trimethylsilyl)phenyl)-[1,2,4]triazolo[4,3-a]pyridin-3(2H)-one; | 38.0351 |
| 124. | 2-(2-ethoxy-3-(2-methylbenzo[d]thiazol-6-yloxy)propyl)-6-(4-(trifluoromethoxy)phenyl)-[1,2,4]triazolo[4,3-a]pyridin-3(2H)-one; | 31.2346 |
| 125. | 2-(4-(4-ethoxypyrimidin-2-yloxy)tetrahydrofuran-3-yl)-6-(4-(trifluoromethoxy)phenyl)-[1,2,4]triazolo[4,3-a]pyridin-3(2H)-one; | 14.1326 |
| 126. | 2-(2-(4-(dimethylamino)-5-fluoropyrimidin-2-yloxy)ethyl)-6-(4-(trifluoromethoxy)phenyl)-[1,2,4]triazolo[4,3-a]pyridin-3(2H)-one; | 32.5571 |
| 127. | 6-(3,5-difluoro-4-phenoxyphenyl)-2-((3-methyl-1,2,4-oxadiazol-5-yl)methyl)-[1,2,4]triazolo[4,3-a]pyridin-3(2H)-one; | 21.5076 |
| 128. | 2-((5-(methoxymethyl)-1,2,4-oxadiazol-3-yl)methyl)-6-(4-(trifluoromethoxy)phenyl)-[1,2,4]triazolo[4,3-a]pyridin-3(2H)-one; | 21.9863 |
| 129. | 2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidine-4-carbonitrile; | 16.1133 |
| 130. | 2-(2-(5-chloro-4-methoxypyrimidin-2-yloxy)ethyl)-6-(4-(trifluoromethoxy)phenyl)-[1,2,4]triazolo[4,3-a]pyridin-3(2H)-one; | 32.4282 |
| 131. | 6-(4-benzoylphenyl)-2-((3-methyl-1,2,4-oxadiazol-5-yl)methyl)-[1,2,4]triazolo[4,3-a]pyridin-3(2H)-one; | 34.7287 |
| 132. | 2-(2-(4-(4-chlorophenoxy)pyrimidin-2-yloxy)ethyl)-6-(4-(trifluoromethoxy)phenyl)-[1,2,4]triazolo[4,3-a]pyridin-3(2H)-one; | 11.019 |
| 133. | 2-(2-(4-(3,3-difluoroazetidin-1-yl)-5-fluoropyrimidin-2-yloxy)ethyl)-6-(4-(trifluoromethoxy)phenyl)-[1,2,4]triazolo[4,3-a]pyridin-3(2H)-one; | 20.4635 |
| 134. | 6-(3,4-dichlorophenyl)-2-((3-methyl-1,2,4-oxadiazol-5-yl)methyl)-[1,2,4]triazolo[4,3-a]pyridin-3(2H)-one; | 15.5405 |
| 135. | 2-(2-(pyrrolo[1,2-a]pyrazin-1-yloxy)ethyl)-6-(4-(trifluoromethoxy)phenyl)-[1,2,4]triazolo[4,3-a]pyridin-3(2H)-one; | 41.4713 |
| 136. | 2-((3-((3-oxo-6-(4-(trifluoromethoxy)phenyl)-[1,2,4]triazolo[4,3-a]pyridin-2(3H)-yl)methyl)-1,2,4-oxadiazol-5-yl)methyl)isoindoline-1,3-dione | 25.2136 |
| 137. | 2-((3-methyl-1,2,4-oxadiazol-5-yl)methyl)-6-(4-(trifluoromethyl)phenyl)-[1,2,4]triazolo[4,3-a]pyridin-3(2H)-one; | 28.8284 |

TABLE 2-continued

Late INa Assay results

| No. | Name | Late INa 1 μM |
|---|---|---|
| 138. | 2-(2-(5-fluoropyrimidin-2-yloxy)ethyl)-6-(4-(trifluoromethoxy)phenyl)-[1,2,4]triazolo[4,3-a]pyridin-3(2H)-one; | 32.4352 |
| 139. | 2-(2-(2-chloropyrimidin-5-yloxy)ethyl)-6-(4-(trifluoromethoxy)phenyl)-[1,2,4]triazolo[4,3-a]pyridin-3(2H)-one; | 20.1502 |
| 140. | 6-(4-(4-fluorophenoxy)phenyl)-2-((5-methyl-1,2,4-oxadiazol-3-yl)methyl)-[1,2,4]triazolo[4,3-a]pyridin-3(2H)-one; | 60.6005 |
| 141. | 2-(2-(isoquinolin-1-yloxy)ethyl)-6-(4-(trifluoromethoxy)phenyl)-[1,2,4]triazolo[4,3-a]pyridin-3(2H)-one; | 29.8617 |
| 142. | 2-((5-cyclopropyl-1,2,4-oxadiazol-3-yl)methyl)-6-(4-(trifluoromethoxy)phenyl)-[1,2,4]triazolo[4,3-a]pyridin-3(2H)-one; | 20.0298 |
| 143. | 6-(4-(4-fluorophenoxy)phenyl)-[1,2,4]triazolo[4,3-a]pyridin-3(2H)-one; | 56.6125 |
| 144. | 2-((5-(pyridin-2-yl)isoxazol-3-yl)methyl)-6-(4-(trifluoromethoxy)phenyl)-[1,2,4]triazolo[4,3-a]pyridin-3(2H)-one; | 19.2199 |
| 145. | 2-((5-(3-methylpyridin-2-yl)isoxazol-3-yl)methyl)-6-(4-(trifluoromethoxy)phenyl)-[1,2,4]triazolo[4,3-a]pyridin-3(2H)-one; | 37.6986 |
| 146. | 6-(4-(4-fluorophenoxy)phenyl)-2-((5-(hydroxymethyl)-1,2,4-oxadiazol-3-yl)methyl)-[1,2,4]triazolo[4,3-a]pyridin-3(2H)-one; | 32.5672 |
| 147. | 2-(1-(3-methyl-1,2,4-oxadiazol-5-yl)ethyl)-6-(4-(trifluoromethoxy)phenyl)-[1,2,4]triazolo[4,3-a]pyridin-3(2H)-one; | 13.4441 |
| 148. | 2-((5-methyl-1,2,4-oxadiazol-3-yl)methyl)-6-(4-(trifluoromethyl)phenyl)-[1,2,4]triazolo[4,3-a]pyridin-3(2H)-one; | 11.6007 |
| 149. | 6-(4-chlorophenyl)-2-((3-methyl-1,2,4-oxadiazol-5-yl)methyl)-[1,2,4]triazolo[4,3-a]pyridin-3(2H)-one; | 26.174 |
| 150. | 6-(3,4-difluorophenyl)-2-((3-methyl-1,2,4-oxadiazol-5-yl)methyl)-[1,2,4]triazolo[4,3-a]pyridin-3(2H)-one; | 12.8483 |
| 151. | 2-cinnamyl-6-(4-(trifluoromethoxy)phenyl)-[1,2,4]triazolo[4,3-a]pyridin-3(2H)-one; | 16.5462 |
| 152. | (S)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one | 10.66 |
| 153. | 2-((3-(methoxymethyl)-1,2,4-oxadiazol-5-yl)methyl)-6-(4-(trifluoromethoxy)phenyl)-[1,2,4]triazolo[4,3-a]pyridin-3(2H)-one; | 23.2052 |
| 154. | 2-((5-(difluoromethyl)-1,2,4-oxadiazol-3-yl)methyl)-6-(4-(trifluoromethoxy)phenyl)-[1,2,4]triazolo[4,3-a]pyridin-3(2H)-one; | 21.0473 |
| 155. | 6-(3-fluoro-4-(trifluoromethoxy)phenyl)-2-((3-methyl-1,2,4-oxadiazol-5-yl)methyl)-[1,2,4]triazolo[4,3-a]pyridin-3(2H)-one; | 18.817 |
| 156. | 2-(2-(4-(2-hydroxyethoxy)pyrimidin-2-yloxy)ethyl)-6-(4-(trifluoromethoxy)phenyl)-[1,2,4]triazolo[4,3-a]pyridin-3(2H)-one; | 6.6206 |
| 157. | 2-((5-(chloromethyl)-1,2,4-oxadiazol-3-yl)methyl)-6-(4-(trifluoromethoxy)phenyl)-[1,2,4]triazolo[4,3-a]pyridin-3(2H)-one; | 22.6872 |
| 158. | (R)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one | 25.2502 |
| 159. | 2-(2-(4-(methylthio)pyrimidin-2-yloxy)ethyl)-6-(4-(trifluoromethoxy)phenyl)-[1,2,4]triazolo[4,3-a]pyridin-3(2H)-one; | 49.6175 |
| 160. | 2-(2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidin-4-yloxy)acetonitrile; | 24.6907 |
| 161. | 6-(4-chloro-3-fluorophenyl)-2-((3-methyl-1,2,4-oxadiazol-5-yl)methyl)-[1,2,4]triazolo[4,3-a]pyridin-3(2H)-one; | 13.8693 |
| 162. | 2-((5-((pyrimidin-2-yloxy)methyl)-1,2,4-oxadiazol-3-yl)methyl)-6-(4-(trifluoromethoxy)phenyl)-[1,2,4]triazolo[4,3-a]pyridin-3(2H)-one; | 18.5454 |
| 163. | 2-((1-methyl-1H-pyrazol-4-yl)methyl)-6-(4-(trifluoromethoxy)phenyl)-[1,2,4]triazolo[4,3-a]pyridin-3(2H)-one; | 11.9553 |
| 164. | 2-((3-methylisoxazol-5-yl)methyl)-6-(4-(trifluoromethoxy)phenyl)-[1,2,4]triazolo[4,3-a]pyridin-3(2H)-one; | 16.9216 |
| 165. | 2-((1-methyl-1H-pyrazol-3-yl)methyl)-6-(4-(trifluoromethoxy)phenyl)-[1,2,4]triazolo[4,3-a]pyridin-3(2H)-one; | 10.8304 |
| 166. | 2-((3-ethyl-1,2,4-oxadiazol-5-yl)methyl)-6-(4-(trifluoromethoxy)phenyl)-[1,2,4]triazolo[4,3-a]pyridin-3(2H)-one; | 24.3827 |
| 167. | 2-((3-ethyl-1,2,4-oxadiazol-5-yl)methyl)-6-(4-(trifluoromethyl)phenyl)-[1,2,4]triazolo[4,3-a]pyridin-3(2H)-one; | 26.1662 |
| 168. | 2-((3-(methoxymethyl)-1,2,4-oxadiazol-5-yl)methyl)-6-(4-(trifluoromethyl)phenyl)-[1,2,4]triazolo[4,3-a]pyridin-3(2H)-one; | 19.1476 |
| 169. | 2-((3-trideuteromethyl-1,2,4-oxadiazol-5-yl)methyl)-6-(4-(trifluoromethoxy)phenyl)-[1,2,4]triazolo[4,3-a]pyridin-3(2H)-one; | 24.0589 |
| 170. | 2-((5-cyclopropyl-1,3,4-thiadiazol-2-yl)methyl)-6-(4-(trifluoromethoxy)phenyl)-[1,2,4]triazolo[4,3-a]pyridin-3(2H)-one; | 18.0428 |
| 171. | 6-(4-(trifluoromethyl)phenyl)-[1,2,4]triazolo[4,3-a]pyridin-3(2H)-one; | 19.6069 |
| 172. | 2-((5-methyloxazol-2-yl)methyl)-6-(4-(trifluoromethyl)phenyl)-[1,2,4]triazolo[4,3-a]pyridin-3(2H)-one; | 24.7699 |

TABLE 2-continued

Late INa Assay results

| No. | Name | Late INa 1 μM |
|---|---|---|
| 173. | 2-((4,5-dimethyloxazol-2-yl)methyl)-6-(4-(trifluoromethyl)phenyl)-[1,2,4]triazolo[4,3-a]pyridin-3(2H)-one; | 22.2478 |
| 174. | 2-(2-(imidazo[1,2-a]pyrazin-8-yloxy)ethyl)-6-(4-(trifluoromethoxy)phenyl)-[1,2,4]triazolo[4,3-a]pyridin-3(2H)-one; | 26.2891 |
| 175. | 2-((5-((pyridin-2-yloxy)methyl)-1,2,4-oxadiazol-3-yl)methyl)-6-(4-(trifluoromethoxy)phenyl)-[1,2,4]triazolo[4,3-a]pyridin-3(2H)-one; | 28.8663 |
| 176. | 2-((5-((2-ethoxyphenoxy)methyl)-1,2,4-oxadiazol-3-yl)methyl)-6-(4-(trifluoromethoxy)phenyl)-[1,2,4]triazolo[4,3-a]pyridin-3(2H)-one; | 25.5442 |
| 177. | 2-(2-(4-isopropoxypyrimidin-2-yloxy)ethyl)-6-(4-(trifluoromethoxy)phenyl)-[1,2,4]triazolo[4,3-a]pyridin-3(2H)-one; | 25.8338 |
| 178. | 2-(2-(4-(2,2,2-trifluoroethoxy)pyrimidin-2-yloxy)ethyl)-6-(4-(trifluoromethoxy)phenyl)-[1,2,4]triazolo[4,3-a]pyridin-3(2H)-one; | 14.2338 |
| 179. | 2-(2-(4-(cyclopropylmethoxy)pyrimidin-2-yloxy)ethyl)-6-(4-(trifluoromethoxy)phenyl)-[1,2,4]triazolo[4,3-a]pyridin-3(2H)-one; | 30.2966 |
| 180. | 6-(4-(trifluoromethoxy)phenyl)-2-(2-(5-(trifluoromethyl)pyrimidin-2-yloxy)ethyl)-[1,2,4]triazolo[4,3-a]pyridin-3(2H)-one; | 22.6454 |
| 181. | 2-((2-cyclopropyloxazol-4-yl)methyl)-6-(4-(trifluoromethoxy)phenyl)-[1,2,4]triazolo[4,3-a]pyridin-3(2H)-one; | 23.8732 |
| 182. | 2-((5-cyclopropyl-1,3,4-oxadiazol-2-yl)methyl)-6-(4-(4-fluorophenoxy)phenyl)-[1,2,4]triazolo[4,3-a]pyridin-3(2H)-one; | 45.9277 |
| 183. | 2-((5-tert-butyloxazol-2-yl)methyl)-6-(4-(trifluoromethoxy)phenyl)-[1,2,4]triazolo[4,3-a]pyridin-3(2H)-one; | 14.6104 |
| 184. | 2-((5-tert-butyloxazol-2-yl)methyl)-6-(4-(trifluoromethyl)phenyl)-[1,2,4]triazolo[4,3-a]pyridin-3(2H)-one; | 18.8675 |
| 185. | 2-methyl-6-(4-(trifluoromethyl)phenyl)-[1,2,4]triazolo[4,3-a]pyridin-3(2H)-one; | 10.0707 |
| 186. | (R)-2-(2-(3-(4-fluorophenoxy)pyrrolidin-1-yl)ethyl)-6-(4-(trifluoromethoxy)phenyl)-[1,2,4]triazolo[4,3-a]pyridin-3(2H)-one; | 37.2878 |
| 187. | 5-methyl-6-(4-(trifluoromethoxy)phenyl)-[1,2,4]triazolo[4,3-a]pyridin-3(2H)-one; | 29.8408 |
| 188. | 5-methyl-2-((3-methyl-1,2,4-oxadiazol-5-yl)methyl)-6-(4-(trifluoromethoxy)phenyl)-[1,2,4]triazolo[4,3-a]pyridin-3(2H)-one; | 17.3208 |
| 189. | 2-(2,2,2-trifluoroethyl)-6-(4-(trifluoromethoxy)phenyl)-[1,2,4]triazolo[4,3-a]pyridin-3(2H)-one; | 15.2595 |
| 190. | 2-isopropyl-6-(4-(trifluoromethoxy)phenyl)-[1,2,4]triazolo[4,3-a]pyridin-3(2H)-one; | 17.5984 |
| 191. | 2-((4-methyloxazol-2-yl)methyl)-6-(4-(trifluoromethoxy)phenyl)-[1,2,4]triazolo[4,3-a]pyridin-3(2H)-one; | 28.8653 |
| 192. | 2-((4-methyloxazol-2-yl)methyl)-6-(4-(trifluoromethyl)phenyl)-[1,2,4]triazolo[4,3-a]pyridin-3(2H)-one; | 34.4214 |
| 193. | 2-((4-cyclopropyloxazol-2-yl)methyl)-6-(4-(trifluoromethoxy)phenyl)-[1,2,4]triazolo[4,3-a]pyridin-3(2H)-one | 33.7808 |
| 194. | 2-((4-cyclopropyloxazol-2-yl)methyl)-6-(4-(trifluoromethyl)phenyl)-[1,2,4]triazolo[4,3-a]pyridin-3(2H)-one; | 21.636 |
| 195. | 6-(4-chlorophenyl)-2-((5-methyloxazol-2-yl)methyl)-[1,2,4]triazolo[4,3-a]pyridin-3(2H)-one | 31.2149 |
| 196. | 8-methyl-6-(4-(trifluoromethoxy)phenyl)-[1,2,4]triazolo[4,3-a]pyridin-3(2H)-one; | 38.29 |
| 197. | 2-((2-methyloxazol-5-yl)methyl)-6-(4-(trifluoromethyl)phenyl)-[1,2,4]triazolo[4,3-a]pyridin-3(2H)-one; | 19.6737 |
| 198. | 2-(3-(4,5-dichloro-2-methoxyphenoxy)-2-hydroxypropyl)-6-(4-(trifluoromethyl)phenyl)-[1,2,4]triazolo[4,3-a]pyridin-3(2H)-one; | 14.7506 |
| 199. | 2-((5-cyclopropyloxazol-2-yl)methyl)-6-(4-(trifluoromethoxy)phenyl)-[1,2,4]triazolo[4,3-a]pyridin-3(2H)-one; | 22.5 |
| 200. | 6-(4-(trifluoromethoxy)phenyl)-[1,2,4]triazolo[4,3-a]pyridin-3(2H)-one; | 26.5 |
| 201. | 2-methyl-6-(4-(trifluoromethoxy)phenyl)-[1,2,4]triazolo[4,3-a]pyridin-3(2H)-one; | 38.7 |

The assay results shown in the above Table 2 establish that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel. In some embodiments, a compound having an activity of reducing late sodium current will also exhibit little or no activity with regard to the L-type calcium channel. For example, a given compound may provide a 30% (or greater, e.g. more than 40%, more than 50%, more than 60%, more than 70%, more than 80%) reduction in late sodium current in the assay described herein, and the same compound may exhibit little or no activity for one or more of the peak sodium current, the hERG potassium channel, and the L-type calcium channel. In this regard, a compound having "little" effect will typically show less then a 30% reduction (e.g. less than a 20% reduction, less than a 15% reduction, less than a 10% reduction) in the given activity (e.g. Peak INa, hERG, L-type calcium), when measured using the assay described herein. In this regard, "no" effect means that any activity measured will differ from the control by less than the standard error of the measurement. The assays conducted to measure activities in this regard should be performed as described above, with the compound at a concentration of 10 μM (or at the upper limit of solubility, if less).

L-type Ca2+ Channel Assay ChanTest

Selected compounds were screened for block of the cardiac L-type $Ca^{2+}$ channel (hCav1.2, encoded by the human CACNA1C gene and coexpressed with the beta 2 subunit, encoded by the human CACNB2 gene, and alpha2delta1, encoded by the CACNA2D1 gene). The $Ca^{2+}$ channel is heterologously expressed in a CHO (Chinese Hamster Ovary) cell line. Cells are maintained following standard tissue culture procedures and stable channel expression is maintained with appropriate selection antibiotics in the culture medium. Cells are harvested for testing on the PatchXpress automated patch clamp (Model 7000A, Molecular Devices, Sunnyvale, Calif.) by washing twice with Hank's Balanced Salt Solution, treating the cells with trypsin, and re-suspending cells in culture medium ($4$-$6 \times 10^6$ cells in 20 mL). Cells in suspension are allowed to recover for 10 minutes in a tissue culture incubator set at 37° C. in a humidified 95% air, 5% $CO_2$ atmosphere.

The following solutions are used for electrophysiological recordings. The external solution contains (mM): 137 NaCl, 4 KCl, 1.8 CaCl2, 1 MgCl2, 10 Glucose, 10 HEPES (pH 7.4 with NaOH). The internal solution contains (mM): 130 Cs Aspartate, 5 MgCl2, 5 EGTA, 4 ATP, 0.1 GTP, 10 HEPES, (pH adjusted to 7.2 with N-methyl-D-glucamine).

Vehicle is applied to nave cells (n≥2, where n=the number cells), for a 5-10 minute exposure interval. Each solution exchange is performed in quadruplicate. At the end of each experiment, a saturating concentration of nifedipine (10 μM) is added to block hCav1.2 current. Leak current is digitally subtracted from the total membrane current record.

Test compound stock solutions are prepared by addition of dimethyl sulfoxide (DMSO) and stored frozen. Each test compound DMSO stock is sonicated (Model 2510/5510, Branson Ultrasonics, Danbury, Conn.), at ambient room temperature for at least 20 minutes to facilitate dissolution. Test compound concentrations are prepared fresh daily by diluting stock solutions into the standard extracellular physiological saline solution (see above). The maximum percent of DMSO added with compound is 0.1%. All test compound and control solutions are placed in a glass-lined 96-well compound plate before loading on PatchXpress.

One or two concentrations (1, 10 μM) of each test compound is applied at five (5) minute intervals via disposable polyethylene micropipette tips to nave cells (n 2, where n=the number cells/concentration). Each test compound concentration is added to the cell in quadruplicate. Total duration of exposure to each test compound concentration is 5 minutes.

Onset and steady state block of hCav1.2 (α1C/β2/α2δ) channels is measured using a stimulus voltage pattern consisting of a depolarizing test pulse (duration, 200 ms; amplitude, 10 mV) at 10 s intervals from a −80 mV holding potential. Peak current is measured during a step to 10 mV.

Example 208

$Na_v1.7$ Screening Assay

Evidence supports a role for the tetrodotoxin-sensitive $Na_v1.7$ in the pathogenesis of pain. In this assay, whole-cell patch-clamp techniques were used to determine the effects of compounds of Formula (I) on human Nav1.7 (hNav1.7+β1 subunits) channels expressed in HEK293 cells. The $Na_v1.7$ cell line was prepared by stably transfecting HEK293 cells with human $Na_v1.7$ α unit and β1 subunit. HEK293 cells stably expressing $huNa_v1.7$ were analyzed by patch clamp techniques and were found to have $Na^+$ currents between −400 and −1800 pA (no currents were recorded in untransfected cells). The $Na^+$ current in these cells was blocked by tetrodotoxin (TTX) with an $IC_{50}$ value of 10-74 nmol/L. Similar results were obtained by use of membrane potential-sensitive dyes.

Stock solutions of compounds of Formula I ("test compounds") were prepared in DMSO at a concentration of 40 mmol/L just prior to use. Each test compound was tested in duplicate at 100 μM, then a 1 in 4 serial dilution to yield 8 concentrations for testing. TTX was used as a control inhibitor of $Na_v1.7$ current.

The effect of test compounds to reduce $Na_v1.7$ $Na^+$ current was measured using a fluorescent dye-based membrane potential assay kit (#R8123) from Molecular Devices (California, USA). Briefly, cells were seeded into poly-D-lysine pre-coated black-wall, clear-bottom 96-well Biocoat plates in 100 μl growth media 24 h prior to assay. On the day of the assay the membrane potential dye was prepared and prewarmed with Hepes-HBSS solution to 37° C. To each well, 100 μl dye was added and incubated at 37° C. for 60 min. Veratridine was added to each well to achieve a final concentration of 50 μmol/L. Test compound was then added to each well in the desired concentration, and fluorescence was recorded. For each test compound data set, an $IC_{50}$ value was calculated based on the assay points generated.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel or L-type calcium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 μM (or at the upper limit of solubility, if less). In particular embodiments, the selectivity of a compound of the disclosure will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current, or the L-type calcium channel.

Example 209

Material and Methods

Expression of Human $Na_v1.1$ cDNA

All wild-type (WT) and mutant constructs have been studied previously by our laboratory (Kahlig, 2008; Lossin, 2002; Rhodes, 2004) and cDNA expression was performed as previously described (Kahlig, 2008). Briefly, expression of $Na_v1.1$ was achieved by transient transfection using Qiagen Superfect reagent (5.5 μg of DNA was transfected at a plasmid mass ratio of 10:1:1 for $\alpha_1$:$\beta_1$:$\beta_2$). The human $\beta_1$ and $\beta_2$ cDNAs were cloned into plasmids containing the marker genes DsRed (DsRed-IRES2-h$\beta_1$) or EGFP (EGFP-IRES2-h$\beta_2$) along with an internal ribosome entry site (IRES). Unless otherwise noted, all reagents were purchased from Sigma-Aldrich (St Louis, Mo., U.S.A.).

Electrophysiology

Whole-cell voltage-clamp recordings are used to measure the biophysical properties of WT and mutant Na$_V$1.1 channels, as described previously (Kahlig, 2008). Briefly, the pipette solution consisted of (in mM) 110 CsF, 10 NaF, 20 CsCl, 2 EGTA, 10 HEPES, with a pH of 7.35 and osmolarity of 300 mOsmol/kg. The bath (control) solution contained in (mM): 145 NaCl, 4 KCl, 1.8 CaCl$_2$, 1 MgCl$_2$, 10 dextrose, 10 HEPES, with a pH of 7.35 and osmolarity of 310 mOsmol/kg. Cells are allowed to stabilize for 10 min after establishment of the whole-cell configuration before current was measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz. For clarity, representative ramp currents are low pass filtered off-line at 50 Hz.

Specific voltage-clamp protocols assessing channel activation, fast inactivation and availability during repetitive stimulation are used as depicted as figure insets. Whole-cell conductance wisas calculated from the peak current amplitude by $G_{Na}=I_{Na}/(V-E_{Na})$ and normalized to the maximum conductance between −80 and +20 mV. Conductance-voltage and steady-state channel availability curves are fit with Boltzmann functions to determine the voltage for half-maximal activation/inactivation ($V_{1/2}$) and a slope factor (k). Time-dependent entry into and recovery from inactivation are evaluated by fitting the peak current recovery with the two exponential function, $I/I_{max}=A_f\times[1-\exp(-t/\tau_f)]+A_s\times[1-\exp(-t/\tau_s)]$, where $\tau_f$ and $\tau_s$ denote time constants (fast and slow components, respectively), $A_f$ and $A_s$ represent the fast and slow fractional amplitudes.

For use-dependent studies, cells are stimulated with depolarizing pulse trains (−10 mV, 5 ms, 300 pulses, 10 Hz) from a holding potential of −120 mV. Currents are then normalized to the peak current recorded in response to the first pulse in each frequency train. For tonic block studies, peak and persistent current are evaluated in response to a 200 ms depolarization to −10 mV (0.2 Hz) following digital subtraction of currents recorded in the presence and absence of 0.5 µM tetrodotoxin (TTX). Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM. Unless otherwise noted, statistical comparisons are made using one-way ANOVA followed by a Tukey post-hoc test in reference to WT-Na$_V$1.1.

In Vitro Pharmacology

A stock solution of 20 mM ranolazine (Gilead, Foster City, Calif.) is prepared in 0.1 M HCl. A fresh dilution of the compound of Formula IA or IB in the bath solution is prepared every experimental day and the pH was readjusted to 7.35. Direct application of the perfusion solution to the clamped cell is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Solutions containing the compounds of the disclosure are perfused for three minutes prior to current recordings to allow equilibrium (tonic) drug block. Tonic block of peak and persistent currents are measured from this steady-state condition. Three sequential current traces are averaged to obtain a mean current for each recording condition (control, ranolazine and TTX). The mean current traces are utilized for offline subtraction and analysis. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition, which are then used for offline subtraction and analysis. Block of ramp current is assessed by voltage ramps to +20 mV from a holding potential of −120 mV at a rate of 20 mV/s stimulated every 30 s. To minimize time-dependent current drift, only one trace recorded during control, compound of the disclosure, or TTX superfusion is analyzed. TTX was applied in the presence of ranolazine. Concentration inhibition curves are fit with the Hill equation: $I/I_{max}=1/[1+10^{\wedge}(\log IC_{50}-I)*k]$, where $IC_{50}$ is the concentration that produces half inhibition and k is the Hillslope factor.

In Vivo Pharmacology

Jugular vein cannulated male Sprague Dawley rats (250-350 g, Charles River Laboratories, Hollister, Calif.) are used to study brain penetration of the compounds of the disclosure in vivo. Animal use is approved by the Institutional Animal Care and Use Committee, Gilead Sciences. Three rats per group are infused intravenously with the compound of the disclosure in saline at 85.5 µg/kg/min. After 1, 2.5 or 5 h animals are sacrificed for plasma and brain collection, and concentrations of the compound of the disclosure are measured by liquid chromatography coupled with tandem mass spectrometry (LC-MS/MS). Brain tissue is homogenated in 1% 2N HCl acidified 5% sodium fluoride (final homogenate was diluted 3-fold). Plasma and brain homogenate samples (50 µl) are precipitated along with deuterated D3-ranolazine as an internal standard, vortexed and centrifuged. The supernatant (50 µL) is transferred and diluted with water (450 µl) prior to injection (10 µl). High performance liquid chromatography wisas performed using a Shimadzu LC-10AD liquid chromatograph and a Luna C18(2), 3 µm, 20×2.0 mm column with a mobile phase consisting of water containing 0.1% formic acid (solution A) and acetonitrile (solution B) carried out under isocratic conditions (75% solution A, 25% solution B; flow rate 0.300 ml/min). Mass spectrometric analyses are performed using an API3000 mass spectrometer (Applied Biosystems, Foster City, Calif.) operating in positive ion mode with MRM transition 428.1>98. Brain-to-plasma ranolazine ratios wareere calculated for each sample as ng ranolazine/g brain divided by ng ranolazine/ml plasma.

Results

Using the above methods it can be demonstrated that the compound of the disclosure have the ability to inhibit WT-Na$_V$1.1 and a panel of Na$_V$1.1 mutant channels associated with the epilepsy and migraine syndromes GEFS+, SMEI and FHM3 demonstrating the ability of the compounds of the disclosure to preferentially block the abnormal increased persistent current carried by these mutant channels. The ability of the compounds of the disclosure to cross the blood brain barrier may also be established using the above methods.

Example 210

Material and Methods

Expression of Human $Na_V1.2$ cDNA

Wild-type (WT) cDNA stably transfected in Chinese hamster ovary (CHO) cells is used to record Na+ currents. Unless otherwise noted, all reagents are purchased from Sigma-Aldrich (St Louis, Mo., U.S.A.).

Electrophysiology

Whole-cell voltage-clamp recordings are used to measure the biophysical properties of WT. Briefly, the pipette solution consists of (in mM) 110 CsF, 10 NaF, 20 CsCl, 2 EGTA, 10 HEPES, with a pH of 7.35 and osmolarity of 300 mOsmol/kg. The bath (control) solution contains in (mM): 145 NaCl, 4 KCl, 1.8 CaCl2, 1 MgCl2, 10 dextrose, 10 HEPES, with a pH of 7.35 and osmolarity of 310 mOsmol/kg. Cells are allowed to stabilize for 10 min after establishment of the whole-cell configuration before current is measured. Series resistance is compensated 90% to assure that the command potential is reached within microseconds with a voltage error <2 mV. Leak currents are subtracted by using an online P/4 procedure and all currents are low-pass Bessel filtered at 5 kHz and digitized at 50 kHz.

For clarity, representative ramp currents are low pass filtered off-line at 50 Hz. Specific voltage-clamp protocols assessing channel activation, fast inactivation and availability during repetitive stimulation are used. Results are presented as mean±SEM, and unless otherwise noted, statistical comparisons are made using one-way ANOVA.

Tonic block of peak current is measured. The mean current traces are utilized for offline subtraction and analysis. Use-dependent block of peak current is measured during pulse number 300 of a pulse train (−10 mV, 5 ms, 300 pulses) at frequencies between 10 and 135 Hz from a holding potential of −120 mV. Two sequential pulse train stimulations are averaged to obtain mean current traces for each recording condition, which are then used for offline subtraction and analysis.

Specific voltage-clamp protocols assessing channel activation, fast inactivation and availability during repetitive stimulation are used. Whole-cell conductance is calculated from the peak current amplitude by $G_{Na}=I_{Na}/(V-E_{Na})$ and normalized to the maximum conductance between −80 and +20 mV. Conductance-voltage and steady-state channel availability curves are fit with Boltzmann functions to determine the voltage for half-maximal activation/inactivation ($V_{1/2}$) and a slope factor (k). Time-dependent entry into and recovery from inactivation are evaluated by fitting the peak current recovery with the two exponential function, $I/I_{max}=A_f\times[1-\exp(-t/\tau_f)]+A_s\times[1-\exp(-t/\tau_s)]$, where $\tau_f$ and $\tau_s$ denote time constants (fast and slow components, respectively), $A_f$ and $A_s$ represent the fast and slow fractional amplitudes.

For use-dependent studies, cells are stimulated with depolarizing pulse trains (−10 mV, 5 ms, 300 pulses, 10 Hz) from a holding potential of −120 mV. Currents are then normalized to the peak current recorded in response to the first pulse in each frequency train. For tonic block studies, peak and persistent current are evaluated in response to a 200 ms depolarization to −10 mV (0.2 Hz) following digital subtraction of currents recorded in the presence and absence of 0.5 μM tetrodotoxin (TTX). Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM. Unless otherwise noted, statistical comparisons are made using one-way ANOVA followed by a Tukey post-hoc test in reference to $WT-Na_V1.2$.

In vitro Pharmacology

Stock solutions of 20 mM of the compounds of the disclosure (Gilead, Foster City, Calif.) are prepared in 0.1M HCl. Fresh dilutions of the compound of the disclosures in the bath solution are prepared every experimental day and the pH is readjusted to 7.35. Direct application of the perfusion solutions to the clamped cells is achieved using the Perfusion Pencil system (Automate, Berkeley, Calif.). Direct cell perfusion is driven by gravity at a flow rate of 350 μL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Ranolazine containing solutions are perfused for three minutes prior to current recordings to allow equilibrium (tonic) drug block. Tonic block of peak and persistent currents are measured from this steady-state condition. Three sequential current traces are averaged to obtain a mean current for each recording condition (control, compounds of the disclosure, and TTX). The mean current traces are utilized for offline subtraction and analysis. Use-dependent block of peak current is measured during pulse number 300 of the pulse train, (−10 mV, 5 ms, 300 pulses, 10 Hz) from a holding potential of 120 mV. Two sequential pulse train stimulations are averaged to obtain mean current traces for each recording condition, which are then used for offline subtraction and analysis. Block of ramp current is assessed by voltage ramps to +20 mV from a holding potential of −120 mV at a rate of 20 mV/s stimulated every 30 s. To minimize time-dependent current drift, only one trace recorded during control, compound of the disclosure, or TTX superfusion is analyzed. TTX is applied in the presence of the compound of the disclosure. Concentration inhibition curves are fit with the Hill equation: $I/I_{max}=1/[1+10^{\wedge}(\log IC_{50}-I)*k]$, where $IC_{50}$ is the concentration that produces half inhibition and k is the Hill slope factor.

Results

It is thus demonstrated that the compounds of the disclosure have the ability to inhibit $WT-Na_v1.2$ demonstrating the ability of the compounds of the disclosure to preferentially block an abnormal increased persistent current carried by this channel.

What is claimed is:

1. A method of treating a disease in a human selected from the group consisting of diabetes, diabetic peripheral neuropathy, migraine, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication, comprising administering to a human in need thereof a therapeutically effective dose of a compound of Formula I:

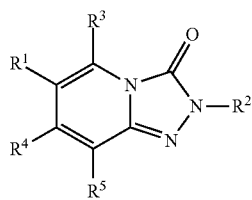

I wherein:
R$^1$ is aryl, pyridinyl, pyridazinyl, pyrimidinyl, quinolonyl, indazolyl, triazolopyridinyl, imidazopyridinyl, thiadiazolyl, or triazolyl;
  wherein said aryl, pyridinyl, pyridazinyl, pyrimidinyl, quinolonyl, indazolyl, triazolopyridinyl, imidazopyridinyl, thiadiazolyl, or triazolyl are substituted with one, two, or three substituents independently selected from the group consisting of hydroxyl, halo, —NO$_2$, CN, —SF$_5$, —Si(CH$_3$)$_3$, —O—CF$_3$, —O—R$^{20}$, —S—R$^{20}$, —C(O)—R$^{20}$, —N(R$^{20}$)(R$^{22}$), —C(O)—N(R$^{20}$)(R$^{22}$), —N(R$^{20}$)—C(O)—R$^{22}$, —N(R$^{20}$)—S(O)$_2$—R$^{26}$, —S(O)$_2$—R$^{20}$, —S(O)$_2$—N(R$^{20}$)(R$^{22}$), C$_{1-3}$ alkoxy, C$_{1-4}$ alkyl, C$_{2-4}$ alkenyl, C$_{2-4}$ alkynyl, cycloalkyl, aryl, heteroaryl, and heterocyclyl, and
    wherein said C$_{1-3}$ alkoxy, C$_{1-4}$ alkyl, C$_{2-4}$ alkenyl, C$_{2-4}$ alkynyl, cycloalkyl, aryl, heteroaryl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —CN, and —O—R$^{20}$,
R$^2$ is hydrogen, C$_{1-15}$ alkyl, C$_{1-8}$ alkoxy, —C(O)—O—R$^{26}$, —C(O)—N(R$^{26}$)(R$^{28}$), —N(R$^{20}$)—S(O)$_2$—R$^{20}$, cycloalkyl, aryl, heteroaryl, or heterocyclyl, wherein said C$_{1-15}$ alkyl is optionally substituted with one, two, or three substituents independently selected from hydroxyl, C$_{1-8}$ alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{24}$, —C(O)—O—R$^{20}$, —C(O)—N(R$^{20}$)(R$^{22}$), —CN, and —O—R$^{20}$, and
  wherein said C$_{1-8}$ alkoxy, C$_{2-4}$ alkenyl, C$_{2-4}$ alkynyl, aryl, heterocyclyl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and
  wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from deuterium, hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;
R$^3$ is selected from the group consisting of hydrogen, hydroxyl, halo, C$_{1-4}$ alkyl, C$_{1-4}$ alkoxy, —R$^{25}$—N(R$^{20}$)(R$^{22}$), —R$^{25}$—O—R$^{20}$, —R$^{25}$—C(O)—O—R$^{20}$, —R$^{25}$—C(O)—N(R$^{20}$)(R$^{22}$), —R$^{25}$—C(O)—O—N(R$^{20}$)(R$^{22}$), —R$^{25}$—N(R$^{20}$)—C(O)—R$^{22}$, and —R$^{25}$—O—C(O)—N(R$^{20}$)(R$^{22}$) and wherein said C$_{1-4}$ alkyl is optionally substituted with one, two, or three substituents independently selected from hydroxyl, and halo;
R$^4$ is selected from the group consisting of hydrogen, optionally substituted C$_{1-4}$ alkyl, aryl, —CF$_3$, -halo, and —O—R$^{24}$, and
  wherein said aryl is optionally further substituted with one, two, or three substituents independently selected from hydroxyl, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and
  wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), C(O)—R$^{20}$, —C(O)—O—R$^{20}$, —C(O)—N(R$^{20}$)(R$^{22}$), —CN, and —O—R$^{20}$;
R$^5$ is selected from the group consisting of hydrogen, optionally substituted alkyl, amino, optionally substituted alkoxy, —CF$_3$, —O—CF$_3$, —CN, and —N(R$^{20}$)C(O)—R$^{22}$;
R$^{20}$ and R$^{22}$ are in each instance independently selected from the group consisting of hydrogen, acyl, C$_{1-15}$ alkyl, C$_{2-15}$ alkenyl, C$_{2-15}$ alkynyl, cycloalkyl, heterocyclyl, aryl, and heteroaryl, and
  wherein said C$_{1-15}$ alkyl, C$_{2-15}$ alkenyl, C$_{2-15}$ alkynyl, cycloalkyl, heterocyclyl, aryl or heteroaryl are optionally substituted with one, two, or three substituents independently selected from hydroxyl, halo, C$_{1-4}$ alkyl, mono- or dialkylamino, aminocarbonyl, —NO$_2$, —SO$_2$R$^{26}$, —CN, C$_{1-3}$ alkoxy, —CF$_3$, —OCF$_3$, aryl, cycloalkyl, and heteroaryl; or
  when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, aralkyl, aryl, aryloxy, aralkyloxy, mono- or dialkylamino, aminocarbonyl, —NO$_2$, —SO$_2$R$^{26}$, —CN, C$_{1-3}$ alkoxy, —CF$_3$, —OCF$_3$, and cycloalkyl;
R$^{25}$ is in each instance independently a bond or selected from C$_{1-6}$ alkylene optionally substituted with one or two C$_{1-3}$ alkyl groups; and
R$^{24}$, R$^{26}$, and R$^{28}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, C$_{1-4}$ alkoxy, —CF$_3$, and —OCF$_3$;
or a pharmaceutically acceptable salt, ester, or stereoisomer thereof,
with the proviso that the compound is not 1-(3,4-difluorobenzyl)-2-oxo-N-(3-(3-oxo-2,3-dihydro-[1,2,4]triazolo[4,3-a]pyridin-6-yl)benzyl)-1,2-dihydropyridine-3-carboxamide.

2. The method of claim 1, wherein R$^1$ is pyridinyl, pyridazinyl, pyrimidinyl, quinolonyl, indazolyl, triazolopyridinyl, imidazopyridinyl, thiadiazolyl, or triazolyl,
  wherein said pyridinyl, pyridazinyl, pyrimidinyl, quinolonyl, indazolyl, triazolopyridinyl, imidazopyridinyl, thiadiazolyl, or triazolyl is substituted with one, two, or three substituents independently selected from the group consisting of hydroxyl, halo, —NO$_2$, CN, —SF$_5$, —Si(CH$_3$)$_3$, —O—CF$_3$, —O—R$^{20}$, —S—R$^{20}$, —C(O)—R²⁰, —N(R²⁰)(R²²), —C(O)—N(R²⁰)(R²²), —N(R²⁰)—C(O)—R²², —N(R²⁰)—S(O)₂—R²⁶, —S(O)₂—R²⁰, —S(O)₂—N(R²⁰)(R²²), C₁₋₃ alkoxy, C₁₋₄ alkyl, C₂₋₄ alkenyl, C₂₋₄ alkynyl, cycloalkyl, aryl, heteroaryl, and heterocyclyl, and wherein said C₁₋₃ alkoxy, C₁₋₄ alkyl, C₂₋₄ alkenyl, C₂₋₄ alkynyl, cycloalkyl, aryl, heteroaryl, or heterocyclyl are optionally substituted with one, two, or three substituents independently selected from hydroxyl, halo, —NO₂, —O—CF₃, —O—CHF₂, aryl, heterocyclyl, heteroaryl, cycloalkyl, —N(R²⁰)(R²²),—C(O)—R²⁰, —C(O)—O—R²⁰, —CN, and —O—R²⁰.

3. The method of claim 1, wherein R¹ is aryl,
wherein said aryl is substituted with one, two, or three substituents independently selected from the group consisting of hydroxyl, halo, —NO₂, —CN, —SF₅, —Si(CH₃)₃, —O—CF₃, —O—R²⁰, —S—R²⁰, —C(O)—R²⁰, —N(R²⁰)(R²²), —C(O)—N(R²⁰)(R²²), —N(R²⁰)—C(O)—R²², —N(R²⁰)—S(O)₂—R²⁶, —S(O)₂—R²⁰, —S(O)₂—N(R²⁰)(R²²), C₁₋₃ alkoxy, C₁₋₄ alkyl, C₂₋₄ alkenyl, C₂₋₄ alkynyl, cycloalkyl, aryl, heteroaryl, and heterocyclyl, and wherein said C₁₋₃ alkoxy, C₁₋₄ alkyl, C₂₋₄ alkenyl, C₂₋₄ alkynyl, aryl, heteroaryl, cycloalkyl, or heterocyclyl are optionally substituted with one, two, or three substituents independently selected from hydroxyl, halo, —NO₂, —O—CF₃, —O—CHF₂, aryl, heterocyclyl, heteroaryl, cycloalkyl, —N(R²⁰)(R²²), —C(O)—R²⁰, —C(O)—O—R²⁰, —CN, and —O—R²⁰.

4. The method of claim 1, wherein R¹ is phenyl,
wherein said phenyl is substituted with one, two, or three substituents independently selected from the group consisting of hydroxyl, halo, —NO₂, —CN, —SF₅, —Si(CH₃)₃, —O—CF₃, —O—R²⁰, —S—R²⁰, —C(O)—R²⁰, C(O)OH, —N(R²⁰)(R²²), —C(O)—N(R²⁰)(R²²), —N(R²⁰)—C(O)—R²², —N(R²⁰)—S(O)₂—R²⁶, —S(O)₂—R²⁰, —S(O)₂—N(R²⁰)(R²²), C₁₋₃ alkoxy, C₁₋₄ alkyl, C₂₋₄ alkenyl, C₂₋₄ alkynyl, cycloalkyl, aryl, heteroaryl, and heterocyclyl, and wherein said C₁₋₃ alkoxy, C₁₋₄ alkyl, C₂₋₄ alkenyl, C₂₋₄ alkynyl, aryl, heteroaryl, cycloalkyl, and heterocyclyl are optionally substituted with one, two, or three substituents independently selected from hydroxyl, halo, —NO₂, —O—CF₃, —O—CHF₂, phenyl, heterocyclyl, heteroaryl, cycloalkyl, —N(R²⁰)(R²²), —C(O)—R²⁰, —C(O)—O—R²⁰, —CN, and —O—R²⁰.

5. The method of claim 1, wherein R² is hydrogen, C₁₋₁₅ alkyl, C₁₋₈ alkoxy, —C(O)—O—R²⁸, —C(O)—N(R²⁶)(R²⁸), —N(R²⁰)—S(O)₂—R²⁰, cycloalkyl, or heterocyclyl,
wherein said C₁₋₁₅ alkyl is optionally substituted with one, two, or three substituents independently selected from hydroxyl, C₁₋₈ alkoxy, halo, —NO₂, —O—CF₃, —O—CHF₂, C₂₋₄ alkenyl, C₂₋₄ alkynyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and wherein said C₁₋₈ alkoxy, C₂₋₄ alkenyl, C₂₋₄ alkynyl, heterocyclyl, or cycloalkyl are optionally further substituted with one, two, or three substituents independently selected from hydroxyl, halo, —NO₂, —O—CF₃, C₁₋₆ alkyl, C₁₋₄ alkoxy, aralkyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and wherein said C₁₋₆ alkyl, C₁₋₄ alkoxy, aralkyl, aryl, heterocyclyl, heteroaryl, or cycloalkyl are optionally further substituted with one, two, or three substituents independently selected from deuterium, hydroxyl, halo, —NO₂, —O—CF₃, —CF₃, —O—CHF₂, —N(R²⁰)(R²²), —C(O)—R²⁰, —C(O)—O—R²⁰, C(O)—O—R²⁰, —C(O)—N(R²⁰)(R²²), —CN, and —O—R²⁰.

6. The method of claim 5, wherein R² is hydrogen, C₁₋₁₅ alkyl, C₁₋₈ alkoxy, —C(O)—O—R²⁶, —C(O)—N(R²⁶)(R²⁸), and —N(R²⁰)—S(O)₂—R²⁰,
wherein said C₁₋₁₅ alkyl is optionally substituted with one, two, or three substituents independently selected from hydroxyl, C₁₋₈ alkoxy, halo, —NO₂, —O—CF₃, —O—CHF₂, C₂₋₄ alkenyl, C₂₋₄ alkynyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and wherein said C₁₋₈ alkoxy, C₂₋₄ alkenyl, C₂₋₄ alkynyl, heterocyclyl, heteroaryl, or cycloalkyl are optionally further substituted with one, two, or three substituents independently selected from hydroxyl, halo, —NO₂, —O—CF₃, C₁₋₆ alkyl, C₁₋₄ alkoxy, aralkyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and wherein said C₁₋₆ alkyl, C₁₋₄ alkoxy, aralkyl, aryl, heterocyclyl, heteroaryl, or cycloalkyl are optionally further substituted with one, two, or three substituents independently selected from deuterium, hydroxyl, halo, —NO₂, —O—CF₃, —CF₃, —O—CHF₂, —N(R²⁰)(R²²), —C(O)—R²⁰, —C(O)—O—R²⁰, —C(O)—N(R²⁰)(R²²), —CN, and —O—R²⁰.

7. A method of treating a disease in a human selected from the group consisting of diabetes, diabetic peripheral neuropathy, migraine, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication, comprising administering to a human in need thereof a therapeutically effective dose of a compound of Formula II:

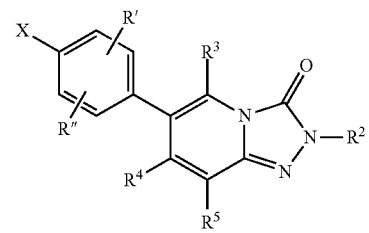

II wherein:
X is selected from the group consisting of hydroxyl, halo, —NO₂, —CN, —SF₅, —Si(CH₃)₃, —O—CF₃, —O—R²⁰, —S—R²⁰, —C(O)—R²⁰, —C(O)OH, —N(R²⁰)(R²²), —C(O)—N(R²⁰)(R²²), —N(R²⁰)—C(O)—R²², —N(R²⁰)—S(O)₂—R²⁶, —S(O)₂—R²⁰, —S(O)₂—N(R²⁰)(R²²), C₁₋₃ alkoxy, C₁₋₄ alkyl, C₂₋₄ alkenyl, C₂₋₄ alkynyl, cycloalkyl, aryl, heteroaryl, and heterocyclyl, and wherein said C₁₋₃ alkoxy, C₁₋₄ alkyl, C₂₋₄ alkenyl, C₂₋₄ alkynyl, aryl, heteroaryl, cycloalkyl, or heterocyclyl are optionally substituted with one, two, or three substituents independently selected from hydroxyl, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —CN, and —O—R$^{20}$;

R' and R" are each independently selected from the group consisting of hydrogen, C$_{1-15}$ alkyl, C$_{1-4}$ alkoxy, hydroxyl, halo, —NO$_2$, —O—CF$_3$, cycloalkyl, aryl, heteroaryl, and heterocyclyl, and;

wherein said C$_{1-15}$ alkyl is optionally substituted with one, two, or three substituents independently selected from hydroxyl, C$_{1-3}$ alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-3}$ alkoxy, C$_{2-4}$ alkenyl, C$_{2-4}$ alkynyl, cycloalkyl, aryl, heterocyclyl, or heteroaryl are optionally further substituted with one, two, or three substituents independently selected from deuterium, hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$—C(O)—N(R$^{20}$)(R$^{22}$), —CN, and —O—R$^{20}$;

R$^2$ is hydrogen, C$_{1-15}$ alkyl, C$_{1-8}$ alkoxy, —C(O)—O—R$^{26}$, —C(O)—N(R$^{26}$)(R$^{28}$), —N(R$^{20}$)—S(O)$_2$—R$^{20}$, cycloalkyl, aryl, heterocyclyl, or heterocyclyl, wherein said C$_{1-8}$ alkyl is optionally substituted with one, two, or three substituents independently selected from hydroxyl, C$_{1-8}$ alkoxy, halo, —NO$_2$, —O—CF$_3$, —O—CHF$_2$, C$_{2-4}$ alkenyl, C$_{2-4}$ alkynyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^2$)(R$^{22}$), —CN, and —O—R$^{20}$, and wherein said C$_{1-8}$ alkoxy, C$_{2-4}$ alkenyl, C$_{2-4}$ alkynyl, aryl, heterocyclyl, heteroaryl, or cycloalkyl are optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said C$_{1-6}$ alkyl, C$_{1-4}$ alkoxy, aralkyl, aryl, heterocyclyl, heteroaryl, or cycloalkyl are optionally further substituted with one, two, or three substituents independently selected from deuterium, hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^3$ is selected from the group consisting of hydrogen, hydroxyl, halo, C$_{1-4}$ alkyl, C$_{1-3}$ alkoxy, —R$^{25}$—N(R$^{20}$)(R$^{22}$), —R$^{25}$—O—R$^{20}$, —R$^{25}$—C(O)—O—R$^{20}$, —R$^{25}$—C(O)—N(R$^{20}$)(R$^{22}$), —R$^{25}$—C(O)—O—N(R$^{20}$)(R$^{22}$), —R$^{25}$—N(R$^{20}$)—C(O)—R$^{22}$, and —R$^{25}$—O—C(O)—N(R$^{20}$)(R$^{22}$), and wherein said C$_{1-4}$ alkyl is optionally substituted with one, two, or three substituents independently selected from hydroxyl and halo;

R$^4$ is selected from the group consisting of hydrogen, optionally substituted alkyl, aryl, —CF$_3$, -halo, and —O—R$^{24}$, and wherein said aryl is optionally further substituted with one, two, or three substituents independently selected from hydroxyl, —NO$_2$, —O—CF$_3$, C$_{1-6}$ alkyl, C$_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$)—C(O)—N(R$^{20}$)(R$^{22}$), —CN, and —O—R$^{20}$; and wherein said C$_{1-6}$ alkyl, C$_{1-4}$ alkoxy, aralkyl, aryl, heterocyclyl, heteroaryl, cycloalkyl, are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$;

R$^5$ is selected from the group consisting of hydrogen, optionally substituted alkyl, amino, optionally substituted alkoxy, —CF$_3$, —O—CF$_3$, —CN, and —N(R$^{20}$)C(O)—R$^{22}$;

R$^{20}$ and R$^{22}$ are in each instance independently selected from the group consisting of hydrogen, acyl, C$_{1-15}$ alkyl, C$_{2-15}$ alkenyl, C$_{2-15}$ alkynyl, cycloalkyl, heterocyclyl, aryl, and heteroaryl, and wherein the C$_{1-15}$ alkyl, C$_{2-15}$ alkenyl, C$_{2-15}$ alkynyl, cycloalkyl, heterocyclyl, aryl, or heteroaryl are optionally substituted with one, two, or three substituents independently selected from hydroxyl, halo, C$_{1-4}$ alkyl, mono- or dialkylamino, aminocarbonyl, —NO$_2$, —SO$_2$R$^{26}$, —CN, C$_{1-3}$ alkoxy, —CF$_3$, —OCF$_3$, aryl, cycloalkyl, and heteroaryl; or when R$^{20}$ and R$^{22}$ are attached to a common nitrogen atom R$^{20}$ and R$^{22}$ may join to form a heterocyclic ring which is then optionally substituted with one, two, or three substituents independently selected from hydroxyl, halo, alkyl, aralkyl, phenyl, phenoxy, aralkyloxy, mono- or dialkylamino, aminocarbonyl, —NO$_2$, —SO$_2$R$^{26}$, —CN, C$_{1-3}$ alkoxy, —CF$_3$, —OCF$_3$, aryl, and cycloalkyl;

R$^{25}$ is in each instance independently a bond or selected from C$_{1-6}$ alkylene optionally substituted with one or two C$_{1-3}$ alkyl groups; and R$^{24}$, R$^{26}$, and R$^{28}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, C$_{1-4}$ alkoxy, —CF$_3$, and —OCF$_3$, or a pharmaceutically acceptable salt, ester, or stereoisomer thereof.

8. The method of claim 7, wherein X is C$_{1-3}$ alkoxy or C$_{1-4}$ alkyl, and wherein said C$_{1-4}$ alkyl is optionally substituted with one, two, or three substituents independently selected from hydroxyl, alkoxy, halo, —NO$_2$, —O—CF$_3$, —O—CHF$_2$, aryl, heterocyclyl, heteroaryl, cycloalkyl, —N(R$^{20}$)(R$^{22}$), —C(O)—R$^{20}$, —C(O)—O—R$^{20}$, —CN, and —O—R$^{20}$, and wherein said C$_{1-3}$ alkoxy is optionally further substituted with one, two, or three substituents independently selected from hydroxyl, halo, —NO$_2$, —O—CF$_3$, C$_{1-6}$ alkyl, C$_{1-4}$ alkoxy, aralkyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰.

9. The method of claim 8, wherein X is —O—CF₃ and each of R' and R" is hydrogen.

10. The method of claim 8, wherein X is —CF₃ and each of R' and R" is hydrogen.

11. The method of claim 1, wherein R² is hydrogen or C₁₋₁₅ alkyl, and wherein said C₁₋₁₅ alkyl is optionally substituted with one, two, or three substituents independently selected from hydroxyl, C₁₋₈ alkoxy, halo, —NO₂, —O—CF₃, —O—CHF₂, C₂₋₄ alkenyl, C₂₋₄ alkynyl, aryl, heterocyclyl, heteroaryl, cycloalkyl, —N(R²⁰)(R²²), —C(O)—R²⁰, —C(O)—O—R²⁰, —C(O)—N(R²⁰)(R²²), and —O—R²⁰, and
  wherein said C₁₋₈ alkoxy, C₂₋₄ alkenyl, C₂₋₄ alkynyl, aryl, heterocyclyl, heteroaryl, or cycloalkyl are optionally further substituted with one, two, or three substituents independently selected from hydroxyl, halo, —NO₂, —O—CF₃, C₁₋₆ alkyl, C₁₋₄ alkoxy, aralkyl, aryl, heterocyclyl, heteroaryl, cycloalkyl, —N(R²⁰)(R²²), —C(O)—R²⁰, —C(O)—O—R²⁰, C(O)—O—R²⁰, —C(O)—N(R²)(R²²), —CN, and —O—R²⁰, and
    wherein said C₁₋₆ alkyl, C₁₋₄ alkoxy, aralkyl, aryl, heterocyclyl, heteroaryl, or cycloalkyl are optionally further substituted with one, two, or three substituents independently selected from deuterium, hydroxyl, halo, —NO₂, —O—CF₃, —CF₃, —O—CHF₂, —N(R²⁰)(R²²), —C(O)—R²⁰, —C(O)—O—R²⁰, —C(O)—N(R²⁰)(R²²), —CN, and O—R²⁰.

12. A method of treating a disease in a human selected from the group consisting of diabetes, diabetic peripheral neuropathy, migraine, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication, comprising administering to a human in need thereof a therapeutically effective dose of a compound of Formula III:

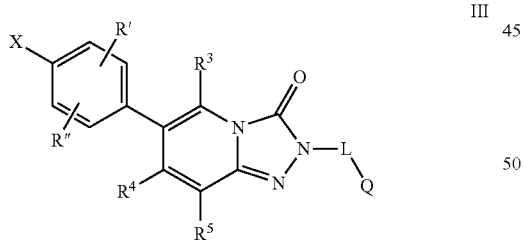

III wherein:
  X is selected from the group consisting of hydroxyl, halo, —NO₂, CN, —SF₅, —Si(CH₃)₃, —O—CF₃, —S—R²⁰, —C(O)—R²⁰, C(O)OH, —N(R²)(R²²), —C(O)—N(R²⁰)(R²²), —N(R²⁰)—C(O)—R²², —N(R²⁰)—S(O)₂—R²⁶, —S(O)₂—R²⁰, —S(O)₂—N(R²⁰)(R²²), C₁₋₃ alkoxy, C₁₋₄ alkyl, C₂₋₄ alkenyl, C₂₋₄ alkynyl, cycloalkyl, aryl, heteroaryl, and heterocyclyl, and
    wherein said alkoxy, C₁₋₄ alkyl, C₂₋₄ alkenyl, C₂₋₄ alkynyl, aryl, heteroaryl, cycloalkyl, or heterocyclyl are optionally substituted with one, two, or three substituents independently selected from hydroxyl, halo, —NO₂, —O—CF₃, —O—CHF₂, aryl, heterocyclyl, heteroaryl, cycloalkyl, —N(R²⁰)(R²²), —C(O)—R²⁰, —C(O)—O—R²⁰, —CN, and —O—R²⁰;
  R' and R" are each independently selected from the group consisting of hydrogen, C₁₋₁₅ alkyl, C₁₋₄ alkoxy, hydroxyl, halo, —NO₂, —O—CF₃, cycloalkyl, aryl, heteroaryl, and heterocyclyl, and;
    wherein said C₁₋₁₅ alkyl is optionally substituted with one, two, or three substituents independently selected from hydroxyl, alkoxy, halo, —NO₂, —O—CF₃, —O—CHF₂, alkenyl, alkynyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and
      wherein said alkoxy, alkenyl, alkynyl, cycloalkyl, aryl, heterocyclyl, or heteroaryl are optionally further substituted with one, two, or three substituents independently selected from deuterium, hydroxyl, halo, —NO₂, —O—CF₃, C₁₋₆ alkyl, C₁₋₄ alkoxy, aralkyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰, and
        wherein said C₁₋₆ alkyl, C₁₋₄ alkoxy, aralkyl, aryl, heterocyclyl, heteroaryl, cycloalkyl, are optionally further substituted with one, two, or three substituents independently selected from hydroxyl, halo, —NO₂, —O—CF₃, —CF₃, —O—CHF₂, —N(R²⁰)(R²²), —C(O)—R²⁰, —C(O)—O—R²⁰, —C(O)—N(R²⁰)(R²²), —CN, and —O—R²⁰;
  L is selected from the group consisting of a bond and straight or branched C₁₋₆ alkylene,
    wherein said straight or branched C₁₋₆ alkylene is optionally further substituted with one, two, or three substituents independently selected from hydroxyl, alkoxy, halo, —NO₂, —O—CF₃, —O—CHF₂, C₂₋₄ alkenyl, C₂₋₄ alkynyl, aryl, heterocyclyl, heteroaryl, cycloalkyl, —N(R²⁰)(R²²), —C(O)—R²⁰, —C(O)—O—R²⁰, —C(O)—N(R²)(R²²), —CN, and —O—R²⁰, and
      wherein said alkoxy, C₂₋₄ alkenyl, C₂₋₄ alkynyl, cycloalkyl, aryl, heterocyclyl, or heteroaryl are optionally further substituted with one, two, or three substituents independently selected from hydroxyl, halo, —NO₂, —O—CF₃, C₁₋₆ alkyl, C₁₋₄ alkoxy, aralkyl, aryl, heterocyclyl, heteroaryl, cycloalkyl, —N(R²⁰)(R²²), —C(O)—R²⁰, —C(O)—O—R²⁰, —C(O)—N(R²⁰)(R²²), —CN, and —O—R²⁰; and
        wherein said C₁₋₆ alkyl, C₁₋₄ alkoxy, aralkyl, aryl, heterocyclyl, heteroaryl, cycloalkyl, are optionally further substituted with one, two, or three substituents independently selected from hydroxyl, halo, —NO₂, —O—CF₃, —CF₃, —O—CHF₂, —N(R²⁰)(R²²), —C(O)—R²⁰, —C(O)—O—R²⁰, —C(O)—N(R²⁰)(R²²), —CN, and —O—R²⁰;
  Q is selected from the group consisting of hydrogen, hydroxyl, C₁₋₄ alkoxy, halo, —NO₂, —O—CF₃, —O—CHF₂, C₂₋₄ alkenyl, C₂₋₄ alkynyl, aryl, heterocyclyl, heteroaryl, cycloalkyl, —N(R²⁰)(R²²), —C(O)—O—R²⁰, —C(O)—N(R²⁰)(R²²), —CN, and —O—R²⁰, and
    wherein said C₁₋₄ alkoxy, C₂₋₄ alkenyl, C₂₋₄ alkynyl, aryl, heterocyclyl, heteroaryl, or cycloalkyl are optionally further substituted with one, two, or three substituents independently selected from deuterium, hydroxyl, halo, —NO₂, —O—CF₃, C₁₋₆ alkyl, C₁₋₄ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^3$ is selected from the group consisting of hydrogen, hydroxyl, halo, $C_{1-4}$ alkyl, $C_{1-3}$ alkoxy, —$R^{25}$—N($R^{20}$)$R^{22}$), —$R^{25}$—O—$R^{20}$, —$R^{25}$—C(O)—O—$R^{20}$, —$R^{25}$—C—N($R^{20}$)($R^{22}$), —$R^{25}$—C(O)—O—N($R^{20}$)($R^{22}$), —$R^{25}$—N($R^{20}$)—C(O)—$R^{22}$, and —$R^{25}$—O—C(O)—N($R^{20}$)($R^{22}$), and wherein said $C_{1-4}$ alkyl is optionally substituted with one, two, or three substituents independently selected from hydroxyl and halo;

$R^4$ is selected from the group consisting of hydrogen, optionally substituted alkyl, aryl, —$CF_3$, -halo, and —O—$R^{24}$, and wherein said aryl is optionally further substituted with one, two, or three substituents independently selected from hydroxyl, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, cycloalkyl, are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

$R^5$ is selected from the group consisting of hydrogen, optionally substituted alkyl, amino, optionally substituted alkoxy, —$CF_3$, —O—$CF_3$, —CN, and —N($R^{20}$)C(O)—$R^{22}$;

$R^{20}$ and $R^{22}$ are in each instance independently selected from the group consisting of hydrogen, acyl, $C_{1-15}$ alkyl, $C_{2-15}$ alkenyl, $C_{2-15}$ alkynyl, cycloalkyl, heterocyclyl, aryl, and heteroaryl, and wherein the $C_{1-15}$ alkyl, $C_{2-15}$ alkenyl, $C_{2-15}$ alkynyl, cycloalkyl, heterocyclyl, aryl, and heteroaryl are optionally substituted with one, two, or three substituents independently selected from hydroxyl, halo, $C_{1-4}$ alkyl, mono- or dialkylamino, aminocarbonyl, —$NO_2$, —$SO_2R^{26}$, —CN, $C_{1-3}$ alkoxy, —$CF_3$, —$OCF_3$, aryl, cycloalkyl, and heteroaryl; or when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, aralkyl, phenyl, phenoxy, aralkyloxy, mono- or dialkylamino, aminocarbonyl, —$NO_2$, —$SO_2R^{26}$, —CN, $C_{1-3}$ alkoxy, —$CF_3$, —$OCF_3$, aryl, and cycloalkyl;

$R^{25}$ is in each instance independently a bond or selected from $C_{1-6}$ alkylene optionally substituted with one or two $C_{1-3}$ alkyl groups; and $R^{24}$ and $R^{26}$ are in each instance independently selected from hydrogen, alkyl, aryl, or cycloalkyl, wherein the alkyl, aryl and cycloalkyl may be further substituted with from 1 to 3 substituents independently selected from hydroxyl, halo, $C_{1-4}$ alkoxy, —$CF_3$, and —$OCF_3$ or a pharmaceutically acceptable salt, ester, or stereoisomer thereof.

13. The method of claim 12,
wherein L is straight or branched $C_{1-6}$ alkylene,
wherein said straight or branched $C_{1-6}$ alkylene is optionally further substituted with one, two, or three substituents independently selected from hydroxyl, alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said alkoxy, $C_{2-4}$ alkenyl, $C_{2-4}$ alkynyl, cycloalkyl, aryl, heterocyclyl, or heteroaryl are optionally further substituted with one, two, or three substituents independently selected from hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{24}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$;

Q is selected from the group consisting of hydrogen, hydroxyl, $C_{1-4}$ alkoxy, halo, —$NO_2$, —O—$CF_3$, —O—$CHF_2$, $C_{2-4}$ alkenyl, $C_{2-4}$ alkynyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$, and wherein said $C_{1-4}$ alkoxy, $C_{2-4}$ alkenyl, $C_{2-4}$ alkynyl, aryl, heterocyclyl, heteroaryl, or cycloalkyl are optionally further substituted with one, two, or three substituents independently selected from deuterium, hydroxyl, halo, —$NO_2$, —O—$CF_3$, $C_{1-6}$ alkyl, $C_{1-4}$ alkoxy, aralkyl, aryl, heterocyclyl, heteroaryl, cycloalkyl, —N($R^{20}$)($R^{22}$), —C(O)—$R^{20}$, —C(O)—O—$R^{20}$, —C(O)—N($R^{20}$)($R^{22}$), —CN, and —O—$R^{20}$; and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —$NO_2$, —O—$CF_3$, —$CF_3$, —O—$CHF_2$, —N($R^{20}$)($R^{22}$), —C(O)—$R^{20}$, —C(O)—O—$R^{20}$, —C(O)—N($R^{20}$)($R^{22}$), —CN, and —O—$R^{20}$.

14. The method of claim 13, wherein $R^3$ is hydrogen or $C_{1-3}$ alkoxy.

15. The method of claim 14, wherein $R^3$ is hydrogen.

16. The method of claim 12, wherein $R^4$ is hydrogen or phenyl substituted with —$OCF_3$.

17. The method of claim 12, wherein $R^5$ is hydrogen or alkyl.

18. The method of claim 12, wherein each of R' and R" is hydrogen.

19. A method of treating a disease in a human selected from the group consisting of diabetes, diabetic peripheral neuropathy, migraine, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication, comprising administering to a human in need thereof a therapeutically effective dose of a compound of Formula IV:

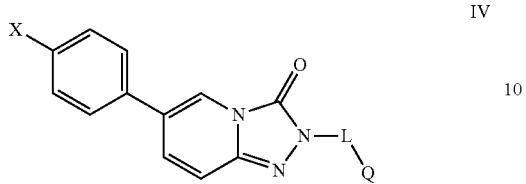

IV wherein:
X is selected from the group consisting of hydroxyl, halo, $-NO_2$, CN, $-SF_5$, $-Si(CH_3)_3$, $-O-CF_3$, $-O-R^{20}$, $-S-R^{20}$, $-C(O)-R^{20}$, $C(O)OH$, $-N(R^{20})(R^{22})$, $-C(O)-N(R^{20})(R^{22})$, $-N(R^{20})-C(O)-R^{22}$, $-N(R^{20})-S(O)_2-R^{26}$, $-S(O)_2-R^{20}$, $-S(O)_2-N(R^{20})(R^{22})$, $C_{1-3}$ alkoxy, $C_{1-4}$ alkyl, $C_{2-4}$ alkenyl, $C_{2-4}$ alkynyl, cycloalkyl, aryl, heteroaryl, and heterocyclyl, and
  wherein said $C_{1-3}$ alkoxy, $C_{1-4}$ alkyl, $C_{2-4}$ alkenyl, $C_{2-4}$ alkynyl, aryl, heteroaryl, cycloalkyl, or heterocyclyl are optionally substituted with one, two, or three substituents independently selected from hydroxyl, halo, $-NO_2$, $-O-CF_3$, $-O-CHF_2$, phenyl, heterocyclyl, heteroaryl, cycloalkyl, $-N(R^{20})(R^{22})$, $-C(O)-R^{20}$, $-C(O)-O-R^{20}$, $-C(O)-O-R^{20}$, $-CN$, and $-O-R^{20}$;
L is selected from the group consisting of a bond and straight or branched $C_{1-6}$ alkylene, and
  wherein said straight or branched $C_{1-6}$ alkylene is optionally further substituted with one, two, or three substituents independently selected from hydroxyl, alkoxy, halo, $-NO_2$, $-O-CF_3$, $-O-CHF_2$, $C_{2-4}$ alkenyl, $C_{2-4}$ alkynyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
    wherein said alkoxy, $C_{2-4}$ alkenyl, $C_{2-4}$ alkynyl, aryl, heterocyclyl, heteroaryl, or cycloalkyl are optionally further substituted with one, two, or three substituents independently selected from hydroxyl, halo, $-NO_2$, $-O-CF_3$, $C_{1-6}$ alkyl, $C_{1-4}$ alkoxy, aralkyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$; and
    wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, $-NO_2$, $-O-CF_3$, $-CF_3$, $-O-CHF_2$, $-N(R^{20})(R^{22})$, $-C(O)-R^{20}$, $-C(O)-O-R^{20}$, $-C(O)-N(R^{20})(R^{22})$, $-CN$, and $-O-R^{20}$;
Q is selected from the group consisting of hydrogen, hydroxyl, alkoxy, halo, $-NO_2$, $-O-CF_3$, $-O-CHF_2$, $C_{2-4}$ alkenyl, $C_{2-4}$ alkynyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
  wherein said alkoxy, $C_{2-4}$ alkenyl, $C_{2-4}$ alkynyl, aryl, heterocyclyl, heteroaryl, or cycloalkyl are optionally further substituted with one, two, or three substituents independently selected from deuterium, hydroxyl, halo, $-NO_2$, $-O-CF_3$, $C_{1-6}$ alkyl, $C_{1-4}$ alkoxy, aralkyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$; and
  wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, $-NO_2$, $-O-CF_3$, $-CF_3$, $-O-CHF_2$, $-N(R^{20})(R^{22})$, $-C(O)-R^{20}$, $-C(O)-O-R^{20}$, $-C(O)-N(R^{20})(R^{22})$, $-CN$, and $-O-R^{20}$;
$R^{20}$ and $R^{22}$ are in each instance independently selected from the group consisting of hydrogen, acyl, $C_{1-15}$ alkyl, $C_{2-15}$ alkenyl, $C_{2-15}$ alkynyl, cycloalkyl, heterocyclyl, aryl, and heteroaryl, and
  wherein the $C_{1-15}$ alkyl, $C_{2-15}$ alkenyl, $C_{2-15}$ alkynyl, cycloalkyl, heterocyclyl, aryl, or heteroaryl are optionally substituted with one, two, or three substituents independently selected from hydroxyl, halo, $C_{1-4}$ alkyl, mono- or dialkylamino, aminocarbonyl, $-NO_2$, $-SO_2R^{26}$, $-CN$, $C_{1-3}$ alkoxy, $-CF_3$, $-OCF_3$, aryl, cycloalkyl, and heteroaryl; or
when $R^{20}$ and $R^{22}$ are attached to a common nitrogen atom $R^{20}$ and $R^{22}$ may join to form a heterocyclic ring which is then optionally substituted with one, two, or three substituents independently selected from hydroxyl, halo, alkyl, aralkyl, aryl, aryloxy, aralkyloxy, mono- or dialkylamino, aminocarbonyl, $-NO_2$, $-SO_2R^{26}$, $-CN$, $C_{1-3}$ alkoxy, $-CF_3$, $-OCF_3$, aryl, and cycloalkyl;
$R^{26}$ is in each instance independently selected from hydrogen, alkyl, aryl, or cycloalkyl, wherein the alkyl, aryl and cycloalkyl may be further substituted with from 1 to 3 substituents independently selected from hydroxyl, halo, $C_{1-4}$ alkoxy, $-CF_3$, and $-OCF_3$;
or a pharmaceutically acceptable salt, ester, or stereoisomer thereof.

20. The method of claim 19, wherein X is $-OCF_3$.
21. The method of claim 19, wherein X is $-CF_3$.
22. The method of claim 20 or 21, wherein L is straight or branched $C_{1-6}$ alkylene,
  wherein said straight or branched $C_{1-6}$ alkylene is optionally further substituted with one, two, or three substituents independently selected from hydroxyl, alkoxy, halo, $-NO_2$, $-O-CF_3$, $-O-CHF_2$, $C_{2-4}$ alkenyl, $C_{2-4}$ alkynyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
    wherein said alkoxy, $C_{2-4}$ alkenyl, $C_{2-4}$ alkynyl, aryl, heterocyclyl, heteroaryl, or cycloalkyl are optionally further substituted with one, two, or three substituents independently selected from hydroxyl, halo, $-NO_2$, $-O-CF_3$, $C_{1-6}$ alkyl, $C_{1-4}$ alkoxy, aralkyl, aryl, heterocyclyl, heteroaryl, cycloalkyl, $-N(R^{20})(R^{22})$, $-C(O)-R^{20}$, $-C(O)-O-R^{20}$, $-C(O)-N(R^{20})(R^{22})$, $-CN$, and $-O-R^{20}$; and
    wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, $-NO_2$, $-O-CF_3$, $-CF_3$, $-O-CHF_2$, $-N(R^{20})(R^{22})$, $-C(O)-R^{20}$, $-C(O)-O-R^{20}$, $-C(O)-N(R^{20})(R^{22})$, $-CN$, and $-O-R^{20}$, and
Q is selected from the group consisting of hydrogen, $C_{2-4}$ alkenyl, $C_{2-4}$ alkynyl, aryl, heteroaryl, cycloalkyl, and $-O-R^{20}$, and wherein said $C_{2-4}$ alkenyl, $C_{2-4}$ alkynyl, aryl, heteroaryl, or cycloalkyl are optionally further substituted with one, two, or three substituents independently selected from hydroxyl, halo, —NO$_2$, —O—CF$_3$, $C_{1-6}$ alkyl, $C_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

23. The method of claim 22, wherein Q is aryl or heteroaryl, and wherein said aryl or heteroaryl is optionally further substituted with one, two, or three substituents independently selected from hydroxyl, halo, —NO$_2$, —O—CF$_3$, $C_{1-6}$ alkyl, $C_{1-4}$ alkoxy, aralkyl, aryl, heterocyclyl, heteroaryl, cycloalkyl, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$, and wherein said $C_{1-6}$ alkyl, $C_{1-4}$ alkoxy, aralkyl, aryl, heterocyclyl, heteroaryl, or cycloalkyl are optionally further substituted with one, two, or three substituents independently selected from hydroxyl, halo, —NO$_2$, —O—CF$_3$, —CF$_3$, —O—CHF$_2$, —N(R$^{20}$)(R$^{22}$), —C(O)—R$^{20}$, —C(O)—O—R$^{20}$, —C(O)—N(R$^{20}$)(R$^{22}$), —CN, and —O—R$^{20}$.

24. A method of treating a disease in a human selected from the group consisting of diabetes, diabetic peripheral neuropathy, migraine, atrial arrhythmias, ventricular arrhythmias, heart failure, diastolic heart failure, systolic heart failure, acute heart failure, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication, comprising administering to a human in need thereof a therapeutically effective dose of a compound selected from the group consisting of:

2-((3-methyl-1,2,4-oxadiazol-5-yl)methyl)-6-(4-(trifluoromethoxy)phenyl)-[1,2,4]triazolo[4,3-a]pyridin-3(2H)-one;

2-((4-methyl-1,2,5-oxadiazol-3-yl)methyl)-6-(4-(trifluoromethoxy)phenyl)-[1,2,4]triazolo[4,3-a]pyridin-3(2H)-one;

2-((5-methyl-1,2,4-oxadiazol-3-yl)methyl)-6-(4-(trifluoromethoxy)phenyl)-[1,2,4]triazolo[4,3-a]pyridin-3(2H)-one;

2-(2-hydroxy-3-(2-methoxyphenoxy)propyl)-6-(4-(trifluoromethoxy)phenyl)-[1,2,4]triazolo[4,3-a]pyridin-3(2H)-one, 2-((5-methylisoxazol-3-yl)methyl)-6-(4-(trifluoromethoxy)phenyl)-[1,2,4]triazolo[4,3-a]pyridin-3(2H)-one;

2-((3,5-dimethylisoxazol-4-yl)methyl)-6-(4-(trifluoromethoxy)phenyl)-[1,2,4]triazolo[4,3-a]pyridin-3(2H)-one;

6-(4-(trifluoromethoxy)phenyl)-2-((5-(3-(trifluoromethyl)phenyl)-1,2,4-oxadiazol-3-yl)methyl)-[1,2,4]triazolo[4,3-a]pyridin-3(2H)-one;

2-(3-(5-methyl-1,2,4-oxadiazol-3-yl)benzyl)-6-(4-(trifluoromethoxy)phenyl)-[1,2,4]triazolo[4,3-a]pyridin-3(2H)-one;

2-((3-(2,6-dichlorophenyl)-1,2,4-oxadiazol-5-yl)methyl)-6-(4-(trifluoromethoxy)phenyl)-[1,2,4]triazolo[4,3-a]pyridin-3(2H)-one;

2-(benzo[c][1,2,5]oxadiazol-5-ylmethyl)-6-(4-(trifluoromethoxy)phenyl)-[1,2,4]triazolo[4,3-a]pyridin-3(2H)-one;

2-((5-(2-methoxyphenyl)-1,2,4-oxadiazol-3-yl)methyl)-6-(4-(trifluoromethoxy)phenyl)-[1,2,4]triazolo[4,3-a]pyridin-3(2H)-one;

2-(4-(trifluoromethoxy)benzyl)-6-(4-(trifluoromethoxy)phenyl)-[1,2,4]triazolo[4,3-a]pyridin-3(2H)-one;

2-(quinolin-2-ylmethyl)-6-(4-(trifluoromethoxy)phenyl)-[1,2,4]triazolo[4,3-a]pyridin-3(2H)-one;

2-(1-(3-ethyl-1,2,4-oxadiazol-5-yl)ethyl)-6-(4-(trifluoromethoxy)phenyl)-[1,2,4]thazolo[4,3-a]pyridin-3(2H)-one;

2-((3-ethyl-1,2,4-oxadiazol-5-yl)methyl)-6-(4-(trifluoromethoxy)phenyl)-[1,2,4]triazolo[4,3-a]pyridin-3(2H)-one, 2-(pyridin-2-ylmethyl)-6-(4-(trifluoromethoxy)phenyl)-[1,2,4]thazolo[4,3-a]pyridin-3(2H)-one;

2-((4-phenyl-1,2,5-oxadiazol-3-yl)methyl)-6-(4-(trifluoromethoxy)phenyl)-[1,2,4]triazolo[4,3-a]pyridin-3(2H)-one, 2-((5-methyl-1,3,4-oxadiazol-2-yl)methyl)-6-(4-(trifluoromethoxy)phenyl)-[1,2,4]triazolo[4,3-a]pyridin-3(2H)-one;

2-(oxazol-2-ylmnethyl)-6-(4-(trifluoromethoxy)phenyl)-[1,2,4]triazolo[4,3-a]pyridin-3(2H)-one;

2-(benzo[d]thiazol-2-ylmethyl)-6-(4-(trifluoromethoxy)phenyl)-[1,2,4]triazolo[4,3-a]pyridin-3(2H)-one;

2-((5-methyl-2-phenyloxazol-4-yl)methyl)-6-(4-(trifluoromethoxy)phenyl)-[1,2,4]thazolo[4,3-a]pyridin-3(2H)-one;

2-((4,5-dimethyloxazol-2-yl)methyl)-6-(4-(trifluoromethoxy)phenyl)-[1,2,4]triazolo[4,3-a]pyridin-3(2H)-one;

2-(2-methoxy-3-(2-methoxyphenoxyl)propyl)-6-(4-(trifluoromethoxy)phenyl)-[1,2,4]triazolo[4,3-a]pyridin-3(2H)-one;

2-(3-phenoxypropyl)-6-(4-(trifluoromethoxy)phenyl)-[1,2,4]triazolo[4,3-a]pyridin-3(2H)-one;

2-((5-methyloxazol-2-yl)methyl)-6-(4-(trifluoromethoxy)phenyl)[1,2,4]triazolo[4,3-a]pyridin-3(2H)-one;

2((3-cyclopropyl-1-methyl-1H-pyrazol-5-yl)methyl)-6-(4-(trifluoromethoxy)phenyl)-[1,2,4]triazolo[4,3-a]pyridin-3(2H)-one;

2-((1,2,4-oxadiazol-3-yl)methyl)-6-(4-(trifluoromethoxy)phenyl)-[1,2,4]triazolo[4,3-a]pyridin-3(2H)-one;

2-(2-phenoxyethyl)-6-(4-(trifluoromethoxy)phenyl)-[1,2,4]triazolo[4,3-a]pyridin-3(2H)-one;

2-((3-benzyl-1,2,4-oxadiazol-5-yl)methyl)-6-(4-(trifluoromethoxy)phenyl)-[1,2,4]triazolo[4,3-a]pyridin-3(2H)-one;

5-methoxy-2((3-methyl-1,2,4-oxadiazol-5-yl)methyl)-6-(4-(trifluoromethoxy)phenyl)-[1,2,4]triazolo[4,3-a]pyridin-3(2H)-one;

2-((5-methyl-1,2,4-oxadiazol-3-yl)methyl)-6-(3-phenoxyphenyl)-[1,2,4]triazolo[4,3-a]pyridin-3(2H)-one;

6-(4-(4-chlorophenoxyl)phenyl)-2-((5-methyl-1,2,4-oxadiazol-3-yl)methyl)-[1,2,4]triazolo[4,3-a]pyridin-3(2H)-one;

2-((3-(2-chlorophenyl)-1,2,4-oxadiazol-5-yl)methyl)-6-(4-(trifluoromethoxy)phenyl)-[1,2,4]triazolo[4,3-a]pyridin-3(2H)-one;

2-(pyridin-2-yl)-6-(4-(trifluoromethoxy)phenyl)-[1,2,4]triazolo[4,3-a]pyridin-3(2H)-one;

2-(2-(1H-pyrazol-1-yl)ethyl)-6-(4-(trifluoromethoxy)phenyl)-[1,2,4]thazolo[4,3-a]pyridin-3(2H)-one;
2(2-(pyridin-2-yl)ethyl)-6-(4-(trifluoromethoxy)phenyl)-[1,2,4]triazolo[4,3-a]pyridin-3(2H)-one;
2-(3-(2-methoxyphenoxyl)propyl)-6-(4-(trifluoromethoxy)phenyl-[1,2,4]thazolo[4,3-a]pyridin-3(2H)-one,
2-(3-(4-chlorophenoxy)-2-hydroxypropyl)-6-(4-(trifluoromethoxy)phenyl)-[1,2,4]triazolo[4,3-a]pyridin-3(2H)-one;
2-(2-(3-phenoxypyrrolidin-1-yl)ethyl)-6-(4-(trifluoromethoxy)phenyl)-[1,2,4]triazolo[4,3-a]pyridin-3(2H)-one;
2-(2-(4-chlorophenoxyl)ethyl)-6-(4-(trifluoromethoxy)phenyl)-[1,2,4]triazolo[4,3-a]pyridin-3(2H)-one;
2-(2-(4-chloro-1H-pyrazol-1-yl)ethyl)-6(4-(trifluoromethoxy)phenyl)-[1,2,4]triazolo[4,3-a]pyridin-3(2H)-one;
2-(2-(3-methyl-1H-pyrazol-1-yl)ethyl)-6-(4-(trifluoromethoxy)phenyl)-[1,2,4]thazolo[4,3-a]pyridin-3(2H)-one;
2-(2-hydroxy-3-phenoxypropyl)-6-(4-(trifluoromethoxy)phenyl-[1,2,4]thazolo[4,3-a]pyridin-3(2H)-one;
2-(2-(2,6-dimethylphenoxy)ethyl)-6-(4-(trifluoromethoxy)phenyl-[1,2,4]triazolo[4,3-a]pyridin-3(2H)-one;
2-(2-(4-phenyl-1H-imidazol-1-yl)ethyl)-6-(4-(trifluoromethoxy)phenyl)-[1,2,4]thazolo[4,3-a]pyridin-3(2H)-one;
2-(2-(2-chlorophenoxyl)ethyl)-6-(4-(trifluoromethoxy)phenyl-[1,2,4]thazolo[4,3-a]pyridin-3(2H)-one;
6-(4-(trifluoromethoxy)phenyl)-2-(2-(3-(trifluoromethyl)pyridin-2-yloxy)ethyl)-[1,2,4]triazolo[4,3-a]pyridin-3(2H)-one;
2-(2-(6-methylpyridin-2-yl)ethyl)-6-(4-(trifluoromethoxy)phenyl)-[1,2,4]triazolo[4,3-a]pyridin-3(2H)-one;
2-(2-(pyridin-2-yloxy)ethyl)-6-(4-(trifluoromethoxy)phenyl)-[1,2,4]triazolo[4,3-a]pyridin-3(2H)-one,
2-(2-(4,4-difluoropiperidin-1-yl)ethyl)-6-(4-(trifluoromethoxy)phenyl)-[1,2,4]triazolo[4,3-a]pyridin-3(2H)-one;
2-(3-(2-fluorophenoxyl)propyl)-6-(4-(trifluoromethoxy)phenyl)-[1,2,4]triazolo[4,3-a]pyridin-3(2H)-one,
2-(3-(2-chlorophenoxyl)propyl)-6-(4-(trifluoromethoxy)phenyl)-[1,2,4]triazolo[4,3-a]pyridin-3(2H)-one;
6-(4-(4-chlorophenoxyl)phenyl)-2-((3-methyl-1,2,4-oxadiazol-5-yl)methyl)-[1,2,4]triazolo[4,3-a]pyridin-3(2H)-one;
2-(2-(3-chlorophenoxyl)ethyl)-6-(4-(trifluoromethoxy)phenyl)-[1,2,4]triazolo[4,3-a]pyridin-3(2H)-one;
2-(2-(4-fluorophenoxyl)ethyl)-6-(4-(trifluoromethoxy)phenyl)-[1,2,4]triazolo[4,3-a]pyridin-3(2H)-one;
2-(2-(3-bromopyridin-2-yl)ethyl)-6-(4-(trifluoromethoxy)phenyl)-[1,2,4]triazolo[4,3-a]pyridin-3(2H)-one;
2-(2-(4-cyclopropylpyridin-2-yl)ethyl)-6-(4-(trifluoromethoxy)phenyl)-[1,2,4]triazolo[4,3-a]pyridin-3(2H)-one;
2-(2-(4-methylpyridin-2-yl)ethyl)-6-(4-(trifluoromethoxy)phenyl)-[1,2,4]triazolo[4,3-a]pyridin-3(2H)-one;
2-(4-fluorophenethyl)-6-(4-(trifluoromethoxy)phenyl)-[1,2,4]triazolo[4,3-a]pyridin-3(2H)-one;
2-(2-(3-cyclopropylpyridin-2-yl)ethyl)-6-(4-(trifluoromethoxy)phenyl)-[1,2,4]triazolo[4,3-a]pyridin-3(2H)-one,
2-(2-(3-methylpyridin-2-yl)ethyl)-6-(4-(trifluoromethoxy)phenyl)-[1,2,4]triazolo[4,3-a]pyridin-3(2H)-one;
6-(4-(trifluoromethoxy)phenyl)-2-((6-(trifluoromethyl)pyridin-2-yl)methyl)-[1,2,4]triazolo[4,3-a]pyridin-3(2H)-one;
2-(2,6-difluorophenethyl)-6-(4-(trifluoromethoxy)phenyl)-[1,2,4]triazolo[4,3-a]pyridin-3(2H)-one;
2-(3-(3-bromo-4-fluorophenyl)propyl)-6-(4-(trifluoromethoxy)phenyl)-[1,2,4]triazolo[4,3-a]pyridin-3(2H)-one;
6-(4-(trifluoromethoxy)phenyl)-2-(2-(6-(trifluoromethyl)pyridin-2-yloxy)ethyl)-[1,2,4]triazolo[4,3-a]pyridin-3(2H)-one;
6-(4-(trifluoromethoxy)phenyl)-2-(3-(2-(trifluoromethyl)phenoxy)propyl)-[1,2,4]triazolo[4,3-a]pyridin-3(2H)-one;
2-(3-(4-fluoro-2-methoxyphenoxy)propyl)-6-(4-(trifluoromethoxy)phenyl)-[1,2,4]triazolo[4,3-a]pyridin-3(2H)-one;
2-(3-(4-chloropyridin-3-yl)prop-2-ynyl)-6-(4-(trifluoromethoxy)phenyl)-[1,2,4]triazolo[4,3-a]pyridin-3(2H)-one;
2-(2-(2-methoxyphenoxyl)ethyl)-6-(4-(trifluoromethoxy)phenyl)-[1,2,4]triazolo[4,3-a]pyridin-3(2H)-one;
2-(3-(3-oxo-6-(4-(trifluoromethoxy)phenyl)-[1,2,4]triazolo[4,3-a]pyridin-2(3H)-yl)propoxy)benzonitrile;
6-(4-(trifluoromethoxy)phenyl)-2-(3-(2-(trifluoromethyl)phenoxy)propyl)-[1,2,4]triazolo[4,3-a]pyridin-3(2H)-one;
(R)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;
2-(2-(pyridin-3-yl)ethyl)-6-(4-(trifluoromethoxy)phenyl)-[1,2,4]triazolo[4,3-a]pyridin-3(2H)-one;
2-(2-(3,3'-bipyridin-6-yl)ethyl)-6-(4-(trifluoromethoxy)phenyl)-[1,2,4]triazolo[4,3-a]pyridin-3(2H)-one;
2-(2-(p-tolyloxy)ethyl)-6-(4-(trifluoromethoxy)phenyl)-[1,2,4]triazolo[4,3-a]pyridin-3(2H)-one;
2-(3-(4-fluorophenyl)propyl)-6-(4-(trifluoromethoxy)phenyl)-[1,2,4]triazolo[4,3-a]pyridin-3(2H)-one;
2-(chroman-2-ylmethyl)-6-(4-(trifluoromethoxy)phenyl)-[1,2,4]triazolo[4,3-a]pyridin-3(2H)-one;
2-(2,4-difluorophenethyl)-6-(4-(trifluoromethoxy)phenyl)-[1,2,4]triazolo[4,3-a]pyridin-3(2H)-one;
2-(3-(pyridazin-3-yloxy)propyl)-6-(4-(trifluoromethoxy)phenyl)-[1,2,4]triazolo[4,3-a]pyridin-3(2H)-one;
2-(3-(2-chlorophenoxy)-2-methoxypropyl)-6-(4-(trifluoromethoxy)phenyl)-[1,2,4]triazolo[4,3-a]pyridin-3(2H)-one;
2-(2-(pyridazin-3-yloxy)ethyl)-6-(4-(trifluoromethoxy)phenyl)-[1,2,4]triazolo[4,3-a]pyridin-3(2H)-one;
2-(2-(5-methylpyrimidin-2-yloxy)ethyl)-6-(4-(trifluoromethoxy)phenyl)-[1,2,4]triazolo[4,3-a]pyridin-3(2H)-one;
2-((3-methyl-1,2,4-oxadiazol-5-yl)methyl)-6-(4-(2,2,2-trifluoroethoxyl)phenyl)-[1,2,4]triazolo[4,3-a]pyridin-3(2H)-one;
2-(2-(2-(3-methyl-1,2,4-oxadiazol-5-yl)phenoxy)ethyl)-6-(4-(trifluoromethoxy)phenyl)-[1,2,4]triazolo[4,3-a]pyridin-3(2H)-one;
2-(3-(pyrazin-2-yloxy)propyl)-6-(4-(trifluoromethoxy)phenyl)-[1,2,4]triazolo[4,3-a]pyridin-3(2H)-one;
2-(2-((5-methyl-1,2,4-oxadiazol-3-yl)methoxy)ethyl)-6-(4-(trifluoromethoxy)phenyl)-[1,2,4]triazolo[4,3-a]pyridin-3(2H)-one;

2-((3-methyl-1,2,4-oxadiazol-5-yl)methyl)-6-(2-methyl-4-(trifluoromethoxy)phenyl)-[1,2,4]triazolo[4,3-a]pyridin-3(2H)-one;

2-(2-(4,6-dimethylpyridin-2-yloxy)ethyl)-6-(4-(trifluoromethoxy)phenyl)-[1,2,4]triazolo[4,3-a]pyridin-3(2H)-one;

2-(3-(2-chlorophenoxy)-2-(pyrimidin-2-yloxy)propyl)-6-(4-(trifluoromethoxy)phenyl)-[1,2,4]triazolo[4,3-a]pyridin-3(2H)-one, 2-(2-(4-cyclopropylpyrimidin-2-yloxy)ethyl)-6-(4-(trifluoromethoxy)phenyl)-[1,2,4]thazolo[4,3-a]pyridin-3(2H)-one;

(S)-2-(3-methoxy-2-(3-(trifluoromethyl)pyridin-2-yloxy)propyl)-6-(4-(trifluoromethoxy)phenyl)-[1,2,4]triazolo[4,3-a]pyridin-3(2H)-one;

2-(2-(5-chloropyrimidin-2-yloxy)ethyl)-6-(4-(trifluoromethoxy)phenyl)-[1,2,4]triazolo[4,3-a]pyridin-3(2H)-one;

6-(4-(4-fluorophenoxyl)phenyl)-2-((3-methyl-1,2,4-oxadiazol-5-yl)methyl)-[1,2,4]triazolo[4,3-a]pyridin-3(2H)-one;

(3-((3-oxo-6-(4-(trifluoromethoxy)phenyl)-[1,2,4]triazolo[4,3-a]pyridin-2(3H)-yl)methyl)-1,2,4-oxadiazol-5-yl)methyl acetate;

(S)-2-(3-(2-chlorophenoxy)-2-methoxypropyl)-6-(4-(trifluoromethoxy)phenyl)-[1,2,4]thazolo[4,3-a]pyridin-3(2H)-one, (R)-2-(3-(2-chlorophenoxy)-2-methoxypropyl)-6-(4-(trifluoromethoxy)phenyl)-[1,2,4]triazolo[4,3-a]pyridin-3(2H)-one;

2-(2-(1-methyl-1H-benzo[d]imidazol-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-hydroxypropyl)-6-(4-(trifluoromethoxy)phenyl)-[1,2,4]thazolo[4,3-a]pyridin-3(2H)-one;

2-(3-(2-ethoxyphenoxy)-2-hydroxypropyl)-6-(4-(trifluoromethoxy)phenyl)-[1,2,4]triazolo[4,3-a]pyridin-3(2H)-one;

2-(3-(biphenyl-2-yloxy)-2-hydroxypropyl)-6-(4-(trifluoromethoxy)phenyl)-[1,2,4]triazolo[4,3-a]pyridin-3(2H)-one;

2-(2-hydroxy-3-(3-oxo-6-(4-(trifluoromethoxy)phenyl)-[1,2,4]triazolo[4,3-a]pyridin-2(3H)-yl)propoxy)benzonitrile;

2-(2-(pyridin-2-yl)propyl)-6-(4-(trifluoromethoxy)phenyl)-[1,2,4]triazolo[4,3-a]pyridin-3(2H)-one;

2-(2-(6-methoxypyridin-2-yl)ethyl)-6-(4-(trifluoromethoxy)phenyl)-[1,2,4]triazolo[4,3-a]pyridin-3(2H)-one;

2-(3-(4-fluoro-2-methoxyphenoxy)-2-methoxypropyl)-6-(4-(trifluoromethoxy)phenyl)-[1,2,4]triazolo[4,3-a]pyridin-3(2H)-one;

2-(2-ethoxy-3-(4-fluoro-2-methoxyphenoxy)propyl)-6-(4-(trifluoromethoxy)phenyl)-[1,2,4]triazolo[4,3-a]pyridin-3(2H)-one;

2-(2-(4-ethoxypyrimidin-2-yloxy)ethyl)-6-(4-(trifluoromethoxy)phenyl)-[1,2,4]triazolo[4,3-a]pyridin-3(2H)-one;

2-(2-hydroxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(2-hydroxy-3-(2-isopropoxyphenoxyl)propyl)-6-(4-(trifluoromethoxy)phenyl)-[1,2,4]triazolo[4,3-a]pyridin-3(2H)-one;

2-(4-(pyrimidin-2-yloxy)tetrahydrofuran-3-yl)-6-(4-(trifluoromethoxy)phenyl)-[1,2,4]triazolo[4,3-a]pyridin-3(2H)-one;

2-((3-methyl-1,2,4-oxadiazol-5-yl)methyl)-6-(4-(trimethylsilyl)phenyl)-[1,2,4]triazolo[4,3-a]pyridin-3(2H)-one;

2-(2-(pyrimidin-2-yl)ethyl)-6-(4-(trifluoromethoxy)phenyl)-[1,2,4]triazolo[4,3-a]pyridin-3(2H)-one;

2-(2-(2-oxo-3-phenoxypyrrolidin-1-yl)ethyl)-6-(4-(trifluoromethoxy)phenyl)-[1,2,4]triazolo[4,3-a]pyridin-3(2H)-one, 2-(2-(pyrimidin-4-yl)ethyl)-6-(4-(trifluoromethoxy)phenyl)-[1,2,4]triazolo[4,3-a]pyridin-3(2H)-one;

2-(2-(pyrazin-2-yl)ethyl)-6-(4-(trifluoromethoxy)phenyl)-[1,2,4]triazolo[4,3-a]pyridin-3(2H)-one;

2-(2-(4-phenylpyrimidin-2-yloxy)ethyl)-6-(4-(trifluoromethoxy)phenyl)-[1,2,4]triazolo[4,3-a]pyridin-3(2H)-one;

2-(2-(5-methoxypyrimidin-2-yloxy)ethyl)-6-(4-(trifluoromethoxy)phenyl)-[1,2,4]triazolo[4,3-a]pyridin-3(2H)-one;

2-(2-(3-methylpyrazin-2-yl)ethyl)-6-(4-(trifluoromethoxy)phenyl)-[1,2,4]triazolo[4,3-a]pyridin-3(2H)-one;

2-(2-(3-bromo-6-methoxypyrid n-2-yl)ethyl)-6-(4-(trifluoromethoxy)phenyl)-[1,2,4]triazolo[4,3-a]pyridin-3(2H)-one;

2-(3-(4-fluoro-3-(oxazol-2-yl)phenyl)propyl)-6-(4-(trifluoromethoxy)phenyl)-[1,2,4]triazolo[4,3-a]pyridin-3(2H)-one;

6-(4-(4-chlorophenoxy)phenyl)-2-(2-(pyrimidin-2-yloxy)ethyl)-[1,2,4]triazolo[4,3-a]pyridin-3(2H)-one;

2-(3-(4-fluoro-3-(pyridin-3-yl)phenyl)propyl)-6-(4-(trifluoromethoxy)phenyl)-[1,2,4]triazolo[4,3-a]pyridin-3(2H)-one;

6-(4-(4-fluorophenoxyl)phenyl)-2-(2-(pyrimidin-2-yloxy)ethyl)-[1,2,4]triazolo[4,3-a]pyridin-3(2H)-one;

2-(2-(pyrimidin-2-yloxy)ethyl)-6-(4-(trimethylsilyl)phenyl)-[1,2,4]triazolo[4,3-a]pyridin-3(2H)-one, 2-(2-ethoxy-3-(2-methylbenzo[d]thiazol-6-yloxy)propyl)-6-(4-(trifluoromethoxy)phenyl)-[1,2,4]triazolo[4,3-a]pyridin-3(2H)-one;

2-(4-(4-ethoxypyrimidin-2-yloxy)tetrahydrofuran-3-yl)-6-(4-(trifluoromethoxy)phenyl)-[1,2,4]triazolo[4,3-a]pyridin-3(2H)-one;

2-(2-(4-(dimethylamino)-5-fluoropyrimidin-2-yloxy)ethyl)-6-(4-(trifluoromethoxy)phenyl)-[1,2,4]triazolo[4,3-a]pyridin-3(2H)-one, 6-(3,5-difluoro-4-phenoxyphenyl)-2-((3-methyl-1,2,4-oxadiazol-5-yl)methyl)-[1,2,4]triazolo[4,3-a]pyridin-3(2H)-one;

2-((5-(methoxymethyl)-1,2,4-oxadiazol-3-yl)methyl)-6-(4-(trifluoromethoxy)phenyl)-[1,2,4]triazolo[4,3-a]pyridin-3(2H)-one;

2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidine-4-carbonitrile;

2-(2-(5-chloro-4-methoxypyrimidin-2-yloxy)ethyl)-6-(4-(trifluoromethoxy)phenyl)-[1,2,4]triazolo[4,3-a]pyridin-3(2H)-one;

6-(4-benzoylphenyl)-2-((3-methyl-1,2,4-oxadiazol-5-yl)methyl)-[1,2,4]triazolo[4,3-a]pyridin-3(2H)-one;

2-(2-(4-(4-chlorophenoxyl)pyrimidin-2-yloxy)ethyl)-6-(4-(trifluoromethoxy)phenyl)-[1,2,4]triazolo[4,3-a]pyridin-3(2H)-one;

2-(2-(4-(3,3-difluoroazetidin-1-yl)-5-fluoropyrimidin-2-yloxy)ethyl)-6-(4-(trifluoromethoxy)phenyl)-[1,2,4]triazolo[4,3-a]pyridin-3(2H)-one;
6-(3,4-dichlorophenyl)-2-((3-methyl-1,2,4-oxadiazol-5-yl)methyl)-[1,2,4]triazolo[4,3-a]pyridin-3(2H)-one;
2-(2-(pyrrolo[1,2-a]pyrazin-1-yloxy)ethyl)-6-(4-(trifluoromethoxy)phenyl)-[1,2,4]triazolo[4,3-a]pyridin-3(2H)-one;
2-((3-((3-oxo-6-(4-(trifluoromethoxy)phenyl)-[1,2,4]triazolo[4,3-a]pyridin-2(3H)-yl)methyl)-1,2,4-oxadiazol-5-yl)methylisoindoline-1,3-dione;
2-((3-methyl-1,2,4-oxadiazol-5-yl)methyl)-6-(4-(trifluoromethyl)phenyl)-[1,2,4]triazolo[4,3-a]pyridin-3(2H)-one;
2-(2-(5-fluoropyrimidin-2-yloxy)ethyl)-6-(4-(trifluoromethoxy)phenyl)-[1,2,4]triazolo[4,3-a]pyridin-3(2H)-one;
2-(2-(2-chloropyrimidin-5-yloxy)ethyl)-6-(4-(trifluoromethoxy)phenyl)-[1,2,4]triazolo[4,3-a]pyridin-3(2H)-one;
6-(4-(4-fluorophenoxyl)phenyl)-2-((5-methyl-1,2,4-oxadiazol-3-yl)methyl)-[1,2,4]triazolo[4,3-a]pyridin-3(2H)-one;
2-(2-(isoquinolin-1-yloxy)ethyl)-6-(4-(trifluoromethoxy)phenyl)-[1,2,4]triazolo[4,3-a]pyridin-3(2H)-one;
2-((5-cyclopropyl-1,2,4-oxadiazol-3-yl)methyl)-6-(4-(trifluoromethoxy)phenyl)-[1,2,4]triazolo[4,3-a]pyridin-3(2H)-one;
6-(4-(4-fluorophenoxyl)phenyl)-[1,2,4]triazolo[4,3-a]pyridin-3(2H)-one;
2-((5-(pyridin-2-yl)isoxazol-3-yl)methyl)-6-(4-(trifluoromethoxy)phenyl)-[1,2,4]triazolo[4,3-a]pyridin-3(2H)-one;
2-((5-(3-methylpyridin-2-yl)isoxazol-3-yl)methyl)-6-(4-(trifluoromethoxy)phenyl)-[1,2,4]triazolo[4,3-a]pyridin-3(2H)-one;
6-(4-(4-fluorophenoxyl)phenyl)-2-((5-(hydroxymethyl)-1,2,4-oxadiazol-3-yl)methyl)-[1,2,4]triazolo[4,3-a]pyridin-3(2H)-one;
2-(1-(3-methyl-1,2,4-oxadiazol-5-yl)ethyl)-6-(4-(trifluoromethoxy)phenyl)-[1,2,4]triazolo[4,3-a]pyridin-3(2H)-one;
2-((5-methyl-1,2,4-oxadiazol-3-yl)methyl)-6-(4-(trifluoromethyl)phenyl)-[1,2,4]triazolo[4,3-a]pyridin-3(2H)-one;
6-(4-chlorophenyl)-2-((3-methyl-1,2,4-oxadiazol-5-yl)methyl)-[1,2,4]triazolo[4,3-a]pyridin-3(2H)-one;
6-(3,4-difluorophenyl)-2-((3-methyl-1,2,4-oxadiazol-5-yl)methyl)-[1,2,4]triazolo[4,3-a]pyridin-3(2H)-one;
2-cinnamyl-6-(4-(trifluoromethoxy)phenyl)-[1,2,4]triazolo[4,3-a]pyridin-3(2H)-one;
(S)-2-((5-(2,2-dimethyl-1,3-dioxolan-4-yl)-1,2,4-oxadiazol-3-yl)methyl)-6-(4-(trifluoromethoxy)phenyl)-[1,2,4]triazolo[4,3-a]pyridin-3(2H)-one;
2-((3-(methoxymethyl)-1,2,4-oxadiazol-5-yl)methyl)-6-(4-(trifluoromethoxy)phenyl)-[1,2,4]triazolo[4,3-a]pyridin-3(2H)-one;
2-((5-(difluoromethyl)-1,2,4-oxadiazol-3-yl)methyl)-6-(4-(trifluoromethoxy)phenyl)-[1,2,4]triazolo[4,3-a]pyridin-3(2H)-one;
6-(3-fluoro-4-(trifluoromethoxy)phenyl)-2-((3-methyl-1,2,4-oxadiazol-5-yl)methyl)-[1,2,4]triazolo[4,3-a]pyridin-3(2H)-one;
2-(2-(4-(2-hydroxyethoxy)pyrimidin-2-yloxy)ethyl)-6-(4-(trifluoromethoxy)phenyl)-[1,2,4]thazolo[4,3-a]pyridin-3(2H)-one;
2-((5-(chloromethyl)-1,2,4-oxadiazol-3-yl)methyl)-6-(4-(trifluoromethoxy)phenyl)-[1,2,4]triazolo[4,3-a]pyridin-3(2H)-one,
(R)-2-((5-(2,2-dimethyl-1,3-dioxolan-4-yl)-1,2,4-oxadiazol-3-yl)methyl)-6-(4-(trifluoromethoxy)phenyl)-[1,2,4]thazolo[4,3-a]pyridin-3(2H)-one;
2-(2-(4-(methylthio)pyrimidin-2-yloxy)ethyl)-6-(4-(trifluoromethoxy)phenyl)-[1,2,4]triazolo[4,3-a]pyridin-3(2H)-one;
2-(2-(2-(3-oxo-6-(4-(trifluoromethoxy)phenyl)-[1,2,4]triazolo[4,3-a]pyridin-2(3H)-yl)ethyloxo-6-(4-(trifluoromethoxy)phenyl)-[1,2,4]triazolo[4,3-a]pyridin-2(3H)-yl)ethoxy)pyrimidin-4-yloxy)acetonitrile;
6-(4-chloro-3-fluorophenyl)-2-((3-methyl-1,2,4-oxadiazol-5-yl)methyl)-[1,2,4]triazolo[4,3-a]pyridin-3(2H)-one;
2-((5-((pyrimidin-2-yloxy)methyl)-1,2,4-oxadiazol-3-yl)methyl)-6-(4-(trifluoromethoxy)phenyl)-[1,2,4]triazolo[4,3-a]pyridin-3(2H)-one;
2-((1-methyl-1H-pyrazol-4-yl)methyl)-6-(4-(trifluoromethoxy)phenyl)-[1,2,4]triazolo[4,3-a]pyridin-3(2H)-one;
2-((3-methylisoxazol-5-yl)methyl)-6-(4-(trifluoromethoxy)phenyl)-[1,2,4]thazolo[4,3-a]pyridin-3(2H)-one;
2-((1-methyl-1H-pyrazol-3-yl)methyl)-6-(4-(trifluoromethoxy)phenyl)-[1,2,4]thazolo[4,3-a]pyridin-3(2H)-one;
2-((3-ethyl-1,2,4-oxadiazol-5-yl)methyl)-6-(4-(trifluoromethoxy)phenyl)-[1,2,4]thazolo[4,3-a]pyridin-3(2H)-one;
2-((3-ethyl-1,2,4-oxadiazol-5-yl)methyl)-6-(4-(trifluoromethyl)phenyl)-[1,2,4]triazolo[4,3-a]pyridin-3(2H)-one;
2-((3-(methoxymethyl)-1,2,4-oxadiazol-5-yl)methyl)-6-(4-(trifluoromethyl)phenyl)-[1,2,4]thazolo[4,3-a]pyridin-3(2H)-one;
2-((3-trideuteromethyl-1,2,4-oxadiazol-5-yl)methyl)-6-(4-(trifluoromethoxy)phenyl)-[1,2,4]thazolo[4,3-a]pyridin-3(2H)-one;
2-((5-cyclopropyl-1,3,4-thiadiazol-2-yl)methyl)-6-(4-(trifluoromethoxy)phenyl)-[1,2,4]triazolo[4,3-a]pyridin-3(2H)-one;
6-(4-(trifluoromethyl)phenyl)-[1,2,4]thazolo[4,3-a]pyridin-3(2H)-one;
2-((5-methyloxazol-2-yl)methyl)-6-(4-(trifluoromethyl)phenyl)-[1,2,4]thazolo[4,3-a]pyridin-3(2H)-one;
2-((4,5-dimethyloxazol-2-yl)methyl)-6-(4-(trifluoromethyl)phenyl)-[1,2,4]thazolo[4,3-a]pyridin-3(2H)-one;
2-(2-(imidazo[1,2-a]pyrazin-8-yloxy)ethyl)-6-(4-(trifluoromethoxy)phenyl)-[1,2,4]thazolo[4,3-a]pyridin-3(2H)-one;
2-((5-((pyridin-2-yloxy)methyl)-1,2,4-oxadiazol-3-yl)methyl)-6-(4-(trifluoromethoxy)phenyl)-[1,2,4]thazolo[4,3-a]pyridin-3(2H)-one;
2-((5-((2-ethoxyphenoxy)methyl)-1,2,4-oxadiazol-3-yl)methyl)-6-(4-(trifluoromethoxy)phenyl)-[1,2,4]thazolo[4,3-a]pyridin-3(2H)-one,
2-(2-(4-isopropoxypyrimidin-2-yloxy)ethyl)-6-(4-(trifluoromethoxy)phenyl)-[1,2,4]triazolo[4,3-a]pyridin-3(2H)-one;
2-(2-(4-(2,2,2-trifluoroethoxy)pyrimidin-2-yloxy)ethyl)-6-(4-(trifluoromethoxy)phenyl)-[1,2,4]triazolo[4,3-a]pyridin-3(2H)-one,
2-(2-(4-(cyclopropylmethoxy)pyrimidin-2-yloxy)ethyl)-6-(4-(trifluoromethoxy)phenyl)-[1,2,4]triazolo[4,3-a]pyridin-3(2H)-one;

6-(4-(trifluoromethoxy)phenyl)-2-(2-(5-(trifluoromethyl)pyrimidin-2-yloxy)ethyl)-[1,2,4]thazolo[4,3-a]pyridin-3(2H)-one;

2-((2-cyclopropyloxazol-4-yl)methyl)-6-(4-(trifluoromethoxy)phenyl)-[1,2,4]thazolo[4,3-a]pyridin-3(2H)-one;

2-((5-cyclopropyl-1,3,4-oxadiazol-2-yl)methyl)-6-(4-(4-fluorophenoxyl)phenyl)-[1,2,4]triazolo[4,3-a]pyridin-3(2H)-one;

2-((5-tert-butyloxazol-2-yl)methyl)-6-(4-(trifluoromethoxy)phenyl)-[1,2,4]triazolo[4,3-a]pyridin-3(2H)-one;

2-((5-tert-butyloxazol-2-yl)methyl)-6-(4-(trifluoromethyl)phenyl)-[1,2,4]triazolo[4,3-a]pyridin-3(2H)-one;

2-methyl-6-(4-(trifluoromethyl)phenyl)-[1,2,4]triazolo[4,3-a]pyridin-3(2H)-one;

(R)-2-(2-(3-(4-fluorophenoxy)pyrrolidin-1-yl)ethyl)-6-(4-(trifluoromethoxy)phenyl)-[1,2,4]triazolo[4,3-a]pyridin-3(2H)-one;

5-methyl-6-(4-(trifluoromethoxy)phenyl)-[1,2,4]triazolo[4,3-a]pyridin-3(2H)-one;

5-methyl-2-((3-methyl-1,2,4-oxadiazol-5-yl)methyl)-6-(4-(trifluoromethoxy)phenyl)-[1,2,4]triazolo[4,3-a]pyridin-3(2H)-one;

2-(2,2,2-trifluoroethyl)-6-(4-(trifluoromethoxy)phenyl)-[1,2,4]thazolo[4,3-a]pyridin-3(2H)-one;

2-isopropyl-6-(4-(trifluoromethoxy)phenyl)-[1,2,4]triazolo[4,3-a]pyridin-3(2H)-one;

2-((4-methyloxazol-2-yl)methyl)-6-(4-(trifluoromethoxy)phenyl)-[1,2,4]triazolo[4,3-a]pyridin-3(2H)-one;

2-((4-methyloxazol-2-yl)methyl)-6-(4-(trifluoromethyl)phenyl)-[1,2,4]triazolo[4,3-a]pyridin-3(2H)-one;

2-((4-cyclopropyloxazol-2-yl)methyl)-6-(4-(trifluoromethoxy)phenyl)-[1,2,4]triazolo[4,3-a]pyridin-3(2H)-one 2-((4-cyclopropyloxazol-2-yl)methyl)-6-(4-(trifluoromethyl)phenyl)-[1,2,4]triazolo[4,3-a]pyridin-3(2H)-one;

6-(4-chlorophenyl)-2-((5-methyloxazol-2-yl)methyl)-[1,2,4]triazolo[4,3-a]pyridin-3(2H)-one;

8-methyl-6-(4-(trifluoromethoxy)phenyl)-[1,2,4]triazolo[4,3-a]pyridin-3(2H)-one;

2-((2-methyloxazol-5-yl)methyl)-6-(4-(trifluoromethyl)phenyl)-[1,2,4]triazolo[4,3-a]pyridin-3(2H)-one;

2-(3-(4,5-dichloro-2-methoxyphenoxy)-2-hydroxypropyl)-6-(4-(trifluoromethyl)phenyl)-[1,2,4]triazolo[4,3-a]pyridin-3(2H)-one;

2-((5-cyclopropyloxazol-2-yl)methyl)-6-(4-(trifluoromethoxy)phenyl)-[1,2,4]triazolo[4,3-a]pyridin-3(2H)-one;

6-(4-(trifluoromethoxy)phenyl)-[1,2,4]triazolo[4,3-a]pyridin-3(2H)-one; and 2-methyl-6-(4-(trifluoromethoxy)phenyl)-[1,2,4]triazolo[4,3-a]pyridin-3(2H)-one, or a pharmaceutically acceptable salt, ester, or stereoisomer thereof.

* * * * *